United States Patent
Van Der Oost et al.

(10) Patent No.: US 12,071,639 B2
(45) Date of Patent: *Aug. 27, 2024

(54) THERMOSTABLE CAS9 NUCLEASES

(71) Applicants: Wageningen Universiteit, Wageningen (NL); Stichting Voor De Technische Wetenschappen, Utrecht (NL)

(72) Inventors: John Van Der Oost, Renkum (NL); Richard Van Kranenburg, Gorinchem (NL); Elleke Fenna Bosma, Denmark (NL); Ioannis Mougiakos, Wageningen (NL); Prarthana Mohanraju, Wageningen (NL)

(73) Assignees: Wageningen Universiteit, Wageningen (NL); Stichting Voor De Technische Wetenschappen, Utrecht (NL)

( * ) Notice: Subject to any disclaimer, the term of this patent is extended or adjusted under 35 U.S.C. 154(b) by 824 days.

This patent is subject to a terminal disclaimer.

(21) Appl. No.: 16/469,691

(22) PCT Filed: Dec. 14, 2017

(86) PCT No.: PCT/EP2017/082870
§ 371 (c)(1),
(2) Date: Jun. 14, 2019

(87) PCT Pub. No.: WO2018/109101
PCT Pub. Date: Jun. 21, 2018

(65) Prior Publication Data
US 2019/0360002 A1   Nov. 28, 2019

(30) Foreign Application Priority Data

Dec. 14, 2016 (WO) ................ PCT/EP2016/081077
Aug. 16, 2017 (WO) ................ PCT/EP2017/070796

(51) Int. Cl.
C12N 9/22    (2006.01)
C12N 15/10   (2006.01)
C12N 15/11   (2006.01)
C12N 15/113  (2010.01)
C12N 15/90   (2006.01)

(52) U.S. Cl.
CPC ............ *C12N 9/22* (2013.01); *C12N 15/102* (2013.01); *C12N 15/11* (2013.01); *C12N 15/113* (2013.01); *C12N 15/902* (2013.01); *C12N 15/907* (2013.01); *C12N 2310/20* (2017.05); *C12N 2330/51* (2013.01)

(58) Field of Classification Search
None
See application file for complete search history.

(56) References Cited

U.S. PATENT DOCUMENTS

| 10,731,142 B2 * | 8/2020 | Van Der Oost | C12N 15/79 |
| 11,242,513 B2 * | 2/2022 | Van Der Oost | C12N 9/22 |
| 11,326,162 B2 * | 5/2022 | Van Der Oost | C12N 15/11 |
| 2002/0106800 A1 * | 8/2002 | Liaw | C12N 1/205 435/488 |
| 2014/0068797 A1 | 3/2014 | Doudna | |
| 2016/0139124 A1 | 5/2016 | Newman | |
| 2018/0171314 A1 * | 6/2018 | Van Der Oost | C12N 9/22 |

FOREIGN PATENT DOCUMENTS

| CN | 102712912 | 10/2012 | |
| JP | 2006230303 | 9/2006 | |
| JP | 2007537724 A | 12/2007 | |
| JP | 2010510776 A | 4/2010 | |
| WO | WO-0192471 A1 * | 12/2001 | ............... C02F 3/34 |
| WO | 2005084409 | 9/2005 | |
| WO | 2008066280 | 6/2008 | |
| WO | 2014144951 | 9/2014 | |
| WO | 2015139008 | 9/2015 | |
| WO | 2016073990 | 5/2016 | |
| WO | WO-2016099887 A1 * | 6/2016 | ............. C12N 15/10 |
| WO | 2016179038 A1 | 11/2016 | |
| WO | 2016186946 A1 | 11/2016 | |

(Continued)

OTHER PUBLICATIONS

Blast alignment of NmCas9 and SEQ ID No. 1 (https://blast.ncbi.nlm.nih.gov/Blast.cgi) (Year: 2022).*
Addgene vector pBAD/His A plasmid, https://www.addgene.org/vector-database/1827/ [retrieved from internet May 26, 2022] (Year: 2022).*
Clustal alignment of SEQ ID No. 1 from instant and other patent documents (https://www.ebi.ac.uk/Tools/msa/clustalo/). (Year: 2022).*
Liu et al., bioRxiv preprint doi: https://doi.org/10.1101/088336; published Nov. 17, 2016 (Year: 2016).*

(Continued)

*Primary Examiner* — Celine X Qian
*Assistant Examiner* — Catherine Konopka
(74) *Attorney, Agent, or Firm* — Riverside Law LLP

(57) ABSTRACT

A polynucleotide encoding a ThermoCas9 protein from *Geobacillus thermodenitrificans* and a constitutive promoter are used to engineer eukaryotic cells, e.g. fungi, yeast or algae, so that the ThermoCas9 endonuclease is integrated and expressed from the genome of the cell. Then, a second expression plasmid is used to transfect these ThermoCas9 expressing cells, the second plasmid containing an inducible promoter and a polynucleotide encoding a guide RNA. The guide RNA combines with the ThermoCas9 to provide the targeted endonuclease activity to cleave the cell DNA at a desired locus or gene of interest. A repair-oligo is also provided to the cell whereby following DNA cleavage, homologous recombination takes place in the cell with the repair-oligo so that either a deletion or substitution of nucleotides in the locus or gene of interest is achieved. Expression vectors and methods of using the vectors to achieve ThermoCas9 mediated gene editing are described whereby higher temperatures, e.g. greater than 30° C., are used.

17 Claims, 32 Drawing Sheets
Specification includes a Sequence Listing.

(56) References Cited

FOREIGN PATENT DOCUMENTS

| WO | 2016198361 A1 | 12/2016 |
| WO | 2018108272 A1 | 6/2018 |

OTHER PUBLICATIONS

A0A150MP45_GEOSE, sequence first published Jun. 8, 2016, annotated Oct. 5, 2016) (Year: 2016).*

Nishimasu et al., Crystal Structure of Cas9 in Complex with Guide RNA and Target DNA. Cell (2014), 156, 935-949 (Year: 2014).*

Jinek et al., Structures of Cas9 Endonucleases Reveal RNA-Mediated Conformational Activation. Science (2014) 343: 1247997-1 ( Year: 2014).*

Nishimasu et al., Crystal Structure of *Staphylococcus aureus* Cas9. Cell (2015), 162: 1113-1126 (Year: 2015).*

Corrected Notice of Allowability dated Nov. 22, 2021 for U.S. Appl. No. 16/469,677 (pp. 1-2).

Corrected Notice of Allowability dated Nov. 23, 2021 for U.S. Appl. No. 16/469,674 (pp. 1-2).

CRISPR-associated endonuclease Cas9 [Geobacillus stearothermophilus] GenBank: KZE96909.1, 2016.

Daas et al., 2016, "Isolation of a genetically accessible thermophilic xylan degrading bacterium from compost." Biotechnol Biofuels, 9:210.

Karvelis et al., (2015) "Rapid characterization of CRISPR-Cas9 protospacer adjacent motif sequence elements," Genome Biology 16:253.

Leenay et al., 2016, "Identifying and Visualizing Functional PAM Diversity across CRISPR-Cas Systems," Molecular Cell, 62(1):137-147.

Notice of Allowance dated Sep. 24, 2021 for U.S. Appl. No. 16/469,677 (pp. 1-17).

Notice of Allowance dated Sep. 28, 2021 for U.S. Appl. No. 16/469,674 (pp. 1-16).

Translation of JP2006230303A "Thermophilic lipase producing bacterium and use thereof", 7 pages.

Harrington et al., "A thermostable Cas9 with increased lifetime in human plasma," Nat Commun. 2017; 8: 1424, 26 pages.

Mougiakos et al., "Next Generation Prokaryotic Engineering: The CRISPR-Cas Toolkit," Trends Biotechnol. Jul. 2016;34(7):575-587.

Mougiakos et al., "Efficient Genome Editing of a Facultative Thermophile Using Mesophilic spCas9," ACS Synth Biol. May 19, 2017;6(5):849-861.

Blenke et al., CRISPR-Cas9 gene editing: Delivery aspects and therapeutic potential, J Control Release. Dec. 28, 2016;244(Pt B):139-148.

"RecName: Full=CRISPR-associated endonuclease Cas9 {ECO:0000256|HAMAP-Rule:MF_01480}; EC=3.1.-.-{ECO:0000256|HAMAP-Rule:MF_01480};", UniProt, (Sep. 7, 2016), Database accession No. A0A178TEJ9, URL: EBI, XP002773239, 2 pages.

Mougiakos Ioannis et al., "Characterizing a thermostable Cas9 for bacterial genome editing and silencing.", Nature Communications, (Nov. 21, 2017), vol. 8, No. 1, doi: 10.1038/s41467-017-01591-4, ISSN 2041-1723, pp. 1-11, XP002779888.

Written Opinion in App. No. SG11201905380U, dated Oct. 5, 2020, 6 pages.

Written Opinion in App. No. SG11201905381X, dated Oct. 3, 2020, 7 pages.

Written Opinion in App. No. SG11201905383Y, dated Sep. 28, 2020, 7 pages.

Written Opinion in App. No. SG11201905378P, dated Oct. 5, 2020, 7 pages.

Blast search and alignment of SEQ ID No. 1, , https://blast.ncbi.nlm.nih.gov/Blast.cgi, [retrieved Jun. 6, 2022] (Year: 2022).

Jinek et al., Structures of Cas9 Endonucleases Reveal RNA-Mediated Conformational Activation. Science (2014), 343: 1247997-1-1247997-11 (Year: 2014).

NCBI, "type II CRISPR RNA-guided endonuclease Cas9 [Geobacillus stearothermophilus]", «NCBI Reference Sequence: WP_064213580.1» 2 pages.

Standage-Beier et al., "Targeted Large-Scale Deletion of Bacterial Genomes Using CRISPR-Nickases," ACS Synth Biol, Nov. 20, 2015;4(11):1217-25.

Cong et al., "Multiplex Genome Engineering Using CRISPR/Cas Systems." Science (2013), 339: 819-823 (Year: 2013).

CRISPR-associated endonuclease Cas9 {ECO:0000256|HAMAP-Rule:MF_01480}; EC=3.1.-.-{ECO:0000256HAMAP-Rule:MF_01480}; Geobacillus stearothermophilus (Bacillus stearothermophilus); UniprotKB/TrEMBL A0A178TEJ9 (Year: 2016) 21 pages.

\* cited by examiner

Match to: DQ453159 DQ453159 Geobacillus virus E2, complete genome(DQ453159) position: 39980-39951, with: spacer4 CRISPR No.4 Spacer No.1 (spacer4_3_1) position: 1-30, Strand: +

(SEQ ID NO:242) 5' ▓▓▓▓▓CUGGCGGUGCGAAUUCUAACCGUCCCGGAA▓▓▓▓▓ 3' <- CRISPR spacer RNA (SEQ ID NO:243) 3' ▓▓▓▓▓AACCGCCACGCTTAAGATTGGCAGGGCCTT▓▓▓ 5' <- Protospacer Sequence (SEQ ID NO:244) 5' ▓▓▓▓▓TTGGCGGTGCGAATTCTAACCGTCCCGGAA▓▓▓▓ 3' <- [Entrez Nucleotide]

Score: 30

Match to: Bacillus alcaayensis strain 24KAM51 LG50_053, whole genome shotgun sequence(NZ_JYCF01000053) position: 110918-110889, with: spacer9 CRISPR No.9 Spacer No.1 (spacer9_9_1) position: 1-30, Strand: +

(SEQ ID NO:245) 5' ▓▓▓▓▓UCUACCUCUACUCUCGAUUCACGAAUCGG▓▓▓ 3' <- CRISPR spacer RNA (SEQ ID NO:246) 3' ▓▓▓▓▓AAGATGGAGATGAGAGCTAAGTGCTTAGCC▓▓▓▓ 5' <- Protospacer Sequence (SEQ ID NO:247) 5' ▓▓▓▓▓TCTACCTCTACTCTCGATTCACGAATCG▓▓▓ 3' <- [Entrez Nucleotide]

Score: 30

Match to: Anoxybacillus flavithermus WK1, complete genome(CP000922) position: 701422-701450, with: spacer5 CRISPR No.5 Spacer No.1 (spacer5_5_1) position: 1-29, Strand: -

(SEQ ID NO:248) 5' ▓▓▓▓▓UCACGGAGCUUUACACAAAUAAAGCCGGA▓▓▓ 3' <- CRISPR spacer RNA (SEQ ID NO:249) 3' ▓▓▓▓▓AGTGCCTCGAAATGTGTTTATTTCGGCCT▓▓▓ 5' <- Protospacer Sequence (SEQ ID NO:250) 5' ▓▓▓▓▓TCACGGAGCTTTACACAAATAAAGCCGGA▓▓▓▓▓ 3' <- [Entrez Nucleotide]

Score: 29

Match to: Geobacillus kaustophilus strain E123 LG51_086, whole genome shotgun sequence(NZ_JYCF01000086) position: 15565-15537, with: spacer5 CRISPR No.5 Spacer No.1 (spacer5_5_1) position: 1-29, Strand: +

(SEQ ID NO:251) 5' ▓▓▓▓▓UCACGGAGCUUUACACAAAUAAAGCCGGA▓▓▓ 3' <- CRISPR spacer RNA (SEQ ID NO:252) 3' ▓▓▓▓▓AGTGCCTCGAAATGTGTTTATTTCGGCCT▓▓▓ 5' <- Protospacer Sequence

Fig. 7B

Colonies are indicated with arrows.

Fig. 18C
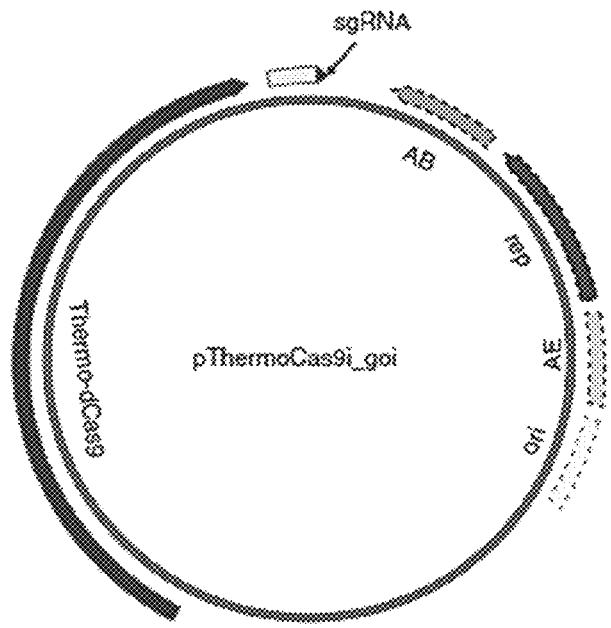
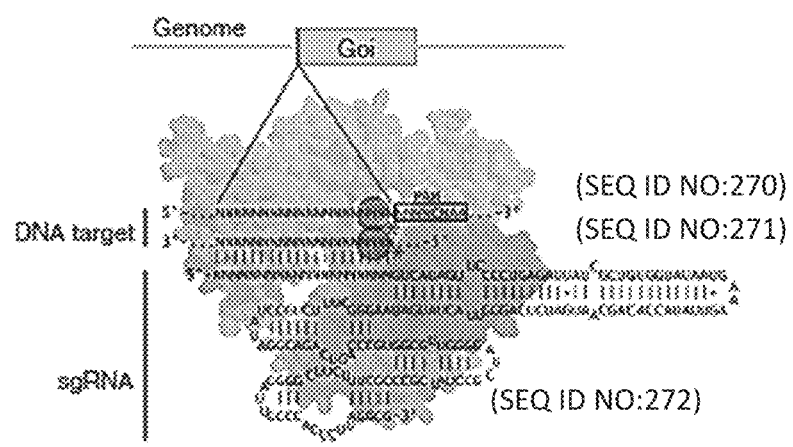
Fig. 18D
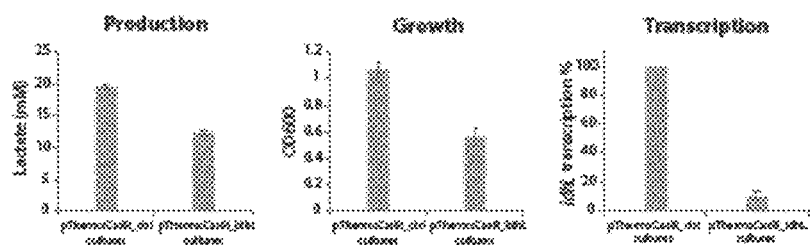

Fig. 20A
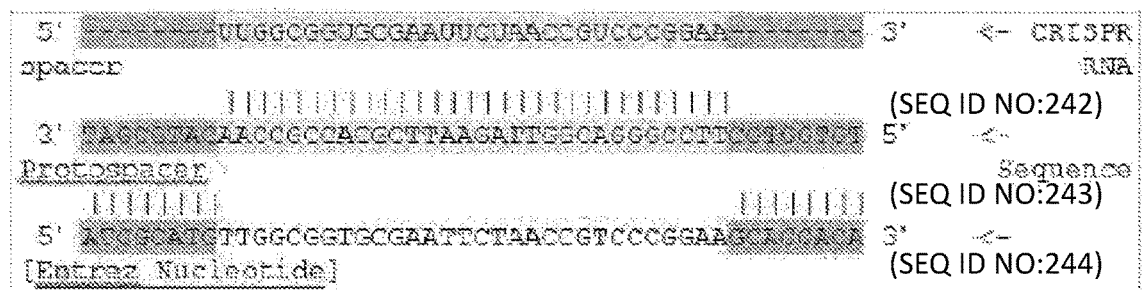
(SEQ ID NO:242)
(SEQ ID NO:243)
(SEQ ID NO:244)
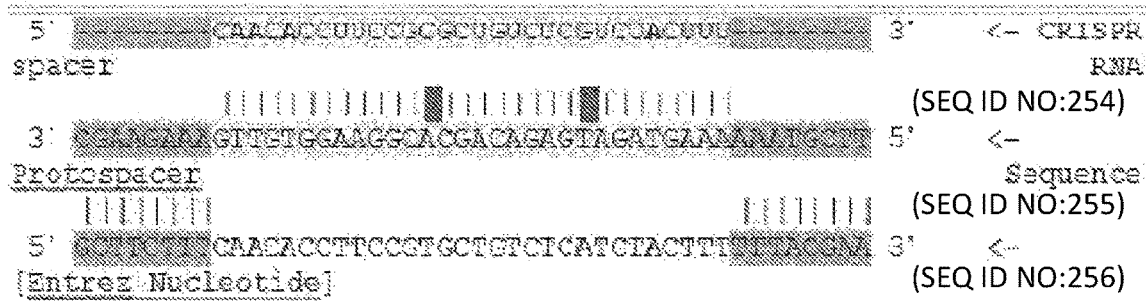
(SEQ ID NO:254)
(SEQ ID NO:255)
(SEQ ID NO:256)
Fig. 20B
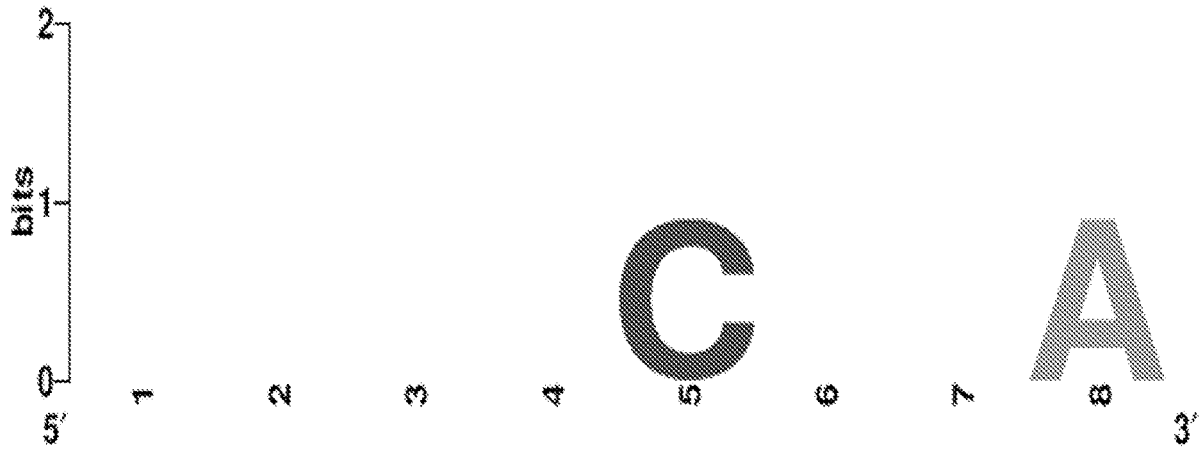

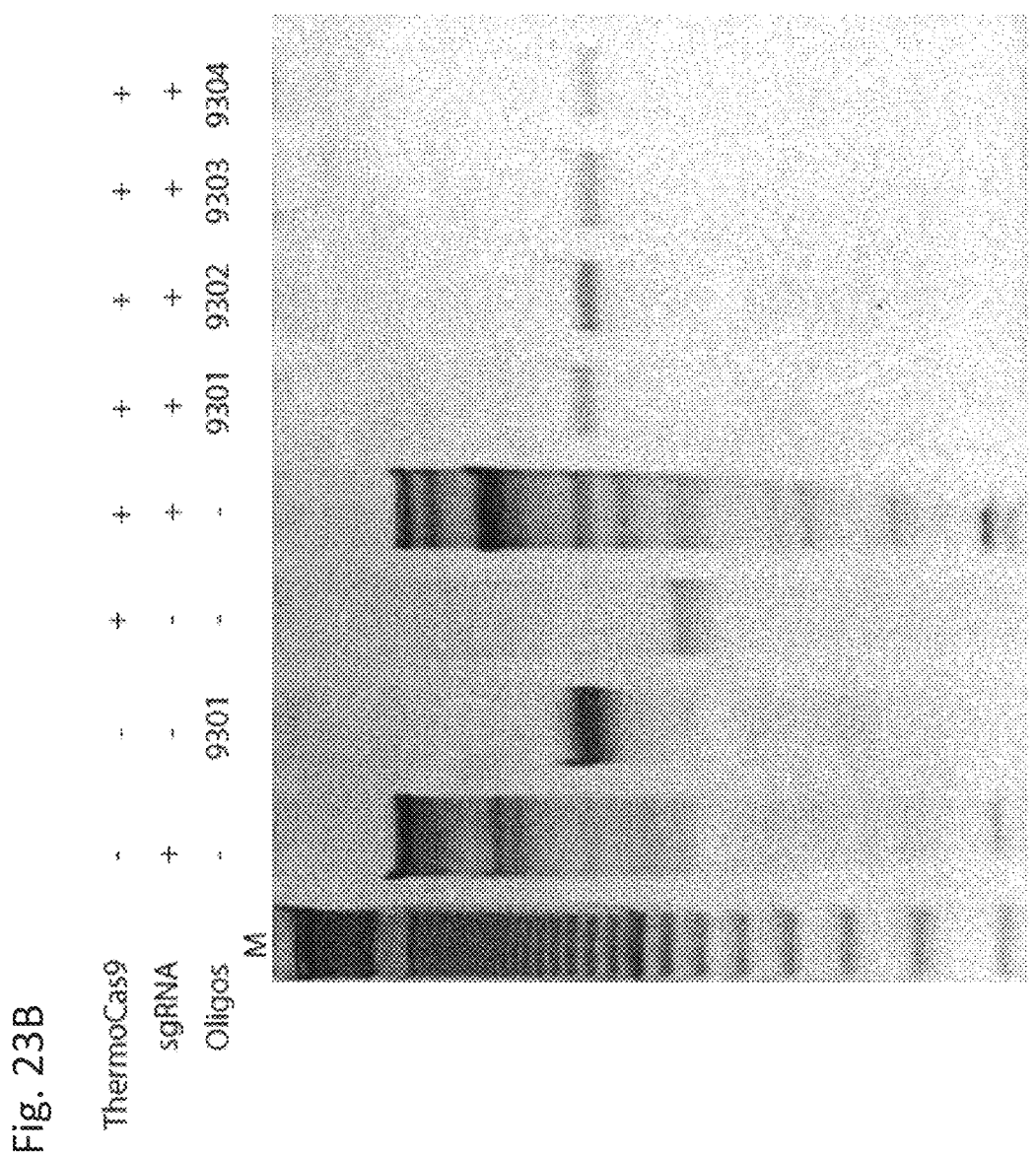

THERMOSTABLE CAS9 NUCLEASES

CROSS-REFERENCE TO RELATED APPLICATIONS

This application is a U.S. national phase application filed under 35 U.S.C. § 371 claiming priority to International Patent Application No. PCT/EP17/082870, filed Dec. 14, 2017, which claims priority to International Patent Application No. PCT/EP16/081077, filed Dec. 14, 2016, and to International Patent Application No. PCT/EP17/071796, filed Aug. 16, 2017, the contents of each of which are incorporated by reference herein in their entireties.

SEQUENCE LISTING

This application contains a Substitute Sequence Listing that is provided herewith in the form of an 152,416 byte ASCII text file named "206071-0016-00US_SubstituteSequenceListing.txt" created on Oct. 19, 2022, the material of which is herein incorporated by reference.

FIELD OF THE INVENTION

The present invention relates to the field of genetic engineering and more particularly to nucleic acid editing and genome modification. The present invention concerns genetic engineering tools in the form of nucleases which can be configured for sequence-directed site-specific binding, nicking, cutting and modification of genetic material; also, ribonucleoproteins which exert activity, particularly nuclease activity, on sequence specific sites of genetic material, and modified nucleases and ribonucleoproteins for use as markers. The invention therefore also concerns associated expression constructs for delivery and expression of nucleases and guide RNAs within non-human cells. Further, the invention concerns the sequence-specific editing of nucleic acids in vitro or in vivo and methods used to achieve that. A particular area to which the invention relates is the genetic manipulation of thermophilic organisms, particularly microorganisms.

BACKGROUND TO THE INVENTION

It was first demonstrated in 2007 that CRISPR-Cas is an adaptive immune system in many bacteria and most archaea (Barrangou et al., 2007, Science 315: 1709-1712), Brouns et al., 2008, Science 321: 960-964). Based on functional and structural criteria, two classes of CRISPR-Cas systems that each comprise three types have so far been characterized, most of which use small RNA molecules as guide to target complementary DNA sequences (Makarova et al., 2015, Nat Rev Microbiol 13: 722-736; Mahanraju et al., 2016, Science 353: aad5147).

In a recent study by the Doudna/Charpentier labs, a thorough characterization of the effector enzyme of the class 2/type II CRISPR-Cas system (Cas9) was performed, including demonstration that the introduction of designed CRISPR RNA guides (with specific spacer sequences) targets complementary sequences (protospacers) on a plasmid, causing double strand breaks of this plasmid (Jinek et al., 2012, Science 337: 816-821). Following Jinek et al., 2012, Cas9 is used as a tool for genome editing.

Cas9 has been used to engineer the genomes of a range of eukaryotic cells (e.g. fish, plant, man) (Charpentier and Doudna, 2013, Nature 495: 50-51).

In addition, Cas9 has been used to improve yields of homologous recombination in bacteria by selecting for dedicated recombination events (Jiang et al., 2013, Nature Biotechnol 31: 233-239). To achieve this, a toxic fragment (Targeting construct) is co-transfected with a rescuing fragment carrying the desired alteration (Editing construct, carrying point mutation or deletions). The Targeting construct consists of Cas9 in combination with a design CRISPR and an antibiotic resistance marker, defining the site of the desired recombination on the host chromosome; in the presence of the corresponding antibiotic, integration of the Targeting construct in the host chromosome is selected for. Only when the additional recombination occurs of the Editing construct with the CRISPR target site on the host chromosome, the host can escape from the auto-immunity problem. Hence, in the presence of the antibiotic, only the desired (marker-free) mutants are able to survive and grow. A related strategy to select for subsequent removal of the integrated Targeting construct from the chromosome is presented as well, generating a genuine marker free mutant.

It has been established in recent years that CRISPR-Cas mediated genome editing constitutes a useful tool for genetic engineering. It has been established that the prokaryotic CRISPR systems serve their hosts as adaptive immune systems (Jinek et al., 2012, Science 337: 816-821) and can be used for quick and effective genetic engineering (Mali et al., 2013, Nat Methods 10:957-963, for example), requiring only modification of the guide sequence in order to target sequences of interest.

However, there is a continuing need for the development of agents with improved sequence-specific nucleic acid detection, cleavage and manipulation under a variety of experimental conditions for application in the area of genetic research and genome editing. In particular, currently available sequence-specific genome editing tools, including Cas9, are not applicable for use in all conditions or organisms, for example, sequence-specific nucleases are relatively thermo-sensitive and therefore not applicable for use in strictly thermophilic microorganisms (which are capable of growth between 41° C. and 122° C. and grow optimally in the ranges of temperatures from >45° C. to 80° C. with hyperthermophiles capable of optimal growth above 80° C.), for example, microorganisms that are used in industrial fermentations or for in vitro laboratory processes conducted at elevated temperatures.

To date there is no experimental evidence for active Cas9 proteins in thermophiles. Based on a comparative genome screening by Chylinski et al. (2014; Nucleic Acids Research 42: 6091-61-05) on the presence of Cas9 in bacteria it was found that the Type II-C CRISPR-Cas system is only present in approximately 3.3% of all bacterial genomes. Among thermophilic bacteria, the Type II system is underrepresented based on statistical analysis (P=0.0019). In addition, no Type II system has been found in archaea however, this could possibly be due to the absence of the RNase III protein (involved in the Type II system) in archaea. Chylinski, et al., (2014; Nucleic Acids Research 42: 6091-6105) did describe the classification and evolution of type II CRISPR-Cas systems, in particular, two species are identified which exhibit these systems, however these species grow maximally at 55° C. and do not exhibit strictly thermophilic growth with optimum growth temperature 60-80° C., with hyperthermophiles capable of growing optimally above 80° C.

Despite the rarity of the CRISPR-Cas system in bacterial genomes and in particular the fact that Cas9 has been found only in bacteria (not archaea) with optimal growth temperatures below 45° C., the inventors have surprisingly discovered several thermostable Cas9 variants which enable genome editing to be carried out at elevated temperatures. The inventors have also discovered optimised protospacer adjacent motif (PAM) sequences that work with the thermostable Cas9 variants to enable genome editing to be carried out over a wide range of temperatures, including at the elevated temperatures. These Cas9 nucleases, and RNA molecules that are designed with knowledge of the associated PAM sequences, provide novel tools for genetic engineering at elevated temperatures and are of particular value in the genetic manipulation of thermophilic organisms; particularly microorganisms.

A phylogenetic re-assessment of the thermophilic genus *Geobacillus* has recently been performed, which resulted in the creation of a new genus, *Parageobacillus*. Consequently, some species previously of the genus *Geobacillus* have been systematically re-assigned to *Parageobacillus* and re-named accordingly (Aliyu et al., (2016) Systematic and Applied Microbiology 39:527-533).

Clustered Regularly Interspaced Short Palindromic Repeats (CRISPR) and the CRISPR-associated (Cas) proteins provide adaptive and heritable immunity in prokaryotes against invading genetic elements (Brouns et al. Science 321, (2008); Barrangou et al. CRISPR provides acquired resistance against viruses in prokaryotes. Science 315, (2007); Wright et al. Cell 164, 29-44 (2016); Mohanraju et al. Science 353, aad5147 (2016)). CRISPR-Cas systems are subdivided into two classes (1 and 2) and six types (I-VI), depending on their complexity and signature protein (Makarova et al. *Nat. Rev. Microbiol.* 13, 722-736 (2015)). Class 2 systems, including type-II CRISPR-Cas9 and type V CRISPR-Cas12a (previously called CRISPR-Cpf1) have recently been exploited as genome engineering tools for both eukaryotes (Komor et al. Cell 168, 20-36 (2017); Puchta, Curr. Opin. Plant Biol. 36, 1-8 (2017); Xu et al. J. Genet. Genomics 42, 141-149 (2015); Tang et al. Nat. Plants 3, 17018 (2017); Zetsche et al. Nat. Biotechnol. 35, 31-34 (2016)) and prokaryotes (Mougiakos, et al. Trends Biotechnol. 34, 575-587 (2016)). These systems are among the simplest CRISPR-Cas systems known as they introduce targeted double stranded DNA breaks (DSBs) based on a ribonucleoprotein (RNP) complex formed by a single Cas endonuclease and an RNA guide.

To date, *Streptococcus pyogenes* Cas9 (SpCas9) is the best characterized and most widely employed Cas9 for genome engineering. Although a few other type-II systems have been characterized, none of them is derived from a thermophilic organism (Nakade, et al. Bioengineered 1-9 (2017). doi:10.1080/21655979.2017.1282018). Characterization of such CRISPR-Cas systems would be interesting to gain fundamental insights as well as to develop novel applications.

Although basic genetic tools are available for a number of thermophiles (Taylor et al. Microb. Biotechnol. 4, 438-448 (2011); Olson, et al. Curr. Opin. Biotechnol. 33, 130-141 (2015); Zeldes, et al. Front. Microbiol. 6, 1209 (2015)), the efficiency of these tools is still too low to enable full exploration and exploitation of this interesting group of organisms. Based on our finding that SpCas9 is not active in vivo ≥42° C., we have previously developed an SpCas9-based engineering tool for facultative thermophiles, combining homologous recombination at elevated temperatures and SpCas9-based counter-selection at moderate temperatures (Mougiakos et al. *ACS Synth. Biol.* 6, 849-861 (2017)). However, a Cas9-based editing and silencing tool for obligate thermophiles is not yet available as SpCas9 is not active at or above 42° C. (Mougiakos et al. *ACS Synth. Biol.* 6, 849-861 (2017)) and to date no thermophilic Cas9 has been characterized.

SUMMARY OF THE INVENTION

The inventors have discovered and characterised ThermoCas9: an RNA-guided DNA-endonuclease from the CRISPR-Cas type-IIC system of the thermophilic bacterium *Geobacillus thermodenitrificans* T12. The inventors have surprisingly shown its in vitro activity over a broad temperature range, demonstrated the importance of the sgRNA-structure for thermostability and applied ThermoCas9 for in vivo genome editing across a wide temperature range.

Accordingly, the present invention provides a method of modifying the genetic material of a eukaryotic cell, comprising (i) integrating a polynucleotide encoding a ThermoCas9 under the control of a first promoter into the genome of the cell, wherein the expressed ThermoCas9 comprises an amino acid sequence of SEQ ID NO: 1 or a sequence of at least 77% identity therewith, or an active fragment thereof; (ii) transforming the cell with an expression vector comprising a polynucleotide sequence encoding a guide RNA and under the control of a second promoter, wherein the guide RNA has a nucleic acid sequence which recognizes a nucleic acid sequence comprised at a desired target locus in the genome of the cell, and (iii) transforming the cell with a repair oligonucleotide.

The ThermoCas9 nuclease of the specified sequence and variant and fragments noted above is the ThermoCas9 of the aspects of the invention described hereinafter. The active fragments of the ThermoCas9 have guide RNA directed endonuclease activity with respect to target sequences in the genome of cells or organisms which are desired to be modified.

The genome of the cell may be modified first to express the ThermoCas9, whether constitutively or inducible, after which the cell is transformed with the expression vector for the gRNA; optionally at the same time or separately of transformation with the repair-oligo. In one possibility, the cell may be transformed simultaneously with all three elements, ThermoCas9 integration vector, gRNA expression vector and repair oligonucleotide.

In alternative aspect, the invention provides a method of modifying the genetic material of a eukaryotic cell, comprising (i) integrating a polynucleotide encoding a ThermoCas9 under the control of a first promoter into the genome of the cell, wherein the expressed ThermoCas9 comprises an amino acid sequence of SEQ ID NO: 1 or a sequence of at least 77% identity therewith, or an active fragment thereof; and (ii) transforming the cell with an expression vector comprising a polynucleotide sequence encoding a guide RNA under the control of the first or of a separate second promoter, wherein the guide RNA has a nucleic acid sequence which recognizes a nucleic acid sequence comprised at a desired target locus in the genome of the cell, and a repair oligonucleotide also under the control of the first or the second promoter, or a separate third promoter.

The repair oligonucleotide is preferably a double-stranded DNA repair oligo; optionally comprising a polynucleotide sequence for insertion into the genome of the cell by way of homologous recombination following guide RNA directed ThermoCas9 endonuclease cutting. Therefore, the repair oligo which does not contain and insert may be used to achieve a deletion of a desired locus or gene segment in the genome of the cell.

In some embodiments, the first promoter is a constitutive promoter, e.g. TEF1 promoter. In other embodiments, the first promoter may be a physical or chemically inducible promoter of the kinds described hereinafter in connection with other aspects of the invention.

Various combinations of promoter are possible in accordance with the invention such that the the second promoter may be a constitutive or inducible promoter. Any third promoter may be a constitutive or inducible promoter.

The cell may be transformed with the expression plasmid(s) and/or the repair-oligo by heat-shock or for example by electroporation.

Certain eukaryotic cells are able to grow at temperatures up to about 62° C.-63° C. Various fungi or algae or blue green algae, for example. Therefore the methods of the invention may be employed wherein the cell is transformed and/or grown following transformation at a temperature in the range 26° C.-63° C.; preferably 31° C.-61° C.; more preferably 35° C.-60° C.; even more preferably 34° C.-41° C., e.g. 37° C. Other temperatures may be used falling within the ranges selected from any of the following ranges, as shown by the upper and lower limit combinations marked "x" in the table below:

b. a polynucleotide sequence encoding a guide RNA, wherein the guide RNA has a nucleic acid sequence which recognizes a nucleic acid sequence comprised in the target locus;
c. a first promoter oriented with respect to polynucleotide sequences of (a) and (b) so as to drive expression thereof in the organism.

In preferred aspects, the prokaryotic organisms are thermophilic bacteria, as further defined hereinafter.

The expression vector of the invention may be used alone or in conjunction with a second expression vector.

Preferably, the sequence of (a) is 3' of the promoter and the sequence of (b) is 3' of the sequence of (b).

Additionally, the expression vector may further comprise a polynucleotide sequence which encodes an homologous recombination (HR) fragment under the control of the first promoter or a separate second promoter.

Where a single expression vector is used in methods of the invention described herein, and there are first and second promoters, the first promoter may be an inducible promoter. The second promoter may be a constitutive promoter or an inducible promoter. When the second promoter is an inducible promoter it may be the same or different as the first inducible promoter.

| Lower limit (° C.) | Upper Limit (° C.) | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|
| | 62 | 61 | 60 | 59 | 58 | 57 | 56 | 55 | 54 | 53 | 52 | 51 | 50 | 49 | 48 | 47 | 46 | 45 | 44 | 43 | 42 | 41 | 40 | 39 | 38 | 37 | 36 | 35 | 34 | 33 |
| 27 | x | x | x | x | x | x | x | x | x | x | x | x | x | x | x | x | x | x | x | x | x | x | x | x | x | x | x | x | x | x |
| 28 | x | x | x | x | x | x | x | x | x | x | x | x | x | x | x | x | x | x | x | x | x | x | x | x | x | x | x | x | x | |
| 29 | x | x | x | x | x | x | x | x | x | x | x | x | x | x | x | x | x | x | x | x | x | x | x | x | x | x | x | x | | |
| 30 | x | x | x | x | x | x | x | x | x | x | x | x | x | x | x | x | x | x | x | x | x | x | x | x | x | x | x | | | |
| 31 | x | x | x | x | x | x | x | x | x | x | x | x | x | x | x | x | x | x | x | x | x | x | x | x | x | x | | | | |
| 32 | x | x | x | x | x | x | x | x | x | x | x | x | x | x | x | x | x | x | x | x | x | x | x | x | x | | | | | |
| 33 | x | x | x | x | x | x | x | x | x | x | x | x | x | x | x | x | x | x | x | x | x | x | x | x | | | | | | |
| 34 | x | x | x | x | x | x | x | x | x | x | x | x | x | x | x | x | x | x | x | x | x | x | x | | | | | | | |
| 35 | x | x | x | x | x | x | x | x | x | x | x | x | x | x | x | x | x | x | x | x | x | x | | | | | | | | |
| 36 | x | x | x | x | x | x | x | x | x | x | x | x | x | x | x | x | x | x | x | x | x | | | | | | | | | |
| 37 | x | x | x | x | x | x | x | x | x | x | x | x | x | x | x | x | x | x | x | x | | | | | | | | | | |
| 38 | x | x | x | x | x | x | x | x | x | x | x | x | x | x | x | x | x | x | x | | | | | | | | | | | |
| 39 | x | x | x | x | x | x | x | x | x | x | x | x | x | x | x | x | x | x | | | | | | | | | | | | |
| 40 | x | x | x | x | x | x | x | x | x | x | x | x | x | x | x | x | x | | | | | | | | | | | | | |
| 41 | x | x | x | x | x | x | x | x | x | x | x | x | x | x | x | x | | | | | | | | | | | | | | |
| 42 | x | x | x | x | x | x | x | x | x | x | x | x | x | x | x | | | | | | | | | | | | | | | |
| 43 | x | x | x | x | x | x | x | x | x | x | x | x | x | x | | | | | | | | | | | | | | | | |
| 44 | x | x | x | x | x | x | x | x | x | x | x | x | x | | | | | | | | | | | | | | | | | |
| 45 | x | x | x | x | x | x | x | x | x | x | x | x | | | | | | | | | | | | | | | | | | |
| 46 | x | x | x | x | x | x | x | x | x | x | x | | | | | | | | | | | | | | | | | | | |
| 47 | x | x | x | x | x | x | x | x | x | x | | | | | | | | | | | | | | | | | | | | |
| 48 | x | x | x | x | x | x | x | x | x | | | | | | | | | | | | | | | | | | | | | |
| 49 | x | x | x | x | x | x | x | x | | | | | | | | | | | | | | | | | | | | | | |
| 50 | x | x | x | x | x | x | x | | | | | | | | | | | | | | | | | | | | | | | |
| 51 | x | x | x | x | x | x | | | | | | | | | | | | | | | | | | | | | | | | |
| 52 | x | x | x | x | x | | | | | | | | | | | | | | | | | | | | | | | | | |
| 53 | x | x | x | x | | | | | | | | | | | | | | | | | | | | | | | | | | |
| 54 | x | x | x | | | | | | | | | | | | | | | | | | | | | | | | | | | |
| 55 | x | x | | | | | | | | | | | | | | | | | | | | | | | | | | | | |
| 56 | x | | | | | | | | | | | | | | | | | | | | | | | | | | | | | |

In some methods of the invention the eukaryotic cell is a fungus, particularly a yeast, e.g. *Saccharomyces* sp., e.g. *S. cerevisiae*.

The present invention also provides a polynucleotide expression vector for modifying the genetic material at a target locus of a prokaryotic host organism which comprises the expression vector, the vector comprising:
 a. a polynucleotide sequence encoding a Cas9 nuclease, wherein the Cas9 nuclease comprises an amino acid sequence of SEQ ID NO: 1 or a sequence of at least 77% identity therewith, or an active fragment thereof;

The inducible promoter(s) may be physically or chemically inducible. Some preferred chemically inducible promoters include a β-glucosidase promoter inducible with cellobiose or a Pm promoter inducible with 3-methylbenzoate. When the second promoter controlling the HR fragment is a constitutive promoter then this may be the P3 promoter.

The arms of the HR fragment may comprise a nucleic acid sequence which allows recombination upstream and downstream, respectively, of a locus of interest in the host organism. In operation, a double recombination event involving each arm (respectively) of the HR fragment, either side of a locus of interest, serves to replace the locus with the HR fragment. Therefore, expression of the guide RNA, the ThermoCas9 and the HR fragment by the vector results in the deletion of a locus of interest, e.g. gene of interest, from the genome of the prokaryotic organism.

The locus of interest herein comprises the target sequence recognized by the guide RNA.

The HR fragment may also comprise an insertion element between the upstream and downstream arms thereof. In this mode of operation, a vector of the invention when expressed in a transformed host cell results in a substitution at the locus of interest. When the insertion element is a gene of interest then expression of the vector in a transformed host results in a gene substitution, e.g. from a native gene in the organism to a new gene of interest, possibly an heterologous gene from another species or organism. In some instances, the new gene of interest may also be provided with a promoter, optionally an inducible promoter so that expression of the new gene can be switched on in the transformed organism as desired.

The locus of interest as described herein may comprise the PAM sequence 5'-NNNNCNN-3' located 3' of the target sequence; optionally at least 2, 3, 4, 5, 6 or more nucleotides from the target sequence.

In preferred vectors, the nucleotide sequence encoding the guide RNA preferably encodes a single guide RNA (sgRNA).

In another aspect, the invention provides methods employing any of the expression vectors of the invention described herein. Therefore, the invention provides a method of modifying the genetic material of a prokaryotic organism comprising transforming the organism with a first expression vector which comprises:

(a) a polynucleotide sequence encoding a Cas9 nuclease, wherein the Cas9 nuclease comprises an amino acid sequence of SEQ ID NO: 1 or a sequence of at least 77% identity therewith, or an active fragment thereof;

(b) a polynucleotide sequence encoding a guide RNA, wherein the guide RNA has a nucleic acid sequence which recognizes a nucleic acid sequence comprised in the target locus;

(c) a first promoter oriented with respect to polynucleotide sequences of (a) and (b) and so as to drive expression thereof in the organism; and, a second expression vector comprising a polynucleotide sequence which encodes an homologous recombination (HR) fragment under the control of a promoter.

In another aspect, the invention provides a method of modifying the genetic material of a prokaryotic organism comprising transforming the organism with a single expression vector comprising (a), (b), and (c) above and also a polynucleotide sequence which encodes an homologous recombination (HR) fragment under the control of the said first promoter or a separate second promoter.

The organism may be transformed e.g. using electroporation.

In methods of the invention, the transformed organism is cultured for a period at a first temperature, and then cultured at a second temperature before or during induction of the promoter of the Cas9 sequence. Advantageously to improve the recombination efficiency, an incubation step may be carried out at the elevated temperature, at which the plasmid cannot replicate.

The first temperature may be 60° C. or less and the second temperature is a higher temperature which may be at least 55° C. Alternatively, the first temperature may be 55° C. or less and the second temperature may be greater than 55° C. The different temperatures to be used may readily be selected by a person of average skill in the art, depending on the particular prokaryotic organism being modified, particularly a thermophilic bacterium.

In some preferred methods, the organism being modified is selected from *Geobacillus thermoglucosidans, Bacillus coagulans* or *Pseudomonas putida*.

Also provided by the invention is a prokaryotic cell, e.g. a bacterial cell, transformed with an expression vector of the invention as hereinbefore defined.

In accordance with the invention is a method of genetically modifying a thermophilic prokaryotic organism comprising transforming with a single expression plasmid as defined above at a first temperature and then subjecting the organism to an elevated temperature during which there is homologous recombination selected over plasmid multiplication. Such elevated temperatures may be in the range 55° C. to 100° C., 60° C. to 100° C., 65° C. to 100° C., 70° C. to 100° C., 75° C. to 100° C., 80° C. to 100° C., 85° C. to 100° C., 90° C. to 100° C., 95° C. to 100° C.

Further, the present invention provides an isolated clustered regularly interspaced short palindromic repeat (CRISPR)-associated (Cas) protein or polypeptide comprising;

a. the amino acid motif EKDGKYYC [SEQ ID NO: 2]; and/or b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or c. the amino acid motif $X_5LKX_6IE$ [SEQ ID NO: 4] wherein $X_5$ is independently selected from Methionine or Phenylalanine and $X_6$ is independently selected from Histidine or Asparagine; and/or d. the amino acid motif $X_7VYSX_8K$ [SEQ ID NO: 5] wherein $X_7$ is Glutamate or Isoleucine and $X_8$ is one of Tryptophan, Serine or Lysine; and/or e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

For the avoidance of doubt proteins, polypeptides or nucleic acids coding for Cas proteins of the present invention may also be referred to as "GtCas9" or "ThermoCas9". "GtCas9" and "ThermoCas9" are used interchangeably throughout the specification and have the same meaning.

A polypeptide in the context of this invention may be viewed as a fragment of the full length Cas protein. Such fragments may be inactive and used in ways and for purposes not associated directly with binding, editing and/or cutting of genetic material, for example for standards in assays or raising antibodies or the like.

In preferred embodiments however, the Cas protein or polypeptide is functional and capable of cleavage, binding, marking or modifying at a temperature in the range 20° C. and 100° C., inclusive, when associated with at least one targeting RNA molecule, and a polynucleotide comprising a target nucleic acid sequence recognised by the targeting RNA molecule.

Preferably the Cas protein or polypeptide is functional and capable of said cleavage, binding, marking or modifying at a temperature in the range 50° C. and 70° C., for example 55° C. or 60° C.

In particular embodiments, the invention may provide a Cas protein or polypeptide comprising the amino acid motif EKDGKYYC [SEQ ID NO: 2]. In other embodiments, the Cas proteins or polypeptides may further comprise the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine.

In other embodiments the Cas proteins or polypeptides defined herein may additionally further comprise the amino acid motif $X_5LKX_6IE$ [SEQ ID NO: 4] wherein $X_5$ is independently selected from Methionine or Phenylalanine and $X_6$ is independently selected from Histidine or Asparagine.

In other embodiments, the Cas proteins or polypeptides defined herein may additionally further comprise the amino acid motif $X_7VYSX_8K$ [SEQ ID NO: 5] wherein $X_7$ is Glutamate or Isoleucine and $X_8$ is one of Tryptophan, Serine or Lysine.

In other embodiments, the Cas proteins or polypeptides defined herein may additionally further comprise the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

In accordance with the present invention, it may be appreciated that a Cas protein or polypeptide of the invention may comprise any of the motifs of SEQ ID NOs 2 to 6, either alone or in combination. The following summarises each of the combinations of motifs which may characterize Cas proteins or polypeptides of the invention:

EKDGKYYC. [SEQ ID NO: 2]

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine.

EKDGKYYC [SEQ ID NO: 2]; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

EKDGKYYC [SEQ ID NO: 2]; and $X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

EKDGKYYC [SEQ ID NO: 2]; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_5LKX_6IE$ [SEQ ID NO: 4] wherein $X_5$ is independently selected from Methionine or Phenylalanine and $X_6$ is independently selected from Histidine or Asparagine; and $X_7VYSX_8K$ [SEQ ID NO: 5] wherein $X_7$ is Glutamate or Isoleucine and $X_8$ is one of Tryptophan, Serine or Lysine.

$X_5LKX_6IE$ [SEQ ID NO: 4] wherein $X_5$ is independently selected from Methionine or Phenylalanine and $X_6$ is independently selected from Histidine or Asparagine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

$X_7VYSX_8K$ [SEQ ID NO: 5] wherein $X_7$ is Glutamate or Isoleucine and $X_8$ is one of Tryptophan, Serine or Lysine; and $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine.

In another aspect, the present invention provides an isolated Cas protein or polypeptide fragment thereof having an amino acid sequence of SEQ ID NO: 1 or a sequence of at least 77% identity therewith, wherein the Cas protein or polypeptide fragment thereof comprises any of the following motifs or amino acids, either alone or in combination:

An RuvC-I domain comprising IGLDIGITSIG [SEQ ID NO: 23], preferably IGLDIGITSIGWAVINLD [SEQ ID NO: 24].

A Bridge domain comprising RSARR [SEQ ID NO: 25], preferably PRRLARSARRRLRRRKHRLERIRRL [SEQ ID NO: 26]; and/or An α-helical/recognition lobe domain comprising WQLR [SEQ ID NO: 27]; and/or An α-helical/recognition lobe domain comprising HLAKRRG [SEQ ID NO: 28], preferably LARILLHLAKRRG [SEQ ID NO: 29]; and/or An α-helical/recognition lobe domain comprising IFAKQ [SEQ ID NO: 30], preferably EIKLIFAKQ [SEQ ID NO: 31]; and/or An α-helical/recognition lobe domain comprising IWASQR [SEQ ID NO: 32]; and/or KVGFCTFEPKEKRAPK [SEQ ID NO: 33]; and/or FTVWEHINKLRL [SEQ ID NO: 34]; and/or An RuvC-II domain comprising the motif IANPVVMRALTQ [SEQ ID NO: 35], preferably IANPWMRALTQARKVVNAIIKKYG [SEQ ID NO: 36]; and/or An RuvC-II domain comprising the motif ELAR [SEQ ID NO: 37], preferably IHIELARE [SEQ ID NO: 38]; and/or An HNH domain comprising the motif QNGKCAY [SEQ ID NO: 39], preferably IVKFKLWSEQNGKCAY [SEQ ID NO: 40]; and/or An HNH domain comprising the motif VDHVIP [SEQ ID NO: 41], preferably VDHVIPYSRSLDDSYTNKVL [SEQ ID NO: 42]; and/or An RuvC-III domain comprising the motif DTRYISR-FLAN [SEQ ID NO: 43]; and/or An RuvC-III domain comprising the motif VYTVNGRITAHLRSRW [SEQ ID NO: 44]; and/or An RuvC-III domain comprising the motif HHAVDA [SEQ ID NO: 45], preferably HHAVDAAIVA [SEQ ID NO: 46]; and/or Preferably, the present invention provides an isolated Cas protein or polypeptide fragment thereof having an amino acid sequence of SEQ ID NO: 1 or a sequence of at least 77% identity therewith, wherein the Cas protein or polypeptide fragment thereof comprises each of the amino acid motifs [SEQ ID NO: 23] to [SEQ ID NO: 46] in combination.

In another aspect, the present invention provides an isolated Cas protein or polypeptide fragment thereof having an amino acid sequence of SEQ ID NO: 1 or a sequence of at least 77% identity therewith. Preferably the Cas protein or polypeptide is capable of binding, cleavage, marking or modifying at a temperature in the range 20° C. and 100° C. inclusive. Preferably the Cas protein or polypeptide is capable of said cleavage, binding, marking or modifying at a temperature in the range between 20° C. and 70° C., for example 25° C., 55° C., 60° C. or 65° C. Preferably the Cas protein or polypeptide is capable of said cleavage, binding, marking or modifying at a temperature in the range between 50° C. and 70° C., for example 55° C. or 60° C. Preferably the Cas protein or polypeptide is capable of said cleavage, binding, marking or modifying at a temperature in the range between 30° C. and 80° C., at a temperature between 37° C. and 78° C., preferably at a temperature above 55° C.; more preferably at a temperature between 55° C. and 80° C.; even more preferably at a temperature between 55° C. and 65° C. or 60° C. and 65° C.

The present invention also provides uses of a targeting RNA molecule and a Cas protein or polypeptide provided herein, for binding, cleaving, marking or modifying a target polynucleotide comprising a target nucleic acid sequence. The targeting RNA molecule recognizes the target nucleic acid sequence on a target nucleic acid strand of the polynucleotide.

The target polynucleotide that comprises the target nucleic acid sequence may be double stranded and so comprise a target nucleic acid strand, comprising said target nucleic acid sequence, and a non-target nucleic acid strand, comprising a protospacer nucleic acid sequence. The protospacer nucleic acid sequence is substantially complementary to the target nucleic acid sequence and pairs with it in the double stranded target polynucleotide. The non-target nucleic acid strand may further comprise a protospacer adjacent motif (PAM) sequence directly adjacent the 3' end of the protospacer sequence. The PAM sequence may be at least 6, 7, or 8 nucleic acids in length. Preferably, the PAM sequence has a cytosine in the fifth position. Preferably the PAM sequence comprises the sequence 5'-NNNNC-3', so that from the 5'-end the PAM sequence begins 5'-NNNNC-3'. Additionally or alternatively, the PAM sequence may have an adenine in the eighth position, so that the PAM sequence comprises the sequence 5'-NNNNNNNA-3', and from the 5'-end the PAM sequence begins 5'-NNNNNNNA-3'. Additionally or alternatively, the PAM sequence may have a cytosine in one or more of the first, second, third, fourth, and sixth positions, such that from the 5'-end the PAM sequence begins 5'-CNNNN-3', 5'-NCNNN-3', 5'-NNCNN-3', 5'-NNNCN-3', and/or 5'-NNNNNC-3'. Optionally the PAM sequence comprises, so that from the 5'-end the PAM sequence begins, 5'-CCCCCCNA-3' [SEQ ID NO: 10], and further preferably the PAM sequence comprises, so that from the 5'-end the PAM sequence begins, 5'-CCCCCCAA-3' [SEQ ID NO: 11]. Other preferred PAM sequences include 5'-ATCCCCAA-3' [SEQ ID NO: 21] and 5'-ACGGCCAA-3' [SEQ ID NO: 22].

Preferably, the Cas protein or polypeptide is capable of the binding, cleaving, marking or modifying at a temperature in the range 40° C. to 80° C. inclusive, preferably in the range 45° C. to 80° C. inclusive, and further preferably in the range 50° C. to 80° C. inclusive. For example, the binding, cleaving, marking or modifying occurs at a temperature of 45° C., 46° C., 47° C., 48° C., 49° C., 50° C., 51° C., 52° C., 53° C., 54° C., 55° C., 56° C., 57° C., 58° C., 59° C., 60° C., 61° C., 62° C., 63° C., 64° C., 65° C., 66° C., 67° C., 68° C., 69° C., 70° C., 71° C., 72° C., 73° C., 74° C., 75° C., 76° C., 77° C., 78° C., 79° C. or 80° C. More preferably the Cas protein or polypeptide is capable of the binding, cleaving, marking or modifying at a temperature in the range 55 to 65° C. In preferred aspects, a Cas protein or polypeptide fragment of the invention may comprises an amino acid sequence of at least 75% identity; preferably at least 85%; more preferably at least 90%; even more preferably at least 95% identity to SEQ ID NO: 1.

The Cas protein or polypeptide may be used in combination with a targeting RNA molecule that recognizes a target nucleic acid sequence on the target nucleic acid strand, where the non-target nucleic acid sequence has a PAM sequence directly adjacent the 3' end of the protospacer sequence on the non-target strand, as disclosed herein. Thus, the PAM sequence may comprise the sequence 5'-NNNNC-3', and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, in the range 50° C. and 70° C. inclusive, or in the range 55° C. and 65° C., inclusive. Preferably from the 5'-end the PAM sequence begins 5'-NNNNC-3' and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, in the range 50° C. and 70° C. inclusive, or in the range 55° C. and 65° C., inclusive. Preferably from the 5'-end the PAM sequence begins 5'-NNNNNNNA-3' and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, the range 50° C. and 70° C. inclusive, or in the range 55° C. and 65° C., inclusive. Further preferably the 5'-end of the PAM sequence begins 5'-NNNNCNNA-3' [SEQ ID NO: 47] and the Cas protein may bind, cleave, mark or modify the target strand at a temperature in the range 20° C. and 100° C. inclusive, preferably in the range 30° C. and 90° C. inclusive, in the range 37° C. and 78° C. inclusive, in the range 40° C. and 80° C. inclusive, in the range 50° C. and 70° C. inclusive, or in the range 55° C. and 65° C., inclusive.

More particularly, a Cas protein or polypeptide of the invention may comprise an amino acid sequence with a percentage identity with SEQ ID NO:1 as follows: at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5% or at least 99.8%. The percentage identity may be at least 89%. The percentage identity may be at least 90%. Preferably the percentage identity will be at least 95%, for example 98%.

The percentage amino acid sequence identity with SEQ ID NO: 1 is determinable as a function of the number of identical positions shared by the sequences in a selected comparison window, taking into account the number of gaps, and the length of each gap, which need to be introduced for optimal alignment of the two sequences.

A Cas protein or polypeptide fragment of the invention may be characterised in terms of both the reference sequence SEQ ID NO: 1 and any aforementioned percentage variant thereof as defined by percentage sequence identity, alone or in combination with any of the aforementioned amino acid motifs (i.e. SEQ ID NOS 2 and/or 3 and/or 4 and/or 5 and/or 6) as essential features.

The invention provides a use of a targeting RNA molecule as provided herein and a Cas protein or polypeptide of the invention for binding, cleaving, marking or modifying a target nucleic acid strand comprising a target nucleic acid sequence. Preferably said binding, cleaving, marking or modifying occurs at a temperature disclosed herein, for example at a temperature of between 20 and 100° C. The invention also provides a method of binding, cleaving, marking or modifying a target nucleic acid sequence in a target nucleic acid strand comprising designing a targeting RNA molecule as provided herein and forming a ribonucleoprotein complex comprising the targeting RNA molecule and a Cas protein or polypeptide of the invention. Preferably the ribonucleoprotein complex binding, cleaving, marking or modifying the target nucleic acid sequence at a temperature disclosed herein, for example at a temperature of between 37 and 100° C.

The uses and methods of the invention may be carried out, and the nucleoproteins of the invention formed and used, in vivo, for example in bacterial cells. The uses and methods of the invention may be carried out, and the nucleoproteins of the invention formed and used, in vivo, except in human cells. Alternatively the uses and methods of the invention may be carried out, and the nucleoproteins of the invention formed and used, in vitro. The Cas protein of the invention may be provided in isolated form, for example when used in vitro or when added to cells by transfection, the Cas protein may be heterologously expressed, for example following transient or stable transformation of the cell by nucleic acid encoding the Cas protein, the targeting RNA molecule may be transcribed from an expression vector following transient or stable transformation of the cell by nucleic acid encoding the RNA molecule, and/or the RNA molecule may be provided in isolated form, for example when used in vitro or when added to cells by transfection. In preferred embodiments, the Cas protein or polypeptide is expressed from the genome of a host cell, following stable intergration of a nucleic acid encoding the Cas protein or polypeptide in the genome of the host cell. Thus the Cas protein and/or RNA molecule may be added to the in vivo or in vitro environment using any artificial or contrived method for adding a protein or nucleic acid molecule to a cell in which it is not otherwise present.

The polynucleotide comprising the target nucleic acid sequence may be cleaved by the Cas protein, and optionally the cleavage may be DNA cleavage. The target nucleic acid strand comprising the target sequence may be double stranded DNA and the method or use may result in a double stranded break in the polynucleotide comprising the target nucleic acid sequence. The polynucleotide comprising the target nucleic acid sequence may be double stranded DNA, the Cas protein may lack the ability to cut the double stranded DNA and the use or method may result in gene silencing of the polynucleotide.

The Cas protein or polypeptide may be provided for the methods, uses and nucleoproteins of the invention at a concentration of 250 nM or less, for example at a concentration of 200 nM or less, 150 nM or less, 100 nM or less, 50 nM or less, 25 nM or less, 10 nM or less, 5 nM or less, 1 nM or less or 0.5 nM or less. Alternatively, the Cas protein or polypeptide may be provided at a concentration of at least 0.5 nM, at least 1 nM, at least 5 nM, at least 10 nM, at least 25 nM, at least 50 nM, at least 100 nM, at least 150 nM, at least 200 nM, or at least 250 nM. The PAM sequence of the invention may have an adenine in the eighth position, so that the PAM sequence comprises the sequence 5'-NNNNNNNA-3', and the concentration of Cas protein or polypeptide may be 100 nM or less, 50 nM or less, 25 nM or less, 10 nM or less, 5 nM or less, 1 nM or less or 0.5 nM or less. The PAM sequence may comprise the sequence 5'-NNNNCNNA-3' [SEQ ID NO: 47], and the concentration of Cas protein or polypeptide may be 100 nM or less, 50 nM or less, 25 nM or less, 10 nM or less, 5 nM or less, 1 nM or less or 0.5 nM or less. The PAM sequence may comprise the sequence 5'-CCCCCCNA-3' [SEQ ID NO: 10], and the concentration of Cas protein or polypeptide may be 100 nM or less, 50 nM or less, 25 nM or less, 10 nM or less, 5 nM or less, 1 nM or less or 0.5 nM or less.

Also, the invention provides nucleic acids encoding any of the aforementioned proteins or polypeptides of the invention. The nucleic acids may be isolated or in the form of expression constructs.

In all aforementioned aspects of the present invention, amino acid residues may be substituted conservatively or non-conservatively. Conservative amino acid substitutions refer to those where amino acid residues are substituted for other amino acid residues with similar chemical properties (e.g., charge or hydrophobicity) and therefore do not alter the functional properties of the resulting polypeptide.

Similarly it will be appreciated by a person of average skill in the art that nucleic acid sequences may be substituted conservatively or non-conservatively without affecting the function of the polypeptide. Conservatively modified nucleic acids are those substituted for nucleic acids which encode identical or functionally identical variants of the amino acid sequences. It will be appreciated by the skilled reader that each codon in a nucleic acid (except AUG and UGG; typically the only codons for methionine or tryptophan, respectively) can be modified to yield a functionally identical molecule. Accordingly, each silent variation (i.e. synonymous codon) of a polynucleotide or polypeptide, which encodes a polypeptide of the present invention, is implicit in each described polypeptide sequence.

The invention provides a transformed cell, having a target nucleic acid sequence in a double stranded target polynucleotide, said cell comprising a Cas protein or polypeptide as provided herein and at least one targeting RNA molecule as provided herein, and an expression vector comprising a nucleic acid encoding at least one of said Cas protein and said targeting RNA molecule. The Cas protein and targeting RNA molecule may enable or permit binding, cleaving, marking or modifying of the target sequence to occur in the transformed cell at a raised temperature, or at a range of temperatures, for example between 37 and 100° C., as disclosed herein. The invention further provides a method of binding, cleaving, marking or modifying a target nucleic acid in a cell comprising either 1) transforming, transfecting or transducing the cell with an expression vector comprising a nucleotide sequence encoding a Cas protein or polypeptide of the invention and a nucleotide sequence encoding a targeting RNA molecule of the invention; or 2) transforming, transfecting or transducing the cell with an expression vector comprising a nucleotide sequence encoding a Cas protein or polypeptide of the invention and a further expression vector comprising a nucleotide sequence encoding a targeting RNA molecule of the invention; or 3) transforming, transfecting or transducing the cell with an expression vector comprising a nucleotide sequence encoding a Cas protein or polypeptide of the invention, and delivering a targeting RNA molecule as provided herein to, or into the cell. The Cas protein or polypeptide may be expressed from the genome of the transformed cell, for example following stable integration into the genome of a nucleotide sequence encoding the Cas protein or polypeptide.

The invention also provides kits comprising one or more of the reagents for carrying out the uses and methods of the invention, or for generating the transformed cells or nucleoprotein complex of the invention, said kits including: a Cas protein or polypeptide of the invention or an expression vector comprising a nucleic acid sequence encoding a Cas protein or polypeptide of the invention; and/or a targeting RNA molecule of the invention or an expression vector comprising a nucleic acid sequence encoding a targeting RNA molecule of the invention. The kits may further include instructions for carrying out the invention, for example instructions for how to design a targeting RNA molecule in accordance with the invention.

RNA Guides and Target Sequences

Cas proteins of the invention allow for sequence-specific binding, cleavage, tagging, marking or modification of target nucleic acids at elevated temperatures. Target nucleic acids may be DNA (single-stranded or double-stranded), RNA or synthetic nucleic acids. A particularly useful application of the present invention is the sequence-specific targeting and modification of genomic DNA by one or more Cas proteins of the invention in complex with one or more guide RNAs (gRNAs) that complementarily bind to a targeted sequence of the genomic DNA. Consequently, the target nucleic acid is preferably double-stranded DNA. Such targeting may be performed in vitro or in vivo. Preferably such targeting is performed in vivo. In this way, Cas proteins of the invention may be used to target and modify specific DNA sequences located in the genomic DNA of a cell. It is envisaged that the Cas system may be used to modify genomes in a variety of cell types of and/or in different organisms.

The gRNAs, also called targeting RNA molecules, recognize the target nucleic acid sequence on the polynucleotide target strand. The RNA molecules may be designed to recognize a target sequence in a double stranded target polynucleotide, wherein the non-target strand comprises a protospacer adjacent motif (PAM) sequence directly adjacent the 3' end of the protospacer sequence. Disclosed herein are PAM sequences that work in an optimal manner with the Cas proteins and polypeptides of the invention. With knowledge of these PAM sequences, gRNAs may be designed for use with the Cas proteins and polypeptides of the invention across the temperature ranges and increased temperatures of the invention.

Accordingly, the present invention provides a ribonucleoprotein complex comprising a Cas protein or a polypeptide of the invention as hereinbefore described, and further comprising at least one RNA molecule which has a targeting function in that it recognizes a particular nucleotide sequence in a target polynucleotide. The present invention also provides use of at least one targeting RNA molecule and a Cas protein or polypeptide for binding, cleaving, marking or modifying a target nucleic acid strand, and a method of binding, cleaving, marking or modifying a target nucleic acid sequence in a target nucleic acid strand using a ribonucleoprotein or nucleoprotein of the invention, as well as transformed non-human cells having the Cas protein or polypeptide and targeting RNA molecule. The target polynucleotide may further comprise a defined PAM sequence directly adjacent the 3' end of a protospacer sequence, in accordance with a PAM sequence provided herein. The PAM sequence may be 6, 7, or 8 nucleic acids in length, or longer, preferably 8 nucleic acids in length. Preferably, the RNA molecule is a single-stranded RNA molecule, e.g. a CRISPR RNA (crRNA) and is associated, e.g. by hybridization with a tracrRNA. The targeting RNA may be a chimera of a crRNA and tracrRNA. The aforementioned RNA molecules may have a ribonucleotide sequence of at least 90% identity, or complementarity to a target nucleotide sequence. Optionally, the RNA molecule has a ribonucleotide sequence of at least 90%, at least 91%, at least 92%, at least 93%, at least 94%, at least 95%, at least 96%, at least 97%, at least 98%, at least 99% or 100% identity or complementarity to a target nucleotide sequence. The preferred target nucleotide sequence is a DNA.

In a preferred aspect, the present invention provides a ribonucleoprotein complex as hereinbefore described, wherein the at least one targeting RNA molecule is substantially complementary along its length to a target DNA sequence.

The targeting RNA molecule may be bound to or associated with the target sequence within the nucleoprotein complex, so that the target polynucleotide, comprising the target sequence and PAM sequence on the non-target strand, may be associated with and so form part of a nucleoprotein complex of the invention.

Alteration of the sequence of the RNA guide which associates with the Cas protein of the invention therefore allows the Cas protein to be programmed to mark or cut double-stranded DNA at sites complementary to the guide RNA.

Preferably, the length of the at least one targeting RNA molecule in a ribonucleoprotein complex of the invention is in the range 35 to 135 residues, optionally in the range 35 to 134 residues, 35 to 133 residues, 35 to 132 residues, 35 to 131 residues, 35 to 130 residues, 35 to 129 residues, 35 to 128 residues, 35 to 127 residues, 35 to 126 residues, 35 to 125 residues, 35 to 124 residues, 35 to 123 residues, 35 to 122 residues, 35 to 121 residues, 35 to 120 residues, 35 to 119 residues, 35 to 118 residues, 35 to 117 residues, 35 to 116 residues, 35 to 115 residues, 35 to 114 residues, 35 to 113 residues, 35 to 112 residues, 35 to 111 residues, 35 to 100 residues, 35 to 109 residues, 35 to 108 residues, 35 to 107 residues, 35 to 106 residues, 35 to 105 residues, 35 to 104 residues, 35 to 103 residues, 35 to 102 residues, 35 to 101 residues, 35 to 100 residues, 35 to 99 residues, 35 to 98 residues, 35 to 97 residues, 35 to 96 residues, 35 to 95 residues, 35 to 94 residues, 35 to 93 residues, 35 to 92 residues, 35 to 91 residues, 35 to 90 residues, 35 to 89 residues, 35 to 88 residues, 35 to 87 residues, 35 to 86 residues, 35 to 85 residues, 35 to 84 residues, 35 to 83 residues, 35 to 82 residues, 35 to 81 residues, 35 to 80 residues, 35 to 79 residues, 35 to 78 residues, 35 to 77 residues, 35 to 76 residues, 35 to 75 residues, 35 to 74 residues, 35 to 73 residues, 35 to 72 residues, 35 to 71 residues, 35 to 70 residues, 35 to 69 residues, 35 to 68 residues, 35 to 67 residues, 35 to 66 residues, 35 to 65 residues, 35 to 64 residues, 35 to 63 residues, 35 to 62 residues, 35 to 61 residues, 35 to 60 residues, 35 to 59 residues, 35 to 58 residues, 35 to 57 residues, 35 to 56 residues, 35 to 55 residues, 35 to 54 residues, 35 to 53 residues, 35 to 52 residues, 35 to 51 residues, 35 to 50 residues, 35 to 49 residues, 35 to 48 residues, 35 to 47 residues, 35 to 46 residues, 35 to 45 residues, 35 to 44 residues, 35 to 43 residues, 35 to 42 residues, 35 to 41 residues, 35 to 40 residues, 35 to 39 residues, 35 to 38 residues, 35 to 37 residues, 35 to 36 residues or 35 residues. Preferably, the length of the at least one RNA molecule is in the range 36 to 174 residues, 37 to 173 residues, 38 to 172 residues, 39 to 171 residues, 40 to 170 residues, 41 to 169 residues, 42 to 168 residues, 43 to 167 residues, 44 to 166 residues, 45 to 165 residues, 46 to 164 residues, 47 to 163 residues, 48 to 162 residues, 49 to 161 residues, 50 to 160 residues, 51 to 159 residues, 52 to 158 residues, 53 to 157 residues, 54 to 156 residues, 36 to 74 residues, 37 to 73 residues, 38 to 72 residues, 39 to 71 residues, 40 to 70 residues, 41 to 69 residues, 42 to 68 residues, 43 to 67 residues, 44 to 66 residues, 45 to 65 residues, 46 to 64 residues, 47 to 63 residues, 48 to 62 residues, 49 to 61 residues, 50 to 60 residues, 51 to 59 residues, 52 to 58 residues, 53 to 57 residues, 54 to 56 residues.

In preferred aspects, the present invention provides a ribonucleoprotein complex, wherein the complementary portion of the at least one RNA molecule is at least 30 residues long. Alternatively, the complementary portion of the at least one RNA molecule may be 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74 or 75 residues long.

The targeting RNA molecule will preferably require a high specificity and affinity for the target nucleic acid sequence. A dissociation constant ($K_d$) in the range 1 µM to 1 µM, preferably 1 nM to 1 pM; more preferably 1-100 pM is desirable as may be determined by native gel electrophoresis, or alternatively isothermal titration calorimetry, surface plasmon resonance, or fluorescence based titration methods. Affinity may be determined using an electrophoretic mobility shift assay (EMSA), also called gel retardation assay (see Semenova et al. (2011) PNAS 108: 10098-10103).

The targeting RNA molecule is preferably modeled on what are known from nature in prokaryotes as CRISPR RNA (crRNA) molecules. The structure of crRNA molecules is already established and explained in more detail in Jore et al., 2011, Nature Structural & Molecular Biology 18: 529-537. In brief, a mature crRNA of type I-E is often 61 nucleotides long and consists of a 5' "handle" region of 8 nucleotides, the "spacer" sequence of 32 nucleotides, and a 3' sequence of 21 nucleotides which form a hairpin with a tetranucleotide loop (FIG. 5). Type I systems differ from type II (Cas9) and details of different systems are described in Van der Oost 2014 Nat Rev Micr 12: 479-492. In type II (Cas9) systems there is a different processing mechanism, making use of a second RNA (tracrRNA) and two ribonucleases. Rather than a hairpin, the mature crRNA in type II remains attached to a fragment of the tracrRNA (FIG. 5). However, the RNA used in the invention does not have to be designed strictly to the design of naturally occurring crRNA, whether in length, regions or specific RNA sequences. What is clear though, is that RNA molecules for use in the invention may be designed based on gene sequence information in the public databases or newly discovered, and then made artificially, e.g. by chemical synthesis in whole or in part. The RNA molecules of the invention may also be designed and produced by way of expression in genetically modified cells or cell free expression systems and this option may include synthesis of some or all of the RNA sequence.

The structure and requirements of crRNA in type II (Cas9) has also been described in Jinek et al., 2012 ibid. In type I, there is a so-called "SEED" portion forming the 5' end of the spacer sequence and which is flanked 5' thereto by the 5' handle of 8 nucleotides. Semenova et al. (2011, PNAS 108: 10098-10103), have found that all residues of the SEED sequence should be complementary to the target sequence, although for the residue at position 6, a mismatch may be tolerated (FIG. 5). In type II, there is a SEED of 10-12 nucleotides that is located at the 3' end of the spacer (FIG. 5) (reviewed by Van der Oost 2014 ibid.). Similarly, when designing and making an RNA component of a ribonucleoprotein complex of the invention directed at a target locus (i.e. sequence), the necessary match and mismatch rules for the type II SEED sequence can be applied.

The invention therefore includes a method of detecting and/or locating a single base change in a target nucleic acid molecule comprising contacting a nucleic acid sample with a ribonucleoprotein complex of the invention as hereinbefore described, or with a Cas protein or polypeptide and separate targeting RNA component of the invention as hereinbefore described, and wherein the sequence of the targeting RNA (including when in the ribonucleoprotein complex) is such that it discriminates between a normal allele and a mutant allele by virtue of a single base change at, for example, position 6 of a contiguous sequence of 8 nucleotide residues.

Without wishing to be bound by a particular theory, a design rule which may be used in preparing a targeting RNA component of ribonucleoprotein complexes of the invention involves the so-called "PAM" (protospacer adjacent motif) sequence in a double stranded target polynucleotide. In the type I-E system of *E. coli*, the PAM sequence may be a conserved triplet of nucleotide residues, such as 5'-CTT-3', 5'-CAT-3', 5'-CCT-3', 5'-CAC-3', 5'-TTT-3', 5'-ATT-3', and 5'-AWG-3', wherein W is A, T or U. In Type I, a PAM sequence located in the targeted strand is usually at a position corresponding to 5' of the SEED. In Type II, however, the PAM is located at the other end, on the displaced, or non-target, strand close to the 3' end of the crRNA spacer, at a position corresponding to 3' of the seed (FIG. 5) (Jinek et al., 2012, op. cit.). For *Streptococcus pyogenes* Cas9, the PAM sequence has a conserved pair of nucleotide residues, 5'-NGG-3'. Recently, different Cas9 variants (Type IIA and Type IIC) (Ran et al., 2015 Nature 520:186-191)—FIG. 1A) have been characterized, and PAMs have been revealed (see Ran et al., 2015, ibid. —FIG. 10). Currently established Cas9 PAMs include: Type IIA 5'-NGGNNNN-3' (*Streptococcus pyogenes*), 5'-NNGTNNN-3' (*Streptococcus pasteurianus*), 5'-NNGGAAN-3' (*Streptococcus thermophilus*), 5'-NNGGGNN-3' (*Staphylococcus aureus*), and Type IIC 5'-NGGNNNN-3' (*Corynebacterium difteriae*), 5'-NNGGGTN-3' (*Campylobacter lari*), 5'-NNNCATN-3' (*Parvobaculum lavamentivorans*), 5'-NNNNGTA-3' (*Neiseria cinerea*). Cas9 of *Geobacillus thermodenitrificans* T12 (this invention) belongs to Type IIC (Ran et al., 2015, ibid.). The inventors have surprisingly found that the choice of PAM sequences for use with the invention can influence the temperature(s) at which the Cas proteins and polypeptides of the invention will interact with a target sequence. In particular, the inventors have found a preference for an 8-mer PAM sequence to confer activity across a broad temperature range, with a cytosine in the $5^{th}$ position after the 3' end of the target sequence, and/or an adenine in the $8^{th}$ position. There is also a preference for cytosine in the $1^{st}$, $2^{nd}$, $3^{rd}$, $4^{th}$ and/or $6^{th}$ position of the PAM sequence after the 3' end of the protospacer sequence.

In particular aspects, interaction with a target sequence within a broad temperature range of, for example 20° C. to 100° C., 20° C. to 80° C., 30 to 80° C., 20° C. to 70° C. or 25° C. to 65° C. may be achieved by utilizing a PAM sequence of 5'-NNNNCVAA-3' [SEQ ID NO: 48]. There is no specific preference for the for the first 4 PAM positions. The first 4 nucleotides can therefore conveniently be any nucleotide (NNNN). Preferably, interaction with a target sequence within such a broad temperature range may be achieved by utilizing a PAM sequence of 5'-NNNNCSAA-3' [SEQ ID NO: 49]. Optimally, the PAM may be of the sequence 5'-NNNNCGAA-3' [SEQ ID NO: 50] or 5'-NNNNCCAA-3' [SEQ ID NO: 51].

Where interaction with a target sequence is required at 30° C., e.g. 30° C. to 100° C., preferably in the range 30° C. to 70° C., 30° C. to 65° C., or 45° C. to 65° C. the PAM sequence may optimally be of the sequence 5'-NNNNC-NAA-3' [SEQ ID NO: 52] or 5'-NNNNCMCA-3' [SEQ ID NO: 53]. There is no specific preference for the for the first 4 PAM positions. The first 4 nucleotides can therefore conveniently be any nucleotide (NNNN). Optionally, for example, the PAM sequence may be 5'-CCCCCNAA-3' or 5'-CCCCCMCA-3'. Optionally, for example, the PAM sequence may be selected from 5'-CCCCCAAA-3', 5'-CCCCCATA-3', 5'-CCCCCAGA-3', 5'-CCCCCACA-3', 5'-CCCCCTAA-3', 5'-CCCCCTTA-3', 5'-CCCCCTGA-3', 5'-CCCCCTCA-3', 5'-CCCCCGAA-3', 5'-CCCCCGTA-3', 5'-CCCCCGGA-3', 5'-CCCCCGCA-3', 5'-CCCCCCAA-3' [SEQ ID NO: 11], 5'-CCCCCCTA-3', 5'-CCCCCCGA-3', or 5'-CCCCCCCA-3'.

In embodiments of the invention, a targeting RNA molecule may have a length in the range of 35-200 residues. In preferred embodiments, the portion of the RNA which is complementary to and used for targeting a desired nucleic acid sequence is from 15 to 32 residues long. In the context of a naturally-occurring crRNA, this would correspond to the spacer portion as shown for example in FIG. 1 of Semenova et al. (2011 ibid.).

A ribonucleoprotein complex of the invention may have a targeting component comprising 8 residues derived from the CRISPR repeat 5' to the RNA sequence which has substantial complementarity to the DNA target sequence. The RNA sequence having complementarity to the DNA target sequence would be understood to correspond in the context of a crRNA as being the spacer sequence. The 5' flanking sequence of the RNA would be considered to correspond to the 5' handle of a crRNA; as shown for example in FIG. 1 of Semenova et al. (2011 ibid.).

A ribonucleoprotein complex of the invention may have a hairpin and tetranucleotide loop forming sequence 3' to the targeting RNA sequence which has complementarity to a DNA target sequence, i.e. 3' to what would correspond to the 3' handle flanking the spacer sequence in a crRNA; for example as shown in FIG. 1 of Semenova et al. (2011 ibid.).

Without wishing to be bound by a particular theory, in a preferred ribonucleoprotein complex and double stranded target polynucleotide, the non-target nucleic acid strand, which does not pair with the targeting RNA of the ribonucleoprotein complex, may comprise a directly 3' adjacent PAM sequence selected from one or more of 5'-NNNNCNNA-3' [SEQ ID NO: 47], 5'-CNNNCNN-3', 5'-NNNCCNN-3', 5'-NNCNCNN-3', 5'-NNNNCCN-3', and 5'-NCNNCNN-3'. Optionally, for example the PAM sequence may be selected from 5'-NNNNC-3', 5'-NNNNCNNA-3' [SEQ ID NO: 47], 5'-CNNNC-3', 5'-CNNNCNNA-3', 5'-NCNNC-3', 5'-NCNNCNNA-3', 5'-NNCNC-3', 5'-NNCNCNNA-3', 5'-NNNCC-3', 5'-NNNCCNNA-3', 5'-NNNNCC-3', 5'-NNNNCCNA-3', 5'-CCNNC-3', 5'-CCNNCNNA-3', 5'-CNCNC-3', 5'-CNCNCNNA-3', 5'-CNNCCN-3', 5'-CNNCCNNA-3', 5'-CNNNCC-3', 5'-CNNNCCNA-3', 5'-CCCNCN-3', 5'-CCCNCNNA-3', 5'-CCNCCN-3', 5'-CCNCCNNA-3', 5'-CCNNCC-3', 5'-CCNNCCNA-3', 5'-CCCCC-3' [SEQ ID NO: 12], 5'-CCCCCNNA-3' [SEQ ID NO: 13], 5'-CCCCCC-3' [SEQ ID NO: 14], 5'-CCCCCCNA-3' [SEQ ID NO: 10], 5'-NCCNC-3', 5'-NCCNCNNA-3', 5'-NCCCC-3', 5'-NCCCCNNA-3', 5'-NCCCCC-3' [SEQ ID NO: 15], 5'-NCCCCCNA-3' [SEQ ID NO: 16], 5'-NNCCC-3', 5'-NNCCCNNA-3', 5'-NNCCCC-3', 5'-NNCCCCNA-3', 5'-NNNCCC-3', and 5'-NNNCCCNA-3'. The PAM sequence may be 5'-CNCCCAC-3' [SEQ ID NO: 17], 5'-CCCCCCAG-3' [SEQ ID NO: 18], 5'-CCCCCCAA-3' [SEQ ID NO: 11], 5'-CCCCCCAT-3' [SEQ ID NO: 19], 5'-CCCCCCAC-3' [SEQ ID NO: 20], 5'-ATCCCCAA-3' [SEQ ID NO: 21], or 5'-ACGGCCAA-3' [SEQ ID NO: 22]. Preferably the PAM sequence will be of the sequence 5'-NNNNCNNA-3' [SEQ ID NO: 47]. However, it will be appreciated that other combinations of nucleotides may be used depending on the desired application and/or concentration of Cas protein or polypeptide. In particular, there is no specific preference for the for the first 4 PAM positions. The first 4 nucleotides can therefore conveniently be any nucleotide (NNNN). These sequences correspond to what is termed "protospacer adjacent motif" or "PAM" in the context of naturally occurring crRNAs. In type IIC CRISPR/Cas systems these PAM sequences facilitate stable interaction with the Cascade/crRNA complex with its dsDNA target, in order to ensure high degree of specificity of the crRNA—both in the natural system targets and therefore preferably also of the RNAs according to the present invention—for the target sequence. Preferably the sequence directly adjacent the protospacer will not be 5'-NNNCATN-3'.

Additionally, the PAM sequence may be of the sequence 5'-NNNNCNNA-3' [SEQ ID NO: 47], for example 5'-NNNNCNAA-3' [SEQ ID NO: 52], or 5'-NNNNCMCA-3' [SEQ ID NO: 53].

One of the limitations of the mesophilic SpCas9 is that it only displays activity between 25 and 44° C.; above these temperatures SpCas9 activity rapidly decreases to undetectable levels (Mougiakos et al., 2017, ACS Synth Biol. 6: 849-861). In contrast to the 25-44° C. range of its mesophilic orthologue SpCas9, ThermoCas9 of the present invention is active in vitro in a much broader temperature range of 20-70° C. The extended activity and stability of Thermo-Cas9 allows for its application in molecular biology techniques that require DNA manipulation at temperatures of 20-70° C., as well as its exploitation in harsh environments that require robust enzymatic activity. ThermoCas9 may also therefore be used as a genome editing tool for both thermophilic and mesophilic organisms.

In addition to having a broad functional temperature activity range, that is, to be functional at both low and high temperatures, for example at both 20° C. and 70° C., or 20° C. and 25° C. or 25° C. and 65° C., the ability to manipulate the range of temperatures at which ThermoCas9 is capable of targeted cleavage or binding or at which targeted cleavage or binding takes place efficiently, by modifying structural features of ThermoCas9 or associated elements (such as, for example, the sgRNA or tracRNA), would enable a greater level of control to be exerted over nucleic acid sequence manipulation. However, until now little was known about the molecular determinants of Cas9 activity at particular temperatures.

The inventors have identified several factors that are important for conferring the thermostability of ThermoCas9, one of which is the PAM preferences of ThermoCas9. The PAM preferences of ThermoCas9 are very strict for activity in the lower part of the temperature range 30° C.), whereas more variety in the PAM is allowed for activity at the moderate to optimal temperatures (37° C. to 60° C.). As such, the PAM sequence may be altered to obtain the most efficient binding, cleavage, marking or modification of the target at a given temperature. This provides a great deal of flexibility in application of the ThermoCas9, depending on the particular application. For instance in some applications a very broad temperature range of target binding, cleavage, marking or modification may be desirable, for example 20° C. to 70° C., preferably 20° C. to 65° C. or 25° C. to 65° C. Binding, cleavage, marking or modification of a target sequence within such a broad temperature range may be achieved by utilizing a PAM sequence of 5'-NNNNCVAA-3' [SEQ ID NO: 48]. Preferably, binding, cleavage, marking or modification of a target sequence within such a broad temperature range may be achieved by utilizing a PAM sequence of 5'-NNNNCSAA-3' [SEQ ID NO: 49], for example 5'-NNNNCGAA-3' [SEQ ID NO: 50] or 5'-NNNNCCAA-3' [SEQ ID NO: 51]. There is no specific preference for the for the first 4 PAM positions. The first 4 nucleotides can therefore conveniently be any nucleotide (NNNN). Optionally, for example 5'-CCCCCGAA-3' or 5'-CCCCCCAA-3' [SEQ ID NO: 11].

Where binding, cleavage, marking or modification of the target is required at 30° C., e.g. 30° C. to 100° C., preferably in the range 30° C. to 70° C., 30° C. to 65° C., or 45° C. to 65° C. the PAM sequence may optimally be of the sequence 5'-NNNNCNAA-3' [SEQ ID NO: 52] or 5'-NNNNCMCA-3' [SEQ ID NO: 53]. There is no specific preference for the for the first 4 PAM positions. The first 4 nucleotides can therefore conveniently be any nucleotide (NNNN). Optionally, for example the PAM sequence may be 5'-CCCCC-NAA-3' or 5'-CCCCCMCA-3'. Optionally, for example the PAM sequence may be selected from 5'-CCCCCAAA-3', 5'-CCCCCATA-3', 5'-CCCCCAGA-3', 5'-CCCCCACA-3', 5'-CCCCCTAA-3', 5'-CCCCCTTA-3', 5'-CCCCCTGA-3', 5'-CCCCCTCA-3', 5'-CCCCCGAA-3', 5'-CCCCCGTA-3', 5'-CCCCCGGA-3', 5'-CCCCCGCA-3', 5'-CCCCCCAA-3' [SEQ ID NO: 11], 5'-CCCCCCTA-3', 5'-CCCCCCGA-3', or 5'-CCCCCCCA-3'.

The PAM sequences of the invention provided herein comprise the sequences disclosed herein, for example as 6-mer, 7-mer or 8-mer sequences. The 6-mer, 7-mer or 8-mer sequences may begin directly 3' of the protospacer sequence on the non-target strand, with no additional nucleic acids interspaced between the protospacer sequence, complimentary to that bound by the target RNA, and the 5' end of the PAM sequence. However, it will be appreciated that there may be additional nucleic acids forming part of the PAM sequence at the 3' end of the 6-mer, 7-mer or 8-mer sequences. Additionally or alternatively, the non-target strand may comprise additional nucleic acids 3' of the PAM sequence.

A nucleoprotein complex of the invention may comprise a ribonucleoprotein complex of the invention and the target nucleic acid strand of nucleic acid, with which the ribonucleoprotein is associated.

Binding, Cleavage, Marking and Modifying Temperatures

The temperature range, including optimal temperature range of the activity, for example nuclease activity, of the Cas proteins of the present invention is significantly higher than that of known Cas9 proteins. Also, the upper extent of the range in which it retains activity is much higher than that of known Cas9 proteins. A higher optimal temperature and functional range provides a significant advantage in genetic engineering at high temperatures and therefore, for example, in the editing of the genomes of thermophilic organisms, many of which have utility in a range of industrial, agricultural and pharmaceutical processes conducted at elevated temperatures. Thus the methods, uses, nucleoproteins and transformed cells of the invention may be useful in industrial processes, for example providing genome editing for metabolic engineering purposes. The presence of the PAM sequences of the invention, directly adjacent to the protospacer sequence in the non-target strand, improve the specificity of the Cas proteins and polypeptides for the target sequences, and support the use of the Cas proteins and polypeptides at higher temperatures and across larger functional temperature ranges.

In accordance with a significantly greater thermostability, Cas proteins of the present invention retain function, for example nuclease activity, across a much greater temperature range of than that of known Cas9 proteins. Also, the upper extent of the range in which it retains activity is much higher than that of known Cas9 proteins. A higher optimal temperature and functional range provides a significant advantage in genetic engineering at high temperatures and therefore, for example, in the editing of the genomes of thermophilic and mesophilic organisms, many of which have utility in a range of industrial, agricultural and pharmaceutical processes conducted at elevated temperatures. The extended activity and stability of ThermoCas9 allows for its application in molecular biology techniques that require DNA manipulation within a broad range of temperatures, for example 20-70° C., as well as its exploitation in harsh environments that require robust enzymatic activity. ThermoCas9 may also therefore be used as a genome editing tool for both thermophilic and mesophilic organisms.

Advantageously, the inventors have also shown that Cas proteins of the invention can also be used to direct transcriptional control of target sequences, for example silencing transcription by sequence-specific binding to target sequences. ThermoCas9 may also therefore be used as a transcriptional control tool in both thermophilic and mesophilic organisms, for example in silencing or activating transcription of target genes. ThermoCas9 may also therefore be used as a gene-silencing tool in both thermophilic and mesophilic organisms.

Advantageously, Cas proteins or polypeptides of the invention are capable of nucleic acid binding, cleavage, marking or modifying at a temperature from 20° C. to 100° C. but are particularly useful at elevated temperatures, for example at a temperature between 41° C. and 122° C., preferably at a temperature between 50° C. and 100° C. Cas proteins and polypeptides of the invention are capable of binding, cleaving, marking or modifying DNA, RNA and synthetic nucleic acids. Cas proteins or polypeptides of the invention may also provide operability for nuclease activity, gene editing and nucleic acid marking applications at temperatures in the range 20 to 50° C., for example.

Where a temperature range is included herein, it is intended that the endpoints are included in the disclosed temperature range, i.e. that the range is "inclusive". For example, where it is stated that there is activity at a temperature in the range between 20° C. and 100° C., the temperatures of 20° C. and 100° C. are included in said range.

Preferably, Cas proteins or polypeptides of the invention, when associated with suitable gRNA (guide RNA, also called targeting RNA molecule) which recognizes a target sequence in the polynucleotide molecule(s) to be bound, cleaved, marked or modified, does so at temperatures in the range 20° C. to 100° C., optionally in the range 20° C. to 70° C., 20° C. to 65° C., 25° C. to 70° C., 25° C. to 65° C., 55° C. to 100° C., 50° C. to 70° C., 55° C. to 70° C., or 55° C. to 65° C.

Preferably, Cas proteins or polypeptides of the invention, when associated with suitable gRNA (guide RNA, also called targeting RNA molecule) which recognizes a target sequence in the polynucleotide molecule(s) to be bound, cleaved, marked or modified, does so at temperatures in the range 50° C. to 100° C., optionally in the range 55° C. to 100° C., 60° C. to 100° C., 65° C. to 100° C., 70° C. to 100° C., 75° C. to 100° C., 80° C. to 100° C., 85° C. to 100° C., 90° C. to 100° C., 95° C. to 100° C. More preferably, Cas proteins of the invention cleave, mark or modify nucleic acids at temperatures in the range 51° C. to 99° C., 52° C. to 98° C., 53° C. to 97° C., 54° C. to 96° C., 55° C. to 95° C., 56° C. to 94° C., 57° C. to 93° C., 58° C. to 92° C., 59° C. to 91° C. 60° C. to 90° C., 61° C. to 89° C., 62° C. to 88° C., 63° C. to 87° C., 64° C. to 86° C., 65° C. to 85° C., 66° C. to 84° C., 67° C. to 83° C., 68° C. to 82° C., 69° C. to 81° C., 70° C. to 80° C., 71° C. to 79° C., 72° C. to 78° C., 73° C. to 77° C., 74° C. to 76° C., or at a temperature of 75° C. Preferably, Cas proteins of the invention bind, cleave, mark or modify nucleic acids at temperatures in the range 60° C. to 80° C., 61° C. to 79° C., 62° C. to 78° C., 63° C. to 77° C., 64° C. to 76° C., 60° C. to 75° C., 60° C. to 70° C. Optimally Cas proteins of the invention bind, cleave, mark or modify nucleic acids at temperatures in the range 60° C. to 65° C., preferably at 65° C.

Target RNA molecules may be designed for use with the Cas proteins and polypeptides of the invention, wherein the target RNA molecules bind to the target sequence in a target strand, and the non-target strand further comprises a PAM sequence provided herein immediately 3' of the protospacer sequence. The PAM sequence may comprise 5'-NNNNNNNA-3', preferably 5'-NNNNCNNA-3' [SEQ ID NO: 47], optionally, for example 5'-CCCCCCNA-3' [SEQ ID NO: 10] or 5'-CCCCCCAA-3' [SEQ ID NO: 11], and the uses, methods, transformed cells, and nucleoproteins of the invention may provide binding, cleaving, marking and/or modifying of the target strand across the temperature range of from 55° C. to 65° C., preferably across the temperature range of from 50° C. to 70° C., from 40° C. to 65° C., from 45° C. to 75° C., from 37° C. to 78° C. and/or from 20° C. to 80° C.

The PAM sequence may be altered to obtain the most efficient cleavage of the target at a given temperature. This provides a great deal of flexibility in application of Cas proteins of the present invention, depending on the particular application. Where binding, cleavage, marking or modifying activity, for example cleavage activity is required within a temperature range of 20° C. to 100° C., preferably 20° C. to 70° C., or 20° C. to 65° C. or 25° C. to 65° C., then activity may be achieved by utilizing a PAM sequence of 5'-NNNNCVAA-3' [SEQ ID NO: 48], preferably, activity within such a temperature range may be achieved by utilizing a PAM sequence of 5'-NNNNCSAA-3' [SEQ ID NO: 49], for example 5'-NNNNCGAA-3' [SEQ ID NO: 50] or 5'-NNNNCCAA-3' [SEQ ID NO: 51]. Optionally, for example 5'-CCCCCGAA-3' [SEQ ID NO: 52] or 5'-CCCCCCAA-3' [SEQ ID NO: 11].

The inventors have found that thermostability of ThermoCas9 increases along with association of a guide (sgRNA) to form a ribonucleoprotein complex. The guide (sgRNA) may suitably comprise a tracrRNA and a crRNA. In such an arrangement, the guide may suitably comprise a crRNA which comprises a nucleotide spacer-fragment and repeat-fragment. The crRNA may suitably be 17-20 nt in length. Optionally, the crRNA may be 17 nt in length. Alternatively, the crRNA may be 18 nt in length, 19 nt in length or 20 nt in length. The guide may also comprise a tracrRNA (anti-repeat fragment (that base pairs with repeat fragment of crRNA)). The tracrRNA and crRNA can be separated by a synthetic linker. The following guide represents a preferred arrangement: 5'-[crRNA (17-20 nucleotide spacer-fragment & repeat-fragment)—(optional: synthetic loop to link the two RNAs)—tracrRNA (anti-repeat fragment (that base pairs with repeat fragment of crRNA) & some variable stem-loop structures (as to which see below), that may be truncated to some extent in some systems)]-3'.

Usually, the tracrRNA will be provided as part of a chimeric single-guide RNA (sgRNA), for example comprising a crRNA and a tracrRNA. The tracrRNA may consist of an anti-repeat region followed by one or more hairpin structures, preferably two or more hairpin structures or more preferably three or more hairpin structures. The presence of the full-length repeat/anti-repeat hairpin (formed by the 3'-end of the crRNA part (repeat) of the and the 5'-end of the complementary tracrRNA part (anti-repeat) in a synthetic sgRNA chimera fused by a 4-nucleotide linker, e.g. 5'-GAAA-3')) at the spacer distal end functions as an anchor to the nuclease, but is not essential to target selection and cleavage activity. For example deletions at the spacer distal end of up to 50-nt long deletion of the tracrRNA part can be tolerated with little to no effect on the DNA cleavage efficiency. Accordingly, for example a deletion of the spacer distal end of the full-length repeat-anti-repeat hairpin may be made up to 50 nt, up to 45 nt, up to 40 nt, up to 35 nt, up to 30 nt, up to 25 nt, up to 20 nt, up to 15 nt, up to 10 nt, or up to 5 nt, without compromise in terms of target DNA cleavage efficiency.

Surprisingly, the inventors have also found that the structure of the tracrRNA influences thermostability of the ThermoCas9 and efficiency of activity, in particular cleavage activity. Specifically, the number of hairpin (or stem-loop) structures in the tracrRNA or the sgRNA can be modified in order to obtain the most efficient binding, cleavage, marking or modifying of the target at a given temperature. This provides a great deal of flexibility in application of Cas proteins of the present invention, depending on the particular application. Optionally, the tracrRNA or the sgRNA may be provided with a nucleic acid sequence which is capable of forming one or more stem-loop structures, two or more stem-loop structures or three or more stem-loop structures. Optionally, the tracrRNA or the sgRNA may be provided with a nucleic acid sequence which is arranged to form one or more stem-loop structures, two or more stem-loop structures or three or more stem-loop structures. Preferably, the sgRNA will be provided with a nucleic acid sequence which is capable of forming at least three stem-loop structures.

Optionally where binding, cleavage, marking or modifying activity, for example cleavage activity is required within a temperature range of 20° C. to 60° C., preferably 37° C. to 60° C., or 37° C., 40° C., 45° C., 50° C., 55° C. or 60° C. then activity may be achieved by utilizing a sgRNA sequence which is capable of forming one or more stem-loop structures.

Optionally where binding, cleavage, marking or modifying activity, for example cleavage activity is required within a temperature range of 20° C. to 65° C., preferably 37° C. to 65° C., more preferably 45° C. to 55° C. or 37° C., 40° C., 45° C., 50° C., 55° C. or 60° C. then activity may be achieved by utilizing a sgRNA sequence which is capable of forming two or more stem-loop structures.

Optionally where binding, cleavage, marking or modifying activity, for example cleavage activity is required within a temperature range of 20° C. to 100° C., preferably 20° C. to 70° C., more preferably 37° C. to 65° C. or 37° C., 40° C., 45° C., 50° C., 55° C., 60° C. or 65° C. then activity may be achieved by utilizing a sgRNA sequence which is capable of forming three or more stem-loop structures.

Preferably, the portion of the sgRNA corresponding to the tracrRNA will comprise the sequence; AAGGGCUUUCUGCCUAUAGGCAGACUGCCC [SEQ ID NO: 54] which exemplifies the 5' hairpin. Preferably, the portion of the sgRNA corresponding to the tracrRNA will further comprise the sequence; GUGGCGUUGGGGAUCGCC-UAUCGCC [SEQ ID NO: 55], which exemplifies the 'middle' hairpin. Preferably, the portion of the sgRNA corresponding to the tracrRNA will further comprise the sequence; CGCUUUCUUCGGGCAUUCCCCACUC-UUAGGCGUUUU [SEQ ID NO: 56], which exemplifies the 3' hairpin.

Preferably, the portion of the sgRNA corresponding to the tracrRNA will comprise the sequence;
AAGGGCUUUCUGCCUAUAGGCA-GACUGCCCGUGGCGUUGGGGAUCGCCUAUCGCC [SEQ ID NO: 57] i.e. including the 5' hairpin and the middle hairpin.

Preferably, the portion of the sgRNA corresponding to the tracrRNA may comprise the sequence;
AAGGGCUUUCUGCCUAUAGGCA-GACUGCCCGUGGCGUUGGGGAUCGCCUAUCGCC GCUUUCUUCGGGCAUUCCCCACUC-UUAGGCGUUUU [SEQ ID NO: 58] i.e. including the 5' hairpin, the middle hairpin and the 3' hairpin.

The inventors have discovered that the number of predicted stem-loops of the tracrRNA scaffold plays a crucial role in DNA cleavage, in particular at elevated temperatures. They have determined that, although the presence of three stem-loops of the tracrRNA scaffold is not essential for cleavage activity, when all three loops are present, the cleavage is most efficient at all temperatures in the range indicating that a full length tracrRNA is required for optimal ThermoCas9-based DNA cleavage at elevated temperatures. In contrast, removal of the 3' hairpin results in a decrease in efficiency of cleavage. Moreover, the inventors found that removal of both the middle and the 3' hairpins, results in a drastically decline in the cleavage efficiency of Thermo-Cas9, particularly at the upper and lower extremes of the functional temperature ranges. Preferably, where binding, cleavage, marking or modification of a target sequence is required at elevated temperatures, for example 45° C. to 100° C., 50° C. to 100° C., 50° C. to 70° C., 50° C. to 65° C., 55° C. to 65° C. or within a broad temperature range such as 20° C. to 100° C., 20° C. to 70° C., 20° C. to 65° C. Preferably, ThermoCas9 associated with a sgRNA with three stem-loop structures will remain stable and capable of binding, cleavage, marking or modification of a target sequence for at least 1 min, at least 2 min, at least 3 min, at least 4 min or at least 5 min, preferably 5 min at a selected temperature in the range 20° C. to 100° C., 20° C. to 70° C., 20° C. to 65° C., 45° C. to 100° C., 50° C. to 100° C., 50° C. to 70° C., 50° C. to 65° C. or 55° C. to 65° C.

Additionally, the inventors have also discovered that the length of the spacer sequence of the sgRNA can be varied in order to manipulate the efficiency of ThermoCas9 activity, for example binding, cleavage, marking or modifying activity. Typically, the spacer sequence will be in the range 18 nt to 25 nt in length. Optionally the spacer sequence will be 18 nt, 19 nt, 20 nt, 21 nt, 22 nt, 23 nt, 24 nt or 25 nt in length. Preferably, spacer lengths of 19 nt, 20 nt, 21 nt or 23 nt will be used, since Cas9 proteins of the invention cleave target sequences with the highest efficiency when associated with sgRNAs with these spacer lengths. The cleavage efficiency drops significantly when a spacer of 18 nt is used. Preferably, the length of the spacer will be 23 nt.

In all aspects of the invention, Cas proteins or polypeptides may be obtained or derived from bacteria, archaea or viruses; or alternatively may be synthesised de novo. In preferred embodiments, a Cas protein or polypeptide of the invention is derived from a thermophilic prokaryotic organism, which may be classified as an archaea or bacterium, but is preferably a bacterium. More preferably a Cas protein or polypeptide of the invention will be derived from a thermophilic bacterium. Herein, the term thermophilic is to be understood as meaning capable of survival and growth at relatively high temperatures, for example in the context of the invention, capable of nucleic acid cleavage, binding or modification at a temperature between 41 and 122° C. (106 and 252° F.). Preferably a Cas protein or polypeptide of the invention may be isolated from one or more thermophilic bacteria and will function above 60° C.

Preferably a Cas protein or polypeptide of the invention may be isolated from one or more thermophilic bacteria and will function in the range 60° C. to 80° C. and optimally between 60° C. and 65° C. In preferred embodiments, a Cas protein or polypeptide of the invention is derived from *Geobacillus* sp. More preferably, a Cas protein of the invention is derived from *Geobacillus thermodenitrificans*. Even more preferably, a Cas protein of the invention is derived from *Geobacillus thermodenitrificans* T12. A Cas protein or polypeptide of the invention may be derived from a virus.

Functional Moieties

Advantageously, the ability of Cas proteins, polypeptides and ribonucleoprotein complexes of the invention to target any polynucleotide sequence in a sequence-specific manner may be exploited in order to modify the target nucleic acid in some way, for example by cleaving it and/or marking it and/or modifying it. It will therefore be appreciated that additional proteins may be provided along with the Cas protein or polypeptide to achieve this. Accordingly, the Cas proteins or polypeptides of the invention may further comprise at least one functional moiety and/or the Cas proteins, polypeptides or ribonucleoprotein complexes of the present invention may be provided as part of a protein complex comprising at least one further protein. In a preferred aspect the present invention provides a Cas protein, polypeptide or a ribonucleoprotein complex wherein the Cas protein or at least one further protein further comprises at least one functional moiety. The at least one functional moiety may be fused or linked to the Cas protein. Preferably, the at least one functional moiety may be translationally fused to the Cas protein through expression in natural or artificial protein expression systems. Alternatively, the at least one functional moiety may be covalently linked by a chemical synthesis step to the Cas protein. Preferably, the at least one functional moiety is fused or linked to the N-terminus and/or the C-terminus of the Cas protein; preferably the C-terminus.

Desirably, the at least one functional moiety will be a protein. It may be a heterologous protein or alternatively may be native to the bacterial species from which the Cas protein was derived. The at least one functional moiety may be a protein; optionally selected from a helicase, a nuclease, a helicase-nuclease, a DNA methylase, a histone methylase, an acetylase, a phosphatase, a kinase, a transcription (co-) activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

In a particularly preferred aspect, the present invention provides a Cas protein, polypeptide, or a ribonucleoprotein complex, wherein the at least one functional moiety is a marker protein, for example GFP.

Nuclease Activity

A Cas ribonucleoprotein of the invention has nucleic acid binding, cleavage, marking or modification activity at a temperature, preferably an elevated temperature, disclosed herein, for example at a temperature between 50° C. and 100° C. The ribonucleoproteins of the invention may be capable of binding, cleaving, marking or modifying DNA, RNA or synthetic nucleic acids. In preferred aspects Cas ribonucleoproteins of the invention are capable of cleaving DNA in a sequence-specific manner, in particular double-stranded DNA.

Cas proteins, polypeptides or ribonucleoproteins of the invention may have more than one nuclease domain. Site-specific nucleases can permit the generation of double strand breaks (DSBs) at selected positions along a strand of DNA. In a target host cell, this enables DSBs to be made at specific pre-selected positions in the genome. The creation of such breaks by site-specific nucleases prompts the endogenous cellular repair machinery to be repurposed in order to insert, delete or modify DNA at desired positions in the genome of interest.

One or more nuclease activity sites of the protein or polypeptide molecule may be inactivated, e.g. so as to allow the activity of another functional moiety linked or fused to the protein or polypeptide, e.g. a nuclease domain such as FokI nuclease.

Therefore notwithstanding the fact that the Cas proteins, polypeptides and ribonucleoproteins of the invention may have endogenous nuclease activity, for certain applications it may be desirable to inactivate the native nuclease activity of the Cas protein and provide a Cas protein or a ribonucleoprotein complex wherein the native Cas9 nuclease activity is inactivated and the Cas protein is linked to at least one functional moiety. Reducing the incidence of mis-targeting events by complementation of the native Cas9 nuclease activity is one such application. This may desirably be achieved by inactivation of the native Cas9 nuclease activity of the Cas protein or ribonucleoprotein complex and provision of a heterologous nuclease, preferably fused to the Cas protein. Accordingly, the present invention provides a Cas protein or a ribonucleoprotein complex, wherein the at least one functional moiety is a nuclease domain, preferably a FokI nuclease domain. In a particularly preferred aspect, the Cas protein or ribonucleoprotein complex of the invention fused to a FokI nuclease domain is provided as part of a protein complex, preferably comprising another Cas protein or ribonucleoprotein complex of the invention fused to a FokI nuclease domain and wherein the two complexes target opposite strands of the target genomic DNA.

For some applications it may be desirable to completely attenuate the nuclease activity of the Cas protein, polypeptide or ribonucleoprotein, for example in applications where the Cas protein or ribonucleoprotein complex is utilised to recognise and modify a specific target sequence in a nucleic acid, for instance to mark it as part of a diagnostic test. In such applications, the nuclease activity of the Cas protein may be inactivated and the functional moiety fused to the Cas protein may be a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

In a preferred aspect, a catalytically inactive, or "dead" Cas protein or polypeptide (dCas) lacking nuclease activity may be bound to a target nucleic acid sequence and thereby sterically repress activity of that sequence. For example, a target RNA may be designed that is complementary to a promoter or exonic sequence of a gene, so that binding of the dCas and target RNA to the gene sterically represses transcriptional initiation or elongation of the gene sequence, thereby repressing expression of the gene. Alternatively, the methods and uses described herein can use modified nuclease variants of gtCas9 that are nickases. A nickase can be created via a mutation in either one of the HNH or the RuvC catalytic domains of the gtCas9 nuclease. This has been shown for *S. pyogenes* Cas9 (spCas) with spCas9-mutants D10A and H840A, which have an inactive RuvC or HNH nuclease domain, respectively. The combination of these two mutations leads to a catalytically dead Cas9 variant (Standage-Beier, K. et al., 2015, *ACS Synth. Biol.* 4, 1217-1225; Jinek, M. et al., 2012, Science 337, 816-821; Xu, T. et al., 2015, Appl. Environ. Microbiol. 81, 4423-4431). Based on sequence homology (FIG. 3), these residues can be D8 (D17 in FIG. 3) and D581 or H582 (FIG. 3) in gtCas9.

Preferably, the mutations D8A and H582A in gtCas9 (ThermoCas9) can be used to create a catalytically inactive, or "dead" Cas protein or polypeptide variant of ThermoCas9 (dCas) which lacks nuclease activity. Such a dCas may usefully find application as, for example, an efficient thermoactive transcriptional silencing CRISPRi tool, being able to steadily and specifically bind to DNA elements without introducing dsDNA breaks. Advantageously, such a system could, amongst other things, greatly facilitate metabolic studies of thermophiles.

In a particularly preferred aspect, the present invention provides a Cas protein or a ribonucleoprotein complex, wherein the nuclease activity of the Cas protein is inactivated and the at least one functional moiety is a marker protein, for example GFP. In this way it may be possible to specifically target a nucleic acid sequence of interest and to visualize it using a marker which generates an optical signal. Suitable markers may include for example, a fluorescent reporter protein, e.g. Green Fluorescent Protein (GFP), Yellow Fluorescent Protein (YFP), Red Fluorescent Protein (RFP), Cyan Fluorescent Protein (CFP) or mCherry. Such a fluorescent reporter gene provides a suitable marker for visualisation of protein expression since its expression can be simply and directly assayed by fluorescence measurement. Alternatively, the reporter nucleic acid may encode a luminescent protein, such as a luciferase (e.g. firefly luciferase). Alternatively, the reporter gene may be a chromogenic enzyme which can be used to generate an optical signal, e.g. a chromogenic enzyme (such as beta-galactosidase (LacZ) or beta-glucuronidase (Gus)). Reporters used for measurement of expression may also be antigen peptide tags. Other reporters or markers are known in the art, and they may be used as appropriate.

Because the marker may be visualized, in certain embodiments where the target nucleic acid is RNA, specifically mRNA, it may be possible to quantify the transcriptional activity of a gene by detection and quantification of the optical signal provided by the marker, particularly where the optical signal generated by the marker is directly proportionate to the quantity of the expression product. Therefore in preferred embodiments of the invention, Cas proteins or ribonucleoproteins of the invention may be used to assay expression products of a gene of interest.

In one aspect, the gtCas9 described herein may be used in a homologous recombination (HR) mediated genome modification method in microbial cells. Such methods involve HR and site-directed gtCas9 activity, whereby counter selection occurs by the gtCas9 activity removing microbes which do not have a desired modification introduced by HR.

Thus the methods and uses provided herein allow the process of homologous recombination to be favoured during a first step such that the microbial genome can be modified with the desired mutation and a second step in which unmodified cells can be targeted by the gtCas9 ribonuclease complex to introduce a DSDB into the genomes of the unmodified cells. Due to an absence of an efficient non-homologous end joining (NHEJ) repair mechanism in the majority of microbes, DSDB typically leads to cell death. Thus, these methods and uses increase overall the population of microbial cells with the desired mutation whilst eliminating any unmodified microbial cells. Preferably, such methods and uses are used in microbes that have substantially no endogenous NHEJ repair mechanism. Alternatively, the methods and uses may be applied to microbes that have an endogenous NHEJ repair mechanism. The methods and uses described herein may be applied to microbes that have an endogenous NHEJ repair mechanism but wherein the NHEJ repair mechanism is either conditionally reduced or the NHEJ activity is knocked out.

The methods and uses provided herein may utilise a sequence of the homologous recombination polynucleotide that has at least one mis-match with the guide RNA, such that the guide RNA is no longer able to recognise the modified genome. This means that the gtCas9 ribonuclease complex will not recognise the modified genome. Therefore, no DSDB can be introduced by the gtCas9 ribonuclease complex and so the modified cells will survive. However, the cells with unmodified genomes will still have substantial complementarity to the guide RNA and consequently can be cleaved site-specifically by the gtCas9 ribonuclease complex.

In another aspect of the methods and uses of the invention, the way in which the gtCas9 ribonucleoase complex is prevented from acting to cleave the microbial genome is not so much to modify or eliminate the sequence targeted by the guide, but rather the PAM required by the gtCas9 ribonuclease complex. The PAM is either modified or eliminated in order to blind the gtCas9 ribonuclease complex to the specific cutting site. Therefore, methods and uses of the invention may include those using a sequence of the homologous recombination polynucleotide that does not include a PAM sequence recognised by the gtCas9 ribonuclease complex. Therefore, no DSDB can be introduced by the gtCas9 ribonuclease complex and so the HR modified cells will survive. However, the unmodified cells will still be recognised by the gtCas9 ribonuclease complex and its guide and so consequently are cleaved site-specifically.

Thus methods and uses are provided herein that rely on HR to modify the genome of the microbe. Preferably, the upstream flank and downstream flanks are 0.5 kilobases (kb) to 1.0 kb each in length. However, recombination using larger or shorter fragments is possible as well. The homologous recombination polynucleotide may further comprise a polynucleotide sequence between the upstream and downstream flanking regions. This polynucleotide sequence could for example contain a modification that is to be introduced into the microbial genome.

Whilst homologous recombination relies upon the upstream and downstream flanks having substantial complementarity to the target regions, mismatches can be accommodated as well. Therefore, in some embodiments, homologous recombination is known to occur between DNA segments with extensive homology to the upstream and downstream flanks. In alternative embodiments, the upstream and downstream flanks have complete complementarity to the target regions. The upstream and downstream flanks need not be identical in size. However, in some instances the upstream and downstream flanks are identical in size. The efficiency of homologous recombination will vary depending on the likelihood of homologous recombination of the smallest fragment length of the flank. However, even if the homologous recombination process is inefficient, advantageously the method described herein will select for any microbial cell that has the desired modification over the unmodified microbial cell. Homologous recombination also allows large deletions (e.g. 50 kb or more) to be made encompassing complete gene clusters. Homologous recombination is also used for recombineering, which is a well-known method to allow for recombination over smaller fragments (45-100 nt). The methods and uses described herein can optionally further comprise at least another homologous recombination polynucleotide or a polynucleotide comprising a sequence encoding a homologous recombination polynucleotide having a sequence substantially complementary to a second target region containing the target in the microbial genome.

In preferred embodiments, the methods and uses described herein utilise a homologous recombination polynucleotide that is DNA. In some embodiments the DNA is single stranded.

In other embodiments, the DNA is double stranded. In further embodiments, the DNA is double stranded and plasmid borne.

HR in the methods and uses provided herein may be used to remove a polynucleotide sequence from the microbial genome. Alternatively, HR in the methods and uses provided herein may be used to insert one or more gene(s), or fragment(s) thereof, in to the microbial genome. As a further alternative, HR in the methods and uses provided herein may be used to modify or replace at least one nucleotide in the microbial genome. Consequently, the methods and uses provided herein may be used for any desired kind of genome modification.

Alternatively, the gtCas9 described herein may be used in a HR mediated genome modification method in microbial cells, whereby the gtCas9 activity introduces DSDB and can induce cellular HR in microbial cells, as has been shown for spCas9 (Jiang et al. (2013) Nature Biotech, 31, 233-239; Xu et al. (2015) Appl Environ Microbiol, 81, 4423-4431; Huang et al. (2015) Acta Biochimica et Biophysica Sinica, 47, 231-243).

Alternatively, homologous recombination may be facilitated through recombineering, e.g., by introducing an oligonucleotide into a microbial cell expressing a gene coding for RecT or beta protein as reviewed by Mougiakos et al. ((2016), Trends Biotechnol. 34: 575-587). In a further embodiment, the Cas9 can be combined with Multiplex Automated Genome Engineering (MAGE) as exemplified by Ronda et al. ((2016), Sci. Rep. 6: 19452.)

Throughout, the reference sequences of the Cas proteins of the invention may be defined as a nucleotide sequence encoding the amino acid sequence. For example the amino acid sequence of the motifs defined in SEQ ID's 2 to 6 also includes all nucleic acid sequences which encode that amino acid sequence.

Accordingly, the present invention also provides an isolated nucleic acid molecule encoding a Cas protein comprising;
a. the amino acid motif EKDGKYYC [SEQ ID NO: 2]; and/or
b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
c. the amino acid motif $X_5LKX_6IE$ [SEQ ID NO: 4] wherein $X_5$ is independently selected from Methionine or Phenylalanine and $X_6$ is independently selected from Histidine or Asparagine; and/or
d. the amino acid motif $X_7VYSX_8K$ [SEQ ID NO: 5] wherein $X_7$ is Glutamate or Isoleucine and $X_8$ is one of Tryptophan, Serine or Lysine; and/or
e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine;
wherein the Cas protein is capable of DNA binding, cleavage, marking or modification between 50° C. and 100° C. when associated with at least one targeting RNA molecule, and a polynucleotide comprising a target nucleic acid sequence recognised by the targeting RNA molecule.

In another aspect the present invention also provides an isolated nucleic acid molecule encoding a clustered regularly interspaced short palindromic repeat (CRISPR)-associated (Cas) protein having an amino acid sequence of SEQ ID NO: 1 or a sequence of at least 77% identity therewith.

In another aspect the present invention also provides an isolated nucleic acid molecule, further comprising at least one nucleic acid sequence encoding a peptide which upon translation is fused to the Cas protein.

In another aspect the present invention also provides an isolated nucleic acid molecule, wherein the at least one nucleic acid sequence fused to the nucleic acid molecule encoding the Cas protein encodes a protein selected from a helicase, a nuclease, a helicase-nuclease, a DNA methylase, a histone methylase, an acetylase, a phosphatase, a kinase, a transcription (co-)-activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

ThermoCas9 Nuclease Activity: Divalent Cations

Previously characterized, mesophilic Cas9 endonucleases employ divalent cations to catalyze the generation of DSBs in target DNA. The inventors have shown that ThermoCas9 can mediate dsDNA cleavage in the presence of any of the following divalent cations: $Mg^{2+}$, $Ca^{2+}$, $Mn^{2+}$, $Co^{2+}$, $Ni^{2+}$, and $Cu^{2+}$.

ThermoCas9 Nuclease Activity: Substrates

The inventors have also surprisingly shown that despite reports that certain type-IIC systems were efficient single stranded DNA cutters ((Ma, et al., *Mol. Cell* 60, 398-407 (2015); Zhang, et al., *Mol. Cell* 60, 242-255 (2015)), ThermoCas9 cannot direct cleavage of ssDNA. The nuclease activity of ThermoCas9 is limited to dsDNA substrates.

Expression Vectors

Nucleic acids of the present invention may be isolated. However, in order that expression of the nucleic acid sensing construct may be carried out in a chosen cell, the polynucleotide sequence encoding the Cas protein or ribonucleoprotein will preferably be provided in an expression construct. In some embodiments, the polynucleotide encoding the Cas protein or ribonucleoprotein will be provided as part of a suitable expression vector. In certain embodiments an expression vector of the present invention (with or without nucleotide sequence encoding amino acid residues which on expression will be fused to a Cas protein) may further comprise a nucleotide sequence encoding a targeting RNA molecule as hereinbefore defined. Consequently, such expression vectors can be used in an appropriate host to generate a ribonucleoprotein complex of the invention which can target a desired nucleotide sequence. Alternatively, nucleotide sequences encoding a targeting RNA molecule as hereinbefore defined may be provided in a separate expression vector or alternatively may be delivered to a target cell by other means.

Suitable expression vectors will vary according to the recipient cell and suitably may incorporate regulatory elements which enable expression in the target cell and preferably which facilitate high-levels of expression. Such regulatory sequences may be capable of influencing transcription or translation of a gene or gene product, for example in terms of initiation, accuracy, rate, stability, downstream processing and mobility.

Such elements may include, for example, strong and/or constitutive promoters, 5' and 3' UTR's, transcriptional and/or translational enhancers, transcription factor or protein binding sequences, start sites and termination sequences, ribosome binding sites, recombination sites, polyadenylation sequences, sense or antisense sequences, sequences ensuring correct initiation of transcription and optionally poly-A signals ensuring termination of transcription and transcript stabilisation in the host cell. The regulatory sequences may be plant-, animal-, bacteria-, fungal- or virus derived, and preferably may be derived from the same organism as the host cell. Clearly, appropriate regulatory elements will vary according to the host cell of interest. For example, regulatory elements which facilitate high-level expression in prokaryotic host cells such as in *E. coli* may include the pLac, T7, P(Bla), P(Cat), P(Kat), trp or tac promoters. Regulatory elements which facilitate high-level expression in eukaryotic host cells might include the AOX1 or GAL1 promoter in yeast or the CMV- or SV40-promoters, CMV-enhancer, SV40-enhancer, Herpes simplex virus VIP16 transcriptional activator or inclusion of a globin intron in animal cells. In plants, constitutive high-level expression may be obtained using, for example, the *Zea mays* ubiquitin 1 promoter or 35S and 19S promoters of cauliflower mosaic virus.

Suitable regulatory elements may be constitutive, whereby they direct expression under most environmental conditions or developmental stages, developmental stage specific or inducible. Preferably, the promoter is inducible, to direct expression in response to environmental, chemical or developmental cues, such as temperature, light, chemicals, drought, and other stimuli. Suitably, promoters may be chosen which allow expression of the protein of interest at particular developmental stages or in response to extra- or intra-cellular conditions, signals or externally applied stimuli. For example, a range of promoters exist for use in *E. coli* which give high-level expression at particular stages of growth (e.g. osmY stationary phase promoter) or in response to particular stimuli (e.g. HtpG Heat Shock Promoter).

Suitable expression vectors may comprise additional sequences encoding selectable markers which allow for the selection of said vector in a suitable host cell and/or under particular conditions.

The invention also includes a method of modifying a target nucleic acid in a cell, comprising transfecting, transforming or transducing the cell with any of the expression vectors as hereinbefore described. The methods of transfection, transformation or transduction are of the types well known to a person of skill in the art. Where there is one expression vector used to generate expression of a ribonucleoprotein complex of the invention and when the targeting RNA is added directly to the cell then the same or a different method of transfection, transformation or transduction may be used. Similarly, when there is one expression vector being used to generate expression of a ribonucleoprotein complex of the invention and when another expression vector is being used to generate the targeting RNA in situ via expression, then the same or a different method of transfection, transformation or transduction may be used.

In other embodiments, mRNA encoding the Cas protein or polypeptide is introduced into a cell so that the Cascade complex is expressed in the cell. The targeting RNA which guides the Cas protein complex to the desired target sequence is also introduced into the cell, whether simultaneously, separately or sequentially from the mRNA, such that the necessary ribonucleoprotein complex is formed in the cell.

Accordingly, the invention also provides a method of modifying, i.e. cleaving, tagging, modifying, marking or binding, a target nucleic acid comprising contacting the nucleic acid with a ribonucleoprotein complex as hereinbefore defined.

In addition, the invention also includes a method of modifying a target nucleic acid comprising contacting the nucleic acid with a Cas protein or polypeptide as hereinbefore defined, in addition to a targeting RNA molecule as hereinbefore defined.

In accordance with the above methods, modification of target nucleic acid may therefore be carried out in vitro and in a cell-free environment. In a cell-free environment, addition of each of the target nucleic acid, the Cas protein and the targeting RNA molecule may be simultaneous, sequential (in any order as desired), or separately. Thus it is possible for the target nucleic acid and targeting RNA to be added simultaneously to a reaction mix and then the Cas protein or polypeptide of the invention to be added separately at a later stage.

Equally, the modification of the target nucleic acid may be made in vivo, that is in situ in a cell, whether an isolated cell or as part of a multicellular tissue, organ or organism. In the context of whole tissue and organs, and in the context of an organism, the method may desirably be carried out in vivo or alternatively may be carried out by isolating a cell from the whole tissue, organ or organism, treating the cell with ribonucleoprotein complex in accordance with the method and subsequently returning the cell treated with ribonucleoprotein complex to its former location, or a different location, whether within the same or a different organism.

In these embodiments, the ribonucleoprotein complex or the Cas protein or polypeptide requires an appropriate form of delivery into the cell. Such suitable delivery systems and methods are well known to persons skilled in the art, and include but are not limited to cytoplasmic or nuclear microinjection. In preferred modes of delivery, an Adeno-associated virus (AAV) is used; this delivery system is not disease causing in humans and has been approved for clinical use in Europe.

Accordingly the present invention provides a method of modifying a target nucleic acid comprising contacting the nucleic acid with:

a. a ribonucleoprotein complex as hereinbefore defined; or
b. a protein or protein complex as hereinbefore defined and an RNA molecule as hereinbefore defined.

In a further aspect the present invention provides a method of modifying a target nucleic acid in a cell, comprising transforming, transfecting or transducing the cell with an expression vector comprising nucleotide sequences encoding a ribonucleoprotein complex as hereinbefore defined; or alternatively transforming, transfecting or transducing the cell with an expression vector comprising nucleotide sequences encoding a protein or protein complex as hereinbefore defined and a further expression vector comprising a nucleotide sequence encoding a targeting RNA molecule as hereinbefore defined.

In a further aspect, the present invention provides a method of modifying a target nucleic acid in a cell comprising transforming, transfecting or transducing the cell with an expression vector comprising nucleotide sequences encoding a protein or protein complex as hereinbefore defined, and then delivering a targeting RNA molecule as hereinbefore defined into the cell.

In embodiments where the guide (i.e. targeting) RNA (gRNA) molecule and the Cas protein or polypeptide are provided separately rather than as part of a ribonucleoprotein complex, the gRNA molecule requires an appropriate form of delivery into a cell, whether simultaneously, separately or sequentially with the Cas protein or protein complex. Such forms of introducing RNA into cells are well known to a person of skill in the art and may include in vitro or ex vivo delivery via conventional transfection methods. Physical methods, such as microinjection and electroporation, as well as calcium co-precipitation, and commercially available cationic polymers and lipids, and cell-penetrating peptides, cell-penetrating (biolistic) particles may each be used. For example, viruses, particularly preferred is AAV, may be used as delivery vehicles, whether to the cytoplasm and/or nucleus, for example via the (reversible) fusion of Cas protein complex of the invention or a ribonucleoprotein complex of the invention to the viral particle.

In another aspect the present invention provides a method of modifying a target nucleic acid, wherein the at least one functional moiety is a marker protein or reporter protein and the marker protein or reporter protein associates with the target nucleic acid; preferably wherein the marker is a fluorescent protein, for example a green fluorescent protein (GFP).

In the aforementioned methods of modifying a target nucleic acid, the functional moiety may be a marker and the marker associates with the target nucleic acid; preferably wherein the marker is a protein; optionally a fluorescent protein, e.g. green fluorescent protein (GFP), yellow fluorescent protein (YFP), red fluorescent protein (RFP) or mCherry. Whether in vitro, ex vivo or in vivo, then methods of the invention can be used to directly visualise a target locus in a nucleic acid molecule, preferably in the form of a higher order structure such as a supercoiled plasmid or chromosome, or a single stranded target nucleic acid such as mRNA. Direct visualisation of a target locus may use electron micrography, or fluorescence microscopy. However, it will be appreciated that in the context of methods of the invention, other kinds of label may be used as the marker including organic dye molecules, radiolabels and spin labels which may be small molecules.

In methods of the invention for modifying a target nucleic acid wherein the target nucleic acid is dsDNA, the functional moiety may be a nuclease or a helicase-nuclease, and the modification is preferably a single stranded or a double stranded break at a desired locus. In this way unique sequence specific cutting of DNA can be engineered by using a suitable functional moiety fused to a ribonucleoprotein complex. The chosen sequence of the RNA component of the final ribonucleoprotein complex provides the desired sequence specificity for the action of the functional moiety.

Therefore, the invention also provides a method of non-homologous end joining of a dsDNA molecule in a cell at a desired locus to remove at least a part of a nucleotide sequence from the dsDNA molecule; optionally to knockout the function of a gene or genes, wherein the method comprises making double stranded breaks using any of the methods of modifying a target nucleic acid as hereinbefore described.

The invention further provides a method of homologous recombination of a nucleic acid into a dsDNA molecule in a cell at a desired locus in order to modify an existing nucleotide sequence or insert a desired nucleotide sequence, wherein the method comprises making a double stranded break at the desired locus using any of the methods of modifying a target nucleic acid as hereinbefore described.

The invention therefore also provides a method of modifying gene expression in an organism comprising modifying a target nucleic acid sequence according to any of the methods hereinbefore described, wherein the nucleic acid is dsDNA and the functional moiety is selected from a DNA modifying enzyme (e.g. a methylase or acetylase), a transcription activator or a transcription repressor.

The invention additionally provides a method of modifying gene expression in an organism comprising modifying a target nucleic acid sequence according to any of the methods hereinbefore described, wherein the nucleic acid is an mRNA and the functional moiety is a ribonuclease; optionally selected from an endonuclease, a 3' exonuclease or a 5' exonuclease.

The target nucleic acid may be DNA, RNA or synthetic nucleic acid. Preferably the target nucleic acid is DNA; preferably dsDNA.

However, the target nucleic acid can be RNA; preferably mRNA. Alternatively therefore, the present invention also provides methods of modifying a target nucleic acid, wherein the target nucleic acid is RNA.

In another aspect the present invention provides a method of modifying a target nucleic acid, wherein the nucleic acid is dsDNA, the at least one functional moiety is a nuclease or a helicase-nuclease, and the modification is a single-stranded or a double-stranded break at a desired locus.

In another aspect the present invention provides a method of modifying a target nucleic acid in a cell, wherein modification results in a silencing of gene expression at a desired locus; and wherein the method includes the steps of;
    a. making double-stranded breaks in the dsDNA molecule; and
    b. repair of the dsDNA molecule in the cell by non-homologous end joining (NHEJ).

In another aspect the present invention provides a method of modifying a target nucleic acid in a cell; wherein the existing nucleotide sequence is modified or deleted and/or a desired nucleotide sequence is inserted at a desired location wherein the method includes the steps of;
    a. making a double stranded break at the desired locus; and
    b. repair of the dsDNA molecule in the cell by homologous recombination.

In another aspect the present invention provides a method of modifying gene expression in a cell comprising modifying a target nucleic acid sequence as hereinbefore described; wherein the nucleic acid is dsDNA and the functional moiety is selected from a DNA modifying enzyme (e.g. a methylase or acetylase), a transcription activator or a transcription repressor.

In another aspect the present invention provides a method of modifying gene expression in a cell comprising modifying a target nucleic acid sequence as hereinbefore described, wherein the nucleic acid is an mRNA and the functional moiety is a ribonuclease; optionally selected from an endonuclease, a 3' exonuclease or a 5' exonuclease.

In another aspect the present invention provides a method of modifying a target nucleic acid as hereinbefore described, wherein the method is carried out at a temperature between 45° C. and 100° C. Preferably, the method is carried out at a temperature at or above 50° C. More preferably, the method is carried out at a temperature between 55° C. and 80° C. Optimally, the method is carried out at a temperature between 60° C. and 65° C. Alternatively, the method may be carried out at a temperature between 20° C. and 45° C. More preferably, at a temperature between 30° C. and 45° C. Even more preferably at a temperature between 37° C. and 45° C.

In any of the methods of modifying a target nucleic acid hereinbefore described, the cell may be a prokaryotic cell or alternatively, may be a eukaryotic cell.

Host Cells

Advantageously, the present invention is of broad applicability and host cells of the present invention may be derived from any genetically tractable organism which can be cultured. Accordingly, the present invention provides a host cell transformed by a method as hereinbefore described. The invention provides a transformed cell, having a target nucleic acid sequence in a double stranded target polynucleotide, said cell comprising a Cas protein or polypeptide as provided herein and at least one targeting RNA molecule as provided herein, and an expression vector comprising a nucleic acid encoding at least one of said Cas protein and said targeting RNA molecule.

Appropriate host cells may be prokaryotic or eukaryotic. In particular, commonly used host cells may be selected for use in accordance with the present invention including prokaryotic or eukaryotic cells which are genetically accessible and which can be cultured, for example prokaryotic cells, fungal cells, plant cells and animal cells. Preferably, host cells will be selected from a prokaryotic cell, a fungal cell, a plant cell, a protist cell or an animal cell. Preferably, host cells will be selected from a prokaryotic cell, a fungal cell, a plant cell, a protist cell or an animal cell except a human cell. Preferably, host cells will not include human cells, including embryonic stem cells. Preferred host cells for use in accordance with the present invention are commonly derived from species which typically exhibit high growth rates, are easily cultured and/or transformed, display short generation times, species which have established genetic resources associated with them or species which have been selected, modified or synthesized for optimal expression of heterologous protein under specific conditions. In preferred embodiments of the invention where the protein of interest is eventually to be used in specific industrial, agricultural, chemical or therapeutic contexts, an appropriate host cell may be selected based on the desired specific conditions or cellular context in which the protein of interest is to be deployed. Preferably the host cell will be a prokaryotic cell. In preferred embodiments the host cell is a bacterial cell. The host cell may for instance be an *Escherichia coli* (*E. coli*) cell. Preferably the host cell will be a cell of a thermophilic bacterium.

Methods and uses of the invention described herein may be used to modify genomes of bacterial cells. In particular embodiments, the bacteria are thermophilic bacteria, preferably the bacteria are selected from: *Acidithiobacillus* species including *Acidithiobacillus caldus*; *Aeribacillus* species including *Aeribacillus pallidus*; *Alicyclobacillus* species including *Alicyclobacillus acidocaldarius*, *Alicyclobacillus acidoterrestris*, *Alicyclobacillus cycloheptanicusl*, *Alicyclobacillus hesperidum*; *Anoxybacillus* species including *Anoxybacillus caldiproteolyticus*, *Anoxybacillus flavithermus*, *Anoxybacillus rupiensis*, *Anoxybacillus tepidamans*; *Bacillus* species including *Bacillus caldolyticus*, *Bacillus caldotenax*, *Bacillus caldovelox*, *Bacillus coagulans*, *Bacillus clausii*, *Bacillus hisashii*, *Bacillus licheniformis*, *Bacillus methanolicus*, *Bacillus smithii* including *Bacillus smithii* ET138, *Bacillus subtilis*, *Bacillus thermocopriae*, *Bacillus thermolactis*, *Bacillus thermoamylovorans*, *Bacillus thermoleovorans*; *Caldibacillus* species including *Caldibacillus debilis*; *Caldicellulosiruptor* species including *Caldicellulosiruptor bescii*, *Caldicellulosiruptor hydrothermalis*, *Caldicellulosiruptor kristjanssonfi*, *Caldicellulosiruptor kronotskyensis*, *Caldicellulosiruptor lactoaceticus*, *Caldicellulosiruptor obsidiansis*, *Caldicellulosiruptor owensensis*, *Caldicellulosiruptor saccharolyticus*; *Clostridium* species including *Clostridium clariflavum*, *Clostridium straminisolvens*, *Clostridium tepidiprofundi*, *Clostridium thermobutyricum*, *Clostridium thermocellum*, *Clostridium thermosuccinogenes*, *Clostridium thermopalmarium*; *Deinococcus* species including *Deinococcus cellulosilyticus*, *Deinococcus deserti*, *Deinococcus geothermalis*, *Deinococcus murrayi*, *Deinococcus radiodurans*; *Defluviitalea* species including *Defluviitalea phaphyphila*, *Desulfotomaculum* species including *Desulfotomaculum carboxydivorans*, *Desulfotomaculum nigrificans*, *Desulfotomaculum salinum*, *Desulfotomaculum solfataricum*; *Desulfurella* species including *Desulfurella acetivorans*; *Desulfurobacterium* species including *Desulfurobacterium thermolithotrophum*; *Geobacillus* species including *Geobacillus icigianus*, *Geobacillus caldoxylosilyticus*, *Geobacillus jurassicus*, *Geobacillus galactosidasius*, *Geobacillus kaustophilus*, *Geobacillus lituanicus*, *Geobacillus stearothermophilus*, *Geobacillus subterraneus*, *Geobacillus thermantarcticus*, *Geobacillus thermocatenulatus*, *Geobacillus thermodenitrificans*, *Geobacillus thermoglucosidans*, *Geobacillus thermoleovorans*, *Geobacillus toebfi*, *Geobacillus uzenensis*, *Geobacillus vulcanfi*, *Geobacillus zalihae*; *Hydrogenobacter* species including *Hydrogenobacter thermophiles*; *Hydrogenobaculum* species including *Hydrogenobaculum acidophilum*; *Ignavibacterium* species including *Ignavibacterium album*; *Lactobacillus* species including *Lactobacillus bulgaricus*, *Lactobacillus delbrueckii*, *Lactobacillus ingluviei*, *Lactobacillus thermotolerans*; *Marinithermus* species including *Marinithermus hydrothermalis*; *Moorella* species including *Moorella thermoacetica*; *Oceanithermus* species including *Oceanithermus desulfurans*, *Oceanithermus profundus*; *Paenibacillus* species including *Paenibacillus* sp. J2, *Paenibacillus marinum*, *Paenibacillus thermoaerophilus*; *Persephonella* species including *Persephonella guaymasensis*, *Persephonella hydrogeniphila*, *Persephonella marina*; *Rhodothermus* species including *Rhodothermus marinus*, *Rhodothermus obamensis*, *Rhodothermus profundi*; *Sulfobacillus* species including *Sulfobacillus acidophilus*; *Sulfurihydrogenibium* species including *Sulfurihydrogenibium azorense*, *Sulfurihydrogenibium kristjanssonii*, *Sulfurihydrogenibium rodmanfi*, *Sulfurihydrogenibium yellowstonense*; *Symbiobacterium* species including *Symbiobacterium thermophilum*, *Symbiobacterium toebfi*; *Thermoanaerobacter* species including *Thermoanaerobacter brockii*, *Thermoanaerobacter ethanolicus*, *Thermoanaerobacter italicus*, *Thermoanaerobacter kivui*, *Thermoanaerobacter marianensis*, *Thermoanaerobacter mathranii*, *Thermoanaerobacter pseudoethanolicus*, *Thermoanaerobacter wiegelii*; *Thermoanaerobacterium* species including *Thermoanaerobacterium aciditolerans*, *Thermoanaerobacterium aotearoense*, *Thermoanaerobacterium ethanolicus*, *Thermoanaerobacterium pseudoethanolicus*, *Thermoanaerobacterium saccharolyticum*, *Thermoanaerobacterium thermosaccharolyticum*, *Thermoanaerobacterium xylanolyticum*; *Thermobacillus* species including *Thermobacillus composti*, *Thermobacillus xylanilyticus*; *Thermocrinis* species including *Thermocrinis albus*, *Thermocrinis ruber*; *Thermodulfatator* species including *Thermodesulfatator atlanticus*, *Thermodesulfatator autotrophicus*, *Thermodesulfatator indicus*; *Thermodesulfobacterium* species including *Thermodesulfobacterium commune*, *Thermodesulfobacterium hydrogeniphilum*; *Thermodesulfobium* species including *Thermodesulfobium narugense*; *Thermodesulfovibrio* species including *Thermodesulfovibrio aggregans*, *Thermodesulfovibrio thiophilus*, *Thermodesulfovibrio yellowstonfi*; *Thermosipho* species including *Thermosipho africanus*, *Thermosipho atlanticus*, *Thermosipho melanesiensis*; *Thermotoga* species including *Thermotoga maritima*, *Thermotoga neopolitana*, *Thermotoga* sp. RQ7; *Thermovibrio* species including *Thermovibrio ammonificans*, *Thermovibrio ruber*, *Thermovirga* species including *Thermovirga lienfi* and *Thermus* species including *Thermus aquaticus*, *Thermus caldophilus*, *Thermus flavus*, *Thermus scotoductus*, *Thermus thermophilus*; *Thiobacillus neapolitanus*.

In another aspect, a method or use described herein can be used to modify bacteria that are mesophilic. In preferred embodiments, the bacteria are selected from: *Acidithiobacillus* species including *Acidithiobacillus caldus*; *Actinobacillus* species including *Actinobacillus succinogenes*; *Anaerobiospirillum* species including *Anaerobiospirillum succiniciproducens*; *Bacillus* species including *Bacillus alcaliphilus*, *Bacillus amyloliquefaciens*, *Bacillus circulans*, *Bacillus cereus*, *Bacillus clausii*, *Bacillus firmus*, *Bacillus halodurans*, *Bacillus hisashii*, *Bacillus lautus*, *Bacillus lentus*, *Bacillus licheniformis*, *Bacillus megaterium*, *Bacillus pumilus*, *Bacillus smithii*, *Bacillus subtilis*, *Bacillus thuringiensis*; *Basfia* species including *Basfia succiniciproducens*; *Brevibacillus* species including *Brevibacillus brevis*; *Brevibacillus laterosporus*; *Clostridium* species including *Clostridium acetobutylicum*, *Clostridium autoethanogenum*, *Clostridium beijerinkii*, *Clostridium carboxidivorans*, *Clostridium cellulolyticum*, *Clostridium ljungdahlii*,

*Clostridium pasteurianum*, *Clostridum perfringens*, *Clostridium ragsdalei*, *Clostridium saccharobutylicum*, *Clostridium saccharoperbutylacetonium*; *Corynebacterium* species including *Corynebacterium glutamicum*; *Desulfitobacterium* species including *Desulfitobacterium dehalogenans*, *Desulfitobacterium hafniense*; *Desulfotomaculum* species including *Desulfotomaculum acetoxidans*, *Desulfotomaculum gibsoniae*, *Desulfotomaculum reducens*, *Desulfotomaculum ruminis*; *Enterobacter* species including *Enterobacter asburiae*; *Enterococcus* species including *Enterococcus faecalis*; *Escherichia* species including *Escherichia coli*; *Lactobacillus* species including *Lactobacillus acidophilus*, *Lactobacillus amylophilus*, *Lactobacillus amylovorus*, *Lactobacillus animalis*, *Lactobacillus arizonensis*, *Lactobacillus bavaricus*, *Lactobacillus brevis*, *Lactobacillus buchneri*, *Lactobacillus bulgaricus*, *Lactobacillus casei*, *Lactobacillus corynoformis*, *Lactobacillus crispatus*, *Lactobacillus curvatus*, *Lactobacillus delbrueckii*, *Lactobacillus fermenturn*, *Lactobacillus gasseri*, *Lactobacillus helveticus*, *Lactobacillus johnsonii*, *Lactobacillus pentosus*, *Lactobacillus plantarum*, *Lactobacillus reuteri*, *Lactobacillus rhamnosus*, *Lactobacillus sakei*, *Lactobacillus salivarius*, *Lactobacillus sanfriscensis*; *Lactococcus* species, including *Lactococcus lactis*; *Mannheimia* species including *Mannheimia succiniciproducens*; *Paenibacillus* species including *Paenibacillus alvei*, *Paenibacillus beijingensis*, *Paenibacillus borealis*, *Paenibacillus dauci*, *Paenibacillus durus*, *Paenibacillus graminis*, *Paenibacillus larvae*, *Paenibacillus lentimorbus*, *Paenibacillus macerans*, *Paenibacillus mucilaginosus*, *Paenibacillus odorifer*, *Paenibacillus polymyxa*, *Paenibacillus stellifer*, *Paenibacillus terrae*, *Paenibacillus wulumuqiensis*; *Pediococcus* species including *Pediococcus acidilactici*, *Pediococcus claussenii*, *Pediococcus ethanolidurans*, *Pediococcus pentosaceus*; *Propionibacterium* species, including *P. acidipropionici*, *P. freudenreichii*, *P. jensenii*; *Salmonella typhimurium*; *Sporolactobacillus* species including *Sporolactobacillus inulinus*, *Sporolactobacillus laevolacticus*; *Staphylococcus aureus*; *Streptococcus* species including *Streptococcus agalactiae*, *Streptococcus bovis*, *Streptococcus equisimilis*, *Streptococcus feacalis*, *Streptococcus mutans*, *Streptococcus oralis*, *Streptococcus pneumonia*, *Streptococcus pyogenes*, *Streptococcus salivarius*, *Streptococcus thermophilus*, *Streptococcus sobrinus*, *Streptococcus uberis*; *Streptomyces* species including *Streptomyces achromogenes*, *Streptomyces avermitilis*, *Streptomyces coelicolor*, *Streptomyces griseus*, *Streptomyces lividans*, *Streptomyces parvulus*, *Streptomyces venezuelae*, *Streptomyces vinaceus*; *Tetragenococcus* species including *Tetragenococcus halophilus* and *Zymomonas* species including *Zymomonas mobilis*. *Pseudomonas* species including *Pseudomonas putida*, *Pseudomonas aeruginosa*, *Pseudomonas alcaligenes*, *Pseudomonas anguilliseptica*, *Pseudomonas argentinensis*, *Pseudomonas borbori*, *Pseudomonas citronellolis*, *Pseudomonas flavescens*, *Pseudomonas mendocina*, *Pseudomonas nitroreducens*, *Pseudomonas oleovorans*, *Pseudomonas pseudoalcaligenes*, *Pseudomonas resinovorans*, *Pseudomonas straminea*, *Pseudomonas asplenii*, *Pseudomonas aurantiaca*, *Pseudomonas aureofaciens*, *Pseudomonas chlororaphis*, *Pseudomonas corrugate*, *Pseudomonas fragi*, *Pseudomonas lundensis*, *Pseudomonas taetrolens*, *Pseudomonas antarctica*, *Pseudomonas azotoformans*, *Pseudomonas blatchfordae'*, *Pseudomonas brassicacearum*, *Pseudomonas brenneri*, *Pseudomonas cedrina*, *Pseudomonas corrugate*, *Pseudomonas fluorescens*, *Pseudomonas gessardii*, *Pseudomonas libanensis*, *Pseudomonas mandelii*, *Pseudomonas marginalis*, *Pseudomonas mediterranea*, *Pseudomonas meridiana*, *Pseudomonas migulae*, *Pseudomonas mucidolens*, *Pseudomonas orientalis*, *Pseudomonas panacis*, *Pseudomonas protegens*, *Pseudomonas proteolytica*, *Pseudomonas rhodesiae*, *Pseudomonas synxantha*, *Pseudomonas thivervalensis*, *Pseudomonas tolaasii*, *Pseudomonas veronii*, *Pseudomonas denitrificans*, *Pseudomonas pertucinogena*, *Pseudomonas cremoricolorata*, *Pseudomonas entomophila*, *Pseudomonas fulva*, *Pseudomonas monteilii*, *Pseudomonas mosselii*, *Pseudomonas oryzihabitans*, *Pseudomonas parafulva*, *Pseudomonas plecoglossicida*, *Pseudomonas putida*, *Pseudomonas balearica*, *Pseudomonas luteola*, *Pseudomonas stutzeri*, *Pseudomonas amygdali*, *Pseudomonas avellanae*, *Pseudomonas caricapapayae*, *Pseudomonas cichorii*, *Pseudomonas coronafaciens*, *Pseudomonas ficuserectae*, '*Pseudomonas helianthi*', *Pseudomonas meliae*, *Pseudomonas savastanoi*, *Pseudomonas syringae*, '*Pseudomonas tomato*', *Pseudomonas viridiflava*, *Pseudomonas abietaniphila*, *Pseudomonas acidophila*, *Pseudomonas agarici*, *Pseudomonas alcaliphila*, *Pseudomonas alkanolytica*, *Pseudomonas amyloderamosa*, *Pseudomonas asplenii*, *Pseudomonas azotifigens*, *Pseudomonas cannabina*, *Pseudomonas coenobios*, *Pseudomonas congelans*, *Pseudomonas costantinii*, *Pseudomonas cruciviae*, *Pseudomonas delhiensis*, *Pseudomonas excibis*, *Pseudomonas extremorientalis*, *Pseudomonas frederiksbergensis*, *Pseudomonas fuscovaginae*, *Pseudomonas gelidicola*, *Pseudomonas grimontii*, *Pseudomonas indica*, *Pseudomonas jessenii*, *Pseudomonas jinjuensis*, *Pseudomonas kilonensis*, *Pseudomonas knackmussii*, *Pseudomonas koreensis*, *Pseudomonas lini*, *Pseudomonas lutea*, *Pseudomonas moraviensis*, *Pseudomonas otitidis*, *Pseudomonas pachastrellae*, *Pseudomonas palleroniana*, *Pseudomonas papaveris*, *Pseudomonas peli*, *Pseudomonas perolens*, *Pseudomonas poae*, *Pseudomonas pohangensis*, *Pseudomonas protegens*, *Pseudomonas psychrophila*, *Pseudomonas psychrotolerans*, *Pseudomonas rathonis*, *Pseudomonas reptilivora*, *Pseudomonas resiniphila*, *Pseudomonas rhizosphaerae*, *Pseudomonas rubescens*, *Pseudomonas salomonii*, *Pseudomonas segitis*, *Pseudomonas septica*, *Pseudomonas simiae*, *Pseudomonas suis*, *Pseudomonas thermotolerans*, *Pseudomonas toyotomiensis*, *Pseudomonas tremae*, *Pseudomonas trivialis*, *Pseudomonas turbinellae*, *Pseudomonas tuticorinensis*, *Pseudomonas umsongensis*, *Pseudomonas vancouverensis*, *Pseudomonas vranovensis*, *Pseudomonas xanthomarina*. Preferably the mesophilic bacterium is *Pseudomonas putida*.

In a further aspect, methods or uses or uses of the invention defined herein could be used to modify the genome of yeast or fungi. In particular embodiments, the fungal species are mesophilic, preferably the fungi is selected from: an *Aspergillus* species including, but not limited to, *Aspergillus nidulans*, *Aspergillus niger*, *Aspergillus oryzae* and *Aspergillus terreus*, more preferably the *Aspergillus* species is *Aspergillus nidulans* or *Aspergillus niger*. Alternatively, the mesophilic fungal species could be a *Candida* species. A method or use defined herein could be used to modify the genome of yeast species including, but not limited to, *Saccharomyces* species including *Saccharomyces cerevisiae*, *Schizosaccharomyces* species including *Schizosaccharomyces pombe*, *Pichia* species including, but not limited to *Pichia pastoris*, *Pichia stipitis*. A method or use defined herein could be used to modify the genome of fungal species including, but not limited to, *Hansenula* species including *Hansenula polymorpha*, *Penicillium* species including, but not limited to *P. brasilianum*, *P. chrysogenum*, *Yarrowia* species including *Yarrowia lipolytica*.

The invention further relates to use of a method as defined herein to modify a yeast or fungal species that are thermophilic, preferably the fungi or yeast is selected from: *Aspergillus* species including *Aspergillus fumigatus*, *Aspergillus nidulans*, *Aspergillus terreus*, *Aspergillus versicolor*, *Canariomyces* species including *Canariomyces thermophile*; *Chaetomium* species including *Chaetomium mesopotamicum*, *Chaetomium thermophilum*; *Candida* species including *Candida bovina*, *Candida sloofii*, *Candida thermophila*, *Candida tropicalis*, *Candida krusei* (=*Issatchenkia orientalis*); *Cercophora* species including *Cercophora coronate*, *Cercophora septentrionalis*; *Coonemeria* species including *Coonemeria aegyptiaca*; *Corynascus* species including *Corynascus thermophiles*; *Geotrichum* species including *Geotrichum candidum*; *Kluyveromyces* species including *Kluyveromyces fragilis*, *Kluyveromyces marxianus*; *Malbranchea* species including *Malbranchea cinnamomea*, *Malbranchea sulfurea*; *Melanocarpus* species including *Melanocarpus albomyces*; *Myceliophtora* species including *Myceliophthora fergusii*, *Myceliophthora thermophila*; *Mycothermus* species including *Mycothermus thermophiles* (=*Scytalidium thermophilum/Torula thermophila*); *Myriococcum* species including *Myriococcum thermophilum*; *Paecilomyces* species including *Paecilomyces thermophila*; *Remersonia* species including *Remersonia thermophila*; *Rhizomucor* species including *Rhizomucor pusillus*, *Rhizomucor tauricus*; *Saccharomyces* species including *Saccharomyces cerevisiae*, *Schizosaccharomyces* species including *Schizosaccharomyces pombe*, *Scytalidiurn* species including *Scytalidium thermophilum*; *Sordaris* species including *Sordaria thermophila*; *Thermoascus* species including *Thermoascus aurantiacus*, *Thermoascus thermophiles*; *Thermomucor* species including *Thermomucor indicae-seudaticae* and *Thermomyces* species including *Thermomyces ibadanensis*, *Thermomyces lanuginosus*.

In the aforementioned lists, microbes identified in bold typeface have been found to be particularly suitable/applicable in use for the present invention.

Some preferred embodiments of the present invention include one or more thermophilic microbes selected from: Thermophilic *bacilli*, including *Aeribacillus*, *Alicyclobacillus*, *Anoxybacillus*, *Bacillus*, *Geobacillus*; *Paenibacillus* species; Thermophilic *clostridia*, including *Anaerobacter*, *Anaerobacterium*, *Caldicellulosiruptor*, *Clostridium*, *Moorella*, *Thermoanaerobacter*, *Thermoanaerobacterium*, *Thermobrachium*, *Thermohalobacter* species or one or more thermophilic *Lactobacillus* species and mesophilic bacteria selected from *Bacillus* species, *Escherichia coli*, *Lactobacillus* species *Lactococcus* species, *Propionibacterium* species and *Pseudomonas* species.

BRIEF DESCRIPTION OF THE FIGURES

The invention will now be described in detail with reference to a specific embodiment and with reference to the accompanying drawings, in which:

FIG. 3, comprising

FIG. 6 shows an alignment of sequences of the *G. thermodenitrificans* T12 type IIc CRISPR system.

FIG. 7, comprising FIG. 7A and FIG. 7B, shows six single hits obtained to provide an in silica PAM prediction for gtCas9.

FIG. 12A through FIG. 12D, shows the results of in vivo genome editing of *Bacillus smithii* ET138 cells using gtCas9 and 8nt PAM sequences, by the growth or absence of colonies of the *Bacillus smithii* ET138 cells on selection plates, as explained in Example 9. Colonies are indicated with arrows in FIG. 12A through FIG. 12C.

Figure 1:
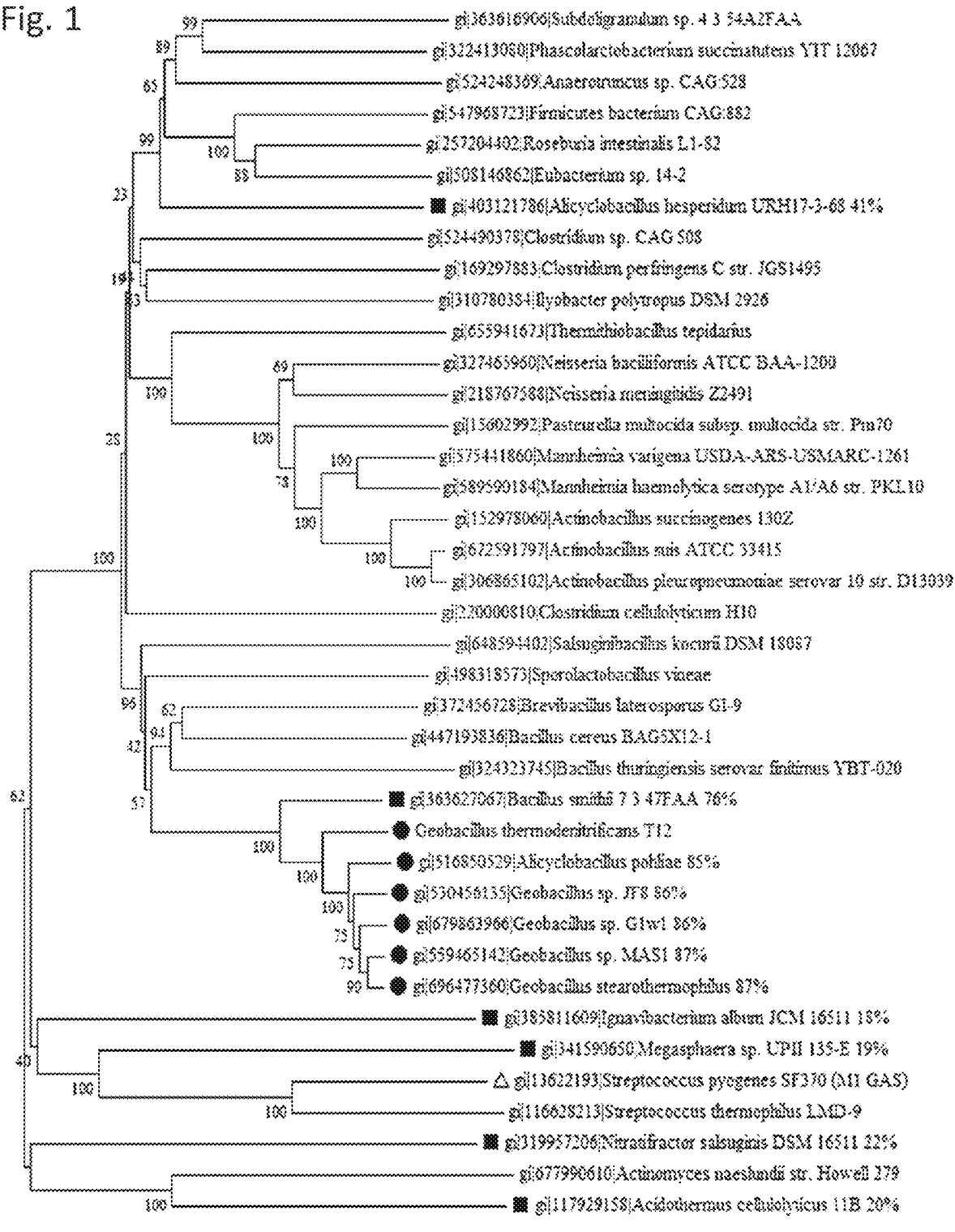
FIG. 1 shows a Neighbour-Joining tree of Cas9 protein sequences. All sequences having a sequence similarity above 40% with strain T12 based on pBLAST or PSI-BLAST were included, as well as currently well-characterized sequences (*S. pyogenes*, *S. thermophiles* and *A. naeslundii*), as well as all currently identified thermophilic sequences also when these were below 40% identity. For all thermophilic sequences, the percentage identity to T12 is indicated after the strain name. Gene identifier (gi) numbers are indicated before the species name. Legend: Closed circles: thermophilic (optimum above 60° C.) Cas9 sequences, closed squares: thermotolerant (optimum <50° C.) Cas9 sequences, open triangle: Cas9 sequence currently most used for genome editing purposes from mesophilic origin; no sign: mesophilic Cas9. Values at the nodes represent 1000-replicate bootstrap values; scale bar represents estimated amino acid substitutions per site.

(A) Schematic representation of the genomic locus encoding ThermoCas9. The domain architecture of ThermoCas9 based on sequence comparison, with predicted active sites residues highlighted in red. A homology model of ThermoCas9 generated using Phyre 2 (Kelley et al. *Nat. Protoc.* 10, 845-858 (2015)) is shown, with different colours for the domains.

(B) Phylogenetic tree of Cas9 orthologues that are highly identical to ThermoCas9. Evolutionary analysis was conducted in MEGA7 (Kumar et al. *Mol. Biol. Evol.* 33, 1870-1874 (2016)).

(C) SDS-PAGE of ThermoCas9 after purification by metal-affinity chromatography and gel filtration. The migration of the obtained single band is consistent with the theoretical molecular weight of 126 kD of the apo-ThermoCas9.

FIG. 16 shows ThermoCas9 PAM analysis.

(A) Schematic illustrating the in vitro cleavage assay for discovering the position and identity (5'-NNNNNNN-3') of the protospacer adjacent motif (PAM). Black triangles indicate the cleavage position.

(B) Sequence logo of the consensus 7 nt long PAM of ThermoCas9, obtained by comparative analysis of the ThermoCas9-based cleavage of target libraries. Letter height at each position is measured by information content.

(C) Extension of the PAM identity to the 8th position by in vitro cleavage assay. Four linearized plasmid targets, each containing a distinct 5'-CCCCCCAN-3' PAM, were incubated with ThermoCas9 and sgRNA at 55° C. for 1 hour, then analysed by agarose gel electrophoresis.

(D) In vitro cleavage assays for DNA targets with different PAMs at 30° C. and 55° C. Sixteen linearized plasmid targets, each containing one distinct 5'-CCCCCNNA-3' [SEQ ID NO: 13] PAM, were incubated with ThermoCas9 and sgRNA, then analysed for cleavage efficiency by agarose gel electrophoresis. See also FIG. 21.

FIG. 17 shows ThermoCas9 is active at a wide temperature range and its thermostability increases when bound to sgRNA.

(A) Schematic representation of the sgRNA and a matching target DNA. Target DNA is shown as a rectangular with black outline, and the PAM is shown as a dark grey, horizontal ellipse with back outline. The crRNA is shown as a dark grey rectangular with black outline and the site where the 3'-end of the crRNA is linked with 5'-end of the tracrRNA is shown as a black, vertical ellipse. The black box with the white letters and the light grey box with the black letters indicate the predicted three and two loops at the 3'-side of the tracrRNA, respectively. The 41-nt truncation of the repeat/anti-repeat region—formed by the complementary 3'-end of the crRNA and the 5'-end of the tracrRNA—is indicated with a long, light grey, vertical, dotted line. The predicted 3' position of the first tracrRNA loop is marked with a black triangle and a black dotted line. The predicted 3' position of the second tracrRNA loop is marked with a white triangle and a black dotted line. The predicted 3' position of the third tracrRNA loop is marked with a white triangle and a white dotted line.

(B) The importance of the predicted three stem-loops of the tracrRNA scaffold was tested by transcribing truncated variants of the sgRNA and evaluating their ability to guide ThermoCas9 to cleave target DNA at various temperatures. Average values of at least two biological replicates are shown, with error bars representing S.D.

(C) To identify the maximum temperature, endonuclease activity of ThermoCas9:sgRNA RNP complex was assayed after incubation at 60° C., 65° C. and 70° C. for 5 or 10 min. The pre-heated DNA substrate was added and the reaction was incubated for 1 hour at the corresponding temperature.

(D) Comparison of active temperature range of ThermoCas9 and SpCas9 by activity assays conducted after 5 min of incubation at the indicated temperature. The pre-heated DNA substrate was added and the reaction was incubated for 1 hour at the same temperature.

Figure 18A:
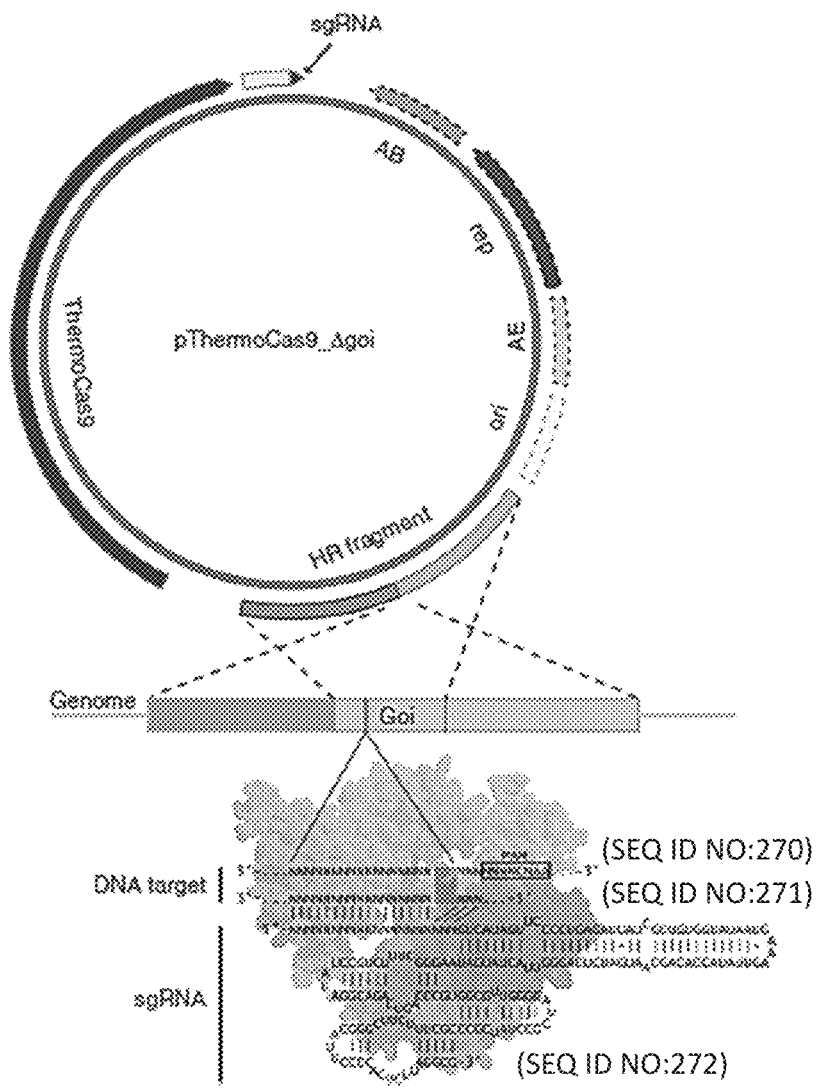
Figure 18B:
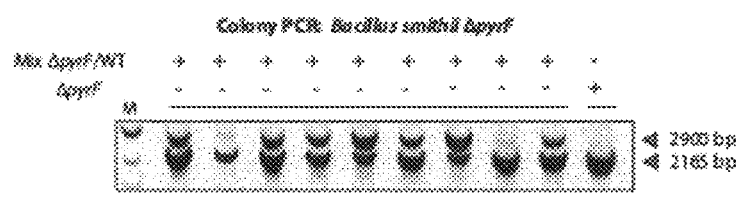

FIG. 18 shows ThermoCas9-based genome engineering in thermophiles.

(A) Schematic overview of the basic pThermoCas9_Δgene-of-interest (goi) construct. The thermocas9 gene was introduced either to the pNW33n (*B. smithii*) or to the pEMG (*P. putida*) vector. Homologous recombination flanks were introduced upstream thermocas9 and encompassed the 1 kb (*B. smithii*) or 0.5 kb (*P. putida*) upstream and 1 kb or 0.5 kb downstream region of the gene of interest (goi) in the targeted genome. A sgRNA-expressing module was introduced downstream the thermocas9 gene. As the origin of replication (on), replication protein (rep), antibiotic resistance marker (AB) and possible accessory elements (AE) are backbone specific, they are represented with dotted outline.

(B) Agarose gel electrophoresis showing the resulting products from genome-specific PCR on ten colonies from the ThermoCas9-based pyrF deletion process from the genome of *B. smithii* ET 138. All ten colonies contained the ΔpyrF genotype and one colony was a clean ΔpyrF mutant, lacking the wild type product.

(C) Schematic overview of the basic pThermoCas9i_goi construct. Aiming for the expression of a catalytically inactive ThermoCas9 (Thermo-dCas9:D8A, H582A mutant), the corresponding mutations were introduced to create the thermo-dcas9 gene. The thermo-dcas9 gene was introduced to the pNW33n vector. An sgRNA-expressing module was introduced downstream the thermo-dcas9.

(D) Graphical representation of the production, growth and RT-qPCR results from the ldhL silencing experiment using Thermo-dCas9. The graphs represent the lactate production, optical density at 600 nm and percentage of ldhL transcription in the repressed cultures compared to the control cultures. Average values from at least two biological replicates are shown, with error bars representing S.D.

Figure 19A:
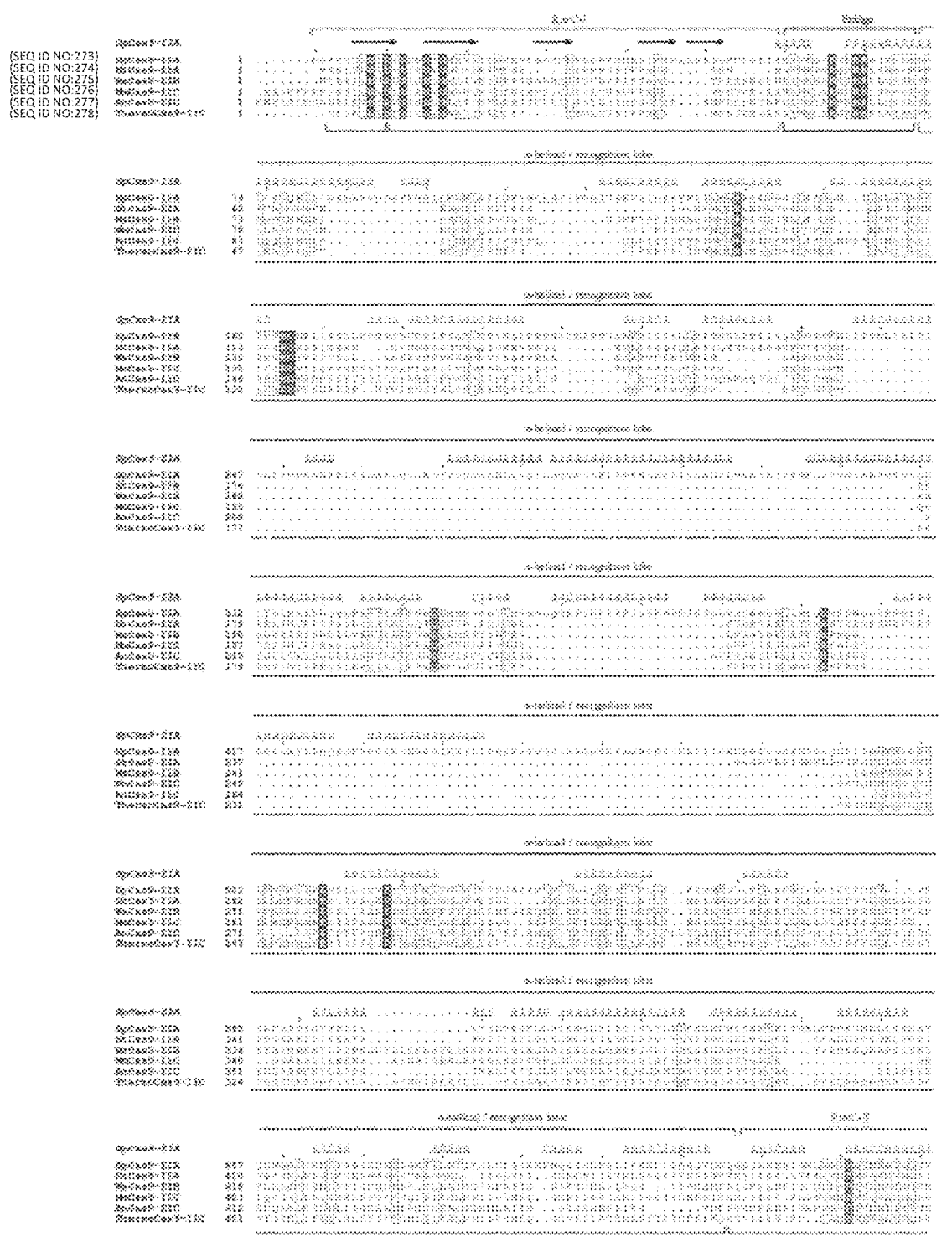
Figure 19B:
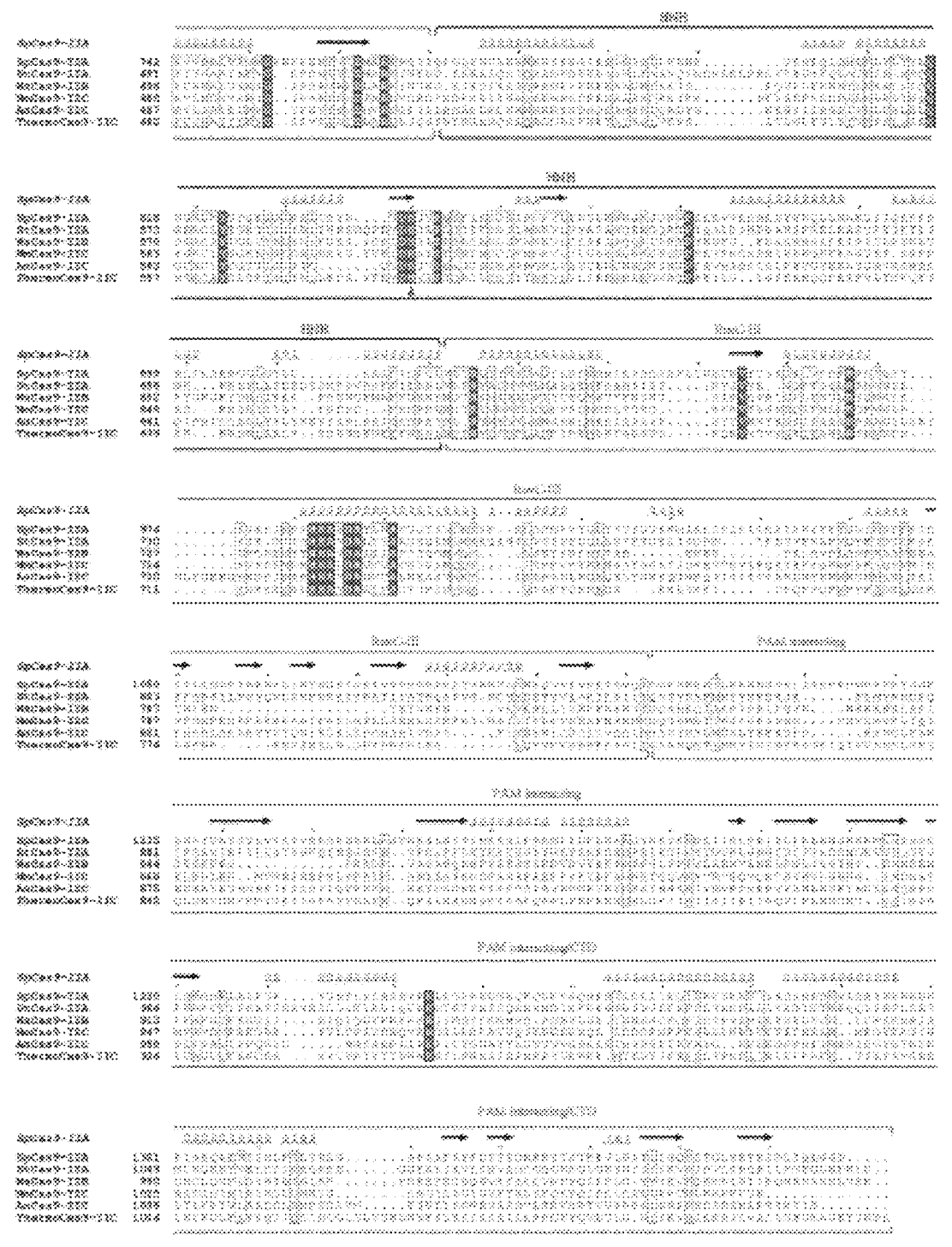

FIG. 19, comprising FIG. 19A and FIG. 19B, shows a multiple sequence alignment of Type II-A, B and C Cas9 orthologues. Cas9 protein sequences of *Streptococcus pyogenes* (Sp), *Streptococcus thermophilus* (St), *Wolinella succinogenes* (Ws), *Neisseria meningitides* (Nm), *Actinomyces naeslundii* (An), and *Geobacillus thermodenitrificans* (Thermo) were aligned using ClustalW1 in MEGA? 2 with default settings; ESPript3 was used to generate the visualization. Strictly conserved residues are shown in white text on grey background; similar residues are shown in black text in white vertical rectangles with black outline. Pyramids indicate the two conserved nuclease domains in all sequences. Horizontal black arrows and curls indicate 13-strands and a-helices, respectively, in the SpCas9 secondary structure (protein database nr 4CMP4). Structural domains are indicated for SpCas9 and ThermoCas9 using the same color scheme as in FIG. 15A.

FIG. 20 shows in silico PAM determination results. Panel (A) shows the two hits obtained with phage genomes using CRISPRtarget6. Panel (B) shows sequence logo of the consensus 7 nt long PAM of ThermoCas9, obtained by in silico PAM analysis. Letter height at each position is measured by information content.

Figure 21:
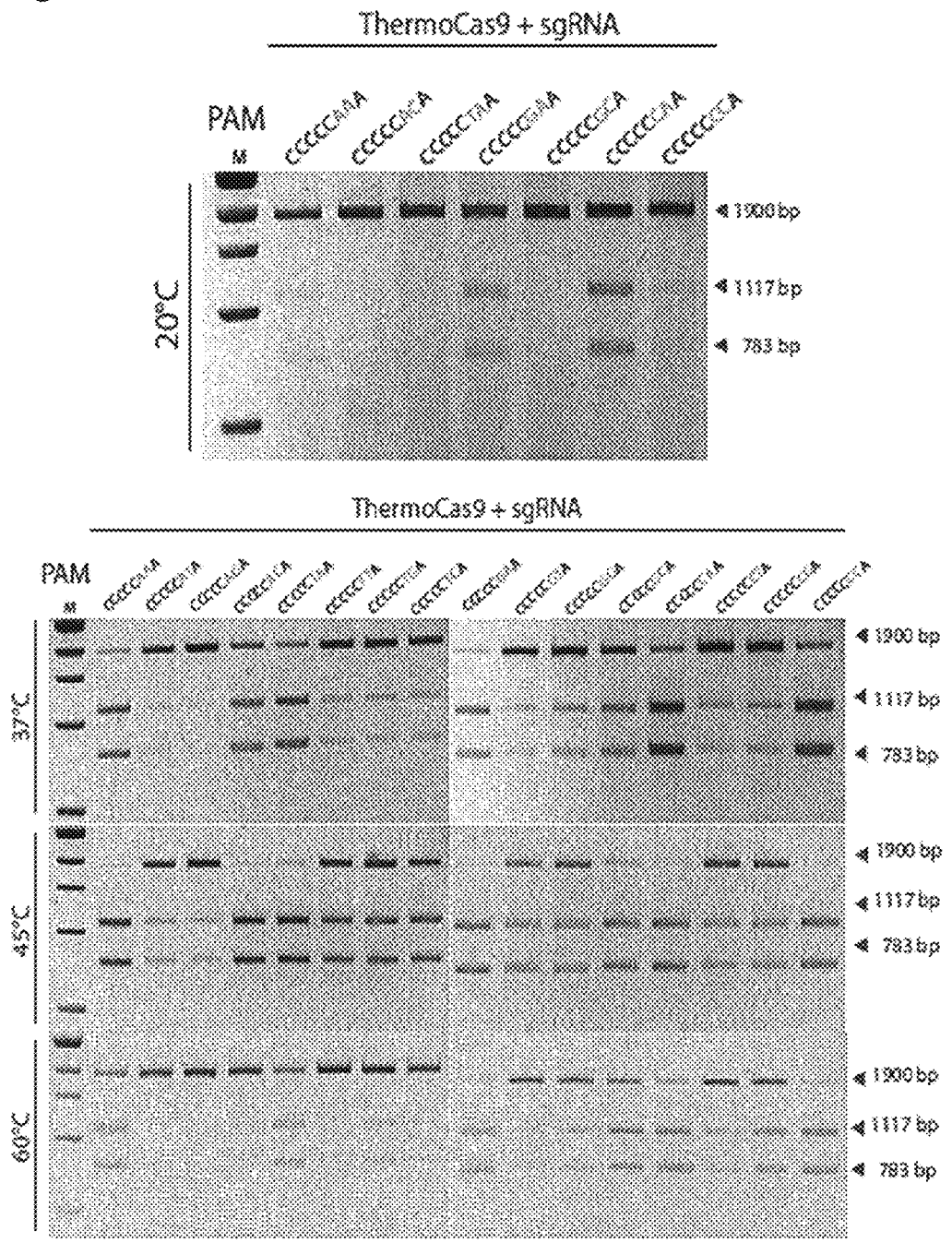

FIG. 21 shows ThermoCas9 PAM discovery. In vitro cleavage assays for DNA targets with different PAMs at 20° C., 3TC, 45° C. and 60° C. Seven (20° C.) or sixteen (3TC, 45° C., 60° C.) linearized plasmid targets, each containing a distinct 5'-CCCCCNNA-3' [SEQ ID NO: 13] PAM, were incubated with ThermoCas9 and sgRNA, then analysed by agarose gel electrophoresis.

Figure 22:
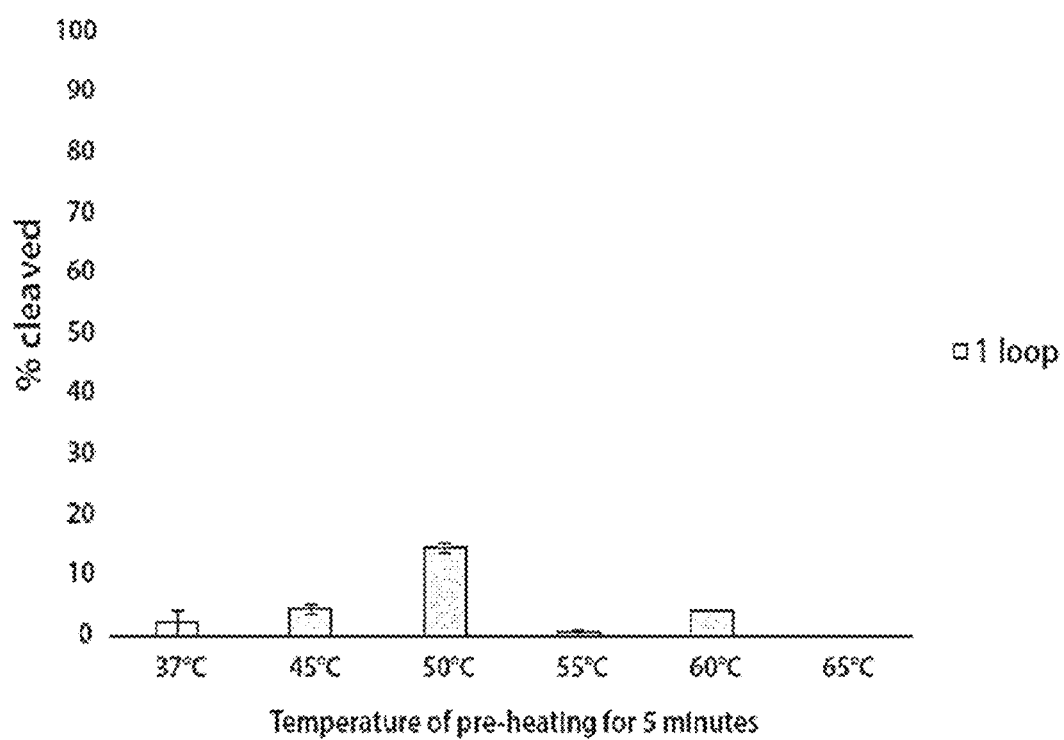

FIG. 22 shows activity of ThermoCas9 at a wide temperature range using sgRNA containing one loop. The importance of the predicted three stem loops of the tracrRNA scaffold was tested by transcribing truncated variations of the sgRNA and evaluating their ability to guide ThermoCas9 to cleave target DNA at various temperatures. Shown above is the effect of one loop on the activity of ThermoCas9 at various temperatures. Average values from at least two biological replicates are shown, with error bars representing S.D.

FIG. 23 shows ThermoCas9 mediates dsDNA targeting using divalent cations as catalysts and does not cleave ssDNA. Panel (A) shows in vitro plasmid DNA cleavage by ThermoCas9 with EDTA and various metal ions. M=1 kb DNA ladder. Panel (B) shows activity of ThermoCas9 on ssDNA substrates. M=10 bp DNA ladder.

Figure 24:
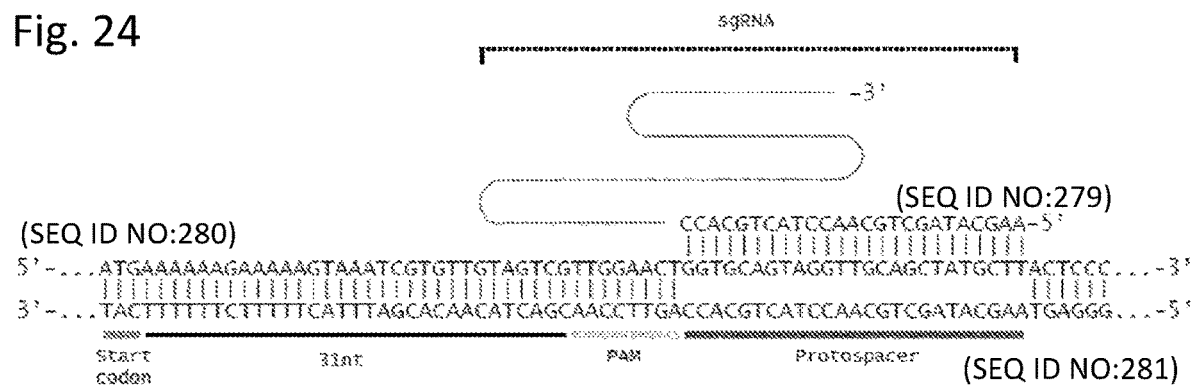

FIG. 24 shows spacer selection for the ldhL silencing experiment. Schematic representation of the spacer (sgRNA)-protospacer annealing during the ldhL silencing process; the selected protospacer resides on the non-template strand and 39 nt downstream the start codon of the ldhL gene.

Figure 25:
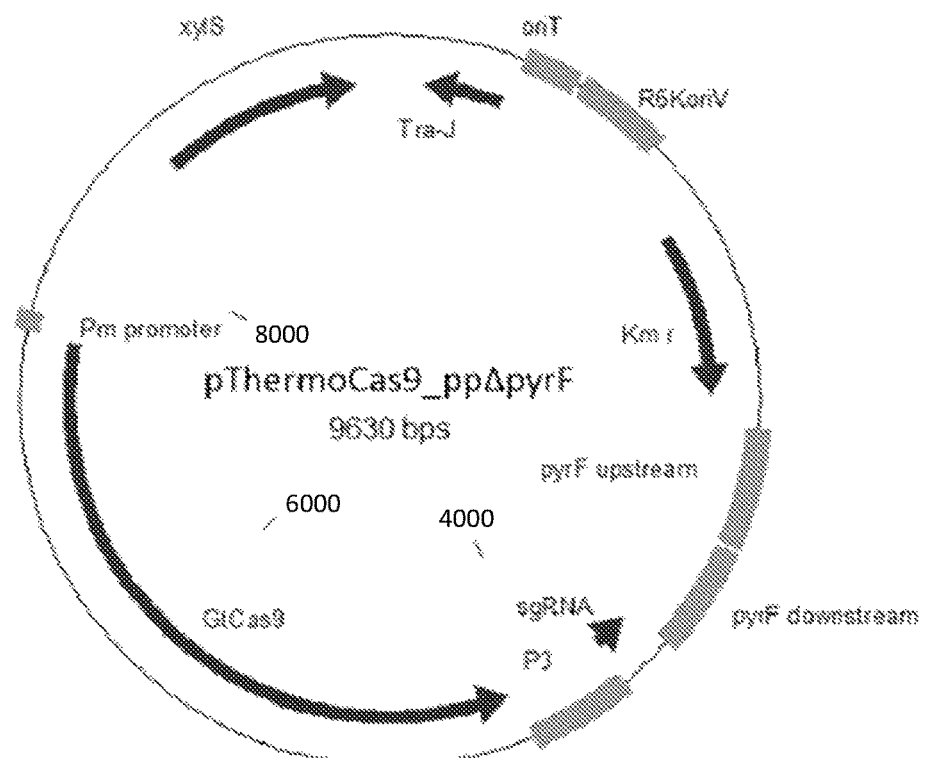

FIG. 25 shows a map of plasmid pThermoCas9_ppΔpyrF consisting of the pEMG backbone, the *Pseudomonas putida* pyrF flanking region and the thermocas9 gene and a *Pseudomonas putida* pyrF targeting sgRNA.

Figure 26:
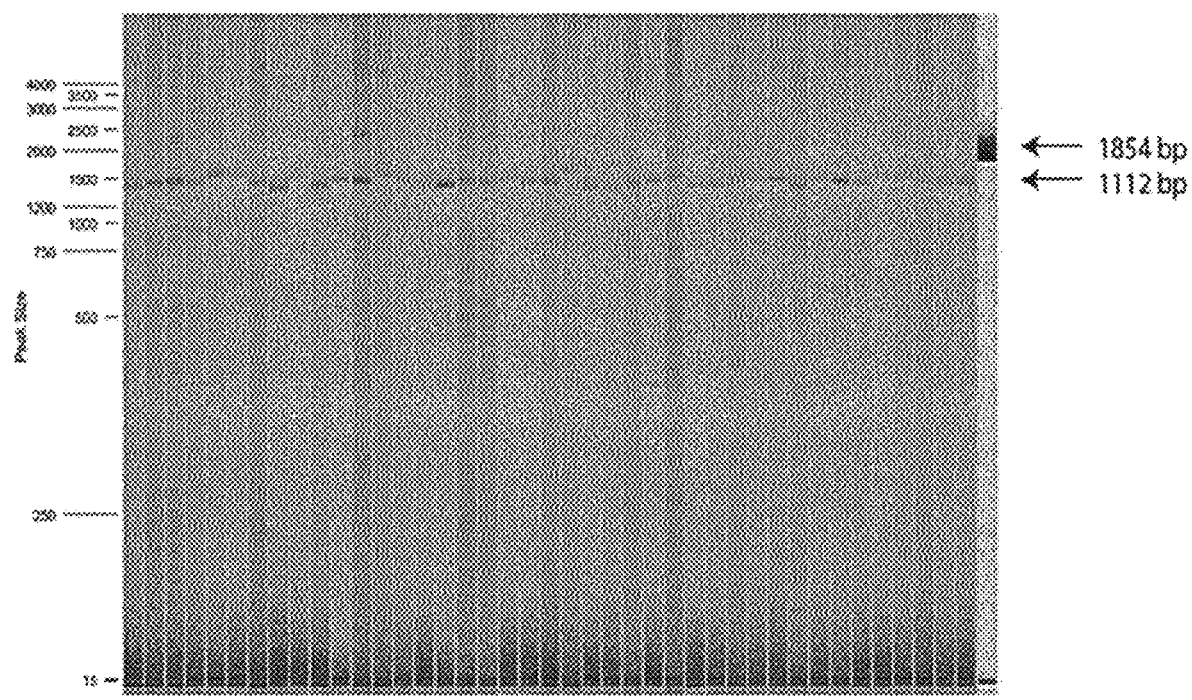

FIG. 26 shows the results of capillary gel electrophoresis showing the resulting products from genome specific PCR on the obtained colonies from the ThermoCas9-based pyrF deletion process from the genome of *Pseudomonas putida*. The 1854 bp band and the 1112 bp band corresponds to the pyrF and ΔpyrF genotype, respectively.

Below are polynucleotide and amino acid sequences of Cas proteins used in accordance with the invention.

*Geobacillus thermodenitrificans* T12 Cas9 protein AA sequence

[SEQ ID NO: 1]

MKYKIGLDIGITSIGWAVINLDIPRIEDLGVRIFDRAENPKTGESLALPR

RLARSARRRLRRRKHRLERIRRLFVREGILTKEELNKLFEKKHEIDVWQL

RVEALDRKLNNDELARILLHLAKRRGFRSNRKSERTNKENSTMLKHIEEN

QSILSSYRTVAEMVVKDPKFSLHKRNKEDNYTNTVARDDLEREIKLIFAK

QREYGNIVCTEAFEHEYISIWASQRPFASKDDIEKKVGFCTFEPKEKRAP

KATYTFQSFTVWEHINKLRLVSPGGIRALTDDERRLIYKQAFHKNKITFH

DVRTLLNLPDDTRFKGLLYDRNTTLKENEKVRFLELGAYHKIRKAIDSVY

GKGAAKSFRPIDFDTFGYALTMFKDDTDIRSYLRNEYEQNGKRMENLADK

VYDEELIEELLNLSFSKFGHLSLKALRNILPYMEQGEVYSTACERAGYTF

TGPKKKQKTVLLPNIPPIANPVVMRALTQARKVVNAIIKKYGSPVSIHIE

LARELSQSFDERRKMQKEQEGNRKKNETAIRQLVEYGLTLNPTGLDIVKF

KLWSEQNGKCAYSLQPIEIERLLEPGYTEVDHVIPYSRSLDDSYTNKVLV

LTKENREKGNRTPAEYLGLGSERWQQFETFVLTNKQFSKKKRDRLLRLHY

DENEENEFKNRNLNDTRYISRFLANFIREHLKFADSDDKQKVYTVNGRIT

AHLRSRWNFNKNREESNLHHAVDAAIVACTTPSDIARVTAFYQRREQNKE

LSKKTDPQFPQPWPHFADELQARLSKNPKESIKALNLGNYDNEKLESLQP

VFVSRMPKRSITGAAHQETLRRYIGIDERSGKIQTVVKKKLSEIQLDKTG

HFPMYGKESDPRTYEAIRQRLLEHNNDPKKAFQEPLYKPKKNGELGPIIR

TIKIIDTTNQVIPLNDGKTVAYNSNIVRVDVFEKDGKYYCVPIYTIDMMK

GILPNKAIEPNKPYSEWKEMTEDYTFRFSLYPNDLIRIEFPREKTIKTAV

GEEIKIKDLFAYYQTIDSSNGGLSLVSHDNNFSLRSIGSRTLKRFEKYQV

DVLGNIYKVRGEKRVGVASSSHSKAGETIRPL*

*Geobacillus thermodenitrificans* T12 Cas9 DNA Sequence

[SEQ ID NO: 7]

ATGAAGTATAAAATCGGTCTTGATATCGGCATTACGTCTATCGGTTGGGC

TGTCATTAATTTGGACATTCCTCGCATCGAAGATTTAGGTGTCCGCATTT

TTGACAGAGCGGAAAACCCGAAAACCGGGGAGTCACTAGCTCTTCCACGT

-continued

```
CGCCTCGCCCGCTCCGCCCGACGTCGTCTGCGGCGTCGCAAACATCGACT
GGAGCGCATTCGCCGCCTGTTCGTCCGCGAAGGAATTTTAACGAAGGAAG
AGCTGAACAAGCTGTTTGAAAAAAAGCACGAAATCGACGTCTGGCAGCTT
CGTGTTGAAGCACTGGATCGAAAACTAAATAACGATGAATTAGCCCGCAT
CCTTCTTCATCTGGCTAAACGGCGTGGATTTAGATCCAACCGCAAGAGTG
AGCGCACCAACAAAGAAAACAGTACGATGCTCAAACATATTGAAGAAAAC
CAATCCATTCTTTCAAGTTACCGAACGGTTGCAGAAATGGTTGTCAAGGA
TCCGAAATTTTCCCTGCACAAGCGTAATAAAGAGGATAATTACACCAACA
CTGTTGCCCGCGACGATCTTGAACGGGAAATCAAACTGATTTTCGCCAAA
CAGCGCGAATATGGGAACATCGTTTGCACAGAAGCATTTGAACACGAGTA
TATTTCCATTTGGGCATCGCAACGCCCTTTTGCTTCTAAGGATGATATCG
AGAAAAAAGTCGGTTTCTGTACGTTTGAGCCTAAAGAAAAACGCGCGCCA
AAAGCAACATACACATTCCAGTCCTTCACCGTCTGGGAACATATTAACAA
ACTTCGTCTTGTCTCCCCGGGAGGCATCCGGGCACTAACCGATGATGAAC
GTCGTCTTATATACAAGCAAGCATTTCATAAAAATAAAATCACCTTCCAT
GATGTTCGAACATTGCTTAACTTGCCTGACGACACCCGTTTTAAAGGTCT
TTTATATGACCGAAACACCACGCTGAAGGAAAATGAGAAAGTTCGCTTCC
TTGAACTCGGCGCCTATCATAAAATACGGAAAGCGATCGACAGCGTCTAT
GGCAAAGGAGCAGCAAAATCATTTCGTCCGATTGATTTTGATACATTTGG
CTACGCATTAACGATGTTTAAAGACGACACCGACATTCGCAGTTACTTGC
GAAACGAATACGAACAAAATGGAAAACGAATGGAAAATCTAGCGGATAAA
GTCTATGATGAAGAATTGATTGAAGAACTTTTAAACTTATCGTTTTCTAA
GTTTGGTCATCTATCCCTTAAAGCGCTTCGCAACATCCTTCCATATATGG
AACAAGGCGAAGTCTACTCAACCGCTTGTGAACGAGCAGGATATACATTT
ACAGGGCCAAAGAAAAAACAGAAAACGGTATTGCTGCCGAACATTCCGCC
GATCGCCAATCCGGTCGTCATGCGCGCACTGACACAGGCACGCAAAGTGG
TCAATGCCATTATCAAAAAGTACGGCTCACCGGTCTCCATCCATATCGAA
CTGGCCCGGGAACTATCACAATCCTTTGATGAACGACGTAAAATGCAGAA
AGAACAGGAAGGAAACCGAAAGAAAAACGAAACTGCCATTCGCCAACTTG
TTGAATATGGGCTGACGCTCAATCCAACTGGGCTTGACATTGTGAAATTC
AAACTATGGAGCGAACAAAACGGAAAATGTGCCTATTCACTCCAACCGAT
CGAAATCGAGCGGTTGCTCGAACCAGGCTATACAGAAGTCGACCATGTGA
TTCCATACAGCCGAAGCTTGGACGATAGCTATACCAATAAAGTTCTTGTG
TTGACAAAGGAGAACCGTGAAAAAGGAAACCGCACCCCAGCTGAATATTT
AGGATTAGGCTCAGAACGTTGGCAACAGTTCGAGACGTTTGTCTTGACAA
ATAAGCAGTTTTCGAAAAAGAAGCGGGATCGACTCCTTCGGCTTCATTAC
GATGAAAACGAAGAAATGAGTTTAAAAATCGTAATCTAAATGATACCCG
TTATATCTCACGCTTCTTGGCTAACTTTATTCGCGAACATCTCAAATTCG
CCGACAGCGATGACAAACAAAAAGTATACACGGTCAACGGCCGTATTACC
GCCCATTTACGCAGCCGTTGGAATTTTAACAAAAACCGGGAAGAATCGAA
TTTGCATCATGCCGTCGATGCTGCCATCGTCGCCTGCACAACGCCGAGCG
ATATCGCCCGAGTCACCGCCTTCTATCAACGGCGCGAACAAAACAAAGAA
CTGTCCAAAAAGACGGATCCGCAGTTTCCGCAGCCTTGGCCGCACTTTGC
TGATGAACTGCAGGCGCGTTTATCAAAAAATCCAAAGGAGAGTATAAAAG
CTCTCAATCTTGGAAATTATGATAACGAGAAACTCGAATCGTTGCAGCCG
GTTTTTGTCTCCCGAATGCCGAAGCGGAGCATAACAGGAGCGGCTCATCA
AGAAACATTGCGGCGTTATATCGGCATCGACGAACGGAGCGGAAAAATAC
AGACGGTCGTCAAAAAGAAACTATCCGAGATCCAACTGGATAAAACAGGT
CATTTCCCAATGTACGGGAAAGAAAGCGATCCAAGGACATATGAAGCCAT
TCGCCAACGGTTGCTTGAACATAACAATGACCCAAAAAAGGCGTTTCAAG
AGCCTCTGTATAAACCGAAGAAGAACGGAGAACTAGGTCCTATCATCCGA
ACAATCAAAATCATCGATACGACAAATCAAGTTATTCCGCTCAACGATGG
CAAAACAGTCGCCTACAACAGCAACATCGTGCGGGTCGACGTCTTTGAGA
AAGATGGCAAATATTATTGTGTCCCTATCTATACAATAGATATGATGAAA
GGGATCTTGCCAAACAAGGCGATCGAGCCGAACAAACCGTACTCTGAGTG
GAAGGAAATGACGGAGGACTATACATTCCGATTCAGTCTATACCCAAATG
ATCTTATCCGTATCGAATTTCCCCGAGAAAAACAATAAAGACTGCTGTG
GGGGAAGAAATCAAAATTAAGGATCTGTTCGCCTATTATCAAACCATCGA
CTCCTCCAATGGAGGGTTAAGTTTGGTTAGCCATGATAACAACTTTTCGC
TCCGCAGCATCGGTTCAAGAACCCTCAAACGATTCGAGAAATACCAAGTA
GATGTGCTAGGCAACATCTACAAAGTGAGAGGGGAAAAGAGAGTTGGGGT
GGCGTCATCTTCTCATTCGAAAGCCGGGGAAACTATCCGTCCGTTATAA
```

DETAILED DESCRIPTION

Example 1: Isolation of Geobacillus thermodenitrificans

G. thermodenitrificans was surprisingly discovered during a search of a library of ±500 isolates for a thermophile capable of degrading lignocellulosic substrates under anaerobic conditions. At first a library of ±500 isolates was established which, after several selection rounds by isolation on cellulose and xylan, was trimmed down to 110 isolates. This library of 110 isolates consisted solely of Geobacillus isolates with G. thermodenitrificans representing 79% of the library.

The isolated G. thermodenitrificans strain has been named "T12". The Cas9 protein from G. thermodenitrificans T12 has been named "gtCas9".

Example 2: Defining the Essential Consensus Sequences for Cas9 in Geobacillus thermodenitrificans The following database searches and alignments were performed:

pBLAST and nBLAST were performed on the in-house BLAST server, in which either the protein or gene sequence of G. thermodenitrificans T12 was used as query sequence. This database was last updated May 2014 and therefore does not contain the most recently added Geobacillus genomes, but normal online BLAST was not used to prevent publication of the T12 sequence. Sequence identities found to be greater than 40% in the BLAST search are included in FIG. 1.

To include more recent sequence data, the sequence of *Geobacillus* MAS1 (most closely related to gtCas9) was used to perform a PSI-BLAST on the NCBI website (Johnson et al., 2008 Nucleic Acids Res. 36 (Web Server issue): W5-9). Two consecutive rounds of PSI-BLAST were performed, in which only sequences that met the following criteria were used for the next round: minimum sequence coverage of 96% in the first round and 97% in the second and third round, minimum identity 40%, only one strain per species.

The sequences resulting from the PSI-BLAST, as well as the sequences with more than 40% identity to T12 from the internal server pBLAST that did not appear in the PSI-BLAST were aligned together with currently well-characterized mesophilic sequences and all currently identified thermophilic sequences also if these were more distantly related, from which a Neighbour-Joining tree was constructed (see FIG. 1). Alignment was performed in Mega6 using ClustalW, after which a tree was constructed using the Neighbour-Joining method and bootstrap analysis was performed using 1000 replicates.

Figure 2:
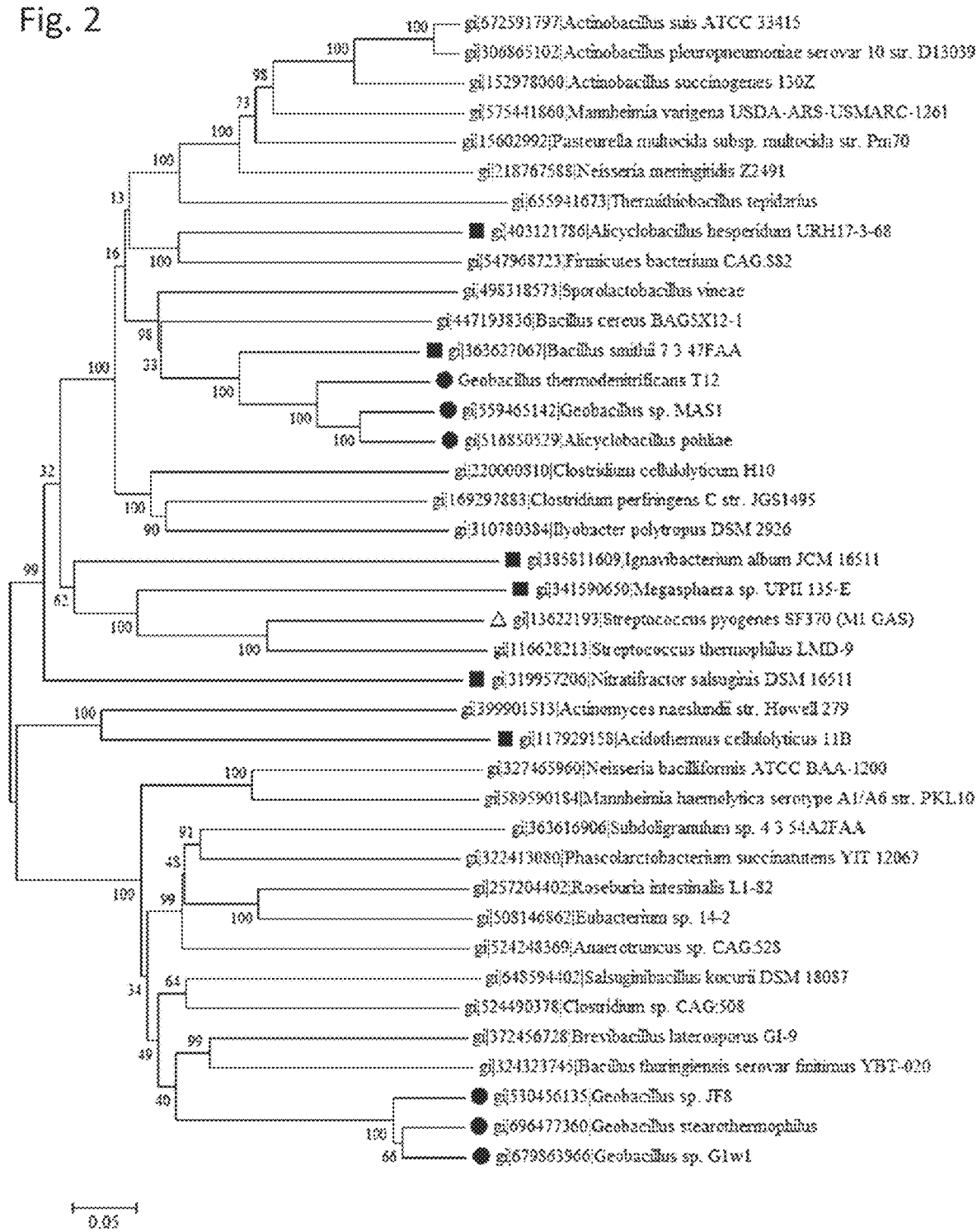
FIG. 2 shows a Neighbour-Joining tree of Cas9 gene sequences. Identity at the gene level was extremely poor; sequences from the same organisms as those used for the protein alignment were used for the gene alignment. Gene identifier (gi) numbers are indicated before the species name. Legend: Closed circles: thermophilic (optimum above 60° C.) Cas9 sequences, closed squares: thermotolerant (optimum <50° C.) Cas9 sequences, open triangle: Cas9 sequence currently most used for genome editing purposes from mesophilic origin; no sign: mesophilic Cas9. Values at the nodes represent 1000-replicate bootstrap values.

When BLASTn was performed using *Geobacillus* sp. MAS1 as the query sequence, only *Geobacillus* sp. JF8 Cas9 was identified with 88% identity, indicating very little homology at the gene level. FIG. 2 is a Neighbour-Joining tree of Clustal-aligned Cas9 gene sequences.

Protein sequences of *G. thermodenitrificans* T12, *A. naeslundii* and *S. pyogenes* were further analyzed for protein domain homology (see FIG. 3) by aligning them in Clone-Manager using BLOSUM62 with default settings.

Figure 3A:
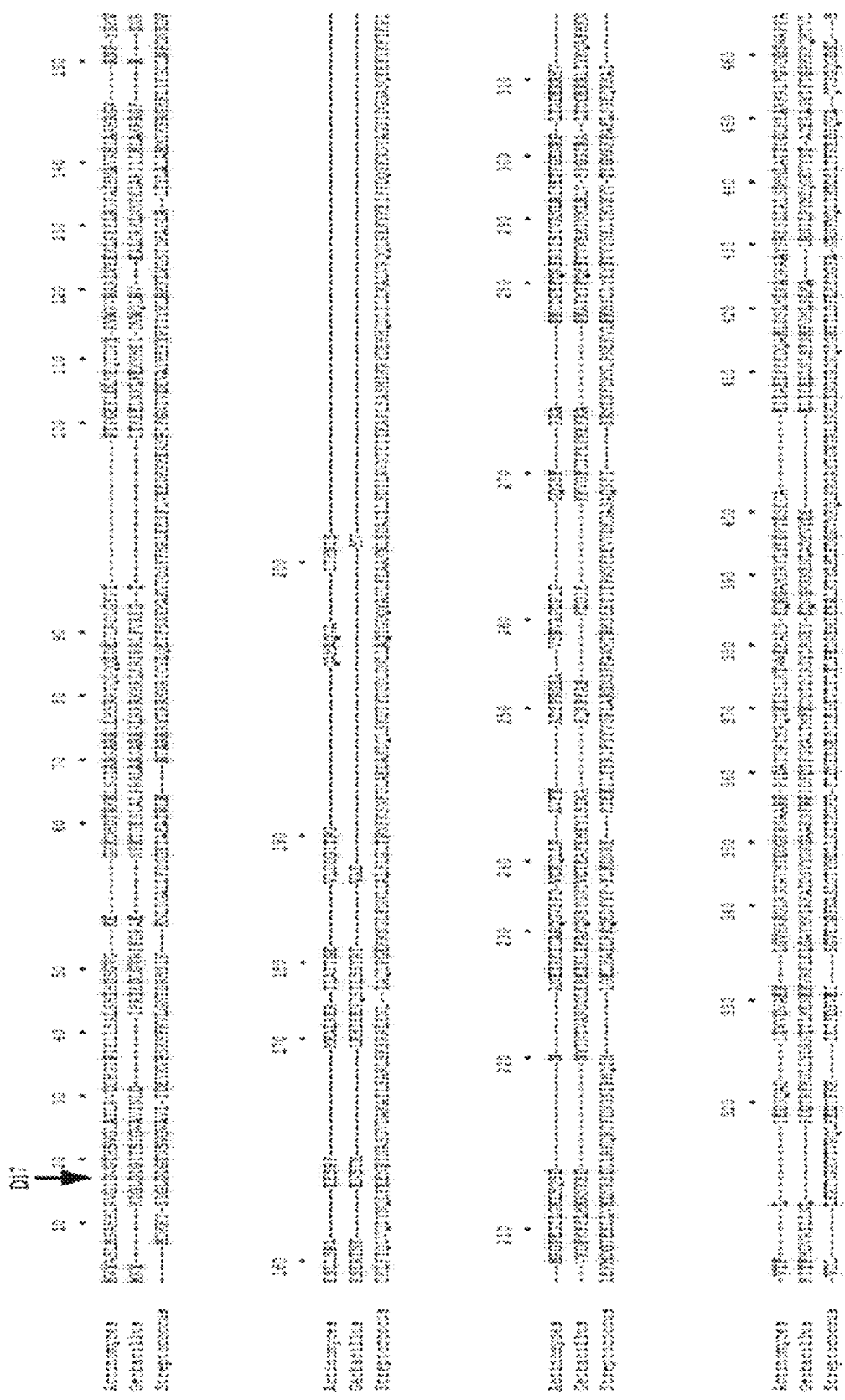
FIG. 3A and FIG. 3B, shows a protein sequence alignment for gtCas9 (SEQ ID NO: 1) (Type II-C) with well-characterized Type II-C (*A. naeslundii*/'ana'; SEQ ID NO: 8) and Type II-A (*S. pyogenes*/'pyo'; SEQ ID NO: 9 and *S. thermophilus*) Cas9 sequences. Important active site residues are well conserved and indicated with black arrows. Protein domains as described for Ana-Cas9 and Pyo-Cas9 (Jinek, et al., 2014, Science 343: 1247997) are indicated with shaded boxes and similarly colored letters. The PAM recognition domain has been determined for the *S. pyogenes* Type II-A system but not for any Type II-C system and is therefore only indicated in the *S. pyogenes* sequence.
Figure 3B:
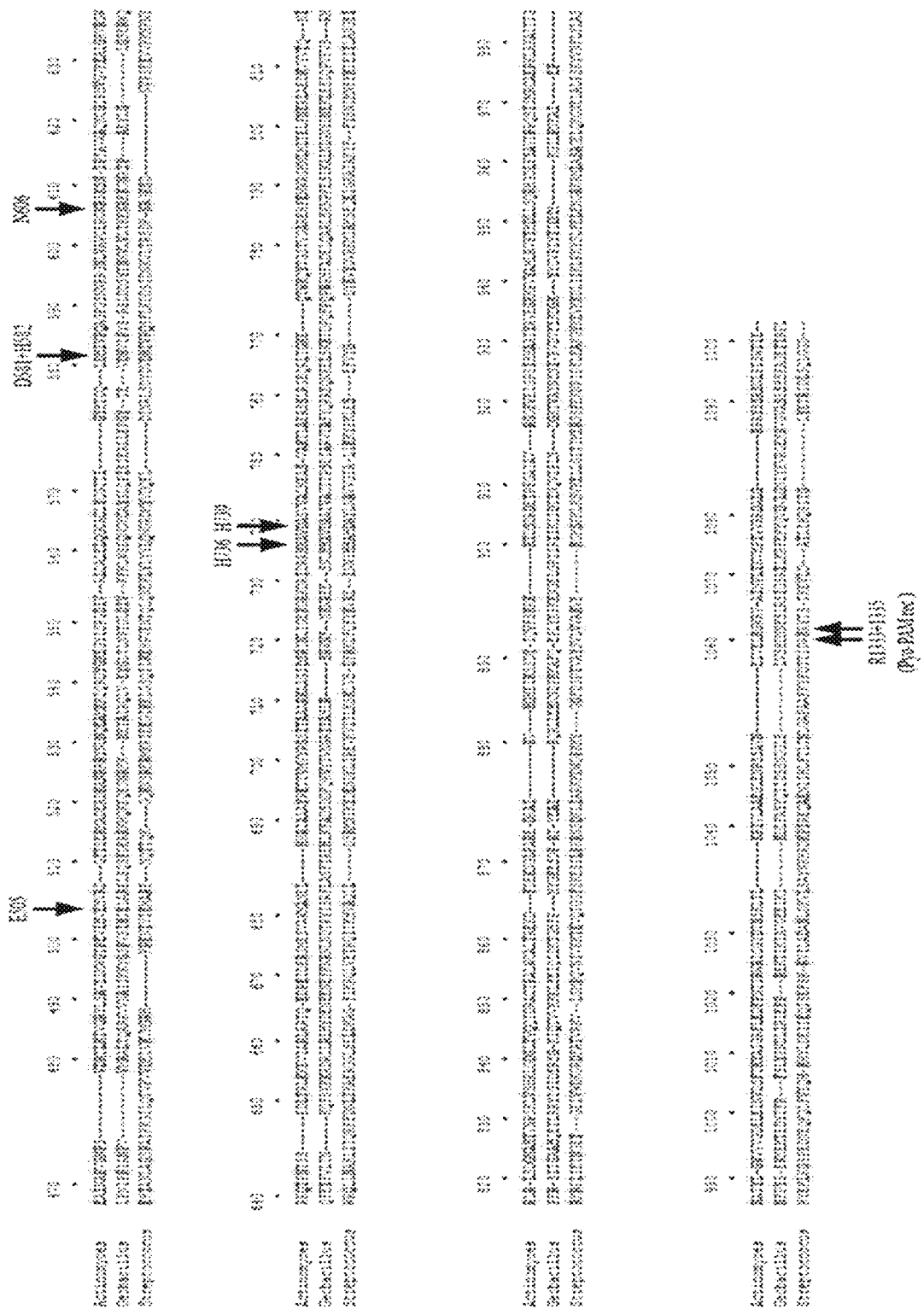
Figure 4:
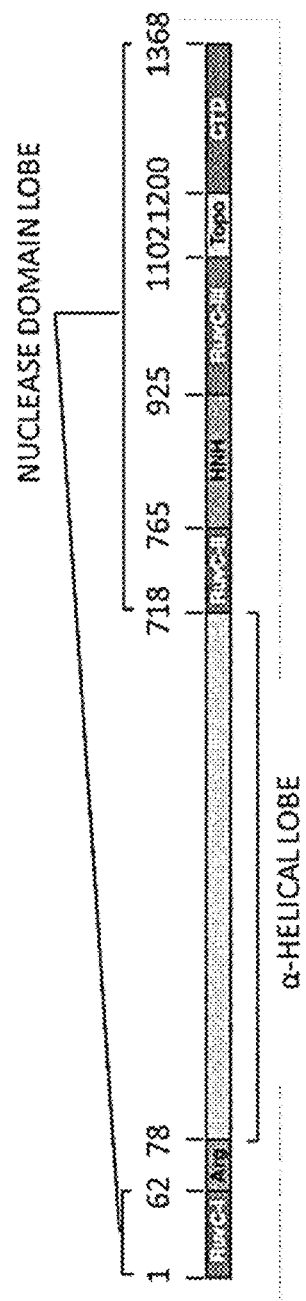
FIG. 4 shows protein architecture of *A. naeslundii* Cas9 (Cas9-Ana) (Jinek et al., 2014). gtCas9 belongs to the same Type II-C CRISPR system and active site residues could be identified.
Figure 5:
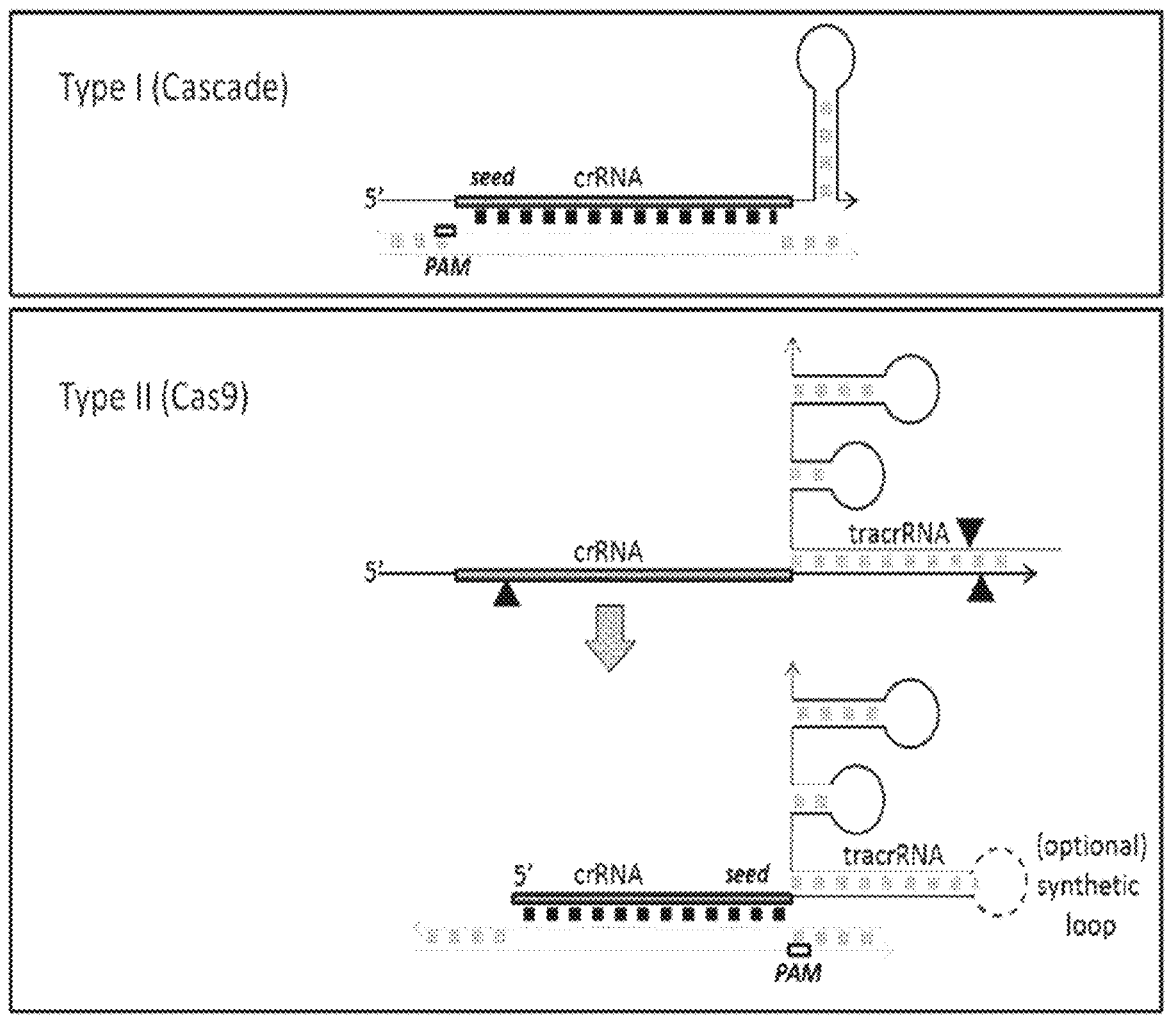
FIG. 5 shows a comparison of crRNA-guided targeting of complementary dsDNA. Base pairing is indicated with dashed lines. RNA is depicted in black, DNA in grey. Base pairing between crRNA spacer and target protospacer is indicated with thick black dashed line, base pairing between DNA strands and between RNA strands is indicated with thick grey dashed lines. The 5' end of the crRNA is indicated. Note that PAM (small white box) in Type I resides downstream of target strand (protospacer), whereas in Type II it resides at the other end on the displaced strand. Likewise, the seed (the predicted sequence of the guide where base pairing with target DNA strand starts, and where no mismatches are allowed) is located close to the PAM, and as such differs in types I and II (Van der Oost, 2014 ibid.). Panel A shows a schematic of a Type I Cascade system of *E. coli*. crRNA has internal spacer (grey box, 31-32 nt that allows for target recognition), flanked bt a 8 nt 5' handle and a 29 nt 3' handle that consists of a stem-loop structure (hairpin) (Jore 2011 ibid.). Panel B shows a schematic of a Type II Cas9 system of *S. pyogenes*. crRNA basepairs with tracrRNA, that allows for processing by RNaseIII (opposite black triangles). Additionally, the 5' end of the crRNA is trimmed by an RNase (black triangle), typically resulting in a 20 nt spacer. Note that a synthetic loop may be introduced to link the crRNA and tracrRNA, resulting in a single guide RNA (sgRNA) (Jinek et al., 2012 ibid.).

Example 3: Identifying Core Amino Acid Motifs which are Essential for the Function of CAS9 and Those which Confer Thermostability in Thermophilic Cas9 Nucleases Percentages identity of the above described aligned protein sequences are provided in FIG. 1. gtCas9 belongs to Type II-C. The best-studied and recently crystallized structure of a Type II-C system is from *Actinomyces naeslundii* (Jinek et al., 2014, Science 343: 1247997). This protein sequence shows only 20% identity to gtCas9 but can be used to estimate highly conserved residues. Two well-characterized Type II-A systems (*S. pyogenes* and *S. thermophilus*) were also included in the analyses (Jinek et al., 2014, Science 343: 1247997; Nishimasu et al., 2014, Cell 156: 935-949). Alignments of these four protein sequences are shown in FIG. 3; FIG. 4 shows the protein architecture as determined for *A. naeslundii* ('Ana-Cas9') (Jinek et al., 2014, Science 343: 1247997). The length of Cas9 from t12 (gtCas9) and *Actinomyces naeslundii* is highly similar (*A. naeslundii* 1101 aa, gtCas9 1082 aa) and gtCas9 is expected to have similar protein architecture but this remains to be determined, as the overall sequence identity to cas9-Ana is only 20%. All active side residues described by Jinek et al. (Jinek et al., 2014, Science 343: 1247997) in Cas9 from *A. naeslundii* and *S. pyogenes* could be identified in gtCas9 (see FIG. 3). The PAM-binding domain has been determined for the *S. pyogenes* Type II-A system but not for any Type II-C system and is therefore only indicated in the *S. pyogenes* sequence. Moreover, the PAM-recognition site varies strongly, not only between CRISPR systems but also between species containing the same system.

Example 4: Determination of the PAM Sequence of *G. thermodenitrificans* gtCas9

It has been established that the prokaryotic CRISPR systems serve their hosts as adaptive immune systems (Jinek et al., 2012, Science 337: 816-821) and can be used for quick and effective genetic engineering (Mali et al., 2013, Nat Methods 10: 957-963.).

Cas9 proteins function as sequence-specific nucleases for the type II CRISPR systems (Makarova et al., 2011, Nat Rev Micro 9: 467-477). Small crRNA molecules, which consist of a "spacer" (target) linked to a repetition region, are the transcription and processing products of a CRISPR loci. "Spacers" naturally originate from the genome of bacteriophages and mobile genetic elements, but they can also be designed to target a specific nucleotide sequence during a genetic engineering process (Bikard et al., 2013, Nucleic Acids Research 41: 7429-7437). The crRNA molecules are employed by the Cas9 as guides for the identification of their DNA targets. The spacer region is identical to the targeted for cleavage DNA region, the "protospacer" (Brouns et al., 2012, Science 337: 808-809). A PAM (Protospacer Adjacent Motif), next to the protospacer, is required for the recognition of the target by the Cas9 (Jinek et al., 2012, Science 337: 816-821).

In order to perform in vitro or in vivo PAM-determination studies for Type II systems, it is necessary to in silico predict the CRISPR array of the system, the tracrRNA-expressing module. The CRISPR array is used for the identification of the crRNA module. The tracrRNA-expressing sequence is located either within a 500 bp-window flanking Cas9 or between the Cas genes and the CRISPR locus (Chylinski, K., et al. (2014) Classification and evolution of type II CRISPR-Cas systems. *Nucleic Acids Res.* 42, 6091-6105). The tracrRNA should consist of a 5'-sequence with high level of complementarity to the direct repeats of the CRISPR array, followed by a predicted structure of no less than two stem-loop structures and a Rho-independent transcriptional termination signal (Ran, F. A., et al. (2015) In vivo genome editing using *Staphylococcus aureus* Cas9. Nature 520, 186-191). The crRNA and tracrRNA molecule can then be used to design a chimeric sgRNA module. The 5'-end of the sgRNA consists of a truncated 20 nt long spacer followed by the 16-20 nt long truncated repeat of the CRISPR array. The repeat is followed by the corresponding truncated anti-repeat and the stem loop of the tracrRNA module. The repeat and anti-repeat parts of the sgRNA are generally connected by a GAAA linker (Karvelis, T., et al. (2015) Rapid characterization of CRISPR-Cas9 protospacer adjacent motif sequence elements. Genome Biol. 16, 253).

The cas genes (the cas9 followed by the cas1 and the cas2 genes) of the *G. thermodenitrificans* T12 type IIc CRISPR system are transcribed using the antisense strand of the T12 chromosome. The cas2 gene is followed by a 100 bp long DNA fragment which upon transcription forms an RNA structure with multiple loops. This structure obviously acts as a transcriptional terminator.

Figure 6:
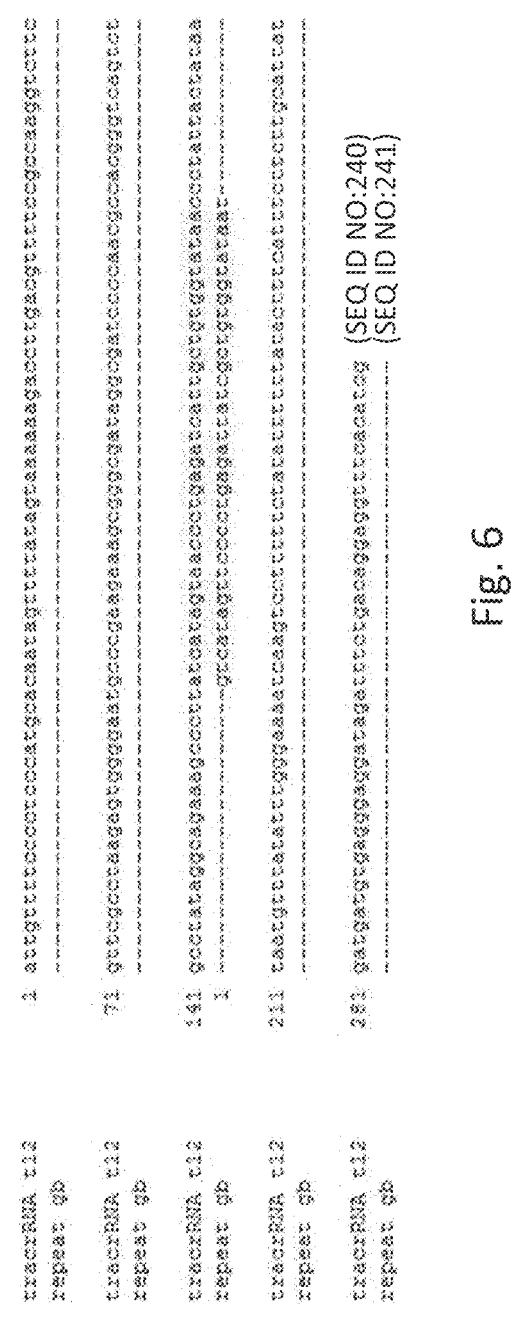

A CRISPR array with 11 repeats and 10 spacer sequences is located upstream of the transcriptional termination sequence and the leader of the array is located at the 5' end of the array. The DNA locus which is transcribed into the tracrRNA is expected to be downstream of the cas9 gene. The alignment of the 325 bp long sequence right downstream of the cas9 gene with the 36 bp long repeat from the CRISPR array revealed that there is a 36 bp long sequence in the tracrRNA locus almost identical to the repeat (shown in FIG. 6). This result led us to the conclusion that the direction of the transcription of the tracrRNA locus should be opposite to the direction of the transcription of the CRISPR array. Consequently the 5'-end of the tracrRNA will be complementary to the 3'-end of the crRNA, leading to the formation of the—required by the Cas9-dual-RNA molecule.

Example 5: Target Generation with Randomized PAM

Two different spacers from the CRISPR II loci of the *G. thermodenitrificans* T12 strain were amplified by PCR using the *G. thermodenitrificans* T12 genomic DNA as template. Two pairs of degenerate primers were used for the amplification of each spacer:

Firstly, a pair that cause the introduction of six random nucleotides upstream of the "protospacer" fragment were used, leading to the production of a pool of protospacers with randomized PAM sequences.

Secondly, a pair that cause the introduction of six random nucleotides downstream of the "protospacer" fragment were used, leading to the production of a pool of protospacers with randomized PAM sequences.

The produced fragments were ligated to the pNW33n vector, producing 4 pools of "protospacer" constructs, with all the possible 4096 different combinations of 6-nucleotide long PAMs each. The assembled DNA was used for the transformation of *G. thermodenitrificans* T12 cells. The cells were plated on chloramphenicol selection and more than $2 \times 10^6$ cells from each protospacer pool will be pooled. The plasmid DNA was extracted from the pools, the target region will be PCR amplified and the products sent for deep sequencing. The PAMs with the fewest reads will be considered active and the process will be repeated only with pNW33n constructs that contain spacers with these PAMs. Reduced transformation efficiency of the *G. thermodenitrificans* T12 will confirm the activity of the PAMs.

Example 6: In Vitro Determination of PAM Sequences for gtCas9

Construction of the pRham:Cas9$_{gt}$ Vector

The cas9$_{gt}$ gene was PCR amplified from the *G. thermodenitrificans* T12 genome, using the BG6927 and BG6928 primers, and combined with the pRham C-His Kan Vector (Lucigen) in one mixture. The mixture was used for transforming *E. cloni* thermo-competent cells according to the provided protocol. 100 µl from the transformation mixture were plated on LB+50kanamycin plates for overnight growth at 37° C. Out of the formed *E. cloni*::pRham:cas9$_{gt}$ single colonies 3 were randomly selected and inoculated in 10 ml LB medium containing 50 µg/ml kanamucin. Glycerol stocks were prepared from the cultures by adding sterile glycerol to 1 ml from each culture up to a final concentration of 20% (v/v). The glycerol stocks were stored at −80° C. The remaining 9 ml from each culture were used for plasmid isolation according to the "GeneJET Plasmid Miniprep Kit" (Thermoscientific) protocol. The plasmids were sent for sequence verification of the cas9$_{gt}$ and one of the plasmids was verified to contain the gene with the right sequence. The corresponding culture was further used for heterologous expression and purification of the gtCas9.

Heterologous Expression of gtCas9 in *E. cloni*::pRham: cas9$_{gt}$ Vector

An *E. cloni*::pRham:cas9$_{gt}$ preculture was prepared after inoculating 10 ml LB+50kanamycin with the corresponding glycerol stocks. After overnight growth at 37° C. and 180 rpm, 2 ml from the preculture were used for inoculating 200 ml of LB+50 kanamycin medium. The *E. cloni*::pRham: cas9$_{gt}$ culture was incubated at 37° C., 180 rpm until an $OD_{600}$ of 0.7. The gtCas9 expression was then induced by adding L-rhamnose to a final concentration of 0.2% w/v. The expression was allowed to proceed for 8 h, after which the cultures were centrifuged for 10 minutes at 4700 rpm, 4° C. to harvest the cells. The medium was discarded and the pelleted cells were either stored at −20° C. or used for the preparation of the cell free extract (CFE) according to the following protocol:

1. Resuspend the pellet in 20 ml Sonication Buffer (20 mM Sodium Phosphate buffer (pH=7.5), 100 mM NaCl, 5 mM MgCl2, 5% (v/v) Glycerol, 1 mM DTT)
2. Disrupt 1 ml of cells by sonication (8 pulses of 30 seconds, cool for 20 seconds on ice in between)
3. Centrifuge for 15 minutes at 35000 g, 4° C. in order to precipitate insoluble parts
4. Remove the supernatant and store it at 4° C. or on ice Designing and Construction of the PAM Library Targeting sgRNA Module for gtCas9

After in silico determination of the tracrRNA expressing DNA module in the genome of *G. thermodenitrificans* T12 strain (see Example 4 above), a single guide (sg)RNA expressing DNA module that combines the crRNA and tracrRNA modules of the CRISPR/Cas9 system in a single molecule was designed. The spacer at the 5'-end of the sgRNA was designed to be complementary to the protospacer of the plasmid library and the module was set under the transcriptional control of a T7 promoter. The pT7_sgRNA DNA module was synthesized by Baseclear and received in a pUC57 vector, forming the pUC57: pT7_sgRNA vector. DH5a competent *E. coli* cells (NEB) were transformed with the vector and the transformation mixture was plated on LB-agar plates containing 100 µg/ml ampicillin. The plates were incubated overnight at 37° C. Three of the formed single colonies were inoculated in 10 ml LB medium containing 100 µg/ml ampicillin. Glycerol stocks were prepared from the cultures by adding sterile glycerol to 1 ml from each culture up to a final concentration of 20% (v/v). The glycerol stocks were stored at −80° C. The remaining 9 ml from each culture were used for plasmid isolation according to the "GeneJET Plasmid Miniprep Kit" (Thermoscientific) protocol. The isolated plasmid was used as a PCR template for amplification of the pT7_sgRNA module. The 218 bp long pT7_sgRNA DNA module (of which the first 18 bp correspond to the pT7) was obtained using the primers BG6574 and BG6575. The complete PCR mixture was run on a 1.5% agarose gel. The band with the desired size was excised and purified according to the "Zymoclean™ Gel DNA Recovery Kit" protocol.

In vitro transcription (IVT) was performed using the "HiScribe™ T7 High Yield RNA Synthesis Kit" (NEB). The purified pT7_sgRNA DNA module was used as template. The IVT mixture was mixed with an equal volume of RNA loading dye (NEB) and heated at 70° C. for 15 minutes in order to disrupt the secondary structure. The heat treated IVT mixture was run on a denaturing Urea-PAGE and the resulting polyacrylamide gel was embaptised for 10 minutes in 100 ml 0.5×TBE buffer containing 10 µl of SYBR Gold (Invitrogen) for staining purposes. The band at the desired size (200 nt) was excised and the sgRNA was purified according to the following RNA purification protocol:
1. Cut RNA gel fragments with a scalpel and add 1 ml of RNA elution buffer, leave overnight at room temperature.
2. Divide 330 µl aliquots into new 1.5 ml tubes.
3. Add 3 volumes (990 µl) of pre-chilled (−20° C.) 100% EtOH.
4. Incubate for 60 minutes at −20° C.
5. Centrifuge for 20 minutes at 13000 rpm in a microfuge at room temperature.
6. Remove EtOH, wash pellet with 1 ml 70% EtOH.
7. Centrifuge for 5 minutes at 13000 rpm in a microfuge at room temperature.
8. Remove 990 µl of the supernatant.
9. Evaporate the rest EtOH in a thermomixer at 55° C. for 15 to 20 minutes.
10. Resuspend pellet in 20 µl MQ, store at −20° C.

Designing and Construction of a 7 nt Long PAM Library, and Linearization of the Library The design and construction of the PAM library was based on the pNW33n vector. A 20 bp long protospacer was introduced to the vector, flanked at its 3' side by a 7 degenerate nucleotides long sequence; the degenerate sequence serves as the PAM and when the protospacer is flanked by a right PAM then it can be recognized as a target by an sgRNA loaded Cas9 and cleaved. The PAM library was prepared according to the following protocol:
1. Prepare the SpPAM double stranded DNA insert by annealing the single stranded DNA oligos 1 (BG6494) and 2 (BG6495)
   I. 10 µl 10×NEBuffer 2.1
   II. 1 µl 50 µM oligo 1 (~1.125 µg)
   III. 1 µl 50 µM oligo 2 (~1.125 µg)
   IV. 85 µl MQ
   V. Incubate the mixture at 94° C. for 5 min and cool down to 37° C. at a rate of 0.03° C./sec
2. Add 1 µl Klenow 3'→5' exo⁻ polymerase (NEB) to each annealed oligos mixture and then add 2.5 µl of 10 µM dNTPs. Incubate at 37° C. for 1 h and then at 75° C. for 20 min.
3. Add 2 µl of the HF-BamHI and 2 µl of the BspHI restriction enzymes to 46 µl of the annealing mixture. Incubate at 37° C. for 1 h. This process will lead to the SpPAMbb insert with sticky ends. Use the Zymo DNA cleaning and concentrator kit (Zymo Research) to clean the created insert.
4. Digest pNW33n with the HF-BamHI and BspHI (NEB) and purify the 3.400 bp long linear pNW33nbb fragment with sticky ends, using the Zymo DNA cleaning and concentrator kit (Zymo Research).
5. Ligate 50 ng of pNW33nBB with 11 ng of the SPPAMbb insert using the NEB T4 ligase according to the provided protocol. Purify the ligation mixture using the Zymo DNA cleaning and concentrator kit (Zymo Research).
6. Transform DH10b electro-competent cells (200 µl of cells with 500 ng of DNA). Recover the cells in SOC medium (200 µl cells in 800 µl SOC) for an hour and then inoculate 50 ml of LB+12.5 µg/ml chloramphenicol with the recovered cells. Incubate overnight the culture at 37° C. and 180 rpm.
7. Isolate plasmid DNA from the culture using the JetStar 2.0 maxiprep kit (GENOMED).
8. Use the SapI (NEB) restriction according to the provided protocol for linearizing the isolated plasmids.

Designing and Execution of the PAM Determination Reactions

The following cleavage reaction was set up for gtCas9-induced introduction of dsDNA breaks to the PAM library members that contain the right PAM downstream of the 3' end of the targeted protospacer:
1. 2.5 µg of E. cloni::pRham:cas9$_{gt}$ CFE per reaction
2. sgRNA to 30 nM final concentration
3. 200 ng of linearized PAM library per reaction
4. 2 µl of cleavage buffer (100 mM Sodium Phosphate buffer (pH=7.5), 500 mM NaCl, 25 mM MgCl2, 25° (v/v) Glycerol, 5 mM DTT)
5. MQ water up to 20 µl final volume The reaction was incubated for 1 h at 60° C. and stopped after adding 4 µl of 6× gel loading dye (NEB). The reaction mixture was then loaded to a 1% agarose gel. The gel was subjected to an 1 h and 15 min long electrophoresis at 100V and then it was incubated for 30 min in 100 ml 0.5×TAE buffer containing 10 µl of SYBR Gold dye (ThermoFisher). After visualizing the DNA bands with blue light, the band that corresponded to the successfully cleaved and PAM containing DNA fragments was cut-off the gel and gel purified using the "Zymoclean™ Gel DNA Recovery Kit" according to the provided protocol.

Tagging of the PAM-Containing gtCAs9 Cleaved DNA Fragments for Sequencing

The Cas9-induced DNA breaks are usually introduced between the $3^{rd}$ and the $4^{th}$ nucleotide of a protospacer, proximally to the PAM sequence. As a result, it is not possible to design a pair of primers that can PCR amplify the PAM-containing part of the cleaved DNA fragments, in order to further on sequence and determine the PAM sequence. For this purpose, a 5-step process was employed:

Step 1: A-Tailing with Taq Polymerase

A-Tailing is a process to add a non-templated adenine to the 3' end of a blunt, double-stranded DNA molecule using Taq polymerase Reaction Components:
  gtCas9-cleaved and PAM-containing DNA fragments—200 ng
  10× ThermoPol® Buffer (NEB)—5 µl
  1 mM dATP—10 µl
  Taq DNA Polymerase (NEB)—0.2 µl
  H₂O—up to 50 µl final reaction volume
  Incubation time—20 min
  Incubation temperature—72° C.

Step 2: Construction of the Sequencing Adaptors

Two complementary short ssDNA oligonucleotides were phosphorylated and annealed to form the sequencing adaptor for the PAM-proximal site of the DNA fragments from step 1. One of the oligonucleotides had an additional thymine at its 3' end, in order to facilitate the ligation of the adaptor to the A-tailed fragments.

Adaptor Oligonucleotides phosphorylation (Separate phosphorylation reactions for each oligo)
  100 µM oligonucleotide stock—2 µL
  10×T4 DNA ligase buffer (NEB)—2 µL
  Sterile MQ water—15 µL
  T4 Polynucleotide Kinase (NEB)—1 µL
  Incubation time—60 min
  Incubation temperature—37° C.
  T4 PNK inactivation—65° C. for 20 min Annealing of the Phosphorylated Oligonucleotides
  Oligonucleotide 1—5 µL from the corresponding phosphorylation mixture
  Oligonucleotide 1—5 µL from the corresponding phosphorylation mixture Sterile MQ water—90 μL
Incubate the phosphorylated oligos at 95° C. for 3 minutes. Cool the reaction slowly at room temperature for ~30 min to 1 hr Step 3: Ligation of the gtCas9-cleaved, A-tailed fragments with the sequencing adaptors The products of step 1 and 2 were ligated according to the following protocol:
10×T4 DNA Ligase Buffer—2 μl
Product step 1—50 ng
Product step 2—4 ng
T4 DNA Ligase—1 μl
Sterile MQ water—to 20 μl
Incubation time—10 min
Incubation temperature—20-25° C.
Heat inactivation at 65° C. for 10 min Step 4: PCR Amplification of a 150-Nucleotides Long PAM-Containing Fragment 5 μl from the ligation mixture of step 4 were used as template for PCR amplification using Q5 DNA polymerase (NEB). The oligonucleotide with the thymine extension from step 2 was employed as the forward primer and the reverse primer was designed to anneal 150 nucleotides downstream of the PAM sequence.

The same sequence was amplified using non-gtCas9 treated PAM-library DNA as template. Both PCR products were gel purified and sent for Illumina HiSeq 2500 paired-end sequencing (Baseclear).

Analysis of the Sequencing Results and Determination of the Candidate PAM Sequences After analysing the sequencing results the following frequency matrices were constructed. The matrices depict the relative abundance of each nucleotide at every PAM position of the gtCas9 digested and non-digested libraries:

|   | pos1 | pos2 | pos3 | pos4 | pos5 | pos6 | pos7 |
|---|---|---|---|---|---|---|---|
| Non-digested | | | | | | | |
| A | 19.22 | 20.83 | 19.12 | 24.43 | 24.59 | 21.75 | 18.22 |
| C | 34.75 | 30 | 31.9 | 30.54 | 25.96 | 27.9 | 27.17 |
| T | 19.16 | 22.19 | 25.34 | 21.28 | 26.09 | 26 | 21.56 |
| G | 26.87 | 26.98 | 23.64 | 23.75 | 23.36 | 24.35 | 33.05 |
| Digested | | | | | | | |
| A | 10.63 | 18.65 | 14.6 | 14.49 | 3.36 | 8.66 | 27.54 |
| C | 66.22 | 49.59 | 56.82 | 60.35 | 92.4 | 62.26 | 34.94 |
| T | 8.09 | 11.21 | 19.12 | 12.15 | 2.35 | 14.66 | 5.58 |
| G | 15.05 | 20.54 | 9.45 | 13.01 | 1.89 | 14.43 | 31.94 |

These results indicate a clear preference for targets with cytosine at the 5$^{th}$ PAM position and preference for targets with cytosines at the first 4 PAM positions.

Example 7: In Silico PAM Prediction for gtCas9

Figure 7B:
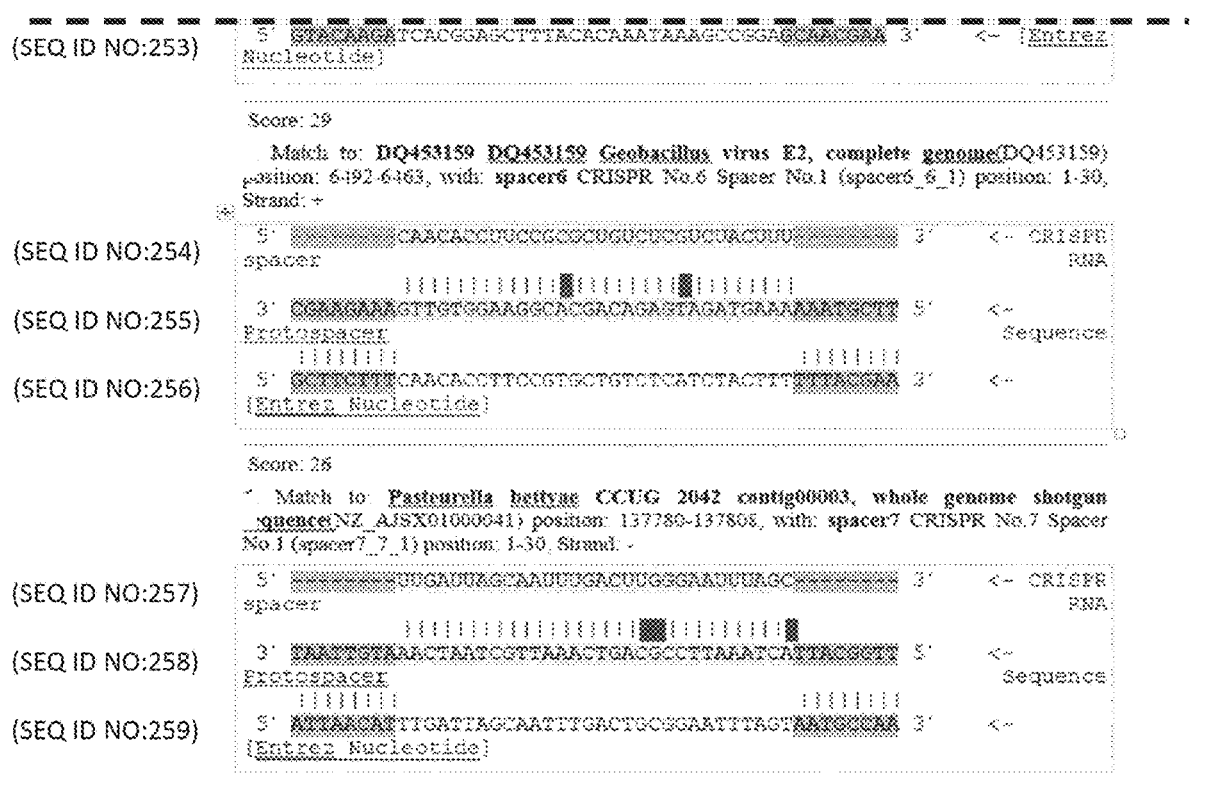
Figure 8:
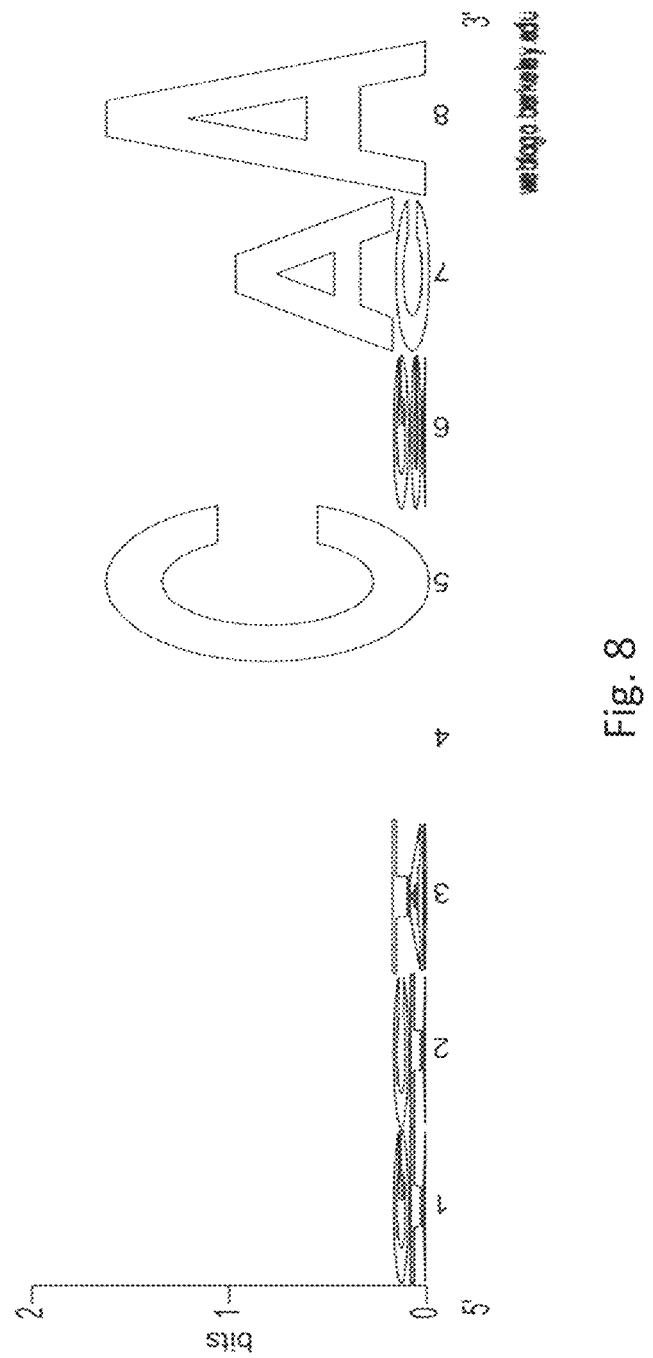
FIG. 8 shows a weblogo combining the results of the alignments illustrated in FIG. 7. The weblogo was generated using weblogo.berkeley.edu.

In silico predictions of MA/Is are possible if enough protospacer sequences are available in genome databases. The in silico prediction of gtCas9 PAM started with identification of hits of spacers from the CRISPR array in the genome of G. thermodenitrificans T12 strain by comparison to sequences in genome databases such as GenBank. The "CRISPR finder" (crispru-psud.fr/Server/) tool was used to identify candidate CRISPR loci in T12. The identified CRISPR loci output was then loaded into "CRISPR target" (bioanalysis.otago.ac.nz/CISPRTarget/_crispr_analysis.html) tool, which searches selected databases and provides an output with matching protospacers. These protospacer sequences were then screened for unique hits and for complementarity to spacers—for example, mismatches in the seed sequence were considered to be likely false positive hits and were excluded from further analysis. Hits with identity to prophage sequences and (integrated) plasmids demonstrated that the obtained hits were true positives. Overall, this process yielded 6 single hits (FIG. 7). Subsequently, the flanking regions (3' for Type II gtCas nuclease) of the remaining, unique protospacer hits were aligned and compared for consensus sequences using a Web-Logo (weblogo.berkeley.edu/logo.cgi) (Crooks G E, Hon G, Chandonia J M, Brenner S E WebLogo: A sequence logo generator, *Genome Research*, 14:1188-1190, (2004)) tool (FIG. 8).

The in silica results were comparable to the in vitro PAM identification experimental results (see Example 6) in which there was a bias for the identity of the 5$^{th}$ residue of the PAM sequence to be a cytosine.

Example 8: Determination of 8 Nucleotide Long PAM Sequences for gtCas9

The in silico data from Example 8 suggested that gtCas9 had some preference for adenosine at the 8$^{th}$ position, therefore further PAM determination experiments were carried out where the 8$^{th}$ position of the PAM sequence was also tested. This is consistent with the characterisation of mesophilic *Brevibacillus laterosporus* SSP360D4 (Karvelis et al., 2015) Cas9 PAM sequence which was found to extend between the 5$^{th}$ and the 8$^{th}$ positions at the 3' end of a protospacer.

Specific 8 Nucleotide-Long Sequence Variants of the PAMs were Trialed with gtCas9:

1)
CNCCCCAC,                               [SEQ ID NO: 17]

2)
CCCCCCAG,                               [SEQ ID NO: 18]

3)
CCCCCCAA,                               [SEQ ID NO: 11]

4)
CCCCCCAT,                               [SEQ ID NO: 19]

5)
CCCCCCAC,                               [SEQ ID NO: 20]

6)
NNNNTNNC (negative control PAM)

Figure 9:
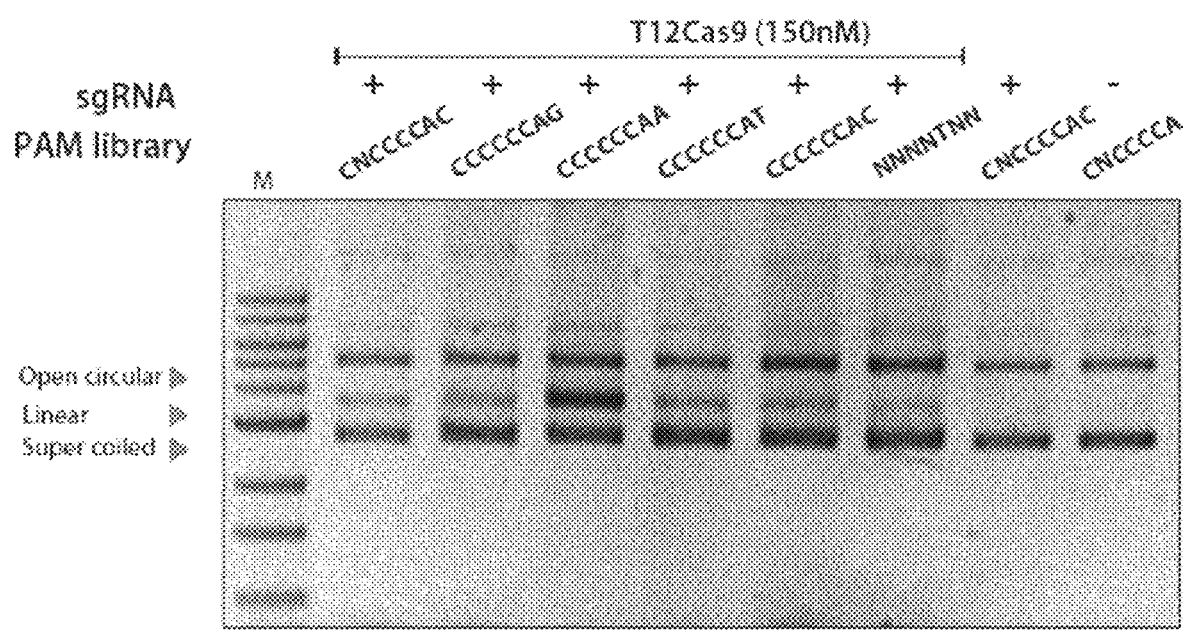
FIG. 9 shows the results of an in vitro cleavage assay at 60° C. targeting plasmids with purified gtCas9. The plasmids included specific 8 nucleotide-long sequence variants of the PAM sequences.

After performing an in vitro cleavage assay at 60° C. targeting these (non-linearized) plasmids with purified gtCas9 and the same sgRNA as before (see Example 6) an increased gtCas9 cleavage activity when the CCCCCCAA [SEQ ID NO: 11] sequence was employed as PAM was observed (FIG. 9). However, cleavage activity was clearly detectable for all the tested PAM sequences, even for the negative control PAM sequence a faint cleavage band was observed. Without wishing to be bound to a particular theory, it is possible that use of high gtCas9 concentration contributed to the cleavage observed with the negative control. It has been generally observed that high Cas9 concentrations in in vitro assays lead to Cas9-induced DNA cleavage without stringent PAM requirement.

Figure 10:
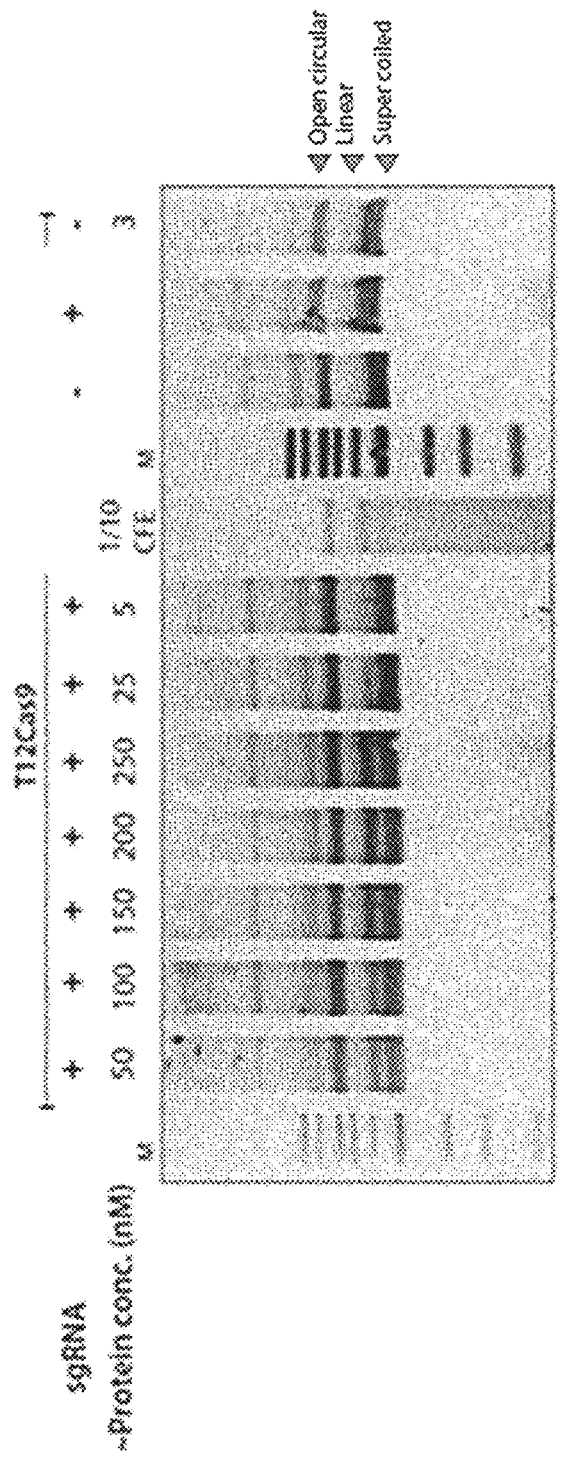
FIG. 10 shows the results of in vitro assays to investigate the effect of gtCas9 concentration, using a targeted plasmid with the CCCCCCAA [SEQ ID NO: 11] PAM sequence.

Cas9 concentration in general is known to influence the efficiency of the Cas9 induced DNA cleavage (higher Cas9 concentration results in higher Cas9 activity). This was also observed when performing in vitro assays using the targeted plasmid with the CCCCCCAA [SEQ ID NO: 11] PAM sequence and different gtCas9 concentrations (FIG. 10)

Figure 11:
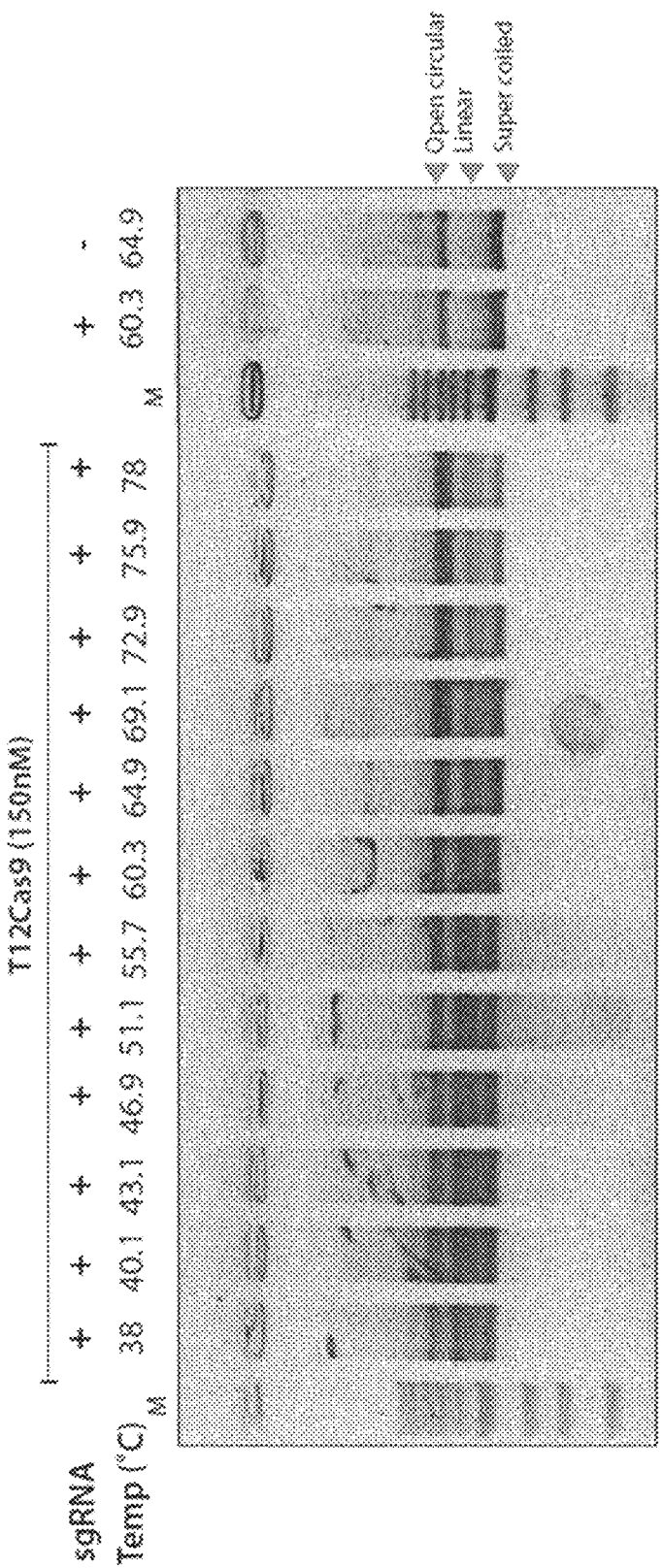
FIG. 11 shows the results of in vitro assays using a targeted plasmid with the CCCCCCAA [SEQ ID NO: 11] PAM sequence over a range of temperatures.

The targeted plasmid with the CCCCCCAA [SEQ ID NO: 11] PAM sequence for in vitro assays as described above was conducted over a wide temperature range between 38 and 78° C. (FIG. 11). Surprisingly, gtCas9 was active at all the temperatures showing the highest activity between 40.1 and 64.9° C.

Thus, the optimal temperature range of Cas9 from *Geobacillus* species is much higher than that of Cas9 proteins which have been characterised to date. Similarly, the upper extent of the range in which it retains nuclease activity is much higher than that of known Cas9 proteins. A higher optimal temperature and functional range provides a significant advantage in genetic engineering at high temperatures and therefore in editing the genomes of thermophilic organisms, which have utility in a range of industrial, agricultural and pharmaceutical processes conducted at elevated temperatures.

Example 9: In Vivo Genome Editing of *Bacillus smithii* ET138 with gtCas9 and 8 Nucleotide Length PAM Sequences To confirm that the 8 nucleotide PAMs were also recognised by gtCas9 in vivo, an experiment was designed to delete the pyrF gene in the genome of *Bacillus smithii* ET138 at 55° C.

This method relies upon providing a homologous recombination template construct in which regions complimentary to the upstream and downstream of the target (pyrF) gene are provided to *B. smithii* ET 138 cells. Introduction of the template allows for the process of homologous recombination to be used to introduce the homologous recombination template (with no pyrF gene) into the genome such that it also replaces the WT pyrF gene in the genome of a cell.

Inclusion of a gtCas9 and a sgRNA in the homologous recombination construct can be used to introduce double stranded DNA breaks (DSDBs) into bacterial genomes that contain WT pyrF. DSDBs in a bacterial genome typically results in cell death. Therefore, a sgRNA that recognises a sequence in the WT pyrF could result in DSDB and death of cells containing the WT pyrF only. Introduction of DSDB is also dependent on a suitable PAM sequence being located downstream at the 3' end of the protospacer that is recognised by gtCas9.

The pNW33n plasmid was used as a backbone to clone:
i) the cas9$_{gt}$ gene under the control of an in-house developed glucose repressible promoter; and
ii) the 1 kb upstream and 1 kb downstream regions of the pyrF gene in the genome of *B. smithii* ET138 as a template for homologous recombination that would result in deletion of the pyrF gene from the genome of *B. smithii* ET138; and
iii) single guide RNA (sgRNA) expressing module under the transcriptional control of a constitutive promoter.

Three separate constructs were generated in which the sequence of the single guide RNAs differed at the first 20 nucleotides, which correspond to the sequence that guides the gtCas9 to its specific DNA target in the genome (also known as the spacer). The three different spacer sequences were designed to target three different candidate protospacers all in the pyrF gene of *B. smithii* ET138. The constructs are herein referred to as constructs 1, 2 and 3 respectively.

The three different targeted protospacers had at their 3'-end the following candidate PAM sequences:
1. TCCATTCC (negative control according to the results of the in vitro assays; 3'-end of the protospacer targeted by the sgRNA encoded on construct number 3)
2. ATCCCCAA (3'-end of the protospacer targeted by the sgRNA encoded on construct number 1; [SEQ ID NO: 21])
3. ACGGCCAA (3'-end of the protospacer targeted by the sgRNA encoded on construct number 2, [SEQ ID NO: 22])

Figure 12:
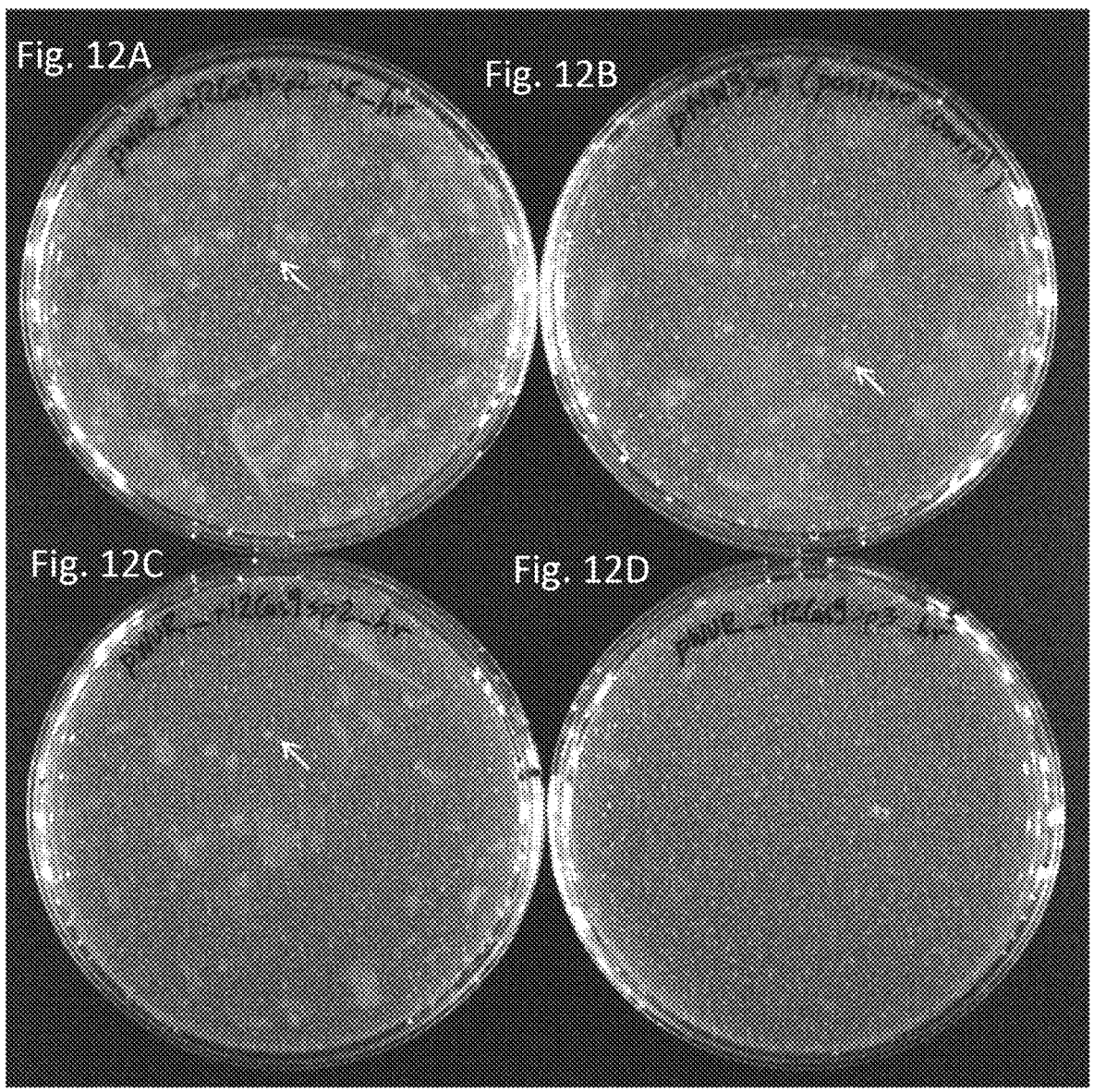
FIG. 12, comprising
Figure 13:
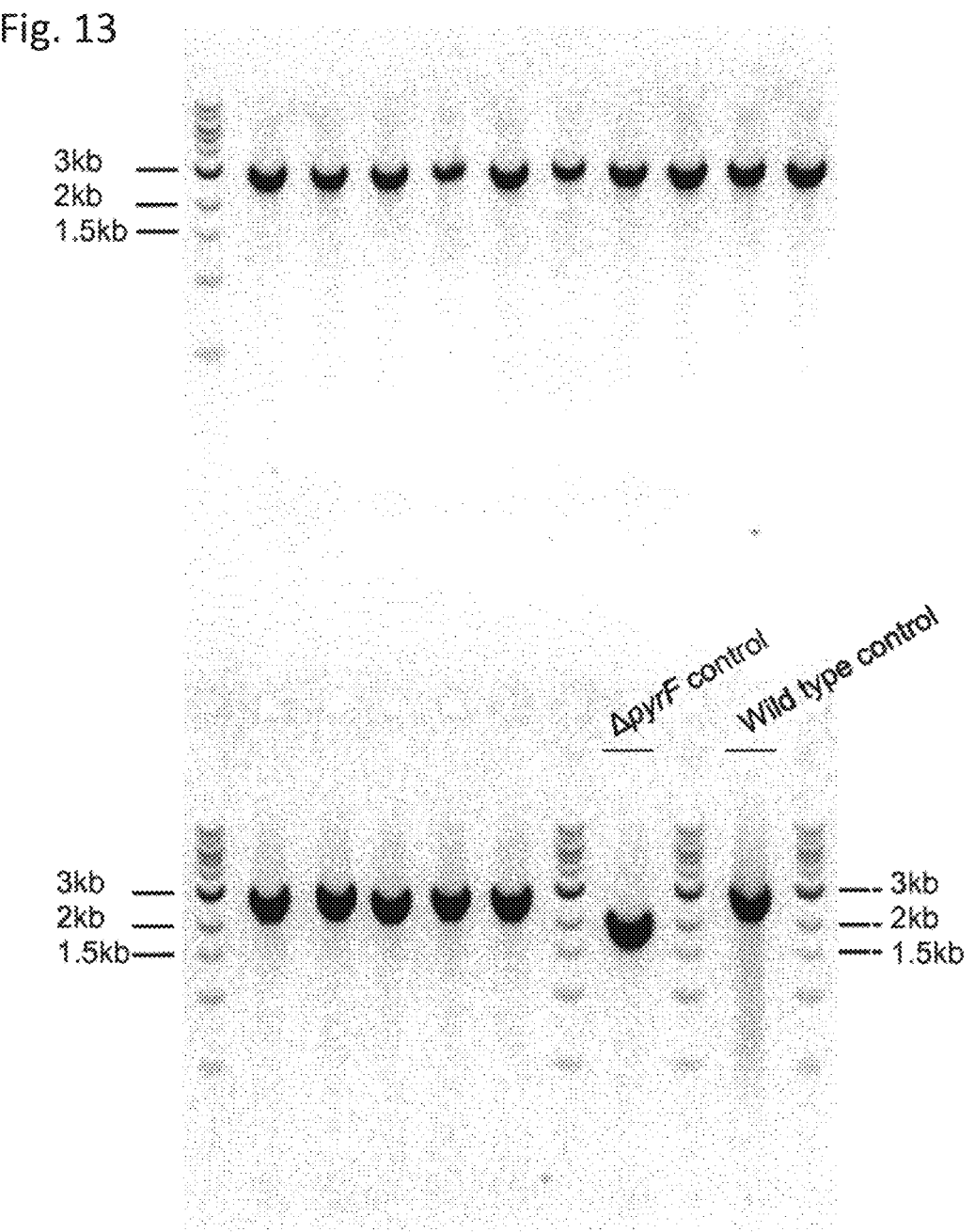
FIG. 13 shows the results of a PCR screen for colonies in which the pyrF gene was deleted. The colonies were generated following transformation of *Bacillus smithii* ET138 cells with construct 3 (negative control). 15 colonies were screened but none showed the deletion genotype −2.1 kb band size and instead all showed the wild type −2.9 kb band size, as explained in Example 9.
Figure 14:
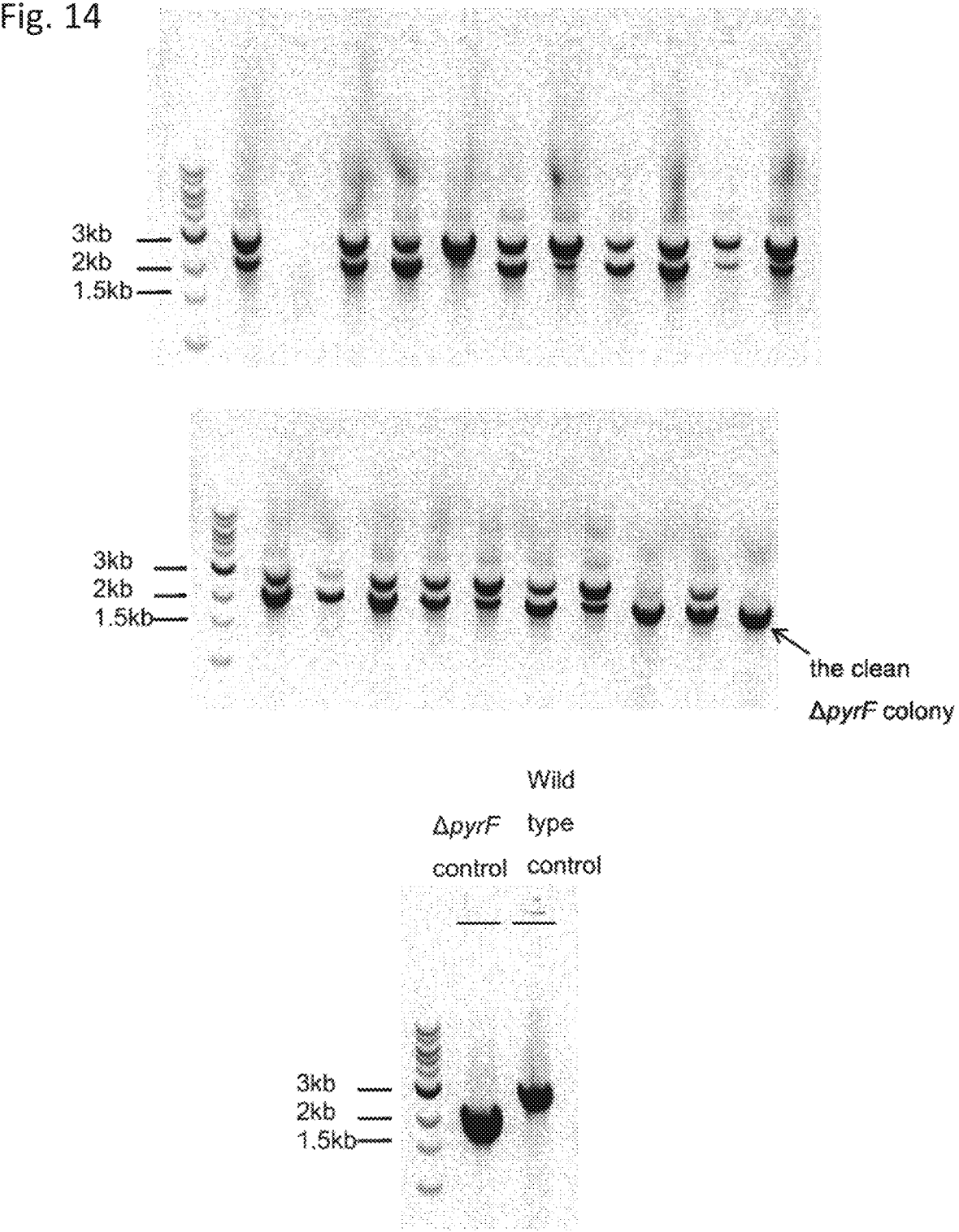
FIG. 14 shows the results of a PCR screen for colonies in which the pyrF gene was deleted. The colonies were generated following transformation of *Bacillus smithii* ET138 cells with construct 1 (PAM sequence ATCCCCAA [SEQ ID NO: 21]). 20 colonies were screened and one showed the deletion genotype −2.1 kb band size whilst the rest showed both the wild type −2.9 kb band size and the deletion genotype −2.1 kb band size, as explained in Example 9. No wild type only genotypes were observed.

After transforming *B. smithii* ET 138 cells with one of the three constructs and plating on selection plates, the following results were obtained:
1. When the cells were transformed with the construct targeting the protospacer that had the negative control TCCATTCC PAM sequence at the 3' end (construct number 3) the transformation efficiency was not affected (FIG. 12 A). The number of colonies was in the same range as the number of colonies after transformation with the pNW33n positive control construct (FIG. 12 B). Of the 15 colonies that were subjected to colony PCR to screen for colonies in which the pyrF gene was deleted, none showed the deletion genotype −2.1 kb expected band size—, all were wild-type −2.9 kb expected band size—(FIG. 13). This indicates that the tested PAM was indeed not recognised by the gtCas9 in vivo.
2. When the cells were transformed with construct number 1 only a few colonies were obtained (FIG. 12 C) when compared to the positive control (cells transformed with pNW33n). 20 colonies were subjected to colony PCR to screen for colonies in which the pyrF gene was deleted. The majority (19) of the colonies contained both the wild type and pyrF deletion genotype whilst one colonies had a pyrF deletion genotype (FIG. 14). This result indicated that the PAM sequence ATCCCCAA [SEQ ID NO: 21] is recognised in vivo by gtCas9 because no WT only genotypes were observed. The reduced transformation efficiency is also indicative that a proportion of the cell population has been reduced, which could be attributable to cell death caused of WT only genotype cells by DSDB due to successful targeting by gtCas9.
3. When the cells were transformed with construct number 2 no colonies were obtained (FIG. 12 D). The lack of colonies is indicative that all of the cell population had been successfully targeted by the gtCas9, which led to cell death caused by DSDB. This suggests that ACGGCCAA [SEQ ID NO: 22] PAM sequence is recognised by gtCas9.

These results indicate that gtCas9 is active at 55° C. in vivo with the above mentioned PAM sequences, a result that comes in agreement with the in vitro PAM determination results. Moreover it can be used as a genome editing tool at the same temperature in combination with a plasmid borne homologous recombination template.

Example 10: ThermoCas9 Identification and Purification

Figure 15A:
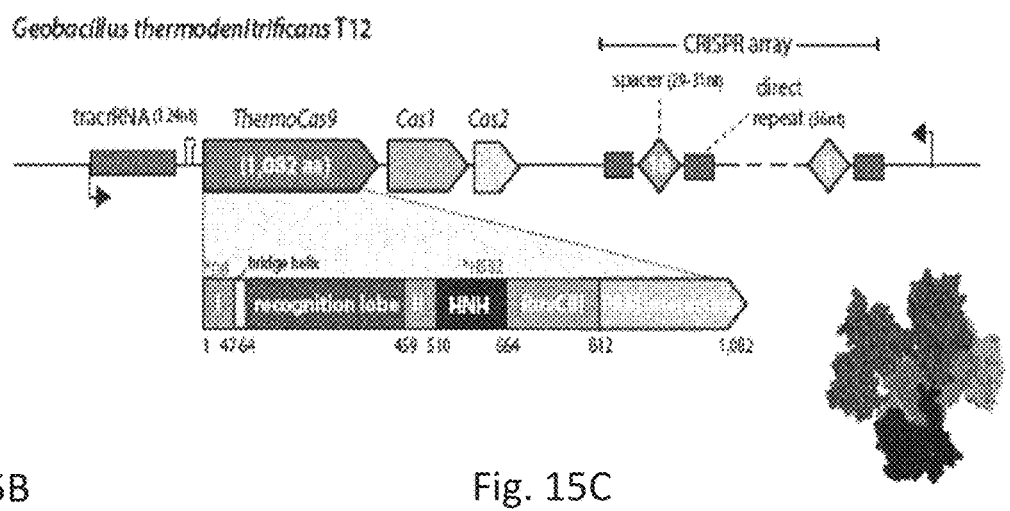
FIG. 15 shows the *Geobacillus thermodenitrificans* T12 type-IIC CRISPR-Cas locus encodes a thermostable Cas9 homolog, ThermoCas9.
Figure 15B:
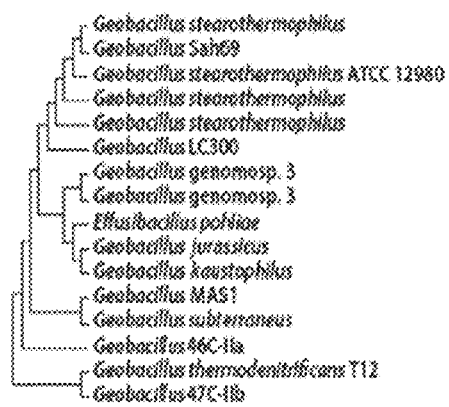

*Geobacillus thermodenitrificans* strain T12, a Gram positive, moderately thermophilic bacterium with an optimal growth temperature at 65° C. (Daas et al. *Biotechnol. Biofuels* 9, 210 (2016)) was isolated and sequenced. Contrary to previous claims that type II CRISPR-Cas systems are not present in thermophilic bacteria (Li et al. *Nucleic Acids Res.* 44, e34-e34 (2016)), the sequencing results revealed the existence of a type-IIC CRISPR-Cas system in the genome of *G. thermodenitrificans* T12 (FIG. 15A). The Cas9 endonuclease of this system (ThermoCas9) was predicted to be relatively small (1082 amino acids) compared to other Cas9 orthologues, such as SpCas9 (1368 amino acids). The size difference is mostly due to a truncated REC lobe, as has been demonstrated for other small Cas9 orthologues (FIG. 19) (Ran et al. *Nature* 520, 186-191 (2015)). Furthermore, ThermoCas9 was expected to be active at least around the temperature optimum of *G. thermodenitrificans* T12 (Daas et al. *Biotechnol. Biofuels* 9, 210 (2016)). Using the ThermoCas9 sequence as query, BLAST-P searches were performed in the NCBI/non-redundant protein sequences dataset, and a number of highly identical Cas9 orthologues were found (87-99% identity at protein level, Table 1), mostly within the *Geobacillus* genus, supporting the idea that ThermoCas9 is part of a highly conserved defense system of thermophilic bacteria (FIG. 15B). These characteristics suggested it may be a potential candidate for exploitation as a genome editing and silencing tool for thermophilic microorganisms, and for conditions at which enhanced protein robustness is required.

Figure 15C:
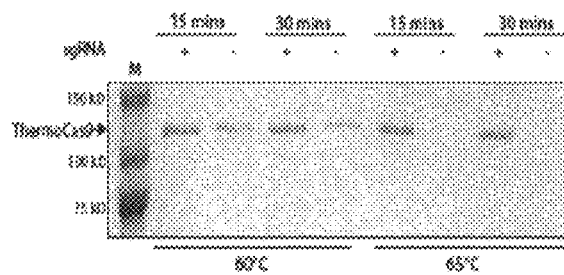

In silico prediction of the crRNA and tracrRNA modules of the *G. thermodenitrificans* T12 CRISPR-Cas system was performed using a previously described approach (Mougiakos et al. *Trends Biotechnol.* 34, 575-587 (2016); Ran et al. *Nature* 520, 186-191 (2015)). Based on this prediction, a 190 nt sgRNA chimera was designed by linking the predicted full size crRNA (30 nt long spacer followed by 36 nt long repeat) and tracrRNA (36 nt long anti-repeat followed by a 88 nt sequence with three predicted hairpin structures). ThermoCas9 was heterologously expressed in *E. coli* and purified to homogeneity. Hypothesizing that the loading of the sgRNA to the ThermoCas9 would stabilize the protein, incubated purified apo-ThermoCas9 and ThermoCas9 loaded with in vitro transcribed sgRNA were incubated at 60° C. and 65° C., for 15 and 30 min. SDS-PAGE analysis showed that the purified ThermoCas9 denatures at 65° C. but not at 60° C., while the denaturation temperature of ThermoCas9-sgRNA complex is above 65° C. (FIG. 15C). The demonstrated thermostability of ThermoCas9 implied its potential as a thermo-tolerant CRISPR-Cas9 genome editing tool, and encouraged us to analyze some relevant molecular features in more detail.

TABLE 1 pBLAST results of Cas9 protein sequences from FIG. 1B compared to ThermoCas9.

| Species | % identity[a] |
| --- | --- |
| *Geobacillus* 47C-IIb | 99 |
| *Geobacillus* 46C-IIa | 89 |
| *Geobacillus* LC300 | 89 |
| *Geobacillus jurassicus* | 89 |
| *Geobacillus* MAS1 | 88 |
| *Geobacillus stearothermophilus* | 88 |
| *Geobacillus stearothermophilus* ATCC 12980 | 88 |
| *Geobacillus* Sah69 | 88 |
| *Geobacillus stearothermophilus* | 88 |
| *Geobacillus kaustophilus* | 88 |
| *Geobacillus stearothermophilus* | 88 |
| *Geobacillus* genomosp. 3 | 87 |
| *Geobacillus* genomosp. 3 | 87 |

TABLE 1-continued pBLAST results of Cas9 protein sequences from FIG. 1B compared to ThermoCas9.

| Species | % identity[a] |
| --- | --- |
| *Geobacillus subterraneus* | 87 |
| *Effusibacillus pohliae* | 86 |

Example 11: ThermoCas9 PAM Determination

Figure 16A:
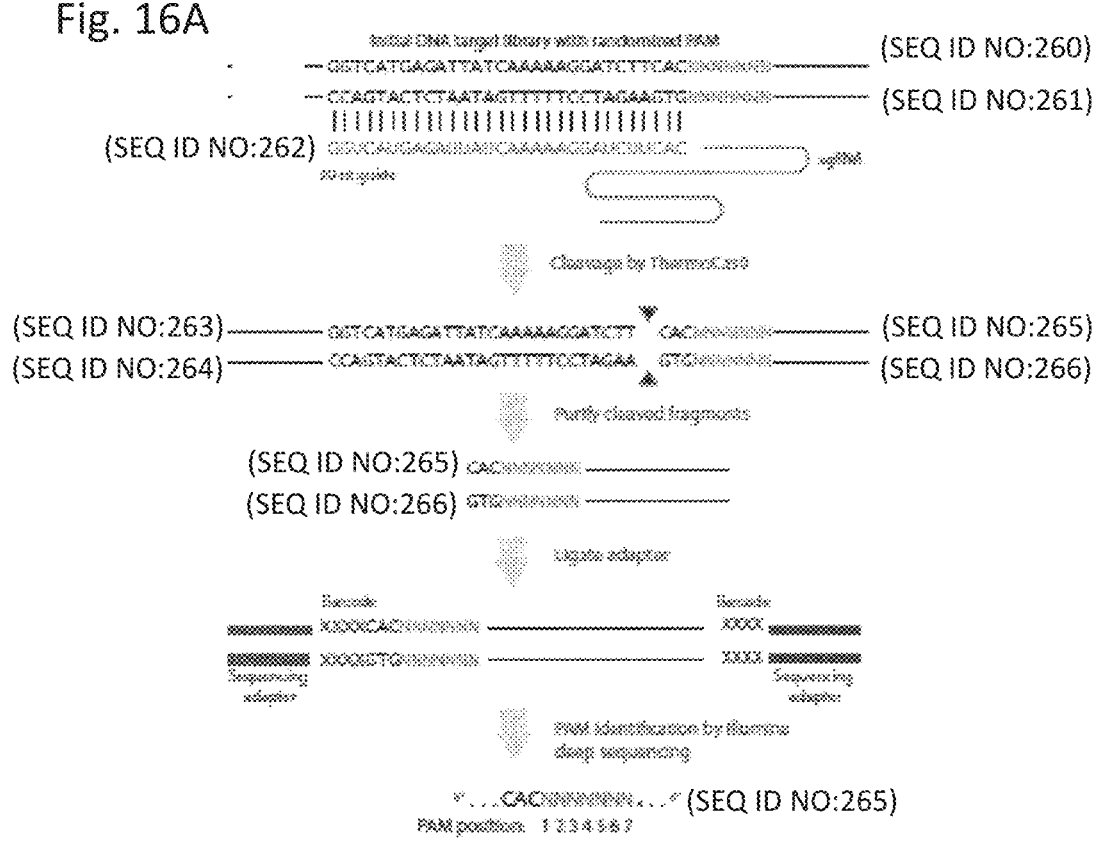
Figure 16B:
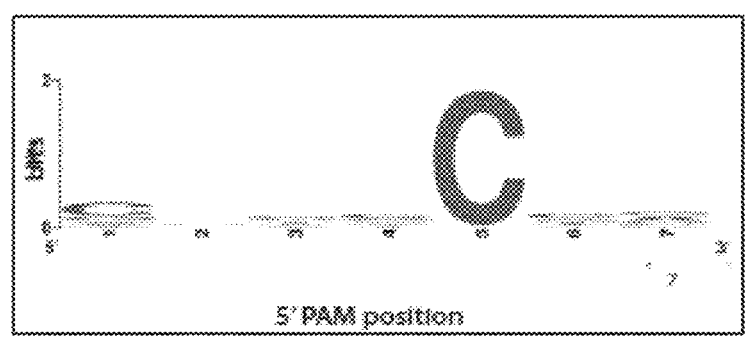
Figure 16C:
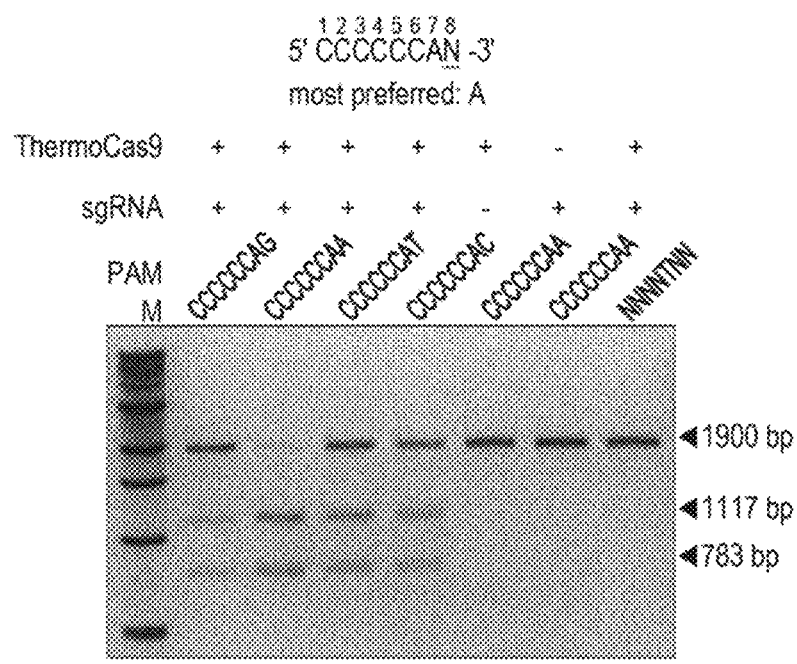

The first step towards the characterization of ThermoCas9 was the in silico prediction of its PAM preferences for successful cleavage of a DNA target. The 10 spacers of the *G. thermodenitrificans* T12 CRISPR locus were used to search for potential protospacers in viral and plasmid sequences using CRISPRtarget (Biswas et al. *RNA Biol.* 10, 817-827 (2013)). As only two hits were obtained with phage genomes (FIG. 20A), it was decided to proceed with an in vitro PAM determination approach. The predicted sgRNA sequence that contained a spacer for ThermoCas9-based targeting linear dsDNA substrates was transcribed with a matching protospacer. The protospacer was flanked at its 3'-end by randomized 7-base pair (bp) sequences. After performing ThermoCas9-based cleavage assays at 55° C., the cleaved members of the library (together with a non-targeted library sample as control) were deep-sequenced and compared in order to identify the ThermoCas9 PAM preference (FIG. 16A). The sequencing results revealed that ThermoCas9 introduces double stranded DNA breaks that, in analogy to mesophilic Cas9 variants, are located mostly between the $3^{rd}$ and the $4^{th}$ PAM proximal nucleotides. Moreover, the cleaved sequences revealed that ThermoCas9 recognizes a 5'-NNNNCNR-3' PAM, with subtle preference for cytosine at the $1^{st}$, $3^{rd}$, $4^{th}$ and $6^{th}$ PAM positions (FIG. 16B). Recent studies have revealed the importance of the $8^{th}$ PAM position for target recognition of certain Type IIC Cas9 orthologues (Karvelis et al. *Genome Biol.* 16, 253 (2015); Kim et al. *Genome Res.* 24, 1012-9 (2014)). For this purpose, and taking into account the results from the in silico ThermoCas9 PAM prediction, additional PAM determination assays were performed. This revealed optimal targeting efficiency in the presence of an adenine at the $8^{th}$ PAM position (FIG. 16C). Interestingly, despite the limited number of hits, the aforementioned in silico PAM prediction (FIG. 20B) also suggested the significance of a cytosine at the $5^{th}$ and an adenine at the $8^{th}$ PAM positions.

Figure 16D:
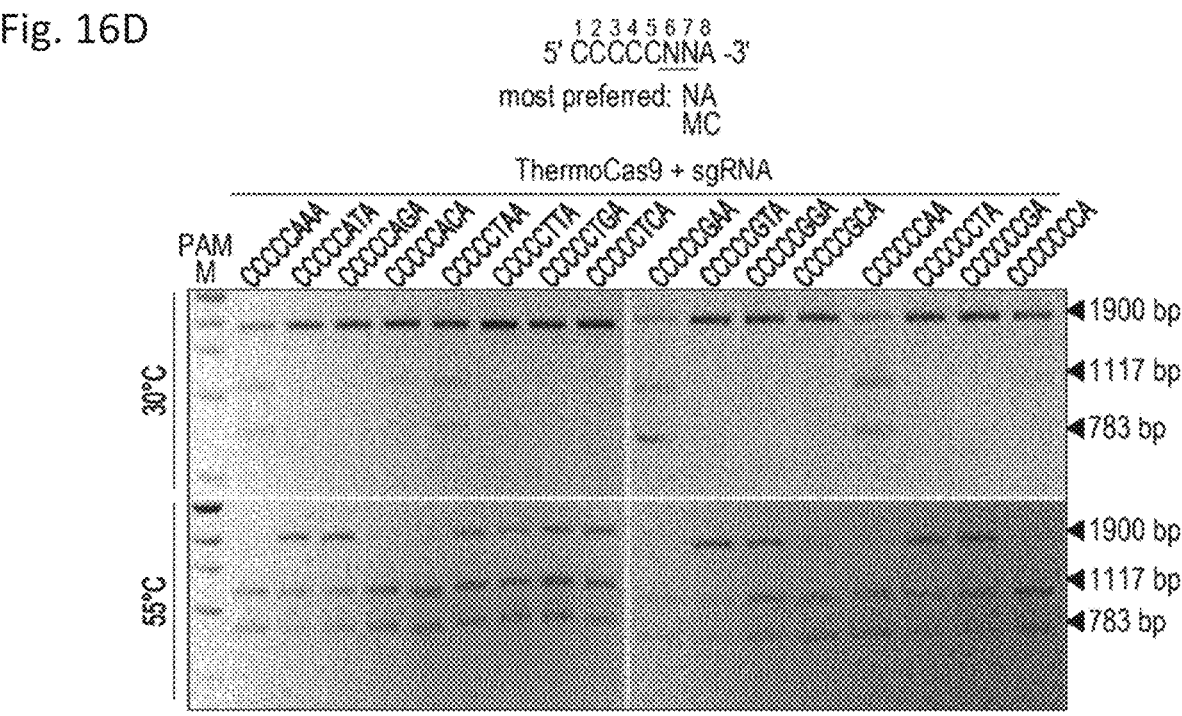

To further clarify the ambiguity of the PAM at the $6^{th}$ and $7^{th}$ PAM positions, a set of 16 different target DNA fragments were generated in which the matching protospacer was flanked by 5'-CCCCCNNA-3' [SEQ ID NO: 13] PAMs. Cleavage assays of these fragments (each with a unique combination of the $6^{th}$ and $7^{th}$ nucleotide) were performed in which the different components (ThermoCas9, sgRNA guide, dsDNA target) were pre-heated separately at different temperatures (20, 30, 37, 45, 55 and 60° C.) for 10 min before combining and incubating them for 1 hour at the corresponding assay temperature. When the assays were performed at temperatures between 37° C. and 60° C., all the different DNA substrates were cleaved (FIG. 16D, FIG. 21). However, the most digested target fragments consisted of PAM sequences ($5^{th}$ to $8^{th}$ PAM positions) 5'-CNAA-3' and 5'-CMCA-3', whereas the least digested targets contained a 5'-CAKA-3' PAM. At 30° C., only cleavage of the DNA substrates with the optimal PAM sequences ($5^{th}$ to $8^{th}$ PAM positions) 5'-CNAA-3' and 5'-CMCA-3' was observed (FIG.

2D). Lastly, at 20° C. only the DNA substrates with ($5^{th}$ to $8^{th}$ PAM positions) 5'-CVAA-3' and 5'-CCCA PAM sequences were targeted (FIG. 21), making these sequences the most preferred PAMs. These findings demonstrate that at its lower temperature limit, ThermoCas9 only cleaves fragments with a preferred PAM. This characteristic could be exploited during in vivo editing processes, for e.g. to avoid off-target effects.

Example 12: Thermostability and Truncations

Figure 17A:
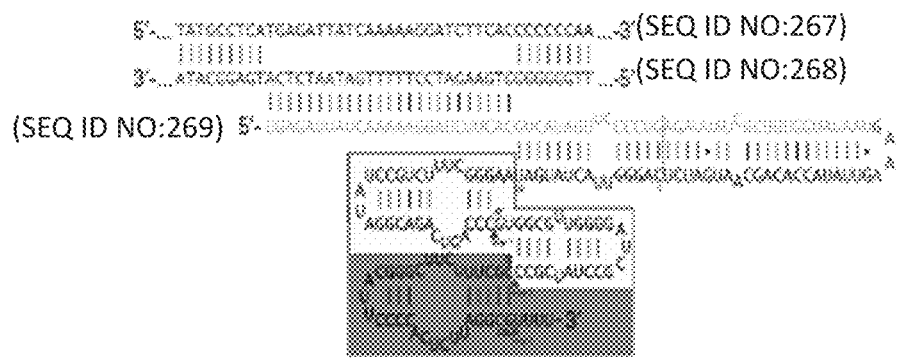
Figure 17B:
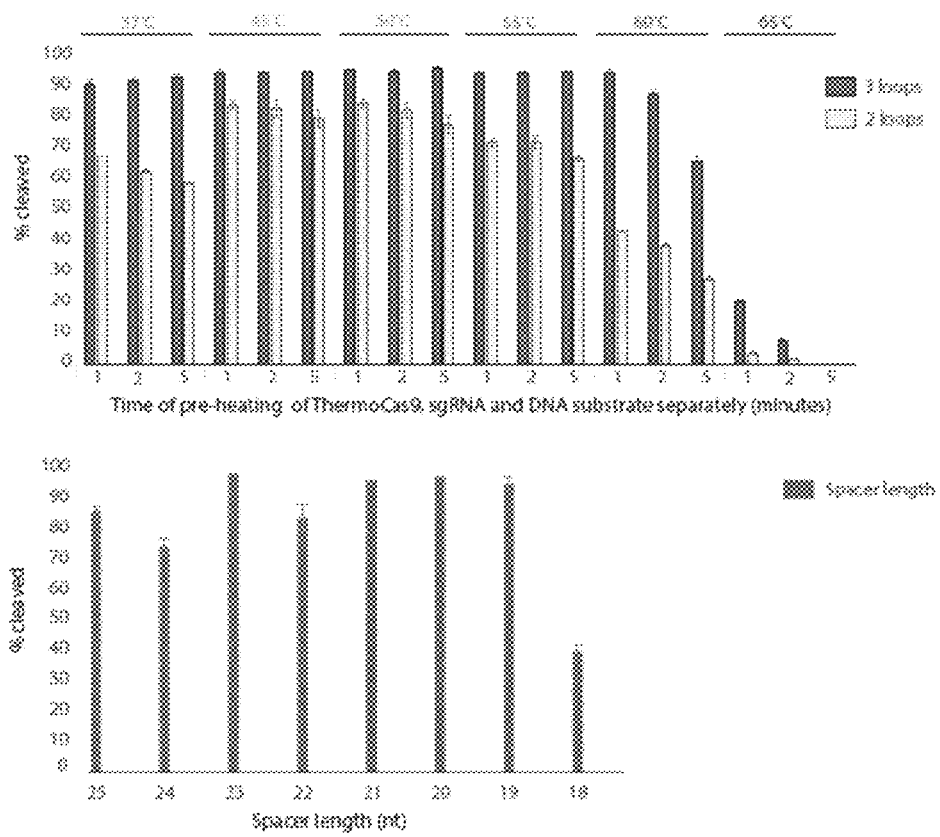

The predicted tracrRNA consists of the anti-repeat region followed by three hairpin structures (FIG. 17A). Using the tracrRNA along with the crRNA to form a sgRNA chimera resulted in successful guided cleavage of the DNA substrate. It was observed that a 41-nt long deletion of the spacer distal end of the full-length repeat-anti-repeat hairpin (FIG. 17A), most likely better resembling the dual guide's native state, had little to no effect on the DNA cleavage efficiency. The effect of further truncation of the predicted hairpins (FIG. 17A) on the cleavage efficiency of ThermoCas9 was evaluated by performing a cleavage time-series in which all the components (sgRNA, ThermoCas9, substrate DNA) were pre-heated separately at different temperatures (37-65° C.) for 1, 2 and 5 min before combining and incubating them for 1 hour at various assay temperatures (37-65° C.). The number of predicted stem-loops of the tracrRNA scaffold seemed to play a crucial role in DNA cleavage; when all three loops were present, the cleavage efficiency was the highest at all tested temperatures, whereas the efficiency decreased upon removal of the 3' hairpin (FIG. 17B). Moreover, the cleavage efficiency drastically dropped upon removal of both the middle and the 3' hairpins (FIG. 22). Whereas pre-heating ThermoCas9 at 65° C. for 1 or 2 min resulted in detectable cleavage, the cleavage activity was abolished after 5 min incubation. The thermostability assay showed that sgRNA variants without the 3' stem-loop result in decreased stability of the ThermoCas9 protein at 65° C., indicating that a full length tracrRNA is required for optimal ThermoCas9-based DNA cleavage at elevated temperatures. Additionally, we also varied the lengths of the spacer sequence (from 25 to 18 nt) and found that spacer lengths of 23, 21, 20 and 19 cleaved the targets with the highest efficiency. The cleavage efficiency drops significantly when a spacer of 18 nt is used.

Figure 17C:
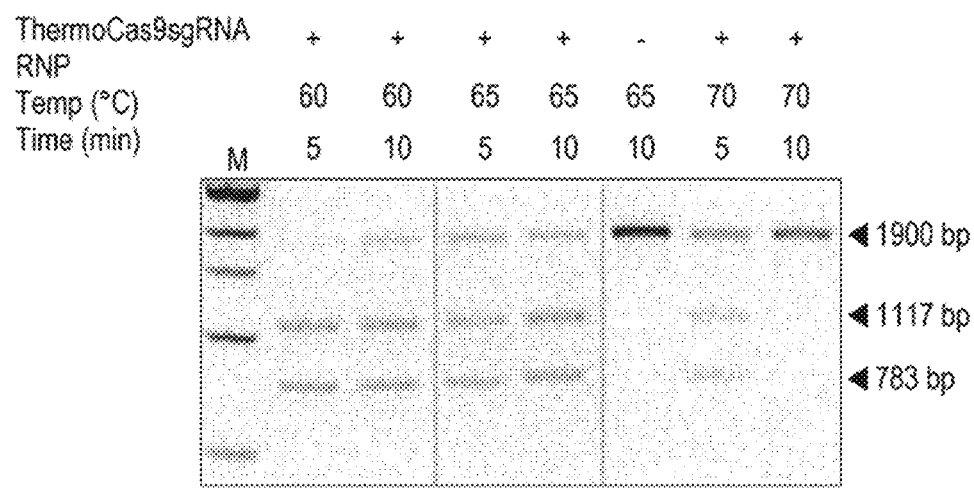
Figure 17D:
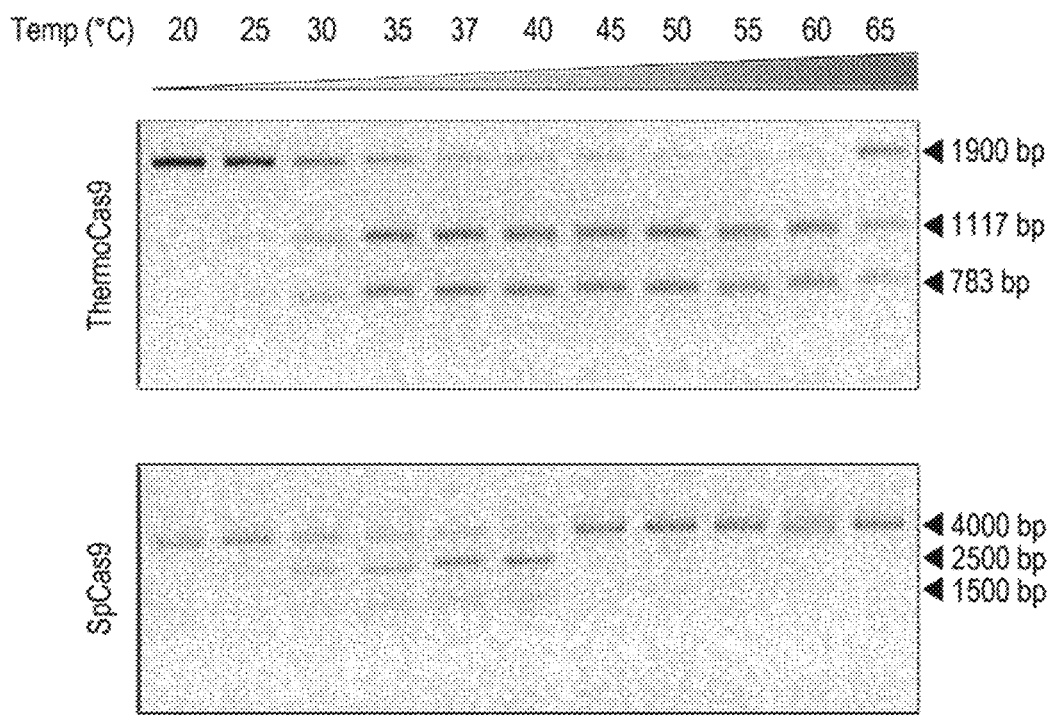

In vivo, the ThermoCas9:sgRNA RNP complex is probably formed within minutes. Together with the above findings, the activity and thermostability of the RNP was evaluated. Pre-assembled RNP complex was heated at 60, 65 and 70° C. for 5 and 10 min before adding pre-heated DNA and subsequent incubation for 1 hour at 60, 65 and 70° C. Strikingly, the ThermoCas9 RNP was active up to 70° C., in spite of its pre-heating for 5 min at 70° C. (FIG. 17C). This finding confirmed our assumption that the ThermoCas9 stability strongly correlates with the association of an appropriate sgRNA guide (Ma et al., *Mol. Cell* 160, 398-407 (2015)). It would be advantageous in some applications for the ThermoCas9 to have a broad temperature activity range, that is, to be functional at both low and high temperatures. Also, in some circumstances, it would be advantageous if the activity of the ThermoCas9 could be restricted to narrower temperature ranges, for example, active at only low or only high temperatures. Consequently, the ability to manipulate the range of temperatures at which ThermoCas9 is capable of targeted cleavage or binding or at which targeted cleavage or binding takes place efficiently, by modifying structural features of ThermoCas9 or associated elements (such as the sgRNA), would enable a greater level of control to be exerted over nucleic acid sequence manipulation. Hence, we set out to compare the ThermoCas9 temperature range to that of the *Streptococcus pyogenes* Cas9 (SpCas9). Both Cas9 homologues were subjected to in vitro activity assays between 20 and 65° C. Both proteins were incubated for 5 min at the corresponding assay temperature prior to the addition of the sgRNA and the target DNA molecules. In agreement with previous analysis, the mesophilic SpCas9 was active only between 25 and 44° C. (FIG. 17D); above these temperature SpCas9 activity rapidly decreased to undetectable levels. In contrast, ThermoCas9 cleavage activity could be detected between 25 and 65° C. (FIG. 17D). This indicates the potential to use ThermoCas9 as a genome editing tool for both thermophilic and mesophilic organisms.

Figure 23A:
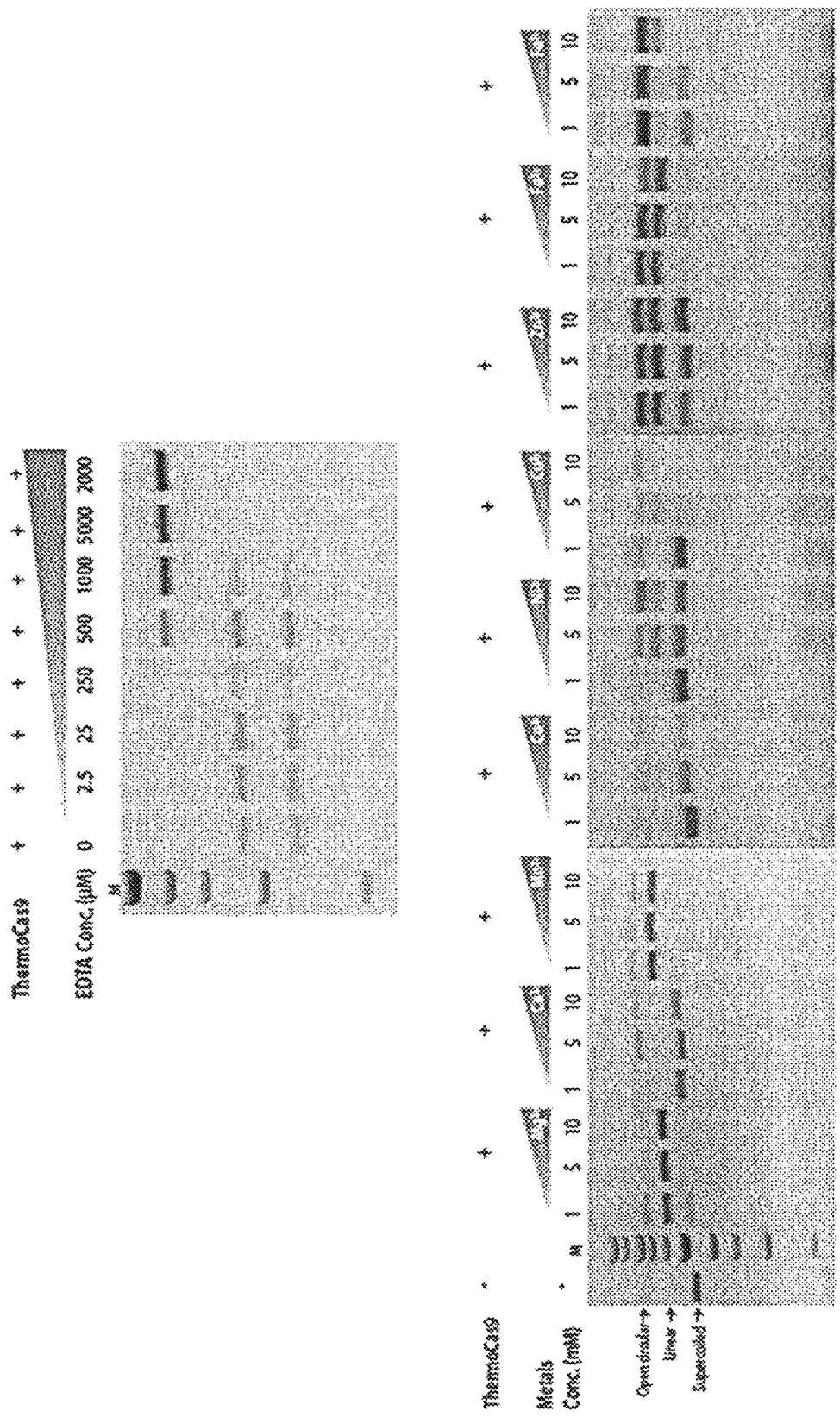

Previously characterized, mesophilic Cas9 endonucleases employ divalent cations to catalyze the generation of DSBs in target DNA (Jinek et al. *Science* 337, 816-821 (2012); Chen et al. *J. Biol. Chem.* 289, 13284-13294 (2014)). To evaluate which cations contribute to DNA cleavage by ThermoCas9, plasmid cleavage assays were performed in the presence of one of the following divalent cations: $Mg^{2+}$, $Ca^{2+}$, $Mn^{2+}$, $Co^{2+}$, $Ni^{2+}$, and $Cu^{2+}$; an assay with the cation-chelating agent EDTA was included as negative control. As expected, target dsDNA was cleaved in the presence of divalent cations and remained intact in the presence of EDTA (FIG. 23A). Based on reports that certain type-IIC systems were efficient single stranded DNA cutters (Ma et al. *Mol. Cell* 60, 398-407 (2015); Zhang et al. *Mol. Cell* 60, 242-255 (2015)), we tested the activity of ThermoCas9 on ssDNA substrates. However, no cleavage was observed, indicating that ThermoCas9 is a dsDNA nuclease (FIG. 23B).

Example 13: ThermoCas9-Based Gene Deletion in the Thermophile *B. smithii*

ThermoCas9 is used as a genome editing tool for thermophilic bacteria. Here it is shown in *Bacillus smithii* ET 138 cultured at 55° C. In order to use a minimum of genetic parts a single plasmid approach was used. A set of pNW33n-based pThermoCas9 plasmids was produced containing the thermocas9 gene under the control of the native xylL promoter ($P_{xylL}$), also a homologous recombination template for repairing Cas9-induced double stranded DNA breaks within a gene of interest, and a sgRNA expressing module under control of the constitutive pta promoter ($P_{pta}$) from *Bacillus coagulans* (FIG. 4A).

The first goal was the deletion of the full length pyrF gene from the genome of *B. smithii* ET 138. The pNW33n-derived plasmids pThermoCas9_bsΔpyrF1 and pThermoCas9_bsΔpyrF2 were used for expression of different ThermoCas9 guides with spacers targeting different sites of the pyrF gene, while a third plasmid (pThermoCas9_ctrl) contained a random non-targeting spacer in the sgRNA expressing module. Transformation of *B. smithii* ET 138 competent cells at 55° C. with the control plasmids pNW33n (no guide) and pThermoCas9_ctrl resulted in the formation of ~200 colonies each. Out of 10 screened pThermoCas9_ctrl colonies, none contained the ΔpyrF genotype, confirming findings from previous studies that homologous recombination in *B. smithii* ET 138 is not sufficient to obtain clean mutants (Mougiakos et al. *ACS Synth. Biol.* 6, 849-861 (2017); Bosma et al. *Microb. Cell Fact.* 14, 99 (2015)). In contrast, transformation with the pThermoCas9_bsΔpyrF1 and pThermoCas9_bsΔpyrF2 plasmids resulted in 20 and 0 colonies respectively, confirming the in vivo activity of ThermoCas9 at 55° C. and verifying the above described broad in vitro temperature range of the protein. Out of ten pThermoCas9_ΔpyrF1 colonies screened, one was a clean ΔpyrF mutant whereas the rest had a mixed wild type/ΔpyrF genotype (FIG. 4B), proving the applicability of the system, as the designed homology directed repair of the targeted pyrF gene was successful. Nonetheless, in the tightly controlled SpCas9-based counter-selection system we previously developed the pyrF deletion efficiency was higher (Olson et al., *Curr. Opin. Biotechnol.* 33, 130-141 (2015)). The low number of obtained transformants and clean mutants in the Thermo-Cas9-based tool can be explained by the low homologous recombination efficiency in *B. smithii* (Olson et al., *Curr. Opin. Biotechnol.* 33, 130-141 (2015)) combined with the constitutive expression of highly active ThermoCas9. It is anticipated that the use of a tightly controllable promoter will increase efficiencies.

Example 14: ThermoCas9-Based Gene Deletion in the Mesophile *Pseudomonas putida*

To broaden the applicability of the ThermoCas9-based genome editing tool, and to evaluate whether in vitro results could be confirmed in vivo, its activity in the mesophilic Gram-negative bacterium *P. putida* KT2440 was evaluated by combining homologous recombination and ThermoCas9-based counter-selection. For this organism, a Cas9-based tool has not been reported to date. Once more, we followed a single plasmid approach. We constructed the pEMG-based pThermoCas9_ppΔpyrF plasmid containing the thermocas9 gene under the control of the 3-methylbenzoate-inducible Pm-promoter, a homologous recombination template for deletion of the pyrF gene and a sgRNA expressing module under the control of the constitutive P3 promoter. After transformation of *P. putida* KT2440 cells and PCR confirmation of plasmid integration, a colony was inoculated in selective liquid medium for overnight culturing at 37° C. The overnight culture was used for inoculation of selective medium and ThermoCas9 expression was induced with 3-methylbenzoate. Subsequently, dilutions were plated on non-selective medium, supplemented with 3-methylbenzoate. For comparison, a parallel experiment without inducing ThermoCas9 expression with 3-methylbenzoate was performed. The process resulted in 76 colonies for the induced culture and 52 colonies for the non-induced control culture. For the induced culture, 38 colonies (50%) had a clean deletion genotype and 6 colonies had mixed wild-type/deletion genotype. On the contrary, only 1 colony (2%) of the non-induced culture had the deletion genotype and there were no colonies with mixed wild-type/deletion genotype retrieved (FIG. 24). These results show that ThermoCas9 can be used as an efficient counter-selection tool in the mesophile *P. putida* KT2440 when grown at 37° C.

Example 15: ThermoCas9-Based Gene Silencing

An efficient thermoactive transcriptional silencing CRISPRi tool is currently not available. Such a system could be useful in a number of applications. For example, such a system would greatly facilitate metabolic studies of thermophiles. A catalytically dead variant of ThermoCas9 could serve this purpose by steadily binding to DNA elements without introducing dsDNA breaks. To this end, we identified the RuvC and HNH catalytic domains of ThermoCas9 and introduced the corresponding D8A and H582A mutations for creating a dead (d) ThermoCas9. After confirmation of the designed sequence, Thermo-dCas9 was heterologously produced, purified and used for an in vitro cleavage assay with the same DNA target as used in the aforementioned ThermoCas9 assays; no cleavage was observed confirming the catalytic inactivation of the nuclease.

Towards the development of a Thermo-dCas9-based CRISPRi tool, we aimed for the transcriptional silencing of the highly expressed ldhL gene from the genome of *B. smithii* ET138. We constructed the pNW33n-based vectors pThermoCas9i_ldhL and pThermoCas9i_ctrl. Both vectors contained the thermo-dCas9 gene under the control of $P_{xylL}$ promoter and a sgRNA expressing module under the control of the constitutive $P_{pta}$ promoter (FIG. 4C). The pThermoCas9i_ldhL plasmid contained a spacer for targeting the non-template DNA strand at the 5' end of the 138 ldhL gene in *B. smithii* ET 138 (Figure S7). The position and targeted strand selection were based on previous studies (Bikard et al. *Nucleic Acids Res.* 41, 7429-7437 (2013); Larson et al. *Nat. Protoc.* 8, 2180-2196 (2013)), aiming for the efficient down-regulation of the ldhL gene. The pThermoCas9i_ctrl plasmid contained a random non-targeting spacer in the sgRNA-expressing module. The constructs were used to transform *B. smithii* ET 138 competent cells at 55° C. followed by plating on LB2 agar plates, resulting in equal amounts of colonies. Two out of the approximately 700 colonies per construct were selected for culturing under microaerobic lactate-producing conditions for 24 hours, as described previously (Bosma et al. *Appl. Environ. Microbiol.* 81, 1874-1883 (2015)). The growth of the pThermoCas9i_ldhL cultures was 50% less than the growth of the pThermoCas9i_ctrl cultures (FIG. 4E). We have previously shown that deletion of the ldhL gene leads to severe growth retardation in *B. smithii* ET 138 due to a lack of Ldh-based $NAD^+$-regenerating capacity under microaerobic conditions (Bosma et al. *Microb. Cell Fact.* 14, 99 (2015)). Thus, the observed decrease in growth is likely caused by the transcriptional inhibition of the ldhL gene and subsequent redox imbalance due to loss of $NAD^+$-regenerating capacity. Indeed, HPLC analysis revealed 40% reduction in lactate production of the ldhL silenced cultures, and RT-qPCR analysis showed that the transcription levels of the ldhL gene were significantly reduced in the pThermoCas9i_ldhL cultures compared to the pThermoCas9i_ctrl cultures (FIG. 4E).

Example 16: Summary

Most CRISPR-Cas applications are based on RNA-guided DNA interference by Class 2 CRISPR-Cas proteins, such as Cas9 and Cas12a (Komor et al., *Cell* 168, 20-36 (2017); Puchta, *Curr. Opin. Plant Biol.* 36, 1-8 (2017); Xu et al. *J. Genet. Genomics* 42, 141-149 (2015); Tang et al. *Nat. Plants* 3, 17018 (2017); Zetsche et al. *Nat. Biotechnol.* 35, 31-34 (2016); Mougiakos et al., *Trends Biotechnol.* 34, 575-587 (2016)). Prior to this work, no Class 2 CRISPR-Cas immune systems were identified and characterized in thermophilic microorganisms, in contrast to the highly abundant Class 1 CRISPR-Cas systems present in thermophilic bacteria and archaea (Makarova et al., *Nat. Rev. Microbiol.* 13, 722-736 (2015); Weinberger et al., *MBio* 3, e00456-12 (2012)), a few of which have been used for genome editing of thermophiles (Li et al. *Nucleic Acids Res.* 44, e34-e34 (2016)). As a result, the application of CRISPR-Cas technologies was mainly restricted to temperatures below 42° C., due to the mesophilic nature of the employed Cas-endonucleases. Hence, this has excluded application of these technologies in obligate thermophiles and in experimental approaches that require elevated temperatures and/or improved protein stability.

The inventors have characterized ThermoCas9, a Cas9 orthologue from the thermophilic bacterium *G. thermodenitrificans* T12, a strain that we previously isolated from compost (Daas et al., *Biotechnol. Biofuels* 9, 210 (2016)). Data mining revealed additional Cas9 orthologues in the genomes of other thermophiles, which were nearly identical to ThermoCas9, for the first time showing that CRISPR-Cas type II systems do exist in thermophiles, at least in some branches of the *Bacillus* and *Geobacillus* genera. The inventors have shown that ThermoCas9 is active in vitro in a wide temperature range of 20-70° C., which is much broader than the 25-44° C. range of its mesophilic orthologue SpCas9. The extended activity and stability of ThermoCas9 allows for its application in molecular biology techniques that require DNA manipulation at temperatures of 20-70° C., as well as its exploitation in harsh environments that require robust enzymatic activity. Furthermore, the inventors have identified several factors that are important for conferring the thermostability of ThermoCas9. Firstly, the inventors have demonstrated that the PAM preferences of Thermo-Cas9 are very strict for activity in the lower part of the temperature range 30° C.), whereas more variety in the PAM is allowed for activity at the moderate to optimal temperatures (37-60° C.). Secondly, the inventors have demonstrated that ThermoCas9 activity and thermostability strongly depends on the association with an appropriate sgRNA guide. Without wishing to be bound by any particular theory, the inventors hypothesise that this stabilization of the multi-domain Cas9 protein is most likely the result of a major conformational change from an open/flexible state to a rather compact state, as described for SpCas9 upon guide binding (Jinek et al. *Science* 343, 1247997-1247997 (2014)).

Based on the here described characterization of the novel ThermoCas9, the inventors have successfully developed genome engineering tools for strictly thermophilic prokaryotes. We showed that ThermoCas9 is active in vivo at 55° C. and 37° C. and we adapted the current Cas9-based engineering technologies for the thermophile *B. smithii* ET 138 and the mesophile *P. putida* KT2440. Due to the wide temperature range of ThermoCas9, it is anticipated that the simple, effective and single plasmid-based ThermoCas9 approach will be suitable for a wide range of thermophilic and mesophilic microorganisms that can grow at temperatures from 37° C. up to 70° C. This complements the existing mesophilic technologies, allowing their use for a large group of organisms for which these efficient tools were thus far unavailable.

Screening natural resources for novel enzymes with desired traits is unquestionably valuable. Previous studies have suggested that the adaptation of a mesophilic Cas9 orthologue to higher temperatures, with directed evolution and protein engineering, would be the best approach towards the construction of a thermophilic Cas9 protein. Instead, we identified a Glade of Cas9 in some thermophilic bacteria, and transformed one of these thermostable ThermoCas9 variants into a powerful genome engineering tool for both thermophilic and mesophilic organisms. With this study, we further stretched the potential of the Cas9-based genome editing technologies and open new possibilities for using Cas9 technologies in novel applications under harsh conditions or requiring activity over a wide temperature range.

Example 17: Materials and Methods a. Bacterial Strains and Growth Conditions

The moderate thermophile *B. smithii* ET 138 ΔsigF ΔhsdR (Mougiakos, et al., (2017) ACS Synth. Biol. 6, 849-861) was used for the gene editing and silencing experiments using ThermoCas9. It was grown in LB2 medium (Bosma, et al. *Microb. Cell Fact.* 14, 99 (2015)) at 55° C. For plates, 30 g of agar (Difco) per liter of medium was used in all experiments. If needed chloramphenicol was added at the concentration of 7 μg/mL. For protein expression, *E. coli* Rosetta (DE3) was grown in LB medium in flasks at 37° C. in a shaker incubator at 120 rpm until an $OD_{600\ nm}$ of 0.5 was reached after the temperature was switched to 16° C. After 30 min, expression was induced by addition of isopropyl-1-thio-β-d-gal-actopyranoside (IPTG) to a final concentration of 0.5 mM, after which incubation was continued at 16° C. For cloning PAM constructs for $6^{th}$ and $7^{th}$, and 8th positions, DH5-alpha competent *E. coli* (NEB) was transformed according to the manual provided by the manufacturer and grown overnight on LB agar plates at 37° C. For cloning degenerate 7-nt long PAM library, electro-competent DH10B *E. coli* cells were transformed according to standard procedures (Sambrook, Fritsch & Maniatis, T. *Molecular cloning: a laboratory manual.* (Cold Spring Harbor Laboratory, 1989) and grown on LB agar plates at 37° C. overnight. *E. coli* DH5α λpir (Invitrogen) was used for *P. putida* plasmid construction using the transformation procedure described by Ausubel et al. (*Current Protocols in Molecular Biology.* (John Wiley & Sons, Inc., 2001). doi: 10.1002/0471142727). For all *E. coli* strains, if required chloramphenicol was used in concentrations of 25 mg/L and kanamycin in 50 mg/L. *Pseudomonas putida* KT2440 (DSM 6125) strains were cultured at 37° C. in LB medium unless stated otherwise. If required, kanamycin was added in concentrations of 50 mg/L and 3-methylbenzoate in a concentration of 3 mM.

b. ThermoCas9 Expression and Purification

ThermoCas9 was PCR-amplified from the genome of *G. thermodenitrificans* T12, then cloned and heterologously expressed in *E. coli* Rosetta (DE3) and purified using FPLC by a combination of $Ni^{2+}$-affinity, anion exchange and gel filtration chromatographic steps. The gene sequence was inserted into plasmid pML-1B (obtained from the UC Berkeley MacroLab, Addgene #29653) by ligation-independent cloning using oligonucleotides (Table 2) to generate a protein expression construct encoding the ThermoCas9 polypeptide sequence (residues 1-1082) fused with an N-terminal tag comprising a hexahistidine sequence and a Tobacco Etch Virus (TEV) protease cleavage site. To express the catalytically inactive ThermoCas9 protein (Thermo-dCas9), the D8A and H582A point mutations were inserted using PCR and verified by DNA sequencing.

TABLE 2

Oligonucleotides used in this study.

| | Oligo | Sequence | Description | SEQ ID |
|---|---|---|---|---|
| PAM Library construction | BG6494 | TATGCCTCATGAGATTATCAAAAAGGATCTTCA CNNNNNNNCTAGATCCTTTTAAATTAAAAATGAA GTTTTAAATCAATC | FW for construction of in vitro target DNA with 7-nt long random PAM sequence | 59 |
| | BG6495 | TATGCCGGATCCTCAGACCAAGTTTACTCATATA TACTTTAGATTGATTTAAAACTTCATTTTAATTT AAAAGGATCTAG | RV for construction of in vitro target DNA sequences | 60 |
| | BG7356 | TCGTCGGCAGCGTCAGATGTGTATAAGAGACAG-T | Adaptor when annealed with BG7357, ligates to A-tailed ThermoCas9 cleaved fragments | 61 |
| | BG7357 | CTGTCTCTTATACACATCTGACGCTGCCGACGA | Adaptor when annealed with BG7356, ligates to A-tailed ThermoCas9 cleaved fragments | 62 |
| | BG7358 | TCGTCGGCAGCGTCAG | FW sequencing adaptor for PCR amplification of the ThermoCas9 cleaved fragments | 63 |
| | BG7359 | GTCTCGTGGGCTCGGAGATGTGTATAAGAGACAG GACCATGATTACGCCAAGC | RV sequencing adaptor for PCR amplification of the ThermoCas9 cleaved fragments | 64 |
| | BG7616 | TCGTCGGCAGCGTCAGATGTGTATAAGAGACAG GGTCATGATTATCAAAAAGGATCTTC | RV sequencing adaptor for PCR amplification of the control fragments | 65 |
| | BG8157 | TATGCCTCATGAGATTATCAAAAAGGATCTTCA CCCCCCCAGCTAGATCCTTTTAAATTAAAAATG AAGTTTTAAATCAATC | FW for construction of in vitro target DNA with PAM "CCCCCAG" | 66 |
| | BG8158 | TATGCCTCATGAGATTATCAAAAAGGATCTTCA CCCCCCAACTAGATCCTTTTAAATTAAAAATGA AGTTTTAAATCAATC | FW for construction of in vitro target DNA with PAM "CCCCCAA" | 67 |
| | BG8159 | TATGCCTCATGAGATTATCAAAAAGGATCTTCA CCCCCCATCTAGATCCTTTTAAATTAAAAATGA AGTTTTAAATCAATC | FW for construction of in vitro target DNA with PAM "CCCCCAT" | 68 |
| | BG8160 | TATGCCTCATGAGATTATCAAAAAGGATCTTCA CCCCCCACCTAGATCCTTTTAAATTAAAAATGA AGTTTTAAATCAATC | FW for construction of in vitro target DNA with PAM "CCCCCAC" | 69 |
| | BG8161 | TATGCCTCATGAGATTATCAAAAAGGATCTTCA CNNNNTNNCTAGATCCTTTTAAATTAAAAATGAA GTTTTAAATCAATC | FW for construction of in vitro target DNA with PAM "NNNNTNN" | 70 |
| | BG8363 | ACGGTTATCCACGAATCAG | FW for PCR linearization of PAM identification libraries | 71 |
| | BG8364 | CGGGATTGACTTTTAAAAAGG | RV for PCR linearization of PAM identification libraries | 72 |
| | BG8763 | TATGCCTCATGAGATTATCAAAAAGGATCTTCA CCCCCCAAACTAGATCCTTTTAAATTAAAAATGA AGTTTTAAATCAATC | FW for construction of in vitro target DNA with PAM position 6&7 "AA" | 73 |
| | BG8764 | TATGCCTCATGAGATTATCAAAAAGGATCTTCA CCCCCCATACTAGATCCTTTTAAATTAAAAATGA AGTTTTAAATCAATC | FW for construction of in vitro target DNA with PAM position 6&7 "AT" | 74 |
| | BG8765 | TATGCCTCATGAGATTATCAAAAAGGATCTTCA CCCCCCAGACTAGATCCTTTTAAATTAAAAATG AAGTTTTAAATCAATC | FW for construction of in vitro target DNA with PAM position 6&7 "AG" | 75 |
| | BG8766 | TATGCCTCATGAGATTATCAAAAAGGATCTTCA CCCCCCACACTAGATCCTTTTAAATTAAAAATGA AGTTTTAAATCAATC | FW for construction of in vitro target DNA with PAM position 6&7 "AC" | 76 |
| | BG8767 | TATGCCTCATGAGATTATCAAAAAGGATCTTCA | FW for construction of in vitro target DNA with PAM position | 77 |

TABLE 2-continued

Oligonucleotides used in this study.

| Oligo | Sequence | Description | SEQ ID |
|---|---|---|---|
| | CCCCCTAACTAGATCCTTTTAAATTAAAAATGA AGTTTTAAATCAATC | 6&7 "TA" | 78 |
| BG8768 | TATGCCTCATGAGATTATCAAAAAGGATCTTCA CCCCCCTAACTAGATCCTTTTAAATTAAAAATGA AGTTTTAAATCAATC | FW for construction of in vitro target DNA with PAM position 6&7 "TT" | 79 |
| BG8769 | TATGCCTCATGAGATTATCAAAAAGGATCTTCA CCCCCCTGACTAGATCCTTTTAAATTAAAAATGA AGTTTTAAATCAATC | FW for construction of in vitro target DNA with PAM position 6&7 "TG" | 80 |
| BG8770 | TATGCCTCATGAGATTATCAAAAAGGATCTTCA CCCCCCTCACTAGATCCTTTTAAATTAAAAATGA AGTTTTAAATCAATC | FW for construction of in vitro target DNA with PAM position 6&7 "TC" | 81 |
| BG8771 | TATGCCTCATGAGATTATCAAAAAGGATCTTCA CCCCCCGAACTAGATCCTTTTAAATTAAAAATG AAGTTTTAAATCAATC | FW for construction of in vitro target DNA with PAM position 6&7 "GA" | 82 |
| BG8772 | TATGCCTCATGAGATTATCAAAAAGGATCTTCA CCCCCCGTACTAGATCCTTTTAAATTAAAAATGA AGTTTTAAATCAATC | FW for construction of in vitro target DNA with PAM position 6&7 "GT" | 83 |
| BG8773 | TATGCCTCATGAGATTATCAAAAAGGATCTTCA CCCCCCGGACTAGATCCTTTTAAATTAAAAATG AAGTTTTAAATCAATC | FW for construction of in vitro target DNA with PAM position 6&7 "GG" | 84 |
| BG8774 | TATGCCTCATGAGATTATCAAAAAGGATCTTCA CCCCCCGCACTAGATCCTTTTAAATTAAAAATG AAGTTTTAAATCAATC | FW for construction of in vitro target DNA with PAM position 6&7 "GC" | 85 |
| BG8775 | TATGCCTCATGAGATTATCAAAAAGGATCTTCA CCCCCCAACTAGATCCTTTTAAATTAAAAATGA AGTTTTAAATCAATC | FW for construction of in vitro target DNA with PAM position 6&7 "CA" | 86 |
| BG8776 | TATGCCTCATGAGATTATCAAAAAGGATCTTCA CCCCCCTACTAGATCCTTTTAAATTAAAAATG AAGTTTTAAATCAATC | FW for construction of in vitro target DNA with PAM position 6&7 "CT" | 87 |
| BG8777 | TATGCCTCATGAGATTATCAAAAAGGATCTTCA CCCCCCGACTAGATCCTTTTAAATTAAAAATG AAGTTTTAAATCAATC | FW for construction of in vitro target DNA with PAM position 6&7 "CG" | 88 |
| BG8778 | TATGCCTCATGAGATTATCAAAAAGGATCTTCA CCCCCCCACTAGATCCTTTTAAATTAAAAATGA AGTTTTAAATCAATC | FW for construction of in vitro target DNA with PAM position 6&7 "CC" | |
| BG6574 | AAGCTTGAAATAATACGACTCACTATAGG | FW for PCR amplification of the sgRNA template for the first PAM identification process (30 nt long spacer) | 89 |
| BG6576 | AAAAAGACCTTGACGTTTTCC | FW for PCR amplification of the sgRNA template for the first PAM identification process | 90 |
| BG9307 | AAGCTTGAAATAATACGACTCACTATAGGTGAGA | FW for PCR amplification of the sgRNA template for all the PAM identification processes except the first one (25 nt long spacer) | 91 |
| BG9309 | AAAACGCCTAAGAGTGGGGAATG | RV for PCR amplification of the sgRNA template for all the PAM identification processes except the first one | 92 |
| BG9310 | AAAAGGCGATAGGCGATCC | RV for PCR amplification of the 3-hairpins long sgRNA template for all the PAM identification processes except the first one | 93 |
| BG9311 | AAAACGGTCAGTCTGCCTATAG | RV for PCR amplification of the 2-hairpins long sgRNA template for all the PAM identification processes except the first one | 94 | sgRNA module for in vitro transcription

TABLE 2-continued

Oligonucleotides used in this study.

| Oligo | Sequence | Description | SEQ ID |
|---|---|---|---|
| BG9308 | AAGCTTGAAATAATACGACTCACTATAGGTGAGATTATCAAAAAGGATCTTCACGTC | pT7 and 25 nt spacer sgRNA Fw | 95 |
| BG10118 | AAGCTTGAAATAATACGACTCACTATAGGAGATTATCAAAAAGGATCTTCACGTCA | pT7 and 24 nt spacer sgRNA Fw | 96 |
| BG10119 | AAGCTTGAAATAATACGACTCACTATAGGAAGATTATCAAAAAGGATCTTCACGTCAG | pT7 and 23 nt spacer sgRNA Fw | 97 |
| BG10120 | AAGCTTGAAATAATACGACTCACTATAGGATTATCAAAAGGATCTTCACGTCATAGT | pT7 and 22 nt spacer sgRNA Fw | 98 |
| BG10121 | AAGCTTGAAATAATACGACTCACTATAGGAATTATCAAAAAGGATCTTCACGTCATAGTT | pT7 and 21 nt spacer sgRNA Fw | 99 |
| BG10122 | AAGCTTGAAATAATACGACTCACTATAGGTTATCAAAAGGATCTTCACGTCATAGTC | pT7 and 20 nt spacer sgRNA Fw | 100 |
| BG10123 | AAGCTTGAAATAATACGACTCACTATAGGTATCAAAAGGATCTTCACGTCATAGTTC | pT7 and 19 nt spacer sgRNA Fw | 101 |
| BG10124 | AAGCTTGAAATAATACGACTCACTATAGGATCAAAAGGATCTTCACGTCATAGTTC | pT7 and 18 nt spacer sgRNA Fw | 102 |
| BG9312 | AAAACGCCTAAGAGTGGGGAATGCCCGAAGAAAGCGGGCGATAGGCGATCC | 3 loops sgRNA OH Rv | 103 |
| BG8191 | AAGCTTGGCGTAATCATGGTC | For the construction of the pThermoCas9_ctrl plasmid & pThermoCas9_bsΔpyrF1/2 | 104 |
| BG8192 | TCATGAGTTCCCATGTTGTG | For the construction of the pThermoCas9_ctrl plasmid & pThermoCas9_bsΔpyrF1/2 | 105 |
| BG8194 | tatgccgaatcacaacatgggaactcatgaGAACATCCTCTTTCTTAG | For the construction of the pThermoCas9_ctrl plasmid & pThermoCas9_bsΔpyrF1/2 | 106 |
| BG8195 | gccgatatcaagacgcgattttatactcatTTAAGGTACCTCCTCGATTG | For the construction of the pThermoCas9_ctrl plasmid & pThermoCas9_bsΔpyrF1/2 | 107 |
| BG8196 | ATGAAGTATAAAATCGTCTTG | For the construction of the pThermoCas9_ctrl plasmid & pThermoCas9_bsΔpyrF1/2 | 108 |
| BG8197 | TAACGGACGGATAGTTTC | For the construction of the pThermoCas9_ctrl plasmid & pThermoCas9_bsΔpyrF1/2 | 109 |
| BG8198 | gaaagcccggggaaactatccgtccgttataAATCAGACAAAATGGCCTGCTTATG | For the construction of the pThermoCas9_ctrl plasmid & pThermoCas9_bsΔpyrF1/2 | 110 |
| BG8263 | gaactgacacttatttcagaatgacGTATAACGGTATCCATTTTAAGATAATCC | For the construction of the pThermoCas9_ctrl plasmid | 111 |
| BG8268 | accgtatacgtccattctgaaataaagtGTCATAGTTCCCCTGAGAT | For the construction of the pThermoCas9_ctrl plasmid | 112 |
| BG8210 | aacagctatgaccatgattacgccaagatCCCCTCCCATGCACAATAG | For the construction of the pThermoCas9_ctrl plasmid & | 113 |
| BG8261 | gaactatgacatatggagttttaaatccagGTATAACGGTATCCATTTTAAGATAATCC | For the construction of the pThermoCas9_bsΔpyrF1 | 114 |
| BG8266 | accgtatactggattaaaactccatgatGTCATAGTTCCCCTGAGAT | For the construction of the pThermoCas9_bsΔpyrF2 | 115 |
| BG8317 | gaactatgaccaccagatcatcaacaagTATAACGGTATCCATTTTAAGAATAATCC | For the construction of the pThermoCas9_ΔbsΔpyrF2 | 116 |
| BG8320 | accgtatactgtgatgtaagctgggtgGTCATAGTTCCCCTGAGAT | For the construction of the pThermoCas9_bsΔpyrF2 | 117 |
| BG9075 | CTATCCGCATTACGTCTATC | For the construction of the pThermoCas91_ctrl | 118 |

TABLE 2-continued

Oligonucleotides used in this study.

| Oligo | Sequence | Description | SEQ ID |
|---|---|---|---|
| BG9076 | GCGTCGACTTCTGTATAGC | For the construction of the pThermoCas9i_ctrl | 119 |
| BG9091 | TGAAGTATAAATCGGTCTTGCTATCGGCATTAC GTCTATC | For the construction of the pThermoCas9i_ctrl | 120 |
| BG9092 | CAAGCTTCGGCTGTATGGAATCACAGCGTCGACT TCTGTATAGC | For the construction of the pThermoCas9i_ctrl | 121 |
| BG9077 | GCTGTGATTCCATACAG | For the construction of the pThermoCas9i_ctrl | 122 |
| BG9267 | GGTGCAGTAGGTTGCAGCTATGCTTGTATAACGG TATCCAT | For the construction of the pThermoCas9i_ctrl | 123 |
| BG9263 | AAGCATAGCTGCAACCTACTGCACCGTCATAGTT CCCCTGAGATTATCG | For the construction of the pThermoCas9i_ctrl | 124 |
| BG9088 | TCATGACCAAAATCCCTTAACG | For the construction of the pThermoCas9i_ctrl | 125 |
| BG9089 | TTAAGGGATTTTGGTCATGAGAACATCCTCTTTCT TAG | For the construction of the pThermoCas9i_ctrl | 126 |
| BG9090 | GCAAGACCGATTTTATACTTCATTTAAG | For the construction of the pThermoCas9i_ctrl | 127 |
| BG9548 | GGATCCCATGACGCTAGTATCCAGCTGGGTCATA GTTCCCCTGAGATTATCG | For the construction of the pThermoCas9i_ldhL | 128 |
| BG9601 | TTCAATATTTTTTTTGAATAAAAAAATACGATACA ATAAAAATGTCTAGAAAAAGATAAAAATG | For the construction of the pThermoCas9i_ldhL | 129 |
| BG9600 | TTTTTATTCAAAAAAATATTGAATTTTAAAA TGATGTGCTAGTATGAAG | For the construction of the pThermoCas9i_ldhL | 130 |
| BG9549 | CCAGCTGGATACTAGCGTCATGGGATCCGTATAA CGGTATCCATTTTAAGAATAATCC | For the construction of the pThermoCas9i_ldhL | 131 |
| BG8552 | TCGGGGGTTCGTTCCCTTG | FW to check genomic pyrF deletion KO check | 132 |
| BG8553 | CTTACACAGCCAGTGACGGAAC | RV to check genomic pyrF deletion KO check | 133 |
| BG2365 | GCCGGCGTCCCGGAAAACGA | For the construction of the pThermoCas9_ppΔpyrF | 134 |
| BG2366 | GCAGGTCGGGTTCCTGCATCCATGCCCCCGAAC T | For the construction of the pThermoCas9_ppΔpyrF | 135 |
| BG2367 | ggcttcggaatcgttccggacgccggcacgCGCATTGGCAAGG CCAAG | For the construction of the pThermoCas9_ppΔpyrF | 136 |
| BG2368 | gacacaggcatcggtgCAGGGTCTCTTGGCAAGTC | For the construction of the pThermoCas9_ppΔpyrF | 137 |
| BG2369 | gccaagagaccctgCACCGATGCCTGTCGAACC | For the construction of the pThermoCas9_ppΔpyrF | 138 |
| BG2370 | cttggcggaaaacgtcaaggtatttacACGCGACATCAACTTCA AGGC | For the construction of the pThermoCas9_ppΔpyrF | 139 |
| BG2371 | atgacgagctgttcaccagcgcTATTATTGAAGCATTTAT CAGGG | For the construction of the pThermoCas9_ppΔpyrF | 140 |
| BG2372 | GTAAAAAGACCTTGACGTTTC | For the construction of the pThermoCas9_ppΔpyrF | 141 |
| BG2373 | tatgaagcgggccattTGAAGACGAAAGGGCCTC | For the construction of the pThermoCas9_ppΔpyrF | 142 |
| BG2374 | taatacgcgtgctggtgaacagctcGTCATAGTTCCCCTGAGA TTATCG | For the construction of the pThermoCas9_ppΔpyrF | 143 |
| BG2375 | tgggtcatgaacatATGAAGTATAAAATCGGTCTTG | For the construction of the pThermoCas9_ppΔpyrF | 144 |
| BG2376 | ccattcgtatcAAATGCCCGCTTCATAAGCAG | For the construction of the pThermoCas9_ppΔpyrF | 145 |
| BG2377 | gattttatacTTCATATGTTCATGACTCCATTATTATTG | For the construction of the pThermoCas9_ppΔpyrF | 146 |
| BG2378 | gggggcatgatgcGTAGGAACCCGACCTGCATTGG | For the construction of the pThermoCas9_ppΔpyrF | 147 |
| BG2381 | ACACGCGGATCACTTACC | For the construction of the pThermoCas9_ppΔpyrF | 148 |
| BG2382 | TGGACGTGTACTTCGACAAC | FW for confirmation of pyrF deletion and pyrF deletion in P. putida | 149 |
| BG2135 | ACACGCGGATGCACTTACC | RV for confirmation of pyrF deletion in P. putida | 150 |

TABLE 2-continued

Oligonucleotides used in this study.

| | Oligo | Sequence | Description | SEQ ID |
|---|---|---|---|---|
| Sequencing primers | BG8196 | TGGACGTGTACTTCGACAAC | thermocas9 seq. 1 | 151 |
| | BG8197 | TAACGGACGGATAGTTTC | thermocas9 seq. 2 | 152 |
| | BG6850 | GCCTCATGAATGCAGCGATGGTCCGGTGTTC | pyrF US | 153 |
| | BG6849 | GCCTCATGAGTTCCCATGTTGTGATTC | pyrF DS | 154 |
| | BG6769 | CAATCCAACTGGGCTTGAC | thermocas9 seq. 3 | 155 |
| | BG6841 | CAAGAACTTTATTGGTATAG | thermocas9 seq. 4 | 156 |
| | BG6840 | TTGCAGAAATGGTTGTCAAG | thermocas9 seq. 5 | 157 |
| | BG9215 | GAGATAATGCCGACTGTAC | pNW33n backbone seq. 1 | 158 |
| | BG9216 | AGGGCTCGCCTTTGGAAG | pNW33n backbone seq. 2 | 159 |
| | BG9505 | GTTGCCAACGTTCTGAG | thermocas9 seq. 6 | 160 |
| | BG9506 | AATCCACGCCGTTTAG | thermocas9 seq. 7 | 161 |
| Cleavage assay | BG8363 | ACGGTTATCCACAGAATCAG | FW for PCR linearization of DNA target | 162 |
| | BG8364 | CGGGATTGACTTTTAAAAAGG | RV for PCR linearization of DNA target | 163 |
| | BG9302 | AAACTTCATTTTTAATTTAAAAGGATCTAGAACCCCCGTGAAGATCCTTTTTGATAATCTCATGACCAAAATCCCTTAACGTGAGTTTTCGTTCCACTGAGCGTCAGACCCCGTAGAAA | Non-template strand oligonucleotide for ssDNA cleavage assays | 164 |
| | BG9303 | TTTCTACGGGGTCTGACGCTCAGTGGAACGAAAACTCACGTTAAGGGATTTGGTCATGAGATTATCAAAAGGATCTTCACCCCCCCAACTAGATCCTTTAAATTAAAAATGAAGTTT | Template strand oligonucleotide for ssDNA cleavage assays | 165 |
| | BG9304 | TTTCTACGGGGTCTGACGCTCAGTGGAACGAAAACTCACGTTAAGGGATTTGGTCATGAGATTATCAAAAGGATCTTCACGGGGGGTTCTAGATCCTTTTAAATTAAAAATGAAGTTT | Template strand oligonucleotide for ssDNA cleavage assays | 166 |
| Thermo Cas9 expression and RT-qPCR | BG7886 | TACTTCCAATCCAATGCAAAGTATAAAATCGGTCTTGATATCG | FW LIC_thermocas9 | 167 |
| | BG7887 | TTATCCACTTCCAATGTTATTATAACGGACGGATAGTTTCCCGGCTTTC | RV LIC_thermocas9 | 168 |
| Thermo Cas9 expression | BG9665 | ATGACGAAAGGAGTTTCTTATTATG | RV qPCR check ldh1 | 169 |
| | BG9666 | AACGGTATTCCGTGATTAAG | FW qPCR check ldh1 | 170 |

Restriction sites are shown in italics. The PAMs are colored red. Spacer regions are shown in bold. Nucleotides in lowercase letters correspond to primer overhangs for HiFi DNA Assembly. LIC: Ligase Independent cloning; FW: Forward primer; RV: Reverse primer.

The proteins were expressed in E. coli Rosetta 2 (DE3) strain. Cultures were grown to an $OD_{600\ nm}$ of 0.5-0.6. Expression was induced by the addition of IPTG to a final concentration of 0.5 mM and incubation was continued at 16° C. overnight. Cells were harvested by centrifugation and the cell pellet was resuspended in 20 mL of Lysis Buffer (50 mM sodium phosphate pH 8, 500 mM NaCl, 1 mM DTT, 10 mM imidazole) supplemented with protease inhibitors (Roche cOmplete, EDTA-free) and lysozyme. Once homogenized, cells were lysed by sonication (Sonoplus, Bandelin) using a using an ultrasonic MS72 microtip probe (Bandelin), for 5-8 minutes consisting of 2 s pulse and 2.5 s pause at 30% amplitude and then centrifuged at 16,000×g for 1 hour at 4° C. to remove insoluble material. The clarified lysate was filtered through 0.22 micron filters (Mdi membrane technologies) and applied to a nickel column (Histrap HP, GE Lifesciences), washed and then eluted with 250 mM imidazole. Fractions containing ThermoCas9 were pooled and dialyzed overnight into the dialysis buffer (250 mM KCl, 20 mM HEPES/KOH, and 1 mM DTT, pH 7.5). After dialysis, sample was diluted 1:1 in 10 mM HEPES/KOH pH 8, and loaded on a heparin FF column pre-equilibrated in IEX-A buffer (150 mM KCl, 20 mM HEPES/KOH pH 8). Column was washed with IEX-A and then eluted with a gradient of IEX-C (2M KCl, 20 mM HEPES/KOH pH 8). The sample was concentrated to 700 µL prior to loading on a gel filtration column (HiLoad 16/600 Superdex 200) via FPLC (AKTA Pure). Fractions from gel filtration were analysed by SDS-PAGE; fractions containing ThermoCas9 were pooled and concentrated to 200 µL (50 mM sodium phosphate pH 8, 2 mM DTT, 5% glycerol, 500 mM NaCl) and either used directly for biochemical assays or frozen at −80° C. for storage.

c. In Vitro Synthesis of sgRNA

The sgRNA module was designed by fusing the predicted crRNA and tracrRNA sequences with a 5'-GAAA-3' linker. The sgRNA-expressing DNA sequence was put under the transcriptional control of the T7 promoter. It was synthesized (Baseclear, Leiden, The Netherlands) and provided in the pUC57 backbone. All sgRNAs used in the biochemical reactions were synthesized using the HiScribe™ T7 High Yield RNA Synthesis Kit (NEB). PCR fragments coding for sgRNAs, with the T7 sequence on the 5' end, were utilized as templates for in vitro transcription reaction. T7 transcription was performed for 4 hours. The sgRNAs were run and excised from urea-PAGE gels and purified using ethanol precipitation.

d. In Vitro Cleavage Assay

In vitro cleavage assays were performed with purified recombinant ThermoCas9. ThermoCas9 protein, the in vitro transcribed sgRNA and the DNA substrates (generated using PCR amplification using primers described in Table 2) were incubated separately (unless otherwise indicated) at the stated temperature for 10 min, followed by combining the components together and incubating them at the various assay temperatures in a cleavage buffer (100 mM sodium phosphate buffer (pH=7), 500 mM NaCl, 25 mM $MgCl_2$, 25 (V/V %) glycerol, 5 mM dithiothreitol (DTT)) for 1 hour. Each cleavage reaction contained 160 nM of ThermoCas9 protein, 4 nM of substrate DNA, and 150 nM of synthetized sgRNA. Reactions were stopped by adding 6× loading dye (NEB) and run on 1.5% agarose gels. Gels were stained with SYBR safe DNA stain (Life Technologies) and imaged with a Gel Doc™ EZ gel imaging system (Bio-rad).

e. Library Construction for In Vitro PAM Screen

For the construction of the PAM library, a 122-bp long DNA fragment, containing the protospacer and a 7-bp long degenerate sequence at its 3'-end, was constructed by primer annealing and Klenow fragment (exo-) (NEB) based extension. The PAM-library fragment and the pNW33n vector were digested by BspHI and BamHI (NEB) and then ligated (T4 ligase, NEB). The ligation mixture was transformed into electro-competent E. coli DH10B cells and plasmids were isolated from liquid cultures. For the 7 nt-long PAM determination process, the plasmid library was linearized by SapI (NEB) and used as the target. For the rest of the assays the DNA substrates were linearized by PCR amplification.

f. PAM Screening Assay

The PAM screening of thermoCas9 was performed using in vitro cleavage assays, which consisted of (per reaction): 160 nM of ThermoCas9, 150 nM in vitro transcribed sgRNA, 4 nM of DNA target, 4 µl of cleavage buffer (100 mM sodium phosphate buffer pH 7.5, 500 mM NaCl, 5 mM DTT, 25% glycerol) and MQ water up to 20 µl final reaction volume. The PAM containing cleavage fragments from the 55° C. reactions were gel purified, ligated with Illumina sequencing adaptors and sent for Illumina HiSeq 2500 sequencing (Baseclear). Equimolar amount of non-thermoCas9 treated PAM library was subjected to the same process and sent for Illumina HiSeq 2500 sequencing as a reference. HiSeq reads with perfect sequence match to the reference sequence were selected for further analysis. From the selected reads, those present more than 1000 times in the ThermoCas9 treated library and at least 10 times more in the ThermoCas9 treated library compared to the control library were employed for WebLogo analysis (Crooks et al., Genome Res. 14, 1188-1190 (2004)).

g. Editing and Silencing Constructs for B. smithii and P. putida

All the primers and plasmids used for plasmid construction were designed with appropriate overhangs for performing NEBuilder HiFi DNA assembly (NEB), and they are listed in Table 2 and 3 respectively. The fragments for assembling the plasmids were obtained through PCR with Q5 Polymerase (NEB) or Phusion Flash High-Fidelity PCR Master Mix (ThermoFisher Scientific), the PCR products were subjected to 1% agarose gel electrophoresis and they were purified using Zymogen gel DNA recovery kit (Zymo Research). The assembled plasmids were transformed to chemically competent E. coli DH5a cells (NEB), or to E. coli DH5α Δpir (Invitrogen) in the case of P. putida constructs, the latter to facilitate direct vector integration. Single colonies were inoculated in LB medium, plasmid material was isolated using the GeneJet plasmid miniprep kit (ThermoFisher Scientific) and sequence verified (GATC-biotech) and 1 µg of each construct transformed of B. smithii ET 138 electro-competent cells, which were prepared according to a previously described protocol (Bosma, et al. Microb. Cell Fact. 14, 99 (2015)). The MasterPure™ Gram Positive DNA Purification Kit (Epicentre) was used for genomic DNA isolation from B. smithii and P. putida liquid cultures.

For the construction of the pThermoCas9_ctrl, pThermoCas9_bsΔpyrF1 and pThermoCas9_bsΔpyrF2 vectors, the pNW33n backbone together with the ΔpyrF homologous recombination flanks were PCR amplified from the pWUR_Cas9sp1_hr vector (Mougiakos, et al. ACS Synth. Biol. 6, 849-861 (2017)) (BG8191 and BG8192). The native $P_{xylA}$ promoter was PCR amplified from the genome of B. smithii ET 138 (BG8194 and BG8195). The thermocas9 gene was PCR amplified from the genome of G. thermodenitrificans T12 (BG8196 and BG8197). The $P_{pta}$ promoter was PCR amplified from the pWUR_Cas9sp1_hr vector (Mougiakos, et al. ACS Synth. Biol. 6, 849-861 (2017)) (BG8198 and BG8261_2/BG8263_nc2/

BG8317_3). The spacers followed by the sgRNA scaffold were PCR amplified from the pUC57_T7t12sgRNA vector (BG8266_2/BG8268_nc2/8320_3 and BG8210).

A four-fragment assembly was designed and executed for the construction of the pThermoCas9i_ldhL vectors. Initially, targeted point mutations were introduced to the codons of the thermocas9 catalytic residues (mutations D8A and H582A), through a two-step PCR approach using pThermoCas9_ctrl as template. During the first PCR step (BG9075, BG9076), the desired mutations were introduced at the ends of the produced PCR fragment and during the second step (BG9091, BG9092) the produced fragment was employed as PCR template for the introduction of appropriate assembly-overhangs. The part of the thermocas9 downstream the second mutation along with the ldhL silencing spacer was PCR amplified using pThermoCas9_ctrl as template (BG9077 and BG9267). The sgRNA scaffold together with the pNW33n backbone was PCR amplified using pThermoCas9_ctrl as template (BG9263 and BG9088). The promoter together with the part of the thermocas9 upstream the first mutation was PCR amplified using pThermoCas9_ctrl as template (BG9089, BG9090)

A two-fragment assembly was designed and executed for the construction of pThermoCas9i_ctrl vector. The spacer sequence in the pThermoCas9i_ldhL vector was replaced with a random sequence containing BaeI restriction sites at both ends. The sgRNA scaffold together with the pNW33n backbone was PCR amplified using pThermoCas9_ctrl as template (BG9548, BG9601). The other half of the construct consisted of Thermo-dCas9 and promoter was amplified using pThermoCas9i_ldhL as template (BG9600, BG9549).

A five-fragment assembly was designed and executed for the construction of the *P. putida* KT2440 vector pThermoCas9_ppΔpyrF. The replicon from the suicide vector pEMG was PCR amplified (BG2365, BG2366). The flanking regions of pyrF were amplified from KT2440 genomic DNA (BG2367, BG2368 for the 576-bp upstream flank, and BG2369, BG2370 for the 540-bp downstream flank). The flanks were fused in an overlap extension PCR using primers BG2367 and BG2370 making use of the overlaps of primers BG2368 and BG2369. The sgRNA was amplified from the pThermoCas9_ctrl plasmid (BG2371, BG2372). The constitutive P3 promoter was amplified from pSW_I-SceI (BG2373, BG2374). This promoter fragment was fused to the sgRNA fragment in an overlap extension PCR using primers BG2372 and BG2373 making use of the overlaps of primers BG2371 and BG2374. ThermoCas9 was amplified from the pThermoCas9_ctrl plasmid (BG2375, BG2376). The inducible Pm-XylS system, to be used for 3-methylbenzoate induction of ThermoCas9 was amplified from pSW_I-SceI (BG2377, BG2378).

TABLE 3

Plasmids used in this study

| Plasmid | Description | Restriction sites used | Primers | Source |
| --- | --- | --- | --- | --- |
| pNW33n | *E. coli-Bacillus* shuttle vector, cloning vector, Cam$^R$ | — | — | BGSC |
| pUC57_T7sgRNAfull | pUC57 vector containing DNA encoding the sgRNA under the control of T7 promoter; serves as a template for in vitro transcription of full length Repeat/Antirepeat sgRNAs | — | — | Baseclear |
| pMA2_T7sgRNAtruncated R/AR | Vector containing DNA encoding the truncated Repeat/Antirepeat part of the sgRNA under the control of T7 promoter; serves as a template for in vitro transcription of truncated Repeat/Antirepeat sgRNAs | — | — | Gen9 |
| pRARE | T7 RNA polymerase based expression vector, Kan$^R$ | — | — | EMD Millipore |
| pML-1B | *E. coli* Rosetta™ (DE3) plasmid, encodes rare tRNAs, Cam$^R$ | — | — | Macrolab, Addgene |
| pEMG | *P. putida* suicide vector, used as template for replicon and Kan$^R$ | — | See Table 2 | 1 |
| pSW_I-SceI | *P. putida* vector containing I-SceI, used as template for xylS and P$_{Pm}$ | — | See Table 2 | 1 |
| pWUR_Cas9sp1_hr | pNW33n with spCas9-module containing spacer targeting the pyrF gene. This plasmid was used as a template for constructing the ThermoCas9 based constructs | — | — | 2 |
| pThermo_Cas9 | thermocas9 with N-term. His-tag and TEV cleavage site in pML-1B. Expression vector for ThermoCas9 | SspI and Ligase Independent Cloning | BG7886 and BG7887 | This study |
| pThermo_dCas9 | cas9dthermocas9 with N-term. His-tag and TEV cleavage site in pML-1B. Expression vector for catalytically inactive (dead) dThermoCas9 | SspI and Ligase Independent Cloning | BG7886 and BG7888 | This study |
| pNW-PAM7nt | Target sequence in pNW33n vector containing a 7-nt degenerate PAM for in vitro PAM determination assay | BamHI and BspHI | See Table 2 | This study |
| pNW63-pNW78 | Target sequence in pNW33n vector containing distinct nucleotides at the 6th and 7th positions of the PAM (CCCCCNNA) | BamHI and BspHI | See Table 2 | This study |
| pThermoCas9_ctrl | pNW33n with ThermoCas9-module[1] containing a non-targeting spacer. Used as a negative control | — | See Table 2 | This study |
| pThermoCas9_bsΔpyrF1 | pNW33n with ThermoCas9-module[1] containing spacer 1 targeting the pyrF gene and the fused us + ds pyrF-flanks | — | See Table 2 | This study |
| pThermoCas9_bsΔpyrF2 | pNW33n with ThermoCas9-module[1] containing spacer 2 targeting the pyrF gene and the fused us + ds pyrF-flanks | — | See Table 2 | This study |
| pThermoCas9i_ctrl | pNW33n with Thermo-dCas9-module[2] containing a non-targeting spacer. Used as a wild-type control | — | See Table 2 | This study |
| pThermoCas9i_ldhL | pNW33n with Thermo-dCas9-module[2] containing spacer 2 targeting the ldhL gene | — | See Table 2 | This study |

TABLE 3-continued

Plasmids used in this study

| Plasmid | Description | Restriction sites used | Primers | Source |
|---|---|---|---|---|
| pThermoCas9_ppΔpyrF | pEMG with ThermoCas9-module[3] for *Pseudomonas putida* containing a spacer targeting the spacer targeting the pyrF gene and the fused us + ds pyrF-flanks | — | See Table 2 | This study |

[1] The ThermoCas9 module contains thermocas9 under the native P$_{xylL}$ promoter followed by the sgRNA under the *B. coagulans* P$_{pta}$ promoter (FIG. 4).
[2] Like the ThermoCas9 module, but with the thermo-dCas9 instead of thermocas9 (FIG. 4).
[3] The ThermoCas9 module for *Pseudomonas putida* contains thermocas9 under the transcriptional control of the inducible Pm-XylS system followed by the sgRNA under the constitutive P3 promoter.

h. Editing Protocol for *P. putida*

Transformation of the plasmid to *P. putida* was performed according to Choi et al. (Choi et al., *J. Microbiol. Methods* 64, 391-397 (2006)). After transformation and selection of integrants, overnight cultures were inoculated. 10 μl of overnight culture was used for inoculation of 3 ml fresh selective medium and after 2 hours of growth at 37° C. ThermoCas9 was induced with 3-methylbenzoate. After an additional 6 h, dilutions of the culture were plated on non-selective medium supplemented with 3-methylbenzoate. For the control culture the addition of 3-methylbenzoate was omitted in all the steps. Confirmation of plasmid integration in the *P. putida* chromosome was done by colony PCR with primers BG2381 and BG2135. Confirmation of pyrF deletion was done by colony PCR with primers BG2381 and BG2382.

i. RNA Isolation

RNA isolation was performed by the phenol extraction based on a previously described protocol (van Hijum et al. *BMC Genomics* 6, 77 (2005)). Overnight 10 mL cultures were centrifuged at 4° C. and 4816×g for 15 min and immediately used for RNA isolation. After removal of the medium, cells were suspended in 0.5 mL of ice-cold TE buffer (pH 8.0) and kept on ice. All samples were divided into two 2 mL screw-capped tubes containing 0.5 g of zirconium beads, 30 μL of 10% SDS, 30 μL of 3 M sodium acetate (pH 5.2), and 500 μL of Roti-Phenol (pH 4.5-5.0, Carl Roth GmbH). Cells were disrupted using a FastPrep-24 apparatus (MP Biomedicals) at 5500 rpm for 45 s and centrifuged at 4° C. and 10 000 rpm for 5 min. 400 μL of the water phase from each tube was transferred to a new tube, to which 400 μL of chloroform-isoamyl alcohol (Carl Roth GmbH) was added, after which samples were centrifuged at 4° C. and 18 400×g for 3 min. 300 μL of the aqueous phase was transferred to a new tube and mixed with 300 μL of the lysis buffer from the high pure RNA isolation kit (Roche). Subsequently, the rest of the procedure from this kit was performed according to the manufacturer's protocol, except for the DNase incubation step, which was performed for 45 min. The concentration and integrity of cDNA was determined using Nanodrop-1000 Integrity and concentration of the isolated RNA was checked on a NanoDrop 1000.

j. Quantification of mRNA by RT-qPCR

First-strand cDNA synthesis was performed for the isolated RNA using SuperScript™ III Reverse Transcriptase (Invitrogen) according to manufacturer's protocol. qPCR was performed using the PerfeCTa SYBR Green Supermix for iQ from Quanta Biosciences. 40 ng of each cDNA library was used as the template for qPCR. Two sets of primers were used; BG9665:BG9666 amplifying a 150-nt long region of the ldhL gene and BG9889:BG9890 amplifying a 150-nt long sequence of the rpoD (RNA polymerase sigma factor) gene which was used as the control for the qPCR. The qPCR was run on a Bio-Rad C1000 Thermal Cycler.

k. HPLC

A high-pressure liquid chromatography (HPLC) system ICS-5000 was used for lactate quantification. The system was operated with Aminex HPX 87H column from Bio-Rad Laboratories and equipped with a UV1000 detector operating on 210 nm and a RI-150 40° C. refractive index detector. The mobile phase consisted of 0.16 N $H_2SO_4$ and the column was operated at 0.8 mL/min. All samples were diluted 4:1 with 10 mM DMSO in 0.01 N $H_2SO_4$.

Example 18 Application of ThermoCas9 in *Geobacillus thermoglucosidans*

ThermoCas9 is evaluated as counter selection tool in *Geobacillus thermoglucosidans* (also known as *Bacillus thermoglucosidasius, Geobacillus thermoglucosidasius*, and *Parageobacillus thermoglucosidasius*) at 55° C. A single-plasmid approach was applied, with the recombination arms and the thermoCas9 gene/sgRNA on the same plasmid. The thermoCas9 gene was placed under control of a β-glucosidase promoter that can be induced by cellobiose (Bartosiak-Jentys, J., Hussein, A. H., Lewis, C. J., Leak, D. J. (2013) Microbiology 159:1267-1275). To improve the recombination efficiency, an incubation step at elevated temperature, at which the plasmid cannot replicate, was added to the workflow. The *G. thermoglucosidans* DSM 2542$^T$ 960 bp ldhL gene (NCBI GeneID:29237966) was chosen as deletion target. Upstream and downstream fragments of 0.9 kb were generated by PCR using primer combinations:

```
2420
(5'-AAAACTCACGTTAAGGGATTTTGGTCATGACCGATTCGGCT
GTTATGGAGAG-3')
and 993
(5'-ATTCAAAGTCAGCATCACATCCAATTACATCAAGCAG-3'),
and 992
(5'-TTGGATGTGATGCTGACTTTGAATACAACAAGGTGAAC-3')
and 2421
(5'-TGCGTCGGAACACCTTCTTCGCGTTTATCGCGGCAAACAGAGCTTT
AAAACCAG-3')
``` both at an annealing temperature of 58° C. and by using chromosomal DNA of *G. thermoglucosidans* ΔsigF (see International (PCT) Application publication No. WO2016/012296) as a template. The vector backbone was amplified in two parts using pThermoCas9_ctrl, as described in Example 13, as a template, introducing the non-targeting spacer sequence (5'-TTATGTTTTCCGGACATAGTACA-3'). One fragment was generated using primer combination

```
2210
(5'-AGGAGGTTGCATATGAAGTATAAAATCGGTCTTG-3')
and 2490
(5'-ACTCTTATTATATAGAAACGCAACTAAGTTAAGCATTGCCATTATAA
CGGACGGATAGTTTCCCC-3').
```

The other fragment was generated using primer combination

```
2489
(5'-AACTTAGTTGCGTTTCTATATAATAAGAGTTATGTTTTCCGGACAT
AGTACAGTCATAGTTCCCCTGAGATTATCG-3')
and 2401
(5'-TCATGACCAAAATCCCTTAACG-3').
```

The β-glucosidase promoter was amplified from *G. thermoglucosidans* ΔsigF (WO2016012296) chromosomal DNA as a template and primer combinations

```
2400
(5'-CGATAAACGCGAAGAAGGTG-3')
and 2208
(5'-TTTTATACTTCATATGCAACCTCCTTTATGTTC-3').
```

The five PCR fragments were created with Phusion Flash High-Fidelity PCR master mix (ThermoFisher) according to the manufacturer's instructions and assembled into a single plasmid by fusing the overlapping regions using the NEBuilder HiFi DNA Assembly Cloning Kit (New England BioLabs) resulting in non-targeting plasmid pRB061.

Plasmid DNA was concentrated using a Zymo DNA Clean and Concentrator spin column (Zymo Research) and eluted into 10 µL H₂O and transformed to electrocompetent *E. coli* TG90 (Gonzy-Treboul, G., Karmzyn-Campelli, C., Stragier, P. 1992. J. Mol. Biol. 224:967-979). Transformants were plated on LB agar plates supplemented with 10 mg/L chloramphenicol and incubated at 37° C. A single colony was selected for plasmid extraction using the ZymoPURE™ Plasmid Midiprep Kit (Zymo Research). Plasmid integrity was confirmed by sequence analysis.

The plasmid containing the targeting spacer (5'-ATAAGGGCAAATGCATAGCTGGC-3') based on a genomic sequence with a PAM sequence of 5'-GGCCC-CAA-3' immediately downstream, was constructed by assembly of two fragments amplified by PCR with the non-targeting plasmid pRB061 as a template, using primer combination

```
2501
(5'-AAGAGATAAGGGCAAATGCATAGCTGGCGTCATAGTTCCCCTGAGA
TTATCG-3')
and 2125
(5'-TCTTCGATGCGAGGAATGTC-3')
and primer combination 1994
(5'-AAACAAACCACCGCTGGTAG-3')
and 2502
(5'-ATGACGCCAGCTATGCATTTGCCCTTATCTCTTATTATATAGAAAC
GCAACTAAG-3').
```

Transformation and plasmid extraction were performed as described above resulting in targeting plasmid pRB063.

The plasmids pRB061 and pRB063 were transformed to *G. thermoglucosidans* ΔsigF (see International (PCT) Application publication No. WO2016/012296) by electroporation as described elsewhere (see WO2016/012296) and plated on TGP plates supplemented with 8 mg/L chloramphenicol. Plates were incubated overnight at 55° C. A single colony was selected and grown overnight at 55° C. in TGP broth supplemented with 8 mg/L chloramphenicol. Subsequently, 1 mL was transferred to 10 mL fresh prewarmed TGP medium supplemented with 8 mg/L chloramphenicol. After an incubation for 8 h to overnight at 68° C., for recombination to occur, 1 mL was transferred to 10 mL fresh prewarmed TGP medium supplemented with 8 mg/L chloramphenicol and 1% (w/v) cellobiose (D(+) cellobiose, Across), to induce the beta-glucosidase promoter, and incubated at 55° C. for 8 h. The cultures were plated at 55° C. on TGP plates containing 1% (w/v) cellobiose. Colony PCR was performed to confirm deletion of the ldhL gene using primers 629 (5'-GACTGGGCGCAAGCGGTGATG-3') and 630 (5'-CCTGTTGCTGATACAAGGTCTAGC-3'). The construct containing the targeting spacer resulted in 16 knockouts out of the 36 colonies analyzed. The random spacer resulted in 1 knockout out of the 78 colonies analyzed. This demonstrates the efficiency of the counter-selection tool for gene deletion in *G. thermoglucosidans*.

| Corbion nr | Sequence 5'-3' |
| --- | --- |
| 629 | GACTGGGCGCAAGCGGTGATG |
| 630 | CCTGTTGCTGATACAAGGTCTAGC |
| 992 | TTGGATGTGATGCTGACTTTGAATACAACAAGGTGAAC |
| 993 | ATTCAAAGTCAGCATCACATCCAATTACATCAAGCAG |
| 1994 | AAACAAACCACCGCTGGTAG |
| 2125 | TCTTCGATGCGAGGAATGTC |

| Corbion nr | Sequence 5'-3' |
|---|---|
| 2208 | TTTTATACTTCATATGCAACCTCCTTTATGTTC |
| 2210 | AGGAGGTTGCATATGAAGTATAAAATCGGTCTTG |
| 2400 | CGATAAACGCGAAGAAGGTG |
| 2401 | TCATGACCAAAATCCCTTAACG |
| 2420 | AAAACTCACGTTAAGGGATTTTGGTCATGACCGATTCGGCTGTTATGGAGAG |
| 2421 | TGCGTCGGAACACCTTCTTCGCGTTTATCGCGGCAAACAGAGCTTTAAAACCAG |
| 2489 | AACTTAGTTGCGTTTCTATATAATAAGAGTTATGTTTTCCGGACATAGTACAGTCATAGTTCCCCTGAGATTATCG |
| 2490 | ACTCTTATTATATAGAAACGCAACTAAGTTAAGCATTGCCATTATAACGGACGGATAGTTCCCC |
| 2501 | aagagATAAGGGCAAATGCATAGCTGGCgtcatagttcccctgagattatcg |
| 2502 | atgacGCCAGCTATGCATTTGCCCTTATctcttattatatagaaacgcaactaag |

Example 19 Application of ThermoCas9 in *Bacillus coagulans*

ThermoCas9 was evaluated as counter selection tool in *Bacillus coagulans* at 55° C. A single-plasmid approach was used, with the recombination arms and the thermoCas9 gene/sgRNA on the same plasmid. The thermoCas9 gene was placed under control of a β-glucosidase promoter that can be induced by cellobiose (Bartosiak-Jentys, J., Hussein, A. H., Lewis, C. J., Leak, D. J. (2013) Microbiology 159:1267-1275). To improve the recombination efficiency an incubation step at elevated temperature, at which the plasmid cannot replicate, was added to the workflow. The *B. coagulans* DSM $1^T$ 759-bp sigF gene (NCBI GeneID: 29812540) was chosen as deletion target. Upstream and downstream fragments of 0.85 kb were generated by PCR using primer combinations 2561
(5'-TCACGTTAAGGGATTTTGGTCATGAGTGAGTCTGGCTATTGACCTGG-3')
and 2562
(5'-ATGAAAAAAGCGCACGTCGGCACGACTCCTTAATTG-3'),
and 2563
(5'-ATTAAGGAGTCGTGCCGACGTGCGCTTTTTTCATTCCC-3')
and 2570
(5'-CACCTTCTTCGCGTTTATCGCGGCACAGGATATAATGGTCGATGTCCTGTTG-3')

both at an annealing temperature of 58° C. and by using chromosomal DNA of *B. coagulans* DSM 1 as a template. The vector backbone was amplified in two parts using pBR061 as a template, introducing the targeting spacer sequence 5'-CGGGGATATGAACCGGATGACTT-3', based on a genomic sequence with a PAM sequence of 5'-ATTT-CAAA-3'. One fragment was generated using primer combination 2571
(5'-CGATAAACGCGAAGAAGGTG-3')
and 2579
(5'-AAGTCATCCGGTTCATATCCCCGACTCTTATTATATAGAAACGCAACTAAGTTAAGC-3').

The other fragment was generated using primer combination 2578
(5'-TAAGAGTCGGGGATATGAACCGGATGACTTGTCATAGTTCCCCTGAGATTATCG-3')
and 2172
(5'-TCATGACCAAAATCCCTTAAC-3').

The four PCR fragments were created with Phusion Flash High-Fidelity PCR master mix (ThermoFisher) according to the manufacturer's instructions, and assembled into a single plasmid by fusing the 25-bp overlapping regions using the NEBuilder HiFi DNA Assembly Cloning Kit (New England BioLabs) resulting in targeting plasmid pMH247. Plasmid DNA was concentrated using a Zymo DNA Clean and Concentrator spin column (Zymo Research) and eluted into 10 μL H$_2$O and transformed to electrocompetent *E. coli* TG90 (Gonzy-Treboul, G., Karmzyn-Campelli, C., Stragier, P. (1992) J. Mol. Biol. 224:967-979). Transformants were plated on LB agar plates supplemented with 10 mg/L chloramphenicol and incubated at 37° C. A single colony was selected for plasmid extraction using the ZymoPURE™ Plasmid Midiprep Kit (Zymo Research). Plasmid integrity was confirmed by sequence analysis. The plasmid was transformed to *B. coagulans* by electroporation as described elsewhere (Kovacs, A. T., van Hartskamp, M., Kuipers, O. P., & van Kranenburg, R. (2010) Applied and Environmental Microbiology, 76(12), 4085-4088) and plated on BC plates supplemented with 7 mg/L chloramphenicol (Kovacs, A. T., van Hartskamp, M., Kuipers, O. P., & van Kranenburg, R. (2010) Applied and Environmental Microbiology, 76(12), 4085-4088). Plates were incubated overnight at 45° C. Two single colonies were selected and grown overnight at 45° C. in BC broth supplemented with 7 mg/L chloramphenicol. Subsequently, 1 ml was transferred to 10 ml fresh, prewarmed BC medium supplemented with 7 mg/L chloramphenicol. After an incubation for 4 h at 65° C., for recombination to occur, the cultures were incubated for 4 hours at 55° C. After this, 1 ml was transferred to 10 ml fresh, prewarmed BC medium supplemented with 7 mg/L chloramphenicol and 1% (w/v) cellobiose, to induce the β-glucosidase promoter, and cultures were incubated overnight at 55° C. The cultures were plated at 55° C. on BC agar plates containing 1% (w/v) cellobiose and colony PCR was performed to check for knockouts using primers 351 (5'-CACCATGTCCCGGACAGCAC-3') and 352 (5'-GCGATGAAATTGGAACACTGAC-3'). For one culture 17 out of 17 tested colonies had the PCR fragment of 2.1 kb confirming the deletion. For the other culture 15 out of 18 tested colonies had the PCR fragment of 2.1 kb confirming the deletion, the other 3 had the PCR fragment of the wild type. This demonstrates the efficiency of the counter-selection tool for gene deletion in *B. coagulans*.

| Corbion nr | Sequence 5'-3' |
|---|---|
| 351 | CACCATGTCCCGGACAGCAC |
| 352 | GCGATGAAATTGGAACACTGAC |
| 2172 | TCATGACCAAAATCCCTTAAC |
| 2561 | TCACGTTAAGGGATTTTGGTCATGAGTGAGTCTGGCTATTGACCTGG |
| 2562 | ATGAAAAAAGCGCACGTCGGCACGACTCCTTAATTG |
| 2563 | ATTAAGGAGTCGTGCCGACGTGCGCTTTTTTCATTCCC |
| 2570 | CACCTTCTTCGCGTTTATCGCGGCACAGGATATAATGGTCGATGTCCTGTTG |
| 2571 | CGATAAACGCGAAGAAGGTG |
| 2578 | TAAGAGTCGGGGATATGAACCGGATGACTTGTCATAGTTCCCCTGAGATTATCG |
| 2579 | AAGTCATCCGGTTCATATCCCCGACTCTTATTATATAGAAACGCAACTAAGTTAAGC |

Example 20 Application of ThermoCas9 in *Pseudomonas putida* Using a Two-Plasmid Approach ThermoCas9 is evaluated as counter selection tool in *Pseudomonas putida* at 30° C. A two-step approach is applied, first integrating the knock-out vector via a single-crossover event and subsequent introduction of the plasmid harbouring the thermoCas9 gene and the sgRNA containing the targeting spacer. The thermoCas9 gene was placed under control of the 3-methylbenzoate inducible Pm promoter. The *P. putida* KT2440, DSM-6125, 702 bp gene pyrF (NCBI GeneID: 1043286) was chosen as a deletion target, as in Example 14]RvK1]. For the construction of an integration vector the 0.5-kb upstream and 0.5-kb downstream regions of pyrF were amplified by PCR with primer combination 2461
(5'-*GCCGGTAGAACTCCGCGAGGTCGTCCAGCCACGGCATTGGCAAGGCCAAG*-3')

and 2462
(5'-*GCGGATAACAATTTCACACAGGAAACAGCTACGCGCATCAACTTCAAGGC*-3')

using the pThermoCas9_ppΔpyrF of Example 14 and FIG. 25 as a template. The vector backbone was amplified by PCR using primer combination 2459
(5'-AGCTGTTTCCTGTGTGAAATTG-3')

and 2460
(5'-GGCTGGACGACCTCGCGGAG-3')

using the pEMG suicide vector (Martinez-Garcia, E., de Lorenzo, V. (2012) Methods Mol. Biol. 813:267-283) as a template. The two PCR fragments were created with Phusion Flash High-Fidelity PCR master mix (ThermoFisher) according to the manufacturer's instructions, using a 58° C. annealing temperature for all reactions, and assembled into a single plasmid by fusion of the vector backbone overlapping regions added to the primers used for the amplification of the upstream and downstream regions, using the NEBuilder HiFi DNA Assembly Cloning Kit (New England BioLabs) resulting in the integration plasmid pRB051. Plasmid DNA was concentrated using a Zymo DNA Clean and Concentrator spin column (Zymo Research) and eluted into 10 μL H₂O and transformed to electrocompetent *E. coli* DH5α λpir (Invitrogen). Transformants were plated on LB agar plates supplemented with 50 mg/L kanamycin and incubated at 37° C. A single colony was selected for plasmid extraction using the ZymoPURE™ Plasmid Midiprep Kit (Zymo Research). Plasmid integrity was confirmed by sequence analysis. The integration plasmid was transformed to electrocompetent *P. putida* KT2440 cells as described elsewhere (see Choi, K. H., A Kumar, and H. P. Schweizer. (2006) *J. Microbiol. Methods* 64: 391-397). Transformants were plated on LB agar plates supplemented with 50 mg/L kanamycin and incubated at 30° C. A single colony was selected for analysis of genomic DNA, isolated using the MasterPure™ DNA Purification Kit (Epicentre). A plasmid integration in the downstream region of pyrF was confirmed by PCR analysis with primers

```
2381
(5'-ACACGGCGGATGCACTTACC-3')
and 2135
(5'-CCGCTTTCTTCGGGCATTCC-3').
```

For a plasmid harboring the ThermoCas9 and corresponding sgRNA elements, a targeting spacer (5'-CCAT-ACCCGCTTTTTCCGCCAGC-3') based on a genomic sequence followed by a 5'-GCCGCCAA-3' PAM sequence was selected. The vector backbone, including the 3-methylbenzoate-inducible Pm-promoter was amplified by PCR with primer combination

```
2467
(5'-GATTTTATACTTCATATGTTCATGACTCCATTATTATTG-3')
and 2468
(5'-CAAGGTCTTTTTTACTAAGTCGAGGGGATCCTCTAGC-3')
``` using pSW(I-SceI) (Wong, S. M., Mekalanos, J. J. (2000) Proc. Natl. Acad. Sci. USA 97:10191-10196) as a template. The ThermoCas9 and corresponding sgRNA fragment were amplified by PCR with primer combinations

```
2469
(5'-CCACACATTATACGAGCCGATGATTAATTGTCAACAGATGGCCCG
CTTCATAAGCAG-3')
and 2470
(5'-TGGAGTCATGAACATATGAAGTATAAAATCGGTCTTG-3')
and 2471
(5'-GATCCCCTCGACTTAGTAAAAAAGACCTTGACGTTTTC-3')
and 2742
(5'-GACAATTAATCATCGGCTCGTATAATGTGTGGCCATACCC
GCTTTTTCCGCCAGCGTCATAGTTCCCCTGAGATTATCG-3')
``` for both using pThermoCas9_ppΔpyrF as a template. The three PCR fragments were created with Phusion Flash High-Fidelity PCR master mix (ThermoFisher) according to the manufacturer's instructions, using a 58° C. annealing temperature for all reactions, and assembled into a single plasmid by fusion of the overlapping regions, using the NEBuilder HiFi DNA Assembly Cloning Kit (New England BioLabs) resulting in the plasmid pRB054. Plasmid DNA was concentrated using a Zymo DNA Clean and Concentrator spin column (Zymo Research) and eluted into 10 μL $H_2O$ and transformed to E. coli DH5a by heat shock (Sambrook, J., en D. W. Russell. (2001) *Molecular cloning: a laboratory manual* 3rd edition. Cold Spring Harbor Laboratory Press, Cold Spring Harbor, New York). Transformants were plated on LB agar plates supplemented with 150 mg/L ampicillin and incubated at 37° C. A single colony was selected for plasmid extraction using the ZymoPURE™ Plasmid Midiprep Kit (Zymo Research). Plasmid integrity was confirmed by sequence analysis.

The pRB054 plasmid was transformed to electrocompetent P. putida KT2440 cells with confirmed pRB051 integration. Transformants were plated on LB agar plates supplemented with 50 mg/L kanamycin and 500 mg/L ampicillin and incubated at 30° C. A single colony was selected for plasmid extraction using the ZymoPURE™ Plasmid Midiprep Kit (Zymo Research). Plasmid integrity was confirmed by sequence analysis. Also genomic DNA was isolated using the MasterPure™ DNA Purification Kit (Epicentre) and pRB051 integration reconfirmed by PCR analysis with primers 2381 (5'-ACACGGCGGATGCACT-TACC-3') and 2135 (5'-CCGCTTTCTTCGGGCATTCC-3'). Subsequently, 10 μL of an overnight culture of the strain with the targeting plasmid was transferred to 3 mL LB medium supplemented with 50 mg/L kanamycin and 500 mg/L ampicillin. After a shaking incubation (180 r.p.m.) of 2 hours at 30° C., 3-methylbenzoate was added to a final concentration of 3 mM. The cultures were incubated, shaking at 30° C. for an additional 4 hours. The culture was plated on LB agar supplemented with 50 mg/L uracil and incubated at 30° C. After overnight growth 96 colonies were transferred to a fresh LB agar plate supplemented with 50 mg/L uracil and incubated for another night at 30° C. Colony PCRs were performed on all grown colonies to check for knockouts using primers 2381 (5'-ACACGGCG-GATGCACTTACC-3') and 2382 (5'-TGGACGTGTACTTCGACAAC-3'). Of the 48 colonies that were tested, 32 colonies yielded a PCR product. All 32 had a fragment of 1112 bp, corresponding to a gene deletion. One of these colonies also gave a 1854 bp fragment indicating a mixed wild-type/deletion genotype in this colony. This demonstrates the efficiency of ThermoCas9 as a counter-selection tool for gene deletion in P. putida at 30° C.

| Corbion nr. | Sequence 5'-3' |
|---|---|
| 2135 | CCGCTTTCTTCGGGCATTCC |
| 2381 | ACACGGCGGATGCACTTACC |
| 2382 | TGGACGTGTACTTCGACAAC |
| 2459 | AGCTGTTTCCTGTGTGAAATTG |
| 2460 | GGCTGGACGACCTCGCGGAG |
| 2461 | GCCGGTAGAACTCCGCGAGGTCGTCCAGCCACGGCATTGGCAAGGCCAAG |
| 2462 | GCGGATAACAATTTCACACAGGAAACAGCTACGCGCATCAACTTCAAGGC |

| Corbion nr. | Sequence 5'-3' |
|---|---|
| 2467 | GATTTTATACTTCATATGTTCATGACTCCATTATTATTG |
| 2468 | CAAGGTCTTTTTTACTAAGTCGAGGGGATCCTCTAGC |
| 2469 | CCACACATTATACGAGCCGATGATTAATTGTCAACAGATGGCCCGCTTCATAAGCAG |
| 2470 | TGGAGTCATGAACATATGAAGTATAAAATCGGTCTTG |
| 2471 | GATCCCCTCGACTTAGTAAAAAAGACCTTGACGTTTTC |
| 2742 | GACAATTAATCATCGGCTCGTATAATGTGTGGCCATACCCGCTTTTTCCGCCAGCGTCATAGTTCCCCTGAGATTATCG |

Example 21 Application of ThermoCas9 in *Saccharomyces cerevisiae*

ThermoCas9 is used as a genome editing tool in the eukaryote *Saccharomyces cerevisiae* at 37° C. A two-step approach was used: first integrating ThermoCas9 for stable expression from the genome and subsequent introduction of a plasmid harbouring the sgRNA along with a linear double-stranded DNA repair-oligo. The ThermoCas9 gene was placed under control of the constitutive TEF1 promoter, the sgRNA under control of the SNR52 promoter and SUP4 terminator. The *S. cerevisiae* CEN.PK113-17A (Entian K D, Miner P (1998) Method Microbiol 26:431-449), 1773 bp gene CAN1 (YEL063C; NCBI GeneID: 856646) was chosen as a deletion target.

A ThermoCas9 integration fragment was maintained on a plasmid constructed by assembly of six fragments. The ThermoCas9 fragment was amplified with primer combination:

2119
(5'-AGCAATCTAATCTAAGTTTTAATTACAAAATGAAGTATAAAATCGGTCTTG-3')
and 2118
(5'-AATGTAAGCGTGACATAACTAATTACATGATTACACCTTCCTCTTCTTCTTGGGTAACGGACGGATAGTTTCCCCGGCTTTC-3')

introducing a nuclear localization signal coding sequence (5'-CCCAAGAAGAAGAGGAAGGTG-3') fused to the 3' end of the ThermoCas9 gene prior to the stop codon using the previously described pThermoCas9_ppApyrF [BR2] (see Example 14) as a template. The CYC1 terminator was amplified with primer combination:

2120
(5'-CCGTTACCCAAGAAGAAGAGGAAGGTGTAATCATGTAATTAGTTATGTCACGCTTAC-3')
and 2105
(5'-ACAAAATGGAATATGTTCATAGGGTAGACGGATAGAGATGGGCCAATACC-3')

using pSF-TEF1-URA3 plasmid (OGS534; Sigma-Aldrich) as a template. The LEU2 locus (YCL018W, Gene ID: 850342) was amplified from genomic DNA of *S. cerevisiae* CEN.PK113-17A with a repaired LEU2 gene (OrganoBalance) with primer combination:

2111
(5'-AACACAGAGTAAATTCCCAAATTATTCCATGTGTTCAAAAACGTTATATTTATAGG-3')
and 2110
(5'-ATTTAAATTTCCGAACTCTCCAAGGCCCTCAGTCTCGACGATCCATATCG-3').

Alternatively, the gene can be amplified from synthetic DNA based on the *S. cerevisiae* S288C LEU2 locus (YCL018W, Gene ID: 850342) including the sequences 523 bp upstream and 104 downstream of the gene. The *S. cerevisiae* ARS replicon was amplified with primer combination:

2104
(5'-TTATCCTATAAATATAACGTTTTTGAACACATGGAATAATTTGGGAATTTACTC-3')
and 2745
(5'-GGGGACTAAAATTTTTTAATATAAATATATAAATTAAAAATAG-3')

using the Vector Conversion Cassette with Sapphire™ Technology (GeneArt Cat. no. A13291) as a template. The *E. coli* pUC replicon was amplified with primer combination:

2116
(5'-GCCGATATCAAGACCGATTTTATACTTCATTTTGTAATTAAAACTTAGATTAGATTGCTATGC-3')
and 2115
(5'-CGCTCATTTGCTCGTCGGGCATCGAATCTCTCTTTGAAAAGATAATGTATGATTATG-3')

using pSF-TEF1-URA3 plasmid (OGS534; Sigma-Aldrich) as a template. The fragment with kanamycin resistance marker and TEF1 promoter was amplified with primer combination:

2109
(5'-AAGCATAATCATACATTATCTTTTCAAAGAGAGATTCGATGCCCGACGAG-3')
and 2114
(5'-AATCTCAGGGGAACTATGACTCCACACCTCTGACCAACGCGATCATTTATCTTTCACTGCGGAGAAG-3')

using pSF-TEF1-URA3 plasmid (OGS534; Sigma-Aldrich) as a template. The six PCR fragments were created with Phusion Flash High-Fidelity PCR master mix (ThermoFisher) according to the manufacturer's instructions and assembled into a single plasmid by fusing the overlapping regions using the NEBuilder HiFi DNA Assembly Cloning Kit (New England BioLabs) resulting in plasmid pRB021. Plasmid DNA was concentrated using a Zymo DNA Clean and Concentrator spin column (Zymo Research) and eluted into 10 µL H$_2$O and transformed to E. coli DH5α by heat-shock (Sambrook, J., en D. W. Russell. 2001. Molecular cloning: a laboratory manual 3rd edition. Cold Spring Harbor Laboratory Press, Cold Spring Harbor, New York). Transformants were plated on LB agar plates supplemented with 50 mg/L kanamycin and incubated at 37° C. A single colony was selected for plasmid extraction using the ZymoPURE™ Plasmid Midiprep Kit (Zymo Research). Plasmid integrity was confirmed by sequence analysis.

The ThermoCas9 gene was integrated in the S. cerevisiae CEN.PK113-17A TDH1 locus (YJL052W) by amplification of the ThermoCas9-LEU2 fragment by PCR using primer combination:

2580
(5'-TTCTTAGGTGCATGCGACGGTATCCACGTGCAGAACAACATAGT
CTGAAGAAGGGGGGGATCCATCTTCGATGGATAGCG-3')
and 2581
(5'-AGAAGAGAAAAGGGTAAAGTTAATGCTTAATCTTGTCTTGG
CTTAAAAAGTAATATGTACGGTCGCCTGACGCATATACC-3')

both with 60 bp tails homologous to either the upstream or downstream region of the TDH1 locus, with pRB021 as a template. The amplified fragment was concentrated using a Zymo DNA Clean and Concentrator spin column (Zymo Research) and eluted into 10 µL H$_2$O. Circa 500 ng of this fragment was transformed to S. cerevisiae CEN.PK113-17A by heat-shock as described elsewhere (R. Daniel Gietz, Robin A. Woods, Methods in Enzymology, Academic Press, 2002, Volume 350, Pages 87-96). Transformants were plated on SM agar plates (Verduyn, C., E. Postma, W. A. Scheffers, and J. P. van Dijken. 1990. J. Gen. Microbiol. 136:395-403.) supplemented with 150 mg/L uracil and incubated at 30° C. for three days. A single colony was selected for genomic DNA extraction using the YeaStar Genomic DNA Kit (Zymo Research) according to manufacturer's Protocol II. Fragment integration and ThermoCas9 sequence was confirmed by sequence analysis.

A S. cerevisiae CAN1 targeting gRNA with a targeting spacer sequence of 5'-GCACCTGGGTTTCTC-CAATAACG-3', based on a genomic sequence with a PAM sequence of 5'-GAATCCAA-3' was expressed from a multicopy plasmid constructed by assembly of three fragments. The SNR promoter was amplified from S. cerevisiae CEN.PK113-17A genomic DNA with primer combination:

2113
(5'-CTACAAATGTGGTATTGGCCCATCTCTATCCGTCTACCCT
ATGAACATATTCC-3')
and 2666
(5'-GGTATAACTTTCATTATACCACAGCGATAATCTCAGGGGA
ACTATGACCGTTATTGGAGAAACCCAGGTGCGATCATTTATCTTTCAC
TGCGGAGAAGTTTCGAACGCCGAAACATGCG-3').

The sgRNA cassette, including CAN1 targeting spacer, was amplified using primer combination:

2665
(5'-CGCATGTTTCGGCGTTCGAAACTTCTCCGCAGTGAAAGATAAAT
GATCGCACCTGGGTTTCTCCAATAACGGTCATAGTTCCCCTGAGATTA
TCGCTGTGGTATAATGAAAGTTATACC-3')
and 2106
(5'-AAAAAACCCCTCAAGACCCGAGACATAAAAAACAAAAA
AACGCCTAAGAGTGGGGAATG-3')

with pThermoCas9_ppΔpyrF as a template. The multicopy backbone was amplified by PCR using primer combination:

2103
(5'-GCATTCCCCACTCTTAGGCGTTTTTTTGTTTTTTATGTCTCGGG
TCTTGAGGGGTTTTTTGTG-3')
and 2108
(5'-GCAGTGAAAGATAAATGATCGCGTTGGTCAGAGGTGTG
GAGTCATAGTTCCCCTGAGATTATCG-3')

using pSF-TEF1-URA3 plasmid (OGS534; Sigma-Aldrich) as a template. The three PCR fragments were created with Phusion Flash High-Fidelity PCR master mix (ThermoFisher) according to the manufacturer's instructions and assembled into a single plasmid by fusing the overlapping regions using the NEBuilder HiFi DNA Assembly Cloning Kit (New England BioLabs) resulting in multi-copy gRNA harbouring plasmid pRB089. Plasmid DNA was concentrated using a Zymo DNA Clean and Concentrator spin column (Zymo Research) and eluted into 10 µL H$_2$O and transformed to E. coli DH5a by heat-shock (Sambrook, J., en D. W. Russell. 2001. Molecular cloning: a laboratory manual 3rd edition. Cold Spring Harbor Laboratory Press, Cold Spring Harbor, New York). Transformants were plated on LB agar plates supplemented with 50 mg/L kanamycin and incubated at 37° C. A single colony was selected for plasmid extraction using the ZymoPURE™ Plasmid Midiprep Kit (Zymo Research). Plasmid integrity was confirmed by sequence analysis.

A repair-oligo consisting of 60 bp upstream and 60 bp downstream of the CAN1 ORF was constructed by annealing primer:

2101
(5'-TTTCAGAGTTCTTCAGACTTCTTAACTCCTGTAAAAACAAAAA
AAAAAAAGGCATAGCAATATGACGTTTTATTACCTTTAATCACATTCCC
ACGCCATTTCGCATTCTCACCCTCATA-3')
and 2102
(5'-TATGAGGGTGAGAATGCGAAATGGCGTGGGAATGTGATTAAAG
GTAATAAAACGTCATATTGCTATGCCTTTTTTTTTTTTGTTTTTACAG
GAGTTAAGAAGTCTGAAGAACTCTGAAA-3').

10 µL of 100 mM both primers was combined, boiled at 99° C. for 5 minutes and subsequently allowed to slowly cool down to room temperature.

Circa 100 ng of the sgRNA harbouring plasmid pRB089 was co-transformed with 200 nmol of the annealed CAN1 repair-oligo to the S. cerevisiae tdh1::ThermoCas9-LEU2 strain by heat-shock, with all steps usually performed at 30° C., now performed at 37° C. Transformants were plated on SM agar plates and incubated at 37° C. for four days. 44 colonies were picked and analyzed by colony PCR with primers 2223 (5'-GGTTGCGAACAGAGTAAACC-3') and 2224 (5'-TCGGGAGCAAGATTGTTGTG-3'). This identified one colony with a 380 bp deletion product, while all other showed a 2153 bp wild-type fragment. This demonstrates ThermoCas9 endonuclease activity in *S. cerevisiae* and its use in genome editing.

| Corbion nr. | Sequence 5'-3' |
|---|---|
| 2101 | TTTCAGAGTTCTTCAGACTTCTTAACTCCTGTAAAAACAAAAAAAAAAAAAGGCATAGCAATATGACGTTTTATTACCTTTAATCACATTCCCACGCCATTTCGCATTCTCACCCTCATA |
| 2102 | TATGAGGGTGAGAATGCGAAATGGCGTGGGAATGTGATTAAAGGTAATAAAACGTCATATTGCTATGCCTTTTTTTTTTTTGTTTTTACAGGAGTTAAGAAGTCTGAAGAACTCTGAAA |
| 2103 | GCATTCCCCACTCTTAGGCGTTTTTTTGTTTTTTATGTCTCGGGTCTTGAGGGGTTTTTTGTG |
| 2104 | TTATCCTATAAATATAACGTTTTTGAACACATGGAATAATTTGGGAATTTACTC |
| 2105 | ACAAAATGGAATATGTTCATAGGGTAGACGGATAGAGATGGGCCAATACC |
| 2106 | AAAAAACCCCTCAAGACCCGAGACATAAAAAACAAAAAAACGCCTAAGAGTGGGAATG |
| 2108 | GCAGTGAAAGATAAATGATCGCGTTGGTCAGAGGTGTGGAGTCATAGTTCCCCTGAGATTATCG |
| 2109 | AAGCATAATCATACATTATCTTTTCAAAGAGAGATTCGATGCCCGACGAG |
| 2110 | ATTTAAATTTCCGAACTCTCCAAGGCCCTCAGTCTCGACGATCCATATCG |
| 2111 | AACACAGAGTAAATTCCCAAATTATTCCATGTGTTCAAAAACGTTATATTTATAGG |
| 2113 | CTACAAATGTGGTATTGGCCCATCTCTATCCGTCTACCCTATGAACATATTCC |
| 2114 | AATCTCAGGGGAACTATGACTCCACACCTCTGACCAACGCGATCATTTATCTTTCACTGCGGAGAAG |
| 2115 | CGCTCATTTGCTCGTCGGGCATCGAATCTCTCTTTGAAAAGATAATGTATGATTATG |
| 2116 | GCCGATATCAAGACCGATTTTATACTTCATTTTGTAATTAAAACTTAGATTAGATTGCTATGC |
| 2118 | AATGTAAGCGTGACATAACTAATTACATGATTACACCTTCCTCTTCTTCTTGGGTAACGGACGGATAGTTTCCCCGGCTTTC |
| 2119 | AGCAATCTAATCTAAGTTTTAATTACAAAATGAAGTATAAAATCGGTCTTG |
| 2120 | CCGTTACCCAAGAAGAAGAGGAAGGTGTAATCATGTAATTAGTTATGTCACGCTTAC |
| 2223 | GGTTGCGAACAGAGTAAACC |
| 2224 | TCGGGAGCAAGATTGTTGTG |
| 2580 | TTCTTAGGTGCATGCGACGGTATCCACGTGCAGAACAACATAGTCTGAAGAAGGGGGGGATCCATCTTCGATGGATAGCG |
| 2581 | AGAAGAGAAAAGGGTAAAGTTAATGCTTAATCTTGTCTTGGCTTAAAAAGTAATATGTACGGTCGCCTGACGCATATACC |
| 2665 | CGCATGTTTCGGCGTTCGAAACTTCTCCGCAGTGAAAGATAAATGATCGCACCTGGGTTTCTCCAATAACGGTCATAGTTCCCCTGAGATTATCGCTGTGGTATAATGAAAGTTATACC |
| 2666 | GGTATAACTTTCATTATACCACAGCGATAATCTCAGGGGAACTATGACCGTTATTGGAGAAACCCAGGTGCGATCATTTATCTTTCACTGCGGAGAAGTTTCGAACGCCGAAACATGCG |
| 2745 | GGGGACTAAAATTTTTAATATAAATATATAAATTAAAAATAG |

The following section of the description consists of numbered paragraphs simply providing statements of the invention already described herein. The numbered paragraphs in this section are not claims. The claims are set forth below in the later section headed "claims".

1. An isolated clustered regularly interspaced short palindromic repeat (CRISPR)-associated (Cas) protein or polypeptide comprising;
   a. the amino acid motif EKDGKYYC [SEQ ID NO: 2]; and/or
   b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
   c. the amino acid motif $X_5LKX_6IE$ [SEQ ID NO: 4] wherein $X_5$ is independently selected from Methionine or Phenylalanine and $X_6$ is independently selected from Histidine or Asparagine; and/or
   d. the amino acid motif $X_7VYSX_8K$ [SEQ ID NO: 5] wherein $X_7$ is Glutamate or Isoleucine and $X_8$ is one of Tryptophan, Serine or Lysine; and/or
   e. the amino acid motif $X_9FYX_{10}X_{11}REQX_{12}KEX_{13}$ [SEQ ID NO: 6] wherein $X_9$ is Alanine or Glutamate, $X_{10}$ is Glutamine or Lysine, $X_{11}$ is Arginine or Alanine, $X_{12}$ is Asparagine or Alanine and $X_{13}$ is Lysine or Serine;
   wherein the Cas protein is capable of nucleic acid cleavage between 50° C. and 100° C. when associated with at least one targeting RNA molecule, and a polynucleotide comprising a target nucleic acid sequence recognised by the targeting RNA molecule.
2. An isolated Cas protein or polypeptide fragment having an amino acid sequence of SEQ ID NO: 1 or a sequence of at least 77% identity therewith, wherein the Cas protein is capable of binding, cleaving, modifying or marking a polynucleotide comprising a target nucleic acid sequence at a temperature between 50° C. and 100° C. when associated with at least one RNA molecule which recognizes the target sequence.
3. A Cas protein or polypeptide fragment as in numbered paragraph 1 or 2, wherein the Cas protein or fragment is capable of nucleic acid binding, cleavage, marking or modification at a temperature between 50° C. and 75° C., preferably at a temperature above 60° C.; more preferably at a temperature between 60° C. and 80° C.; more preferably at a temperature between 60° C. and 65° C.
4. A Cas protein or polypeptide fragment as in any of numbered paragraphs 1 to 3, wherein the nucleic acid binding, cleavage, marking or modification is DNA cleavage.
5. A Cas protein or polypeptide fragment as in any preceding numbered paragraph, wherein the amino acid sequence comprises an amino acid sequence of SEQ ID NO: 1 or a sequence of at least 77% identity therewith.
6. A Cas protein or polypeptide fragment as in any preceding numbered paragraph, wherein the Cas protein is obtainable from a bacterium, archaeon or virus.
7. A Cas protein or polypeptide fragment as in any preceding numbered paragraph, wherein the Cas protein is obtainable from *Geobacillus* sp., preferably from *Geobacillus thermodenitrificans*.
8. A ribonucleoprotein complex comprising a Cas protein as in any preceding numbered paragraph, and comprising at least one targeting RNA molecule which recognises a sequence in a target polynucleotide.
9. A ribonucleoprotein complex as in numbered paragraph 8, wherein the targeting RNA molecule comprises a crRNA and optionally a tracrRNA.
10. A ribonucleoprotein complex as in any of numbered paragraphs 7 to 9, wherein the length of the at least one RNA molecule is in the range 35-135 nucleotide residues.
11. A ribonucleoprotein complex as in numbered paragraph 8 or 9, wherein the target sequence is 31 or 32 nucleotide residues in length.
12. A Cas protein or polypeptide as in any of numbered paragraphs 1 to 7 or a ribonucleoprotein complex as in any of 8 to 11, wherein the protein or polypeptide is provided as part of a protein complex comprising at least one further functional or non-functional protein.
13. A Cas protein, polypeptide, or ribonucleoprotein complex as in numbered paragraph 12, wherein the Cas protein or polypeptide, and/or the at least one further protein further comprise at least one functional moiety.
14. A Cas protein or polypeptide, or ribonucleoprotein complex as in numbered paragraph 13, wherein the at least one functional moiety is fused or linked to the N-terminus and/or the C-terminus of the Cas protein, polypeptide or ribonucleoprotein complex; preferably the N-terminus.
15. A Cas protein or polypeptide, or a ribonucleoprotein complex as in numbered paragraph 13 or 14, wherein the at least one functional moiety is a protein; optionally selected from a helicase, a nuclease, a helicase-nuclease, a DNA methylase, a histone methylase, an acetylase, a phosphatase, a kinase, a transcription (co-) activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.
16. A Cas protein or polypeptide, or a ribonucleoprotein complex as in numbered paragraph 15, wherein the native activity of the Cas9 nuclease activity is inactivated and the Cas protein is linked to at least one functional moiety.
17. A Cas protein or polypeptide, or a ribonucleoprotein complex as in numbered paragraph 15 or 16, wherein the at least one functional moiety is a nuclease domain; preferably a FokI nuclease domain.
18. A Cas protein or polypeptide, or a ribonucleoprotein complex as in any of numbered paragraphs 15 to 17, wherein the at least one functional moiety is a marker protein, for example GFP.
19. An isolated nucleic acid molecule encoding a Cas protein or polypeptide, comprising;
   a. the amino acid motif EKDGKYYC [SEQ ID NO: 2]; and/or
   b. the amino acid motif $X_1X_2CTX_3X_4$ [SEQ ID NO: 3] wherein $X_1$ is independently selected from Isoleucine, Methionine or Proline, $X_2$ is independently selected from Valine, Serine, Asparagine or Isoleucine, $X_3$ is independently selected from Glutamate or Lysine and $X_4$ is one of Alanine, Glutamate or Arginine; and/or
   c. the amino acid motif $X_5LKX_6IE$ [SEQ ID NO: 4] wherein $X_5$ is independently selected from Methionine or Phenylalanine and $X_6$ is independently selected from Histidine or Asparagine; and/or d. the amino acid motif X$_7$VYSX$_8$K [SEQ ID NO: 5] wherein X$_7$ is Glutamate or Isoleucine and X$_8$ is one of Tryptophan, Serine or Lysine; and/or
e. the amino acid motif X$_9$FYX$_{10}$X$_{11}$REQX$_{12}$KEX$_{13}$ [SEQ ID NO: 6] wherein X$_9$ is Alanine or Glutamate, X$_{10}$ is Glutamine or Lysine, X$_{11}$ is Arginine or Alanine, X$_{12}$ is Asparagine or Alanine and X$_{13}$ is Lysine or Serine;

wherein the Cas protein or polypeptide is capable of DNA binding, cleavage, marking or modification between 50° C. and 100° C. when associated with at least one targeting RNA molecule, and a polynucleotide comprising a target nucleic acid sequence recognised by the targeting RNA molecule.

20. An isolated nucleic acid molecule encoding a clustered regularly interspaced short palindromic repeat (CRISPR)-associated (Cas) protein having an amino acid sequence of SEQ ID NO: 1 or a sequence of at least 77% identity therewith; or a polypeptide fragment thereof.

21. An isolated nucleic acid molecule as in numbered paragraph 19 or 20, further comprising at least one nucleic acid sequence encoding an amino acid sequence which upon translation is fused with the Cas protein or polypeptide.

22. An isolated nucleic acid molecule as in numbered paragraph 21, wherein the at least one nucleic acid sequence fused to the nucleic acid molecule encoding the Cas protein or polypeptide, encodes a protein selected from a protein selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag.

23. An expression vector comprising a nucleic acid molecule as in any of numbered paragraphs 19 to 22.

24. An expression vector as in numbered paragraph 23, further comprising a nucleotide sequence encoding at least one targeting RNA molecule.

25. A method of modifying a target nucleic acid comprising contacting the nucleic acid with:
a. a ribonucleoprotein complex of any of numbered paragraphs 6 to 11; or
b. a protein or protein complex of any of numbered paragraphs 12 to 18 and at least one targeting RNA molecule as defined in any of numbered paragraphs 6 to 11; and wherein said method is not used in human cells.

26. A method of modifying a target nucleic acid in a non-human cell, comprising transforming, transfecting or transducing the cell with an expression vector of numbered paragraph 24; or alternatively transforming, transfecting or transducing the cell with an expression vector of numbered paragraph 23 and a further expression vector comprising a nucleotide sequence encoding a targeting RNA molecule as defined in any of numbered paragraphs 6 to 11.

27. A method of modifying a target nucleic acid in a non-human cell comprising transforming, transfecting or transducing the cell with an expression vector of numbered paragraph 23, and then delivering a targeting RNA molecule as defined in any of numbered paragraphs 6 to 11 to or into the cell.

28. A method of modifying a target nucleic acid as in any of numbered paragraphs 25 to 28, wherein the at least one functional moiety is a marker protein or reporter protein and the marker protein or reporter protein associates with the target nucleic acid; preferably wherein the marker is a fluorescent protein, for example a green fluorescent protein (GFP).

29. A method as in any of numbered paragraphs 25 to 28, wherein the target nucleic acid is DNA; preferably dsDNA.

30. A method as in any of numbered paragraphs 25 to 28, wherein the target nucleic acid is RNA.

31. A method of modifying a target nucleic acid as in numbered paragraph 29, wherein the nucleic acid is dsDNA, the at least one functional moiety is a nuclease or a helicase-nuclease, and the modification is a single-stranded or a double-stranded break at a desired locus.

32. A method of silencing gene expression at a desired locus according to any of the methods in any of numbered paragraphs 26, 27, 29 or 31.

33. A method of modifying or deleting and/or inserting a desired nucleotide sequence at a desired location according to any of the methods as in any of numbered paragraphs 26, 27, 29 or 31.

34. A method of modifying gene expression in a non-human cell comprising modifying a target nucleic acid sequence as in a method of any of numbered paragraphs 25 to 29; wherein the nucleic acid is dsDNA and the functional moiety is selected from a DNA modifying enzyme (e.g. a methylase or acetylase), a transcription activator or a transcription repressor.

35. A method of modifying gene expression in a non-human cell comprising modifying a target nucleic acid sequence as in a method of numbered paragraph 30, wherein the nucleic acid is an mRNA and the functional moiety is a ribonuclease; optionally selected from an endonuclease, a 3' exonuclease or a 5' exonuclease.

36. A method of modifying a target nucleic acid as in any of numbered paragraphs 25 to 35, wherein the method is carried out at a temperature between 50° C. and 100° C.

37. A method of modifying a target nucleic acid as in numbered paragraph 36, wherein the method is carried out at a temperature at or above 60° C., preferably between 60° C. and 80° C., more preferably between 60° C. and 65° C.

38. A method as in any of numbered paragraphs 25 to 37 wherein the cell is a prokaryotic cell.

39. A method as in any of numbered paragraphs 25 to 38 wherein the cell is a eukaryotic cell.

40. A host cell transformed by a method as in any of numbered paragraphs 22 to 36; wherein the cell is not a human cell.

The following section of the description consists of further numbered paragraphs simply providing statements of the invention already described herein. The numbered paragraphs in this section are not claims. The claims are set forth below in the later section headed "claims".

1. Use of at least one targeting RNA molecule and a Cas protein for binding, cleaving, marking or modifying a double stranded target polynucleotide comprising a target nucleic acid sequence, wherein:
the double stranded target polynucleotide comprises a target nucleic acid strand, comprising said target nucleic acid sequence, and a non-target nucleic acid strand, comprising a protospacer nucleic acid sequence complementary to the target nucleic acid sequence;

the Cas protein has an amino acid sequence of SEQ ID NO: 1 or a sequence of at least 77% identity therewith;

the at least one targeting RNA molecule recognizes the target sequence;

the non-target nucleic acid strand further comprises a protospacer adjacent motif (PAM) sequence directly adjacent to the 3' end of the protospacer nucleic acid sequence, wherein the PAM sequence comprises 5'-NNNNCNN-3'; and wherein said use is not in a human cell.

2. A use as in paragraph 1, wherein the binding, cleaving, marking or modifying occurs at a temperature between 20° C. and 100° C., at a temperature between 30° C. and 80° C., at a temperature between 37° C. and 78° C., preferably at a temperature above 55° C.; more preferably at a temperature between 55° C. and 80° C.; even more preferably at a temperature between 55° C. and 65° C. or 60° C. and 65° C.

3. A use as in paragraph 1 or paragraph 2, wherein the polynucleotide comprising the target nucleic acid sequence is cleaved by the Cas protein, preferably wherein said cleavage is DNA cleavage.

4. A use as in any of paragraphs 1 to 3 wherein the target nucleic acid strand comprising the target sequence is double stranded DNA and said use results in a double stranded break in the polynucleotide comprising the target nucleic acid sequence.

5. A use as in paragraph 1 or paragraph 2 wherein the polynucleotide comprising the target nucleic acid sequence is double stranded DNA, the Cas protein lacks the ability to cut the double stranded DNA and said use results in gene silencing of the polynucleotide.

6. A use as in paragraph 5, wherein the polynucleotide comprising the Cas protein contains the mutations D8A and H582A.

7. A use as in any preceding paragraph wherein the PAM sequence comprises 5'-NNNNCNNA-3' [SEQ ID NO: 47].

8. A use as in any preceding paragraph, wherein the PAM sequence comprises 5'-NNNNCSAA-3' [SEQ ID NO: 48].

9. A use as in paragraph 8, wherein the PAM sequence comprises 5'-NNNNCCAA-3' [SEQ ID NO: 50].

10. A use as in paragraph 8 or paragraph 9, wherein the binding, cleaving, marking or modifying occurs at a temperature between 20° C. and 70° C.

11. A use as in any of paragraphs 7 to 10, wherein binding, cleaving, marking or modifying occurs at a temperature between 25° C. and 65° C.

12. A use as in any preceding paragraph, wherein the Cas protein is obtainable from a bacterium, archaeon or virus, preferably from a thermophilic bacterium.

13. A use as in any preceding paragraph, wherein the Cas protein is obtainable from *Geobacillus* sp., preferably from *Geobacillus thermodenitrificans*.

14. A use as in any preceding paragraph, wherein the targeting RNA molecule comprises a crRNA and a tracrRNA.

15. A use as in any preceding paragraph, wherein the length of the at least one targeting RNA molecule is in the range 35-200 nucleotide residues.

16. A use as in any preceding paragraph, wherein the target nucleic acid sequence is from 15 to 32 nucleotide residues in length.

17. A use as in any preceding paragraph, wherein the Cas protein further comprises at least one functional moiety.

18. A use as in any preceding paragraph wherein the Cas protein is provided as part of a protein complex comprising at least one further functional or non-functional protein, optionally wherein the at least one further protein further comprises at least one functional moiety.

19. A use as in paragraph 17 or paragraph 18, wherein the Cas protein or further protein comprises at least one functional moiety fused or linked to the N-terminus and/or the C-terminus of the Cas protein or protein complex; preferably the C-terminus.

20. A use as in any of paragraphs 17 to 19, wherein the at least one functional moiety is a protein; optionally selected from a helicase, a nuclease, a helicase-nuclease, a DNA methylase, a histone methylase, an acetylase, a phosphatase, a kinase, a transcription (co-) activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag, for example a green fluorescent protein (GFP).

21. A use as in paragraph 20, wherein the native activity of the Cas9 nuclease is inactivated and the Cas protein is linked to at least one functional moiety.

22. A use as in paragraph 20 or paragraph 21, wherein the at least one functional moiety is a nuclease domain; preferably a FokI nuclease domain.

23. A use as in any of paragraphs 20 to 22, wherein the at least one functional moiety is a marker protein.

24. A method of binding, cleaving, marking or modifying a double stranded target polynucleotide, wherein the double stranded target polynucleotide comprises a target nucleic acid strand comprising a target nucleic acid sequence, and a non-target nucleic acid strand comprising a protospacer nucleic acid sequence complementary to the target nucleic acid sequence, said method comprising:

a. designing at least one targeting RNA molecule, wherein the targeting RNA molecule recognizes the target sequence in the target strand, and the non-target strand further comprises a protospacer adjacent motif (PAM) sequence directly adjacent the 3' end of the protospacer sequence, wherein the PAM sequence comprises 5'-NNNNCNN-3';

b. forming a ribonucleoprotein complex comprising the targeting RNA molecule and a Cas protein, wherein the isolated Cas protein has an amino acid sequence of SEQ ID NO: 1 or a sequence of at least 77% identity therewith; and c. the ribonucleoprotein complex binding, cleaving, marking or modifying the target polynucleotide; and wherein said method is not used in human cells.

25. A method as in paragraph 24, wherein the binding, cleaving, marking or modifying occurs at a temperature between 20° C. and 100° C., at a temperature between 30° C. and 80° C., at a temperature between 37° C. and 78° C., preferably at a temperature above 55° C.; more preferably at a temperature between 55° C. and 80° C.; even more preferably at a temperature between 55° C. and 65° C. or 60° C. and 65° C.

26. A method as in paragraph 24 or paragraph 25, wherein the double stranded target polynucleotide comprising the target nucleic acid sequence is cleaved by the Cas protein, preferably wherein said cleavage is DNA cleavage.
27. A method as in any of paragraphs 24 to 26, wherein the target polynucleotide is double stranded DNA and said use results in a double stranded break in the polynucleotide.
28. A method as in paragraph 24 or paragraph 25, wherein the target polynucleotide comprising the target nucleic acid sequence is double stranded DNA, the Cas protein lacks the ability to cut the double stranded DNA and said method results in gene silencing of the target polynucleotide.
29. A method as in any of paragraphs 24 to 28 wherein the PAM sequence comprises 5'-NNNNCNNA-3' [SEQ ID NO: 47].
30. A method as in paragraph 29, wherein the PAM sequence comprises 5'-NNNNCSAA-3' [SEQ ID NO: 48].
31. A method as in paragraph 30, wherein the PAM sequence comprises 5'-NNNNCCAA-3' [SEQ ID NO: 50].
32. A method as in paragraph 30 or paragraph 31, wherein the binding, cleaving, marking or modifying occurs at a temperature between 20° C. and 70° C.,
33. A method as in any of paragraphs 29 to 32, wherein binding, cleaving, marking or modifying occurs at a temperature between 25° C. and 65° C.
34. A method as in any of paragraphs 24 to 33, wherein the Cas protein is obtainable from a bacterium, archaeon or virus, preferably from a thermophilic bacterium.
35. A method as in any of paragraphs 24 to 34, wherein the Cas protein is obtainable from *Geobacillus* sp., preferably from *Geobacillus thermodenitrificans*.
36. A method as in any of paragraphs 24 to 35, wherein the targeting RNA molecule comprises a crRNA and a tracrRNA.
37. A method as in any of paragraphs 24 to 36, wherein the length of the at least one targeting RNA molecule is in the range 35-200 nucleotide residues.
38. A method as in any of paragraphs 24 to 37, wherein the target nucleic acid sequence is from 15 to 32 nucleotide residues in length.
39. A method as in any of paragraphs 24 to 39, wherein the Cas protein further comprises at least one functional moiety.
40. A method as in any of paragraphs 24 to 40, wherein the Cas protein is provided as part of a protein complex comprising at least one further functional or non-functional protein, optionally wherein the at least one further protein further comprises at least one functional moiety.
41. A method as in paragraph 39 or 40, wherein the Cas protein or further protein comprises at least one functional moiety fused or linked to the N-terminus and/or the C-terminus of the Cas protein or protein complex; preferably the C-terminus.
42. A method as in any of paragraphs 39 to 41, wherein the at least one functional moiety is a protein; optionally selected from a helicase, a nuclease, a helicase-nuclease, a DNA methylase, a histone methylase, an acetylase, a phosphatase, a kinase, a transcription (co-) activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag, for example a green fluorescent protein (GFP).
43. A method as in paragraph 42, wherein the native activity of the Cas9 nuclease is inactivated and the Cas protein is linked to at least one functional moiety.
44. A method as in paragraph 42 or paragraph 43, wherein the at least one functional moiety is a nuclease domain; preferably a FokI nuclease domain.
45. A method as in any of paragraphs 42 to 44, wherein the at least one functional moiety is a marker protein.
46. A use as in paragraph 20 or method as in paragraph 42, wherein the double stranded target polynucleotide is dsDNA, the at least one functional moiety is a nuclease or a helicase-nuclease, and the modification is a single-stranded or a double-stranded break at a desired locus.
47. A use as in paragraph 20 or method as in paragraph 42, wherein the double stranded target polynucleotide is dsDNA and the functional moiety is selected from a DNA modifying enzyme (e.g. a methylase or acetylase), a transcription activator or a transcription repressor and the binding, cleaving, marking or modifying results in modification of gene expression.
48. A use as in paragraph 20 or method as in paragraph 42, wherein said binding, cleaving, marking or modifying occurs in vivo.
49. A use or method as in paragraph 48, wherein said binding, cleaving, marking or modifying occurs in a thermophilic organism, preferably a thermophilic prokaryotic organism, more preferably *Geobacillus* sp.
50. A use or method as in paragraph 48, wherein said binding, cleaving, marking or modifying occurs in a mesophilic organism, preferably a mesophilic prokaryotic organism, more preferably *Pseudomonas* sp.
51. A use as in any of paragraphs 1 to 4, 7 to 23 or 46, or a method as in any of paragraphs 24 to 27, 29 to 46 wherein the binding, cleaving, marking or modifying results in modifying or deleting and/or inserting a desired nucleotide sequence at a desired location, and/or wherein the binding, cleaving, marking or modifying results in silencing gene expression at a desired locus.
52. A transformed non-human cell, having a double stranded target polynucleotide comprising a target nucleic acid sequence, wherein the double stranded target polynucleotide comprises a target nucleic acid strand, comprising said target nucleic acid sequence, and a non-target nucleic acid strand, comprising a protospacer nucleic acid sequence complementary to the target nucleic acid sequence, said cell comprising:
a clustered regularly interspaced short palindromic repeat (CRISPR)-associated (Cas) protein having an amino acid sequence of SEQ ID NO: 1 or a sequence of at least 77% identity therewith;
at least one targeting RNA molecule which recognizes the target nucleic acid sequence in the target nucleic acid strand, wherein the non-target strand further comprises a protospacer adjacent motif (PAM) sequence directly adjacent the 3' end of the protospacer sequence, wherein the PAM sequence comprises 5'-NNNNCNN-3'; and
an expression vector comprising a nucleic acid encoding at least one of said Cas protein and said targeting RNA molecule.
53. A transformed cell as in paragraph 52, wherein the Cas protein and targeting RNA molecule enable binding, cleaving, marking or modifying of the target polynucleotide in the cell and the binding, cleaving, marking or modifying occurs at a temperature between 20° C. and 100° C., at a temperature between 30° C. and 80° C., at a temperature between 37° C. and 78° C., preferably at a temperature above 55° C.; more preferably at a temperature between 55° C. and 80° C.; even more preferably at a temperature between 55° C. and 65° C. or 60° C. and 65° C.

54. A transformed cell as in paragraph 52 or paragraph 53, wherein the target nucleic acid strand comprising the target nucleic acid sequence is cleaved by the Cas protein, preferably wherein said cleavage is DNA cleavage.

55. A transformed cell as in any of paragraphs 52 to 54, wherein the target polynucleotide comprising the target sequence is double stranded DNA and said binding, cleaving, marking or modifying results in a double stranded break in the target polynucleotide.

56. A transformed cell as in paragraph 52 or paragraph 53, wherein the target polynucleotide comprising the target nucleic acid sequence is double stranded DNA, the Cas protein lacks the ability to cut the double stranded DNA and said binding, cleaving, marking or modifying results in gene silencing of the target polynucleotide.

57. A transformed cell as in any of paragraphs 52 to 56, wherein the PAM sequence comprises 5'-NNNNCNNA-3' [SEQ ID NO: 47].

58. A transformed cell as in paragraph 57, wherein the PAM sequence comprises 5'-NNNNCSAA-3' [SEQ ID NO: 48].

59. A transformed cell as in paragraph 58, wherein the PAM sequence comprises 5'-NNNNCCAA-3' [SEQ ID NO: 50].

60. A transformed cell as in paragraph 58 or paragraph 59, wherein the binding, cleaving, marking or modifying occurs at a temperature between 20° C. and 70° C.

61. A transformed cell as in any of paragraphs 57 to 60, wherein binding, cleaving, marking or modifying occurs at a temperature between 25° C. and 65° C.

62. A transformed cell as in any of paragraphs 52 to 61, wherein the Cas protein is obtainable from a bacterium, archaeon or virus, preferably from a thermophilic bacterium.

63. A transformed cell as in any of paragraphs 52 to 62, wherein the Cas protein is obtainable from *Geobacillus* sp., preferably from *Geobacillus thermodenitrificans*.

64. A transformed cell as in any of paragraphs 52 to 63, wherein the cell is a prokaryotic cell.

65. A transformed cell as in any of paragraphs 52 to 63, wherein the cell is a eukaryotic cell.

66. A transformed cell as in any of paragraphs 52 to 65, wherein the targeting RNA molecule comprises a crRNA and a tracrRNA.

67. A transformed cell as in any of paragraphs 52 to 66, wherein the length of the at least one targeting RNA molecule is in the range 35-200 nucleotide residues.

68. A transformed cell as in any of paragraphs 52 to 67, wherein the target nucleic acid sequence is from 15 to 32 nucleotide residues in length.

69. A transformed cell as in any of paragraphs 52 to 68, wherein the Cas protein further comprises at least one functional moiety.

70. A transformed cell as in any of paragraphs 52 to 69, wherein the Cas protein is provided as part of a protein complex comprising at least one further functional or non-functional protein, optionally wherein the at least one further protein further comprises at least one functional moiety.

71. A transformed cell as in paragraph 69 or 70, wherein the Cas protein or further protein comprises at least one functional moiety fused or linked to the N-terminus and/or the C-terminus of the Cas protein or protein complex; preferably the N-terminus.

72. A transformed cell as in any of paragraphs 69 to 71, wherein the at least one functional moiety is a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag, for example a green fluorescent protein (GFP).

73. A transformed cell as in paragraph 72, wherein the native activity of the Cas9 nuclease is inactivated and the Cas protein is linked to at least one functional moiety.

74. A transformed cell as in any of paragraphs 69 to 73, wherein the at least one functional moiety is a nuclease domain; preferably a FokI nuclease domain.

75. A transformed cell as in any of paragraphs 69 to 73, wherein the at least one functional moiety is a marker protein.

76. A transformed cell as in any of paragraphs 69 to 74, wherein the double stranded target polynucleotide is dsDNA, the at least one functional moiety is a nuclease or a helicase-nuclease, and the modification is a single-stranded or a double-stranded break at a desired locus.

77. A transformed cell as in any of paragraphs 69 to 73 or method as in paragraph 42, wherein the double stranded target polynucleotide is dsDNA and the functional moiety is selected from a DNA modifying enzyme (e.g. a methylase or acetylase), a transcription activator or a transcription repressor and the binding, cleaving, marking or modifying results in modification of gene expression.

78. A transformed cell as in any of paragraphs 69 to 74 wherein the Cas protein is expressed from an expression vector.

79. A transformed cell as in any of paragraphs 52 to 78 wherein the binding, cleaving, marking or modifying results in modifying or deleting and/or inserting a desired nucleotide sequence at a desired location, and/or wherein the binding, cleaving, marking or modifying results in silencing gene expression at a desired locus.

80. A nucleoprotein complex comprising a Cas protein, at least one targeting RNA molecule which recognises a target nucleic acid sequence in a double stranded target polynucleotide, and the target polynucleotide, wherein the Cas protein has an amino acid sequence of SEQ ID NO: 1 or a sequence of at least 77% identity therewith;

the double stranded target polynucleotide comprises a target nucleic acid strand, comprising said target nucleic acid sequence, and a non-target nucleic acid strand, comprising a protospacer nucleic acid sequence complementary to the target nucleic acid sequence and a protospacer adjacent motif (PAM) sequence directly adjacent the 3' end of the protospacer sequence, wherein the PAM sequence comprises 5'-NNNNCNN-3'; wherein the nucleoprotein complex is not in a human cell.

81. A nucleoprotein complex as in paragraph 80, wherein the nucleoprotein complex occurs at a temperature between 20° C. and 100° C., at a temperature between 30° C. and 80° C., at a temperature between 37° C. and 78° C., preferably at a temperature above 55° C.; more preferably at a temperature between 55° C. and 80° C.; even more preferably at a temperature between 55° C. and 65° C. or 60° C. and 65° C.

82. A nucleoprotein complex as in paragraph 80 or claim 81, wherein the double stranded target polynucleotide comprising the target nucleic acid sequence is cleaved by the Cas protein, preferably wherein said cleavage is DNA cleavage.

83. A nucleoprotein complex as in any of paragraphs 80 to 82, wherein the target polynucleotide comprising the target sequence is double stranded DNA and said binding, cleaving, marking or modifying results in a double stranded break in the target polynucleotide.

84. A nucleoprotein complex as in paragraph 80 or paragraph 81, wherein the target polynucleotide comprising the target nucleic acid sequence is double stranded DNA, the Cas protein lacks the ability to cut the double stranded DNA and the presence of said nucleoprotein complex results in gene silencing of the target polynucleotide.

85. A nucleoprotein complex as in any of paragraphs 80 to 84, wherein the PAM sequence comprises 5'-NNNNCNNA-3' [SEQ ID NO: 47].

86. A nucleoprotein complex as in paragraph 85, wherein the PAM sequence comprises 5'-NNNNCSAA-3' [SEQ ID NO: 48].

87. A nucleoprotein complex as in paragraph 86, wherein the PAM sequence comprises 5'-NNNNCCAA-3' [SEQ ID NO: 50].

88. A nucleoprotein complex as in paragraph 86 or paragraph 87, wherein the binding, cleaving, marking or modifying occurs at a temperature between 20° C. and 70° C.

89. A nucleoprotein complex as in any of paragraphs 85 to 88, wherein binding, cleaving, marking or modifying occurs at a temperature between 25° C. and 65° C.

90. A nucleoprotein complex as in any of paragraphs 80 to 89, wherein the Cas protein is obtainable from a bacterium, archaeon or virus, preferably from a thermophilic bacterium.

91. A nucleoprotein complex as in any of paragraphs 80 to 90, wherein the Cas protein is obtainable from *Geobacillus* sp., preferably from *Geobacillus thermodenitrificans*.

92. A nucleoprotein complex as in any of paragraphs 80 to 91, wherein the nucleoprotein complex is in a prokaryotic cell.

93. A nucleoprotein complex as in any of paragraphs 80 to 91, wherein the nucleoprotein complex is in a eukaryotic cell.

94. A nucleoprotein complex as in any of paragraphs 80 to 93, wherein the targeting RNA molecule comprises a crRNA and a tracrRNA.

95. A nucleoprotein complex as in any of paragraphs 80 to 94, wherein the length of the at least one targeting RNA molecule is in the range 35-200 nucleotide residues.

96. A nucleoprotein complex as in any of paragraphs 80 to 95, wherein the target nucleic acid sequence is from 15 to 32 nucleotide residues in length.

97. A nucleoprotein complex as in any of paragraphs 80 to 96, wherein the Cas protein further comprises at least one functional moiety.

98. A nucleoprotein complex as in any of paragraphs 80 to 97, wherein the Cas protein is provided as part of a protein complex comprising at least one further functional or non-functional protein, optionally wherein the at least one further protein further comprises at least one functional moiety.

99. A nucleoprotein complex as in paragraph 97 or 98, wherein the Cas protein or further protein comprises at least one functional moiety fused or linked to the N-terminus and/or the C-terminus of the Cas protein or protein complex; preferably the C-terminus.

100. A nucleoprotein complex as in any of paragraphs 97 to 99, wherein the at least one functional moiety is a protein; optionally selected from a helicase, a nuclease, a helicase-nuclease, a DNA methylase, a histone methylase, an acetylase, a phosphatase, a kinase, a transcription (co-)activator, a transcription repressor, a DNA binding protein, a DNA structuring protein, a marker protein, a reporter protein, a fluorescent protein, a ligand binding protein, a signal peptide, a subcellular localisation sequence, an antibody epitope or an affinity purification tag, for example a green fluorescent protein (GFP).

101. A nucleoprotein complex as in paragraph 100, wherein the native activity of the Cas9 nuclease is inactivated and the Cas protein is linked to at least one functional moiety.

102. A nucleoprotein complex as in any of paragraphs 97 to 101, wherein the at least one functional moiety is a nuclease domain; preferably a FokI nuclease domain.

103. A nucleoprotein complex as in any of paragraphs 97 to 101, wherein the at least one functional moiety is a marker protein.

104. A nucleoprotein complex as in any of paragraphs 97 to 102, wherein the nucleic acid is dsDNA, the at least one functional moiety is a nuclease or a helicase-nuclease, and the target polynucleotide has a single-stranded or a double-stranded break at a desired locus.

105. A nucleoprotein complex as in any of paragraphs 97 to 101, wherein the nucleic acid is dsDNA and the functional moiety is selected from a DNA modifying enzyme (e.g. a methylase or acetylase), a transcription activator or a transcription repressor and the nucleoprotein complex formation results in modification of gene expression.

106. A nucleoprotein complex as in any of paragraphs 80 to 105, wherein the nucleoprotein formation results in modifying or deleting and/or inserting a desired nucleotide sequence at a desired location, and/or wherein the nucleoprotein complex formation results in silencing gene expression at a desired locus.

The invention claimed is:

1. A polynucleotide expression vector for modifying the genetic material at a target locus of a host organism which comprises the expression vector, the vector comprising:
   a) a polynucleotide sequence encoding a ThermoCas9 nuclease, wherein the ThermoCas9 nuclease comprises the amino acid sequence of SEQ ID NO: 1 or a sequence of at least 89% identity therewith, or an active fragment thereof;
   b) a polynucleotide sequence encoding a guide RNA, wherein the guide RNA has a nucleic acid sequence which recognizes a target nucleic acid sequence comprised in the target locus; and
   c) a first promoter oriented with respect to polynucleotide sequences of (a) and (b) so as to drive expression thereof in the organism, wherein said first promoter is an inducible promoter.

2. The vector as claimed in claim 1, wherein the sequence of (a) is 3' of the promoter and the sequence of (b) is 3' of the sequence of (a).

3. The vector as claimed in claim 1, wherein the first promoter is selected from the group consisting of a β-glucosidase promoter inducible with cellobiose and a Pm promoter inducible with 3-methylbenzoate.

4. The vector as claimed in claim 1, further comprising a homologous recombination (HR) fragment comprising at least one HR recombination arm.

5. The vector as claimed in claim 4, wherein the HR fragment comprises two recombination arms which allow recombination upstream and downstream, respectively, of a locus of interest in the host organism; and further wherein the locus of interest comprises the target sequence.

6. The vector as claimed in claim 5, wherein the HR fragment further comprises an insertion element between the upstream and downstream arms thereof; wherein the insertion element comprises a gene of interest.

7. The vector as claimed in claim 6, wherein a suitable promoter in operational orientation provides for expression of the gene of interest in the host organism.

8. The vector as claimed in claim 7, wherein the suitable promoter is tac.

9. The vector as claimed in claim 5, wherein the locus of interest comprises the PAM sequence 5'-NNNNCNN-3' located 3' of the target sequence.

10. The vector as claimed in claim 9, wherein the locus of interest comprises a PAM sequence selected from SEQ ID NO: 10, SEQ ID NO: 11, SEQ ID NO: 21 and SEQ ID NO: 22.

11. The vector as claimed in claim 4, wherein the guide RNA is a single guide RNA (sgRNA).

12. A method of modifying the genetic material of an organism comprising transforming the organism with a first expression vector of claim 4, and a second expression vector comprising a promoter and a polynucleotide sequence which encodes a homologous recombination (HR) fragment and which is under the transcriptional control of the promoter.

13. The method as claimed in claim 12, wherein the transformed organism is cultured for a period at a first temperature, and then cultured at a second temperature before or during induction of the promoter of the ThermoCas9 sequence; wherein the first temperature is 60° C. or less and the second temperature is a higher temperature which is at least 55° C.

14. The method as claimed in claim 12, wherein the organism is a prokaryote selected from the group consisting of:
   (a) a thermophilic bacterium,
   (b) a bacterium with growth temperature optimum of at least 40° C.; and
   (c) a soil bacterium.

15. A method of modifying the genetic material of a prokaryotic organism comprising transforming the organism with an expression vector of claim 4.

16. A prokaryotic cell transformed with an expression vector of claim 1.

17. A polynucleotide expression vector for modifying the genetic material at a target locus of a host organism which comprises the expression vector, the vector comprising:
   a) a polynucleotide sequence encoding a ThermoCas9 nuclease, wherein the ThermoCas9 nuclease comprises the amino acid sequence of SEQ ID NO: 1 or a sequence of at least 89% identity therewith, or an active fragment thereof;
   b) a polynucleotide sequence encoding a guide RNA, wherein the guide RNA has a nucleic acid sequence which recognizes a target nucleic acid sequence comprised in the target locus;
   c) a first promoter oriented with respect to polynucleotide sequence of (a) so as to drive expression thereof in the organism, wherein said first promoter is an inducible promoter; and
   d) a second promoter oriented with respect to polynucleotide sequence of (b) so as to drive expression thereof in the organism.

* * * * *

SEQUENCE LISTING

<160> NUMBER OF SEQ ID NOS: 281

<210> SEQ ID NO 1
<211> LENGTH: 1082
<212> TYPE: PRT
<213> ORGANISM: Geobacillus thermodenitrificans T12

<400> SEQUENCE: 1

```
Met Lys Tyr Lys Ile Gly Leu Asp Ile Gly Ile Thr Ser Ile Gly Trp
 1               5                  10                  15

Ala Val Ile Asn Leu Asp Ile Pro Arg Ile Glu Asp Leu Gly Val Arg
                20                  25                  30

Ile Phe Asp Arg Ala Glu Asn Pro Lys Thr Gly Glu Ser Leu Ala Leu
            35                  40                  45

Pro Arg Arg Leu Ala Arg Ser Ala Arg Arg Arg Leu Arg Arg Arg Lys
        50                  55                  60

His Arg Leu Glu Arg Ile Arg Arg Leu Phe Val Arg Glu Gly Ile Leu
 65                  70                  75                  80

Thr Lys Glu Glu Leu Asn Lys Leu Phe Glu Lys Lys His Glu Ile Asp
                85                  90                  95

Val Trp Gln Leu Arg Val Glu Ala Leu Asp Arg Lys Leu Asn Asn Asp
            100                 105                 110

Glu Leu Ala Arg Ile Leu Leu His Leu Ala Lys Arg Arg Gly Phe Arg
        115                 120                 125

Ser Asn Arg Lys Ser Glu Arg Thr Asn Lys Glu Asn Ser Thr Met Leu
130                 135                 140

Lys His Ile Glu Glu Asn Gln Ser Ile Leu Ser Ser Tyr Arg Thr Val
145                 150                 155                 160

Ala Glu Met Val Val Lys Asp Pro Lys Phe Ser Leu His Lys Arg Asn
                165                 170                 175

Lys Glu Asp Asn Tyr Thr Asn Thr Val Ala Arg Asp Asp Leu Glu Arg
            180                 185                 190

Glu Ile Lys Leu Ile Phe Ala Lys Gln Arg Glu Tyr Gly Asn Ile Val
        195                 200                 205

Cys Thr Glu Ala Phe Glu His Glu Tyr Ile Ser Ile Trp Ala Ser Gln
    210                 215                 220

Arg Pro Phe Ala Ser Lys Asp Asp Ile Glu Lys Lys Val Gly Phe Cys
225                 230                 235                 240

Thr Phe Glu Pro Lys Glu Lys Arg Ala Pro Lys Ala Thr Tyr Thr Phe
                245                 250                 255

Gln Ser Phe Thr Val Trp Glu His Ile Asn Lys Leu Arg Leu Val Ser
            260                 265                 270

Pro Gly Gly Ile Arg Ala Leu Thr Asp Asp Glu Arg Arg Leu Ile Tyr
        275                 280                 285

Lys Gln Ala Phe His Lys Asn Lys Ile Thr Phe His Asp Val Arg Thr
    290                 295                 300

Leu Leu Asn Leu Pro Asp Asp Thr Arg Phe Lys Gly Leu Leu Tyr Asp
305                 310                 315                 320

Arg Asn Thr Thr Leu Lys Glu Asn Glu Lys Val Arg Phe Leu Glu Leu
                325                 330                 335

Gly Ala Tyr His Lys Ile Arg Lys Ala Ile Asp Ser Val Tyr Gly Lys
            340                 345                 350

Gly Ala Ala Lys Ser Phe Arg Pro Ile Asp Phe Asp Thr Phe Gly Tyr
        355                 360                 365
```

```
Ala Leu Thr Met Phe Lys Asp Asp Thr Asp Ile Arg Ser Tyr Leu Arg
370                 375                 380

Asn Glu Tyr Glu Gln Asn Gly Lys Arg Met Glu Asn Leu Ala Asp Lys
385                 390                 395                 400

Val Tyr Asp Glu Glu Leu Ile Glu Leu Leu Asn Leu Ser Phe Ser
        405                 410                 415

Lys Phe Gly His Leu Ser Leu Lys Ala Leu Arg Asn Ile Leu Pro Tyr
        420                 425                 430

Met Glu Gln Gly Glu Val Tyr Ser Thr Ala Cys Glu Arg Ala Gly Tyr
        435                 440                 445

Thr Phe Thr Gly Pro Lys Lys Gln Lys Thr Val Leu Leu Pro Asn
450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                485                 490                 495

Ile His Ile Glu Leu Ala Arg Glu Leu Ser Gln Ser Phe Asp Glu Arg
                500                 505                 510

Arg Lys Met Gln Lys Glu Gln Glu Gly Asn Arg Lys Lys Asn Glu Thr
        515                 520                 525

Ala Ile Arg Gln Leu Val Glu Tyr Gly Leu Thr Leu Asn Pro Thr Gly
        530                 535                 540

Leu Asp Ile Val Lys Phe Lys Leu Trp Ser Glu Gln Asn Gly Lys Cys
545                 550                 555                 560

Ala Tyr Ser Leu Gln Pro Ile Glu Ile Glu Arg Leu Leu Glu Pro Gly
                565                 570                 575

Tyr Thr Glu Val Asp His Val Ile Pro Tyr Ser Arg Ser Leu Asp Asp
                580                 585                 590

Ser Tyr Thr Asn Lys Val Leu Val Leu Thr Lys Glu Asn Arg Glu Lys
        595                 600                 605

Gly Asn Arg Thr Pro Ala Glu Tyr Leu Gly Leu Gly Ser Glu Arg Trp
610                 615                 620

Gln Gln Phe Glu Thr Phe Val Leu Thr Asn Lys Gln Phe Ser Lys Lys
625                 630                 635                 640

Lys Arg Asp Arg Leu Leu Arg Leu His Tyr Asp Glu Asn Glu Glu Asn
                645                 650                 655

Glu Phe Lys Asn Arg Asn Leu Asn Asp Thr Arg Tyr Ile Ser Arg Phe
                660                 665                 670

Leu Ala Asn Phe Ile Arg Glu His Leu Lys Phe Ala Asp Ser Asp Asp
                675                 680                 685

Lys Gln Lys Val Tyr Thr Val Asn Gly Arg Ile Thr Ala His Leu Arg
                690                 695                 700

Ser Arg Trp Asn Phe Asn Lys Asn Arg Glu Glu Ser Asn Leu His His
705                 710                 715                 720

Ala Val Asp Ala Ala Ile Val Ala Cys Thr Thr Pro Ser Asp Ile Ala
                725                 730                 735

Arg Val Thr Ala Phe Tyr Gln Arg Arg Glu Gln Asn Lys Glu Leu Ser
                740                 745                 750

Lys Lys Thr Asp Pro Gln Phe Pro Gln Pro Trp Pro His Phe Ala Asp
        755                 760                 765

Glu Leu Gln Ala Arg Leu Ser Lys Asn Pro Lys Glu Ser Ile Lys Ala
770                 775                 780
```

```
Leu Asn Leu Gly Asn Tyr Asp Asn Glu Lys Leu Glu Ser Leu Gln Pro
785                 790                 795                 800

Val Phe Val Ser Arg Met Pro Lys Arg Ser Ile Thr Gly Ala Ala His
            805                 810                 815

Gln Glu Thr Leu Arg Arg Tyr Ile Gly Ile Asp Glu Arg Ser Gly Lys
        820                 825                 830

Ile Gln Thr Val Val Lys Lys Leu Ser Glu Ile Gln Leu Asp Lys
            835                 840                 845

Thr Gly His Phe Pro Met Tyr Gly Lys Glu Ser Asp Pro Arg Thr Tyr
        850                 855                 860

Glu Ala Ile Arg Gln Arg Leu Leu Glu His Asn Asn Asp Pro Lys Lys
865                 870                 875                 880

Ala Phe Gln Glu Pro Leu Tyr Lys Pro Lys Asn Gly Glu Leu Gly
                885                 890                 895

Pro Ile Ile Arg Thr Ile Lys Ile Ile Asp Thr Thr Asn Gln Val Ile
            900                 905                 910

Pro Leu Asn Asp Gly Lys Thr Val Ala Tyr Asn Ser Asn Ile Val Arg
        915                 920                 925

Val Asp Val Phe Glu Lys Asp Gly Lys Tyr Tyr Cys Val Pro Ile Tyr
        930                 935                 940

Thr Ile Asp Met Met Lys Gly Ile Leu Pro Asn Lys Ala Ile Glu Pro
945                 950                 955                 960

Asn Lys Pro Tyr Ser Glu Trp Lys Glu Met Thr Glu Asp Tyr Thr Phe
                965                 970                 975

Arg Phe Ser Leu Tyr Pro Asn Asp Leu Ile Arg Ile Glu Phe Pro Arg
            980                 985                 990

Glu Lys Thr Ile Lys Thr Ala Val Gly Glu Glu Ile Lys Ile Lys Asp
            995                 1000                1005

Leu Phe Ala Tyr Tyr Gln Thr Ile Asp Ser Ser Asn Gly Gly Leu
    1010                1015                1020

Ser Leu Val Ser His Asp Asn Asn Phe Ser Leu Arg Ser Ile Gly
    1025                1030                1035

Ser Arg Thr Leu Lys Arg Phe Glu Lys Tyr Gln Val Asp Val Leu
    1040                1045                1050

Gly Asn Ile Tyr Lys Val Arg Gly Glu Lys Arg Val Gly Val Ala
    1055                1060                1065

Ser Ser Ser His Ser Lys Ala Gly Glu Thr Ile Arg Pro Leu
    1070                1075                1080

<210> SEQ ID NO 2
<211> LENGTH: 8
<212> TYPE: PRT
<213> ORGANISM: Geobacillus thermodenitrificans T12

<400> SEQUENCE: 2

Glu Lys Asp Gly Lys Tyr Tyr Cys
1               5

<210> SEQ ID NO 3
<211> LENGTH: 6
<212> TYPE: PRT
<213> ORGANISM: Artificial Sequence
<220> FEATURE:
<223> OTHER INFORMATION: amino acid motif from Cas9
<220> FEATURE:
<221> NAME/KEY: X
<222> LOCATION: (1)..(1)
```

```
<223> OTHER INFORMATION: Isoleucine, Methionine or Proline
<220> FEATURE:
<221> NAME/KEY: X
<222> LOCATION: (2)..(2)
<223> OTHER INFORMATION: Valine, Serine, Asparagine or Isoleucine
<220> FEATURE:
<221> NAME/KEY: X
<222> LOCATION: (5)..(5)
<223> OTHER INFORMATION: Glutamate or Lysine
<220> FEATURE:
<221> NAME/KEY: X
<222> LOCATION: (6)..(6)
<223> OTHER INFORMATION: Alanine, Glutamate or Arginine

<400> SEQUENCE: 3

Xaa Xaa Cys Thr Xaa Xaa
1               5

<210> SEQ ID NO 4
<211> LENGTH: 6
<212> TYPE: PRT
<213> ORGANISM: Artificial Sequence
<220> FEATURE:
<223> OTHER INFORMATION: amino acid motif from G. thermodenitrificans
      T12 Cas9
<220> FEATURE:
<221> NAME/KEY: X
<222> LOCATION: (1)..(1)
<223> OTHER INFORMATION: Methionine or Phenylalanine
<220> FEATURE:
<221> NAME/KEY: X
<222> LOCATION: (4)..(4)
<223> OTHER INFORMATION: Histidine or Asparagine

<400> SEQUENCE: 4

Xaa Leu Lys Xaa Ile Glu
1               5

<210> SEQ ID NO 5
<211> LENGTH: 6
<212> TYPE: PRT
<213> ORGANISM: Artificial Sequence
<220> FEATURE:
<223> OTHER INFORMATION: amino acid motif from G. thermodenitrificans
      T12
<220> FEATURE:
<221> NAME/KEY: X
<222> LOCATION: (1)..(1)
<223> OTHER INFORMATION: Glutamate or Isoleucine
<220> FEATURE:
<221> NAME/KEY: X
<222> LOCATION: (5)..(5)
<223> OTHER INFORMATION: Tryptophan, Serine or Lysine

<400> SEQUENCE: 5

Xaa Val Tyr Ser Xaa Lys
1               5

<210> SEQ ID NO 6
<211> LENGTH: 12
<212> TYPE: PRT
<213> ORGANISM: Artificial sequence
<220> FEATURE:
<223> OTHER INFORMATION: amino acid motif from thermophilic Cas9
<220> FEATURE:
<221> NAME/KEY: X
<222> LOCATION: (1)..(1)
<223> OTHER INFORMATION: Alanine or Glutamate
<220> FEATURE:
<221> NAME/KEY: X
<222> LOCATION: (4)..(4)
<223> OTHER INFORMATION: Glutamine or Lysine
<220> FEATURE:
```

```
<221> NAME/KEY: X
<222> LOCATION: (5)..(5)
<223> OTHER INFORMATION: Arginine or Alanine
<220> FEATURE:
<221> NAME/KEY: X
<222> LOCATION: (9)..(9)
<223> OTHER INFORMATION: Asparagine or Alanine
<220> FEATURE:
<221> NAME/KEY: X
<222> LOCATION: (12)..(12)
<223> OTHER INFORMATION: Lysine or Serine

<400> SEQUENCE: 6

Xaa Phe Tyr Xaa Xaa Arg Glu Gln Xaa Lys Glu Xaa
1               5                   10

<210> SEQ ID NO 7
<211> LENGTH: 3249
<212> TYPE: DNA
<213> ORGANISM: Geobacillus thermodenitrificans T12

<400> SEQUENCE: 7
atgaagtata aaatcggtct tgatatcggc attacgtcta tcggttgggc tgtcattaat     60
ttggacattc ctcgcatcga agatttaggt gtccgcattt ttgacagagc ggaaaacccg    120
aaaaccgggg agtcactagc tcttccacgt cgcctcgccc gctccgcccg acgtcgtctg    180
cggcgtcgca acatcgact ggagcgcatt cgccgcctgt tcgtccgcga aggaatttta    240
acgaaggaag agctgaacaa gctgtttgaa aaaaagcacg aaatcgacgt ctggcagctt    300
cgtgttgaag cactggatcg aaaactaaat aacgatgaat tagcccgcat ccttcttcat    360
ctggctaaac ggcgtggatt tagatccaac cgcaagagtg agcgcaccaa caagaaaaac    420
agtacgatgc tcaaacatat tgaagaaaac caatccattc tttcaagtta ccgaacggtt    480
gcagaaatgg ttgtcaagga tccgaaattt tccctgcaca agcgtaataa agaggataat    540
tacaccaaca ctgttgcccg cgacgatctt gaacggaaaa tcaaactgat tttcgccaaa    600
cagcgcgaat atgggaacat cgtttgcaca gaagcatttg aacacgagta tatttccatt    660
tgggcatcgc aacgcccttt tgcttctaag gatgatatcg agaaaaaagt cggtttctgt    720
acgtttgagc ctaaagaaaa acgcgcgcca aaagcaacat acacattcca gtccttcacc    780
gtctgggaac atattaacaa acttcgtctt gtctccccgg gaggcatccg ggcactaacc    840
gatgatgaac gtcgtcttat atacaagcaa gcatttcata aaaataaaat caccttccat    900
gatgttcgaa cattgcttaa cttgcctgac gacacccgtt ttaaaggtct tttatatgac    960
cgaaacacca cgctgaagga aaatgagaaa gttcgcttcc ttgaactcgg cgcctatcat   1020
aaaatacgga agcgatcga cagcgtctat ggcaaggag cagcaaaatc atttcgtccg   1080
attgattttg atacatttgg ctacgcatta acgatgttta aagacgacac cgacattcgc   1140
agttacttgc gaaacgaata cgaacaaaat ggaaaacgaa tggaaaatct agcggataaa   1200
gtctatgatg aagaattgat tgaagaactt ttaaacttat cgttttctaa gtttggtcat   1260
ctatccctta agcgcttcg caacatcctt ccatatatgg aacaaggcga agtctactca   1320
accgcttgtg aacgagcagg atatacattt acagggccaa agaaaaaaca gaaaacggta   1380
ttgctgccga acattccgcc gatcgccaat ccggtcgtca tgcgcgcact gacacaggca   1440
cgcaaagtgg tcaatgccat tatcaaaaag tacggctcac cggtctccat ccatatcgaa   1500
ctggcccggg aactatcaca atccctttgat gaacgacgta aaatgcagaa agaacaggaa   1560
ggaaaccgaa agaaaaacga aactgccatt cgccaacttg ttgaatatgg gctgacgctc   1620
```

```
aatccaactg ggcttgacat tgtgaaattc aaactatgga gcgaacaaaa cggaaaatgt    1680
gcctattcac tccaaccgat cgaaatcgag cggttgctcg aaccaggcta tacagaagtc    1740
gaccatgtga ttccatacag ccgaagcttg gacgatagct ataccaataa agttcttgtg    1800
ttgacaaagg agaaccgtga aaaggaaac cgcaccccag ctgaatattt aggattaggc     1860
tcagaacgtt ggcaacagtt cgagacgttt gtcttgacaa ataagcagtt ttcgaaaaag    1920
aagcgggatc gactccttcg gcttcattac gatgaaaacg aagaaaatga gtttaaaaat    1980
cgtaatctaa atgatacccg ttatatctca cgcttcttgg ctaactttat tcgcgaacat    2040
ctcaaattcg ccgacagcga tgacaaacaa aaagtataca cggtcaacgg ccgtattacc    2100
gcccatttac gcagccgttg gaattttaac aaaaaccggg aagaatcgaa tttgcatcat    2160
gccgtcgatg ctgccatcgt cgcctgcaca acgccgagcg atatcgcccg agtcaccgcc    2220
ttctatcaac ggcgcgaaca aaacaaagaa ctgtccaaaa agacggatcc gcagtttccg    2280
cagccttggc cgcactttgc tgatgaactg caggcgcgtt tatcaaaaaa tccaaaggag    2340
agtataaaag ctctcaatct tggaaattat gataacgaga aactcgaatc gttgcagccg    2400 gttttttgtct cccgaatgcc gaagcggagc ataacaggag cggctcatca agaaacattg    2460
cggcgttata tcggcatcga cgaacggagc ggaaaaatac agacggtcgt caaaaagaaa    2520
ctatccgaga tccaactgga taaaacaggt catttcccaa tgtacgggaa agaaagcgat    2580
ccaaggacat atgaagccat cgccaacgg ttgcttgaac ataacaatga cccaaaaaag     2640
gcgtttcaag agcctctgta taaccgaag aagaacggag aactaggtcc tatcatccga      2700
acaatcaaaa tcatcgatac gacaaatcaa gttattccgc tcaacgatgg caaaacagtc    2760
gcctacaaca gcaacatcgt gcgggtcgac gtctttgaga agatggcaa atattattgt      2820 gtccctatct atacaataga tatgatgaaa gggatcttgc caaacaaggc gatcgagccg    2880
aacaaaccgt actctgagtg gaaggaaatg acggaggact atacattccg attcagtcta    2940
tacccaaatg atcttatccg tatcgaattt ccccgagaaa aaacaataaa gactgctgtg    3000
ggggaagaaa tcaaaattaa ggatctgttc gcctattatc aaaccatcga ctcctccaat    3060
ggagggttaa gtttggttag ccatgataac aacttttcgc tccgcagcat cggttcaaga    3120
accctcaaac gattcgagaa ataccaagta gatgtgctag gcaacatcta caaagtgaga    3180
ggggaaaaga gagttggggt ggcgtcatct tctcattcga aagccgggga aactatccgt    3240
ccgttataa                                                          3249

<210> SEQ ID NO 8
<211> LENGTH: 1045
<212> TYPE: PRT
<213> ORGANISM: Actinomyces naeslundii

<400> SEQUENCE: 8

Met Trp Tyr Ala Ser Leu Met Ser Ala His His Leu Arg Val Gly Ile
1               5                   10                  15

Asp Val Gly Thr His Ser Val Gly Leu Ala Thr Leu Arg Val Asp Asp
            20                  25                  30

His Gly Thr Pro Ile Glu Leu Leu Ser Ala Leu Ser His Ile His Asp
        35                  40                  45

Ser Gly Val Gly Lys Glu Gly Lys Lys Asp His Asp Thr Arg Lys Lys
    50                  55                  60

Leu Ser Gly Ile Ala Arg Arg Ala Arg Arg Leu Leu His Arg Arg
65                  70                  75                  80
```

```
Thr Gln Leu Gln Gln Leu Asp Glu Val Leu Arg Asp Leu Gly Phe Pro
                85                  90                  95
Ile Pro Thr Pro Gly Glu Phe Leu Asp Leu Asn Glu Gln Thr Asp Pro
            100                 105                 110
Tyr Arg Val Trp Arg Val Arg Ala Arg Leu Val Glu Glu Lys Leu Pro
            115                 120                 125
Glu Glu Leu Arg Gly Pro Ala Ile Ser Met Ala Val Arg His Ile Ala
        130                 135                 140
Arg His Arg Gly Trp Arg Asn Pro Tyr Ser Lys Val Glu Ser Leu Leu
145                 150                 155                 160
Ser Pro Ala Asn Ala Asn Glu Ile Arg Lys Ile Cys Ala Arg Gln Gly
                165                 170                 175
Val Ser Pro Asp Val Cys Lys Gln Leu Leu Arg Ala Val Phe Lys Ala
            180                 185                 190
Asp Ser Pro Arg Gly Ser Ala Val Ser Arg Val Ala Pro Asp Pro Leu
            195                 200                 205
Pro Gly Gln Gly Ser Phe Arg Arg Ala Pro Lys Cys Asp Pro Glu Phe
        210                 215                 220
Gln Arg Phe Arg Ile Ile Ser Ile Val Ala Asn Leu Arg Ile Ser Glu
225                 230                 235                 240
Thr Lys Gly Glu Asn Arg Pro Leu Thr Ala Asp Glu Arg Arg His Val
                245                 250                 255
Val Thr Phe Leu Thr Glu Asp Ser Gln Ala Asp Leu Thr Trp Val Asp
            260                 265                 270
Val Ala Glu Lys Leu Gly Val His Arg Arg Asp Leu Arg Gly Thr Ala
            275                 280                 285
Val His Thr Asp Asp Gly Glu Arg Ser Ala Ala Arg Pro Pro Ile Asp
        290                 295                 300
Ala Thr Asp Arg Ile Met Arg Gln Thr Lys Ile Ser Ser Leu Lys Thr
305                 310                 315                 320
Trp Trp Glu Glu Ala Asp Ser Glu Gln Arg Gly Ala Met Ile Arg Tyr
                325                 330                 335
Leu Tyr Glu Asp Pro Thr Asp Ser Glu Cys Ala Glu Ile Ile Ala Glu
            340                 345                 350
Leu Pro Glu Glu Asp Gln Ala Lys Leu Asp Ser Leu His Leu Pro Ala
            355                 360                 365
Gly Arg Ala Ala Tyr Ser Arg Glu Ser Leu Thr Ala Leu Ser Asp His
        370                 375                 380
Met Leu Ala Thr Thr Asp Asp Leu His Glu Ala Arg Lys Arg Leu Phe
385                 390                 395                 400
Gly Val Asp Asp Ser Trp Ala Pro Pro Ala Glu Ala Ile Asn Ala Pro
                405                 410                 415
Val Gly Asn Pro Ser Val Asp Arg Thr Leu Lys Ile Val Gly Arg Tyr
            420                 425                 430
Leu Ser Ala Val Glu Ser Met Trp Gly Thr Pro Glu Val Ile His Val
            435                 440                 445
Glu His Val Arg Asp Gly Phe Thr Ser Glu Arg Met Ala Asp Glu Arg
        450                 455                 460
Asp Lys Ala Asn Arg Arg Tyr Asn Asp Asn Gln Glu Ala Met Lys
465                 470                 475                 480
Lys Ile Gln Arg Asp Tyr Gly Lys Glu Gly Tyr Ile Ser Arg Gly Asp
                485                 490                 495
```

```
Ile Val Arg Leu Asp Ala Leu Glu Leu Gln Gly Cys Ala Cys Leu Tyr
            500                 505                 510

Cys Gly Thr Thr Ile Gly Tyr His Thr Cys Gln Leu Asp His Ile Val
            515                 520                 525

Pro Gln Ala Gly Pro Gly Ser Asn Asn Arg Arg Gly Asn Leu Val Ala
            530                 535                 540

Val Cys Glu Arg Cys Asn Arg Ser Lys Ser Asn Thr Pro Phe Ala Val
545                 550                 555                 560

Trp Ala Gln Lys Cys Gly Ile Pro His Val Gly Val Lys Glu Ala Ile
                565                 570                 575

Gly Arg Val Arg Gly Trp Arg Lys Gln Thr Pro Asn Thr Ser Ser Glu
            580                 585                 590

Asp Leu Thr Arg Leu Lys Lys Glu Val Ile Ala Arg Leu Arg Arg Thr
            595                 600                 605

Gln Glu Asp Pro Glu Ile Asp Glu Arg Ser Met Glu Ser Val Ala Trp
            610                 615                 620

Met Ala Asn Glu Leu His His Arg Ile Ala Ala Ala Tyr Pro Glu Thr
625                 630                 635                 640

Thr Val Met Val Tyr Arg Gly Ser Ile Thr Ala Ala Arg Lys Ala
                645                 650                 655

Ala Gly Ile Asp Ser Arg Ile Asn Leu Ile Gly Glu Lys Gly Arg Lys
                660                 665                 670

Asp Arg Ile Asp Arg Arg His His Ala Val Asp Ala Ser Val Val Ala
            675                 680                 685

Leu Met Glu Ala Ser Val Ala Lys Thr Leu Ala Glu Arg Ser Ser Leu
            690                 695                 700

Arg Gly Glu Gln Arg Leu Thr Gly Lys Glu Gln Thr Trp Lys Gln Tyr
705                 710                 715                 720

Thr Gly Ser Thr Val Gly Ala Arg Glu His Phe Glu Met Trp Arg Gly
                725                 730                 735

His Met Leu His Leu Thr Glu Leu Phe Asn Glu Arg Leu Ala Glu Asp
                740                 745                 750

Lys Val Tyr Val Thr Gln Asn Ile Arg Leu Arg Leu Ser Asp Gly Asn
            755                 760                 765

Ala His Thr Val Asn Pro Ser Lys Leu Val Ser His Arg Leu Gly Asp
            770                 775                 780

Gly Leu Thr Val Gln Gln Ile Asp Arg Ala Cys Thr Pro Ala Leu Trp
785                 790                 795                 800

Cys Ala Leu Thr Arg Glu Lys Asp Phe Asp Lys Asn Gly Leu Pro
                805                 810                 815

Ala Arg Glu Asp Arg Ala Ile Arg Val His Gly His Glu Ile Lys Ser
            820                 825                 830

Ser Asp Tyr Ile Gln Val Phe Ser Lys Arg Lys Lys Thr Asp Ser Asp
            835                 840                 845

Arg Asp Glu Thr Pro Phe Gly Ala Ile Ala Val Arg Gly Gly Phe Val
            850                 855                 860

Glu Ile Gly Pro Ser Ile His His Ala Arg Ile Tyr Arg Val Glu Gly
865                 870                 875                 880

Lys Lys Pro Val Tyr Ala Met Leu Arg Val Phe Thr His Asp Leu Leu
                885                 890                 895

Ser Gln Arg His Gly Asp Leu Phe Ser Ala Val Ile Pro Pro Gln Ser
            900                 905                 910
```

-continued

Ile Ser Met Arg Cys Ala Glu Pro Lys Leu Arg Lys Ala Ile Thr Thr
            915                 920                 925

Gly Asn Ala Thr Tyr Leu Gly Trp Val Val Gly Asp Glu Leu Glu
        930                 935                 940

Ile Asn Val Asp Ser Phe Thr Lys Tyr Ala Ile Gly Arg Phe Leu Glu
945                 950                 955                 960

Asp Phe Pro Asn Thr Thr Arg Trp Arg Ile Cys Gly Tyr Asp Thr Asn
                965                 970                 975

Ser Lys Leu Thr Leu Lys Pro Ile Val Leu Ala Ala Glu Gly Leu Glu
            980                 985                 990

Asn Pro Ser Ser Ala Val Asn Glu Ile Val Glu Leu Lys Gly Trp Arg
            995                 1000                1005

Val Ala Ile Asn Val Leu Thr Lys Val His Pro Thr Val Val Arg
        1010                1015                1020

Arg Asp Ala Leu Gly Arg Pro Arg Tyr Ser Ser Arg Ser Asn Leu
        1025                1030                1035

Pro Thr Ser Trp Thr Ile Glu
        1040                1045

<210> SEQ ID NO 9
<211> LENGTH: 1160
<212> TYPE: PRT
<213> ORGANISM: Streptococcus pyogenes

<400> SEQUENCE: 9

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Arg
            180                 185                 190

Lys Gln Arg Thr Phe Asp Asn Gly Ser Ile Pro His Gln Ile His Leu
        195                 200                 205

Gly Glu Leu His Ala Ile Leu Arg Arg Gln Glu Asp Phe Tyr Pro Phe
    210                 215                 220

Leu Lys Asp Asn Arg Glu Lys Ile Glu Lys Ile Leu Thr Phe Arg Ile
225                 230                 235                 240

-continued

Pro Tyr Tyr Val Gly Pro Leu Ala Arg Gly Asn Ser Arg Phe Ala Trp
            245                 250                 255

Met Thr Arg Lys Ser Glu Glu Thr Ile Thr Pro Trp Asn Phe Glu Glu
            260                 265                 270

Val Val Asp Lys Gly Ala Ser Ala Gln Ser Phe Ile Glu Arg Met Thr
            275                 280                 285

Asn Phe Asp Lys Asn Leu Pro Asn Glu Lys Val Leu Pro Lys His Ser
        290                 295                 300

Leu Leu Tyr Glu Tyr Phe Thr Val Tyr Asn Glu Leu Thr Lys Val Lys
305                 310                 315                 320

Tyr Val Thr Glu Gly Met Arg Lys Pro Ala Phe Leu Ser Gly Glu Gln
                325                 330                 335

Lys Lys Ala Ile Val Asp Leu Leu Phe Lys Thr Asn Arg Lys Val Thr
                340                 345                 350

Val Lys Gln Leu Lys Glu Asp Tyr Phe Lys Lys Ile Glu Cys Phe Asp
            355                 360                 365

Ser Val Glu Ile Ser Gly Val Glu Asp Arg Phe Asn Ala Ser Leu Gly
        370                 375                 380

Thr Tyr His Asp Leu Leu Lys Ile Ile Lys Asp Lys Asp Phe Leu Asp
385                 390                 395                 400

Asn Glu Glu Asn Glu Asp Ile Leu Glu Asp Ile Val Leu Thr Leu Thr
                405                 410                 415

Leu Phe Glu Asp Arg Glu Met Ile Glu Glu Arg Leu Lys Thr Tyr Ala
            420                 425                 430

His Leu Phe Asp Asp Lys Val Met Lys Gln Leu Lys Arg Arg Arg Tyr
            435                 440                 445

Thr Gly Trp Gly Arg Leu Ser Arg Lys Leu Ile Asn Gly Ile Arg Asp
        450                 455                 460

Lys Gln Ser Gly Lys Thr Ile Leu Asp Phe Leu Lys Ser Asp Gly Phe
465                 470                 475                 480

Ala Asn Arg Asn Phe Met Gln Leu Ile His Asp Asp Ser Leu Thr Phe
                485                 490                 495

Lys Glu Asp Ile Gln Lys Ala Gln Val Ser Gly Gln Gly Asp Ser Leu
            500                 505                 510

His Glu His Ile Ala Asn Leu Ala Gly Ser Pro Ala Ile Lys Lys Gly
        515                 520                 525

Ile Leu Gln Thr Val Lys Val Val Asp Glu Leu Val Lys Val Met Gly
530                 535                 540

Arg His Lys Pro Glu Asn Ile Val Ile Glu Met Ala Arg Glu Asn Gln
545                 550                 555                 560

Thr Thr Gln Lys Gly Gln Lys Asn Ser Arg Glu Arg Met Lys Arg Ile
                565                 570                 575

Glu Glu Gly Ile Lys Glu Leu Gly Ser Gln Ile Leu Lys Glu His Pro
            580                 585                 590

Val Glu Asn Thr Gln Leu Gln Asn Glu Lys Leu Tyr Leu Tyr Tyr Leu
        595                 600                 605

Gln Asn Gly Arg Asp Met Tyr Val Asp Gln Glu Leu Asp Ile Asn Arg
610                 615                 620

Leu Ser Asp Tyr Asp Val Asp His Ile Val Pro Gln Ser Phe Leu Lys
625                 630                 635                 640

Asp Asp Ser Ile Asp Asn Lys Val Leu Thr Arg Ser Asp Lys Asn Arg
                645                 650                 655

```
Gly Lys Ser Asp Asn Val Pro Ser Glu Val Val Lys Met Lys
            660                 665                 670

Asn Tyr Trp Arg Gln Leu Leu Asn Ala Lys Leu Ile Thr Gln Arg Lys
        675                 680                 685

Phe Asp Asn Leu Thr Lys Ala Glu Arg Gly Gly Leu Ser Glu Leu Asp
    690                 695                 700

Lys Ala Gly Phe Ile Lys Arg Gln Leu Val Glu Thr Arg Gln Ile Thr
705                 710                 715                 720

Lys His Val Ala Gln Ile Leu Asp Ser Arg Met Asn Thr Lys Tyr Asp
                725                 730                 735

Glu Asn Asp Lys Leu Ile Arg Glu Val Lys Val Ile Thr Leu Lys Ser
            740                 745                 750

Lys Leu Val Ser Asp Phe Arg Lys Asp Phe Gln Phe Tyr Lys Val Arg
        755                 760                 765

Glu Ile Asn Asn Tyr His His Ala His Asp Ala Tyr Leu Asn Ala Val
    770                 775                 780

Val Gly Thr Ala Leu Ile Lys Lys Tyr Pro Lys Leu Glu Ser Glu Phe
785                 790                 795                 800

Val Tyr Gly Asp Tyr Lys Val Tyr Asp Val Arg Lys Met Ile Ala Lys
                805                 810                 815

Ser Glu Gln Glu Ile Gly Lys Ala Thr Ala Lys Tyr Phe Phe Tyr Ser
            820                 825                 830

Asn Ile Met Asn Phe Phe Lys Thr Glu Ile Thr Leu Ala Asn Gly Glu
        835                 840                 845

Ile Arg Lys Arg Pro Leu Ile Glu Thr Asn Gly Glu Thr Gly Glu Ile
850                 855                 860

Val Trp Asp Lys Gly Arg Asp Phe Ala Thr Val Arg Lys Val Leu Ser
865                 870                 875                 880

Met Pro Gln Val Asn Ile Val Lys Lys Thr Glu Val Gln Thr Gly Gly
                885                 890                 895

Phe Ser Lys Glu Ser Ile Leu Pro Lys Arg Asn Ser Asp Lys Leu Ile
            900                 905                 910

Ala Arg Lys Lys Asp Trp Asp Pro Lys Lys Tyr Gly Gly Phe Asp Ser
        915                 920                 925

Pro Thr Val Ala Tyr Ser Val Leu Val Val Ala Lys Val Glu Lys Gly
    930                 935                 940

Lys Ser Lys Lys Leu Lys Ser Val Lys Glu Leu Leu Gly Ile Thr Ile
945                 950                 955                 960

Met Glu Arg Ser Ser Phe Glu Lys Asn Pro Ile Asp Phe Leu Glu Ala
                965                 970                 975

Lys Gly Tyr Lys Glu Val Lys Lys Asp Leu Ile Ile Lys Leu Pro Lys
            980                 985                 990

Tyr Ser Leu Phe Glu Leu Glu Asn Gly Arg Lys Arg Met Leu Ala Ser
        995                 1000                1005

Ala Gly Glu Leu Gln Lys Gly Asn Glu Leu Ala Leu Pro Ser Lys
    1010                1015                1020

Tyr Val Asn Phe Leu Tyr Leu Ala Ser His Tyr Glu Lys Leu Lys
    1025                1030                1035

Gly Ser Pro Glu Asp Asn Glu Gln Lys Gln Leu Phe Val Glu Gln
    1040                1045                1050

His Lys His Tyr Leu Asp Glu Ile Ile Glu Gln Ile Ser Glu Phe
    1055                1060                1065
```

Ser Lys Arg Val Ile Leu Ala Asp Ala Asn Leu Asp Lys Val Leu
    1070            1075                1080

Ser Ala Tyr Asn Lys His Arg Asp Lys Pro Ile Arg Glu Gln Ala
    1085            1090                1095

Glu Asn Ile Ile His Leu Phe Thr Leu Thr Asn Leu Gly Ala Pro
    1100            1105                1110

Ala Ala Phe Lys Tyr Phe Asp Thr Thr Ile Asp Arg Lys Arg Tyr
    1115            1120                1125

Thr Ser Thr Lys Glu Val Leu Asp Ala Thr Leu Ile His Gln Ser
    1130            1135                1140

Ile Thr Gly Leu Tyr Glu Thr Arg Ile Asp Leu Ser Gln Leu Gly
    1145            1150                1155

Gly Asp
    1160

<210> SEQ ID NO 10
<211> LENGTH: 8
<212> TYPE: DNA
<213> ORGANISM: Artificial sequence
<220> FEATURE:
<223> OTHER INFORMATION: PAM
<220> FEATURE:
<221> NAME/KEY: misc_feature
<222> LOCATION: (7)..(7)
<223> OTHER INFORMATION: n is a, c, g, or t

<400> SEQUENCE: 10 cccccna                                                             8

<210> SEQ ID NO 11
<211> LENGTH: 8
<212> TYPE: DNA
<213> ORGANISM: Artificial Sequence
<220> FEATURE:
<223> OTHER INFORMATION: PAM

<400> SEQUENCE: 11 cccccaa                                                             8

<210> SEQ ID NO 12
<211> LENGTH: 5
<212> TYPE: DNA
<213> ORGANISM: Artificial Sequence
<220> FEATURE:
<223> OTHER INFORMATION: PAM

<400> SEQUENCE: 12 ccccc                                                               5

<210> SEQ ID NO 13
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (6)..(7)
<223> OTHER INFORMATION: n is a, c, g, or t

<400> SEQUENCE: 13 cccccnna                                                            8

```
<210> SEQ ID NO 14
<211> LENGTH: 6
<212> TYPE: DNA
<213> ORGANISM: Artificial Sequence
<220> FEATURE:
<223> OTHER INFORMATION: PAM

<400> SEQUENCE: 14 cccccc                                                                    6

<210> SEQ ID NO 15
<211> LENGTH: 6
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(1)
<223> OTHER INFORMATION: n is a, c, g, or t

<400> SEQUENCE: 15 nccccc                                                                    6

<210> SEQ ID NO 16
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (7)..(7)
<223> OTHER INFORMATION: n is a, c, g, or t

<400> SEQUENCE: 16 nccccna                                                                   8

<210> SEQ ID NO 17
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (2)..(2)
<223> OTHER INFORMATION: n is a, c, g, or t

<400> SEQUENCE: 17 cnccccac                                                                  8

<210> SEQ ID NO 18
<211> LENGTH: 8
<212> TYPE: DNA
<213> ORGANISM: Artificial Sequence
<220> FEATURE:
<223> OTHER INFORMATION: PAM

<400> SEQUENCE: 18 ccccccag                                                                  8

<210> SEQ ID NO 19
<211> LENGTH: 8
<212> TYPE: DNA
```

```
<213> ORGANISM: Artificial Sequence
<220> FEATURE:
<223> OTHER INFORMATION: PAM

<400> SEQUENCE: 19 cccccat                                                                    8

<210> SEQ ID NO 20
<211> LENGTH: 8
<212> TYPE: DNA
<213> ORGANISM: Artificial Sequence
<220> FEATURE:
<223> OTHER INFORMATION: PAM

<400> SEQUENCE: 20 ccccccac                                                                   8

<210> SEQ ID NO 21
<211> LENGTH: 8
<212> TYPE: DNA
<213> ORGANISM: Artificial Sequence
<220> FEATURE:
<223> OTHER INFORMATION: PAM

<400> SEQUENCE: 21 atccccaa                                                                   8

<210> SEQ ID NO 22
<211> LENGTH: 8
<212> TYPE: DNA
<213> ORGANISM: Artificial Sequence
<220> FEATURE:
<223> OTHER INFORMATION: PAM

<400> SEQUENCE: 22 acggccaa                                                                   8

<210> SEQ ID NO 23
<211> LENGTH: 11
<212> TYPE: PRT
<213> ORGANISM: Artificial Sequence
<220> FEATURE:
<223> OTHER INFORMATION: RuvC-1 domain motif

<400> SEQUENCE: 23

Ile Gly Leu Asp Ile Gly Ile Thr Ser Ile Gly
1               5                   10

<210> SEQ ID NO 24
<211> LENGTH: 18
<212> TYPE: PRT
<213> ORGANISM: Artificial Sequence
<220> FEATURE:
<223> OTHER INFORMATION: RuvC-I domain motif

<400> SEQUENCE: 24

Ile Gly Leu Asp Ile Gly Ile Thr Ser Ile Gly Trp Ala Val Ile Asn
1               5                   10                  15

Leu Asp

<210> SEQ ID NO 25
<211> LENGTH: 5
<212> TYPE: PRT
<213> ORGANISM: Artificial Sequence
<220> FEATURE:
<223> OTHER INFORMATION: Bridge domain motif
```

<400> SEQUENCE: 25

Arg Ser Ala Arg Arg
1               5

<210> SEQ ID NO 26
<211> LENGTH: 25
<212> TYPE: PRT
<213> ORGANISM: Artificial Sequence
<220> FEATURE:
<223> OTHER INFORMATION: Bridge domain motif

<400> SEQUENCE: 26

Pro Arg Arg Leu Ala Arg Ser Ala Arg Arg Leu Arg Arg Arg Lys
1               5                   10                  15

His Arg Leu Glu Arg Ile Arg Arg Leu
            20                  25

<210> SEQ ID NO 27
<211> LENGTH: 4
<212> TYPE: PRT
<213> ORGANISM: Artificial Sequence
<220> FEATURE:
<223> OTHER INFORMATION: alpha-helical/recognition lobe domain motif

<400> SEQUENCE: 27

Trp Gln Leu Arg
1

<210> SEQ ID NO 28
<211> LENGTH: 7
<212> TYPE: PRT
<213> ORGANISM: Artificial Sequence
<220> FEATURE:
<223> OTHER INFORMATION: alpha-helical/recognition lobe domain

<400> SEQUENCE: 28

His Leu Ala Lys Arg Arg Gly
1               5

<210> SEQ ID NO 29
<211> LENGTH: 13
<212> TYPE: PRT
<213> ORGANISM: Artificial Sequence
<220> FEATURE:
<223> OTHER INFORMATION: alpha-helical/recognition lobe domain

<400> SEQUENCE: 29

Leu Ala Arg Ile Leu Leu His Leu Ala Lys Arg Arg Gly
1               5                   10

<210> SEQ ID NO 30
<211> LENGTH: 5
<212> TYPE: PRT
<213> ORGANISM: Artificial Sequence
<220> FEATURE:
<223> OTHER INFORMATION: alpha-helical/recognition lobe domain

<400> SEQUENCE: 30

Ile Phe Ala Lys Gln
1               5

<210> SEQ ID NO 31
<211> LENGTH: 9
<212> TYPE: PRT
<213> ORGANISM: Artificial Sequence

```
<220> FEATURE:
<223> OTHER INFORMATION: alpha-helical/recognition lobe domain

<400> SEQUENCE: 31

Glu Ile Lys Leu Ile Phe Ala Lys Gln
1               5

<210> SEQ ID NO 32
<211> LENGTH: 6
<212> TYPE: PRT
<213> ORGANISM: Artificial Sequence
<220> FEATURE:
<223> OTHER INFORMATION: alpha-helical/recognition lobe domain

<400> SEQUENCE: 32

Ile Trp Ala Ser Gln Arg
1               5

<210> SEQ ID NO 33
<211> LENGTH: 16
<212> TYPE: PRT
<213> ORGANISM: Artificial Sequence
<220> FEATURE:
<223> OTHER INFORMATION: alpha-helical/recognition lobe domain motif

<400> SEQUENCE: 33

Lys Val Gly Phe Cys Thr Phe Glu Pro Lys Glu Lys Arg Ala Pro Lys
1               5                   10                  15

<210> SEQ ID NO 34
<211> LENGTH: 12
<212> TYPE: PRT
<213> ORGANISM: Artificial Sequence
<220> FEATURE:
<223> OTHER INFORMATION: alpha-helical/recognition lobe domain motif

<400> SEQUENCE: 34

Phe Thr Val Trp Glu His Ile Asn Lys Leu Arg Leu
1               5                   10

<210> SEQ ID NO 35
<211> LENGTH: 12
<212> TYPE: PRT
<213> ORGANISM: Artificial Sequence
<220> FEATURE:
<223> OTHER INFORMATION: RuvC-II domain motif

<400> SEQUENCE: 35

Ile Ala Asn Pro Val Val Met Arg Ala Leu Thr Gln
1               5                   10

<210> SEQ ID NO 36
<211> LENGTH: 25
<212> TYPE: PRT
<213> ORGANISM: Artificial Sequence
<220> FEATURE:
<223> OTHER INFORMATION: RuvC-II domain motif

<400> SEQUENCE: 36

Ile Ala Asn Pro Val Val Met Arg Ala Leu Thr Gln Ala Arg Lys Val
1               5                   10                  15

Val Asn Ala Ile Ile Lys Lys Tyr Gly
            20                  25

<210> SEQ ID NO 37
<211> LENGTH: 4
```

```
<212> TYPE: PRT
<213> ORGANISM: Artificial Sequence
<220> FEATURE:
<223> OTHER INFORMATION: RuvC-II domain motif

<400> SEQUENCE: 37

Glu Leu Ala Arg
1

<210> SEQ ID NO 38
<211> LENGTH: 8
<212> TYPE: PRT
<213> ORGANISM: Artificial Sequence
<220> FEATURE:
<223> OTHER INFORMATION: RuvC-II domain motif

<400> SEQUENCE: 38

Ile His Ile Glu Leu Ala Arg Glu
1               5

<210> SEQ ID NO 39
<211> LENGTH: 7
<212> TYPE: PRT
<213> ORGANISM: Artificial Sequence
<220> FEATURE:
<223> OTHER INFORMATION: HNH domain motif

<400> SEQUENCE: 39

Gln Asn Gly Lys Cys Ala Tyr
1               5

<210> SEQ ID NO 40
<211> LENGTH: 16
<212> TYPE: PRT
<213> ORGANISM: Artificial Sequence
<220> FEATURE:
<223> OTHER INFORMATION: HNH domain motif

<400> SEQUENCE: 40

Ile Val Lys Phe Lys Leu Trp Ser Glu Gln Asn Gly Lys Cys Ala Tyr
1               5                   10                  15

<210> SEQ ID NO 41
<211> LENGTH: 6
<212> TYPE: PRT
<213> ORGANISM: Artificial Sequence
<220> FEATURE:
<223> OTHER INFORMATION: HNH domain motif

<400> SEQUENCE: 41

Val Asp His Val Ile Pro
1               5

<210> SEQ ID NO 42
<211> LENGTH: 20
<212> TYPE: PRT
<213> ORGANISM: Artificial Sequence
<220> FEATURE:
<223> OTHER INFORMATION: HNH domain motif

<400> SEQUENCE: 42

Val Asp His Val Ile Pro Tyr Ser Arg Ser Leu Asp Asp Ser Tyr Thr
1               5                   10                  15

Asn Lys Val Leu
            20
```

```
<210> SEQ ID NO 43
<211> LENGTH: 11
<212> TYPE: PRT
<213> ORGANISM: Artificial Sequence
<220> FEATURE:
<223> OTHER INFORMATION: RuvC-III domain motif

<400> SEQUENCE: 43

Asp Thr Arg Tyr Ile Ser Arg Phe Leu Ala Asn
1               5                   10

<210> SEQ ID NO 44
<211> LENGTH: 16
<212> TYPE: PRT
<213> ORGANISM: Artificial Sequence
<220> FEATURE:
<223> OTHER INFORMATION: RuvC-III domain motif

<400> SEQUENCE: 44

Val Tyr Thr Val Asn Gly Arg Ile Thr Ala His Leu Arg Ser Arg Trp
1               5                   10                  15

<210> SEQ ID NO 45
<211> LENGTH: 6
<212> TYPE: PRT
<213> ORGANISM: Artificial Sequence
<220> FEATURE:
<223> OTHER INFORMATION: RuvC-III domain motif

<400> SEQUENCE: 45

His His Ala Val Asp Ala
1               5

<210> SEQ ID NO 46
<211> LENGTH: 10
<212> TYPE: PRT
<213> ORGANISM: Artificial Sequence
<220> FEATURE:
<223> OTHER INFORMATION: RuvC-III domain motif

<400> SEQUENCE: 46

His His Ala Val Asp Ala Ala Ile Val Ala
1               5                   10

<210> SEQ ID NO 47
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(7)
<223> OTHER INFORMATION: n is a, c, g, or t

<400> SEQUENCE: 47 nnnncnna                                                                8

<210> SEQ ID NO 48
<211> LENGTH: 8
<212> TYPE: DNA
<213> ORGANISM: Artificial Sequence
<220> FEATURE:
<223> OTHER INFORMATION: PAM
<220> FEATURE:
```

```
<221> NAME/KEY: misc_feature
<222> LOCATION: (1)..(4)
<223> OTHER INFORMATION: n is a, c, g, or t

<400> SEQUENCE: 48 nnnncvaa                                                                 8

<210> SEQ ID NO 49
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(4)
<223> OTHER INFORMATION: n is a, c, g, or t

<400> SEQUENCE: 49 nnnncsaa                                                                 8

<210> SEQ ID NO 50
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(4)
<223> OTHER INFORMATION: n is a, c, g, or t

<400> SEQUENCE: 50 nnnncgaa                                                                 8

<210> SEQ ID NO 51
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(4)
<223> OTHER INFORMATION: n is a, c, g, or t

<400> SEQUENCE: 51 nnnnccaa                                                                 8

<210> SEQ ID NO 52
<211> LENGTH: 8
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(4)
<223> OTHER INFORMATION: n is a, c, g, or t
<220> FEATURE:
<221> NAME/KEY: misc_feature
<222> LOCATION: (6)..(6)
<223> OTHER INFORMATION: n is a, c, g, or t

<400> SEQUENCE: 52 nnnncnaa                                                                 8

<210> SEQ ID NO 53
<211> LENGTH: 8
```

```
<212> TYPE: DNA
<213> ORGANISM: Artificial Sequence
<220> FEATURE:
<223> OTHER INFORMATION: PAM
<220> FEATURE:
<221> NAME/KEY: misc_feature
<222> LOCATION: (1)..(4)
<223> OTHER INFORMATION: n is a, c, g, or t

<400> SEQUENCE: 53 nnnncmca                                                                    8

<210> SEQ ID NO 54
<211> LENGTH: 30
<212> TYPE: RNA
<213> ORGANISM: Artificial Sequence
<220> FEATURE:
<223> OTHER INFORMATION: tracrRNA 5' hairpin

<400> SEQUENCE: 54
aagggcuuuc ugccuauagg cagacugccc                                           30

<210> SEQ ID NO 55
<211> LENGTH: 25
<212> TYPE: RNA
<213> ORGANISM: Artificial Sequence
<220> FEATURE:
<223> OTHER INFORMATION: tracrRNA 'middle' hairpin

<400> SEQUENCE: 55
guggcguugg ggaucgccua ucgcc                                                25

<210> SEQ ID NO 56
<211> LENGTH: 36
<212> TYPE: RNA
<213> ORGANISM: Artificial Sequence
<220> FEATURE:
<223> OTHER INFORMATION: tracrRNA 3' hairpin

<400> SEQUENCE: 56
cgcuuucuuc gggcauuccc cacucuuagg cguuuu                                    36

<210> SEQ ID NO 57
<211> LENGTH: 55
<212> TYPE: RNA
<213> ORGANISM: Artificial Sequence
<220> FEATURE:
<223> OTHER INFORMATION: tracrRNA 5' hairpin and middle hairpin

<400> SEQUENCE: 57
aagggcuuuc ugccuauagg cagacugccc guggcguugg ggaucgccua ucgcc               55

<210> SEQ ID NO 58
<211> LENGTH: 91
<212> TYPE: RNA
<213> ORGANISM: Artificial Sequence
<220> FEATURE:
<223> OTHER INFORMATION: tracrRNA  5' hairpin, middle hairpin and 3'
      hairpin.

<400> SEQUENCE: 58
aagggcuuuc ugccuauagg cagacugccc guggcguugg ggaucgccua ucgcccgcuu          60
ucuucgggca uuccccacuc uuaggcguuu u                                         91

<210> SEQ ID NO 59
<211> LENGTH: 81
```

```
<212> TYPE: DNA
<213> ORGANISM: Artificial Sequence
<220> FEATURE:
<223> OTHER INFORMATION: BG6494
<220> FEATURE:
<221> NAME/KEY: misc_feature
<222> LOCATION: (35)..(41)
<223> OTHER INFORMATION: n is a, c, g, or t

<400> SEQUENCE: 59
tatgcctcat gagattatca aaaggatct tcacnnnnnn nctagatcct tttaaattaa    60
aaatgaagtt ttaaatcaat c                                            81

<210> SEQ ID NO 60
<211> LENGTH: 81
<212> TYPE: DNA
<213> ORGANISM: Artificial Sequence
<220> FEATURE:
<223> OTHER INFORMATION: BG6495

<400> SEQUENCE: 60
tatgccggat cctcagacca agtttactca tatatacttt agattgattt aaaacttcat    60
ttttaattta aaaggatcta g                                             81

<210> SEQ ID NO 61
<211> LENGTH: 34
<212> TYPE: DNA
<213> ORGANISM: Artificial Sequence
<220> FEATURE:
<223> OTHER INFORMATION: BG7356

<400> SEQUENCE: 61
tcgtcggcag cgtcagatgt gtataagaga cagt                              34

<210> SEQ ID NO 62
<211> LENGTH: 33
<212> TYPE: DNA
<213> ORGANISM: Artificial Sequence
<220> FEATURE:
<223> OTHER INFORMATION: BG7357

<400> SEQUENCE: 62
ctgtctctta tacacatctg acgctgccga cga                               33

<210> SEQ ID NO 63
<211> LENGTH: 16
<212> TYPE: DNA
<213> ORGANISM: Artificial Sequence
<220> FEATURE:
<223> OTHER INFORMATION: BG7358

<400> SEQUENCE: 63
tcgtcggcag cgtcag                                                   16

<210> SEQ ID NO 64
<211> LENGTH: 53
<212> TYPE: DNA
<213> ORGANISM: Artificial Sequence
<220> FEATURE:
<223> OTHER INFORMATION: BG7359

<400> SEQUENCE: 64
gtctcgtggg ctcggagatg tgtataagag acaggaccat gattacgcca agc          53

<210> SEQ ID NO 65
```

```
<211> LENGTH: 61
<212> TYPE: DNA
<213> ORGANISM: Artificial Sequence
<220> FEATURE:
<223> OTHER INFORMATION: BG7616

<400> SEQUENCE: 65
tcgtcggcag cgtcagatgt gtataagaga cagggtcatg agattatcaa aaaggatctt      60
c                                                                      61

<210> SEQ ID NO 66
<211> LENGTH: 82
<212> TYPE: DNA
<213> ORGANISM: Artificial Sequence
<220> FEATURE:
<223> OTHER INFORMATION: BG8157

<400> SEQUENCE: 66
tatgcctcat gagattatca aaaggatct tcacccccc agctagatcc ttttaaatta      60
aaaatgaagt tttaaatcaa tc                                               82

<210> SEQ ID NO 67
<211> LENGTH: 82
<212> TYPE: DNA
<213> ORGANISM: Artificial Sequence
<220> FEATURE:
<223> OTHER INFORMATION: BG8158

<400> SEQUENCE: 67
tatgcctcat gagattatca aaaggatct tcacccccc aactagatcc ttttaaatta      60
aaaatgaagt tttaaatcaa tc                                               82

<210> SEQ ID NO 68
<211> LENGTH: 82
<212> TYPE: DNA
<213> ORGANISM: Artificial Sequence
<220> FEATURE:
<223> OTHER INFORMATION: BG8159

<400> SEQUENCE: 68
tatgcctcat gagattatca aaaggatct tcacccccc atctagatcc ttttaaatta      60
aaaatgaagt tttaaatcaa tc                                               82

<210> SEQ ID NO 69
<211> LENGTH: 82
<212> TYPE: DNA
<213> ORGANISM: Artificial Sequence
<220> FEATURE:
<223> OTHER INFORMATION: BG8160

<400> SEQUENCE: 69
tatgcctcat gagattatca aaaggatct tcacccccc acctagatcc ttttaaatta      60
aaaatgaagt tttaaatcaa tc                                               82

<210> SEQ ID NO 70
<211> LENGTH: 81
<212> TYPE: DNA
<213> ORGANISM: Artificial Sequence
<220> FEATURE:
<223> OTHER INFORMATION: BG8161
<220> FEATURE:
<221> NAME/KEY: misc_feature
<222> LOCATION: (35)..(38)
<223> OTHER INFORMATION: n is a, c, g, or t
```

-continued

```
<220> FEATURE:
<221> NAME/KEY: misc_feature
<222> LOCATION: (40)..(41)
<223> OTHER INFORMATION: n is a, c, g, or t

<400> SEQUENCE: 70
tatgcctcat gagattatca aaaggatct tcacnnnntn nctagatcct tttaaattaa      60
aaatgaagtt ttaaatcaat c                                              81

<210> SEQ ID NO 71
<211> LENGTH: 20
<212> TYPE: DNA
<213> ORGANISM: Artificial Sequence
<220> FEATURE:
<223> OTHER INFORMATION: BG8363

<400> SEQUENCE: 71
acggttatcc acagaatcag                                                20

<210> SEQ ID NO 72
<211> LENGTH: 22
<212> TYPE: DNA
<213> ORGANISM: Artificial Sequence
<220> FEATURE:
<223> OTHER INFORMATION: BG8364

<400> SEQUENCE: 72
cgggattgac ttttaaaaaa gg                                             22

<210> SEQ ID NO 73
<211> LENGTH: 82
<212> TYPE: DNA
<213> ORGANISM: Artificial Sequence
<220> FEATURE:
<223> OTHER INFORMATION: BG8763

<400> SEQUENCE: 73
tatgcctcat gagattatca aaaggatct tcaccccca aactagatcc ttttaaatta      60
aaaatgaagt ttaaatcaa tc                                              82

<210> SEQ ID NO 74
<211> LENGTH: 82
<212> TYPE: DNA
<213> ORGANISM: Artificial Sequence
<220> FEATURE:
<223> OTHER INFORMATION: BG8764

<400> SEQUENCE: 74
tatgcctcat gagattatca aaaggatct tcaccccca tactagatcc ttttaaatta      60
aaaatgaagt ttaaatcaa tc                                              82

<210> SEQ ID NO 75
<211> LENGTH: 82
<212> TYPE: DNA
<213> ORGANISM: Artificial Sequence
<220> FEATURE:
<223> OTHER INFORMATION: BG8765

<400> SEQUENCE: 75
tatgcctcat gagattatca aaaggatct tcaccccca gactagatcc ttttaaatta      60
aaaatgaagt ttaaatcaa tc                                              82

<210> SEQ ID NO 76
```

```
<211> LENGTH: 82
<212> TYPE: DNA
<213> ORGANISM: Artificial Sequence
<220> FEATURE:
<223> OTHER INFORMATION: BG8766

<400> SEQUENCE: 76
tatgcctcat gagattatca aaaggatct tcaccccca cactagatcc ttttaaatta      60
aaaatgaagt tttaaatcaa tc                                              82

<210> SEQ ID NO 77
<211> LENGTH: 82
<212> TYPE: DNA
<213> ORGANISM: Artificial Sequence
<220> FEATURE:
<223> OTHER INFORMATION: BG8767

<400> SEQUENCE: 77
tatgcctcat gagattatca aaaggatct tcacccccct aactagatcc ttttaaatta     60
aaaatgaagt tttaaatcaa tc                                              82

<210> SEQ ID NO 78
<211> LENGTH: 82
<212> TYPE: DNA
<213> ORGANISM: Artificial Sequence
<220> FEATURE:
<223> OTHER INFORMATION: BG8768

<400> SEQUENCE: 78
tatgcctcat gagattatca aaaggatct tcacccccct tactagatcc ttttaaatta     60
aaaatgaagt tttaaatcaa tc                                              82

<210> SEQ ID NO 79
<211> LENGTH: 82
<212> TYPE: DNA
<213> ORGANISM: Artificial Sequence
<220> FEATURE:
<223> OTHER INFORMATION: BG8769

<400> SEQUENCE: 79
tatgcctcat gagattatca aaaggatct tcacccccct gactagatcc ttttaaatta     60
aaaatgaagt tttaaatcaa tc                                              82

<210> SEQ ID NO 80
<211> LENGTH: 82
<212> TYPE: DNA
<213> ORGANISM: Artificial Sequence
<220> FEATURE:
<223> OTHER INFORMATION: BG8770

<400> SEQUENCE: 80
tatgcctcat gagattatca aaaggatct tcacccccct cactagatcc ttttaaatta     60
aaaatgaagt tttaaatcaa tc                                              82

<210> SEQ ID NO 81
<211> LENGTH: 82
<212> TYPE: DNA
<213> ORGANISM: Artificial Sequence
<220> FEATURE:
<223> OTHER INFORMATION: BG8771
```

```
<400> SEQUENCE: 81
tatgcctcat gagattatca aaaggatct tcaccccccg aactagatcc ttttaaatta      60
aaaatgaagt tttaaatcaa tc                                              82

<210> SEQ ID NO 82
<211> LENGTH: 82
<212> TYPE: DNA
<213> ORGANISM: Artificial Sequence
<220> FEATURE:
<223> OTHER INFORMATION: BG8772

<400> SEQUENCE: 82
tatgcctcat gagattatca aaaggatct tcaccccccg tactagatcc ttttaaatta      60
aaaatgaagt tttaaatcaa tc                                              82

<210> SEQ ID NO 83
<211> LENGTH: 82
<212> TYPE: DNA
<213> ORGANISM: Artificial Sequence
<220> FEATURE:
<223> OTHER INFORMATION: BG8773

<400> SEQUENCE: 83
tatgcctcat gagattatca aaaggatct tcaccccccg gactagatcc ttttaaatta      60
aaaatgaagt tttaaatcaa tc                                              82

<210> SEQ ID NO 84
<211> LENGTH: 82
<212> TYPE: DNA
<213> ORGANISM: Artificial Sequence
<220> FEATURE:
<223> OTHER INFORMATION: BG8774

<400> SEQUENCE: 84
tatgcctcat gagattatca aaaggatct tcaccccccg cactagatcc ttttaaatta      60
aaaatgaagt tttaaatcaa tc                                              82

<210> SEQ ID NO 85
<211> LENGTH: 82
<212> TYPE: DNA
<213> ORGANISM: Artificial Sequence
<220> FEATURE:
<223> OTHER INFORMATION: BG8775

<400> SEQUENCE: 85
tatgcctcat gagattatca aaaggatct tcaccccccc aactagatcc ttttaaatta      60
aaaatgaagt tttaaatcaa tc                                              82

<210> SEQ ID NO 86
<211> LENGTH: 82
<212> TYPE: DNA
<213> ORGANISM: Artificial Sequence
<220> FEATURE:
<223> OTHER INFORMATION: BG8776

<400> SEQUENCE: 86
tatgcctcat gagattatca aaaggatct tcaccccccc tactagatcc ttttaaatta      60
aaaatgaagt tttaaatcaa tc                                              82

<210> SEQ ID NO 87
```

<211> LENGTH: 82
<212> TYPE: DNA
<213> ORGANISM: Artificial Sequence
<220> FEATURE:
<223> OTHER INFORMATION: BG8777

<400> SEQUENCE: 87
tatgcctcat gagattatca aaaggatct tcaccccccc gactagatcc ttttaaatta    60
aaaatgaagt tttaaatcaa tc                                            82

<210> SEQ ID NO 88
<211> LENGTH: 82
<212> TYPE: DNA
<213> ORGANISM: Artificial Sequence
<220> FEATURE:
<223> OTHER INFORMATION: BG8778

<400> SEQUENCE: 88
tatgcctcat gagattatca aaaggatct tcaccccccc cactagatcc ttttaaatta    60
aaaatgaagt tttaaatcaa tc                                            82

<210> SEQ ID NO 89
<211> LENGTH: 29
<212> TYPE: DNA
<213> ORGANISM: Artificial Sequence
<220> FEATURE:
<223> OTHER INFORMATION: BG6574

<400> SEQUENCE: 89
aagcttgaaa taatacgact cactatagg                                     29

<210> SEQ ID NO 90
<211> LENGTH: 22
<212> TYPE: DNA
<213> ORGANISM: Artificial Sequence
<220> FEATURE:
<223> OTHER INFORMATION: BG6576

<400> SEQUENCE: 90
aaaaaagacc ttgacgttttt cc                                           22

<210> SEQ ID NO 91
<211> LENGTH: 57
<212> TYPE: DNA
<213> ORGANISM: Artificial Sequence
<220> FEATURE:
<223> OTHER INFORMATION: BG9307

<400> SEQUENCE: 91
aagcttgaaa taatacgact cactataggt gagattatca aaaggatct tcacgtc       57

<210> SEQ ID NO 92
<211> LENGTH: 23
<212> TYPE: DNA
<213> ORGANISM: Artificial Sequence
<220> FEATURE:
<223> OTHER INFORMATION: BG9309

<400> SEQUENCE: 92
aaaacgccta agagtgggga atg                                           23

<210> SEQ ID NO 93
<211> LENGTH: 19
<212> TYPE: DNA
<213> ORGANISM: Artificial Sequence

```
<220> FEATURE:
<223> OTHER INFORMATION: BG9310

<400> SEQUENCE: 93
aaaaggcgat aggcgatcc                                               19

<210> SEQ ID NO 94
<211> LENGTH: 23
<212> TYPE: DNA
<213> ORGANISM: Artificial Sequence
<220> FEATURE:
<223> OTHER INFORMATION: BG9311

<400> SEQUENCE: 94
aaaacgggtc agtctgccta tag                                          23

<210> SEQ ID NO 95
<211> LENGTH: 57
<212> TYPE: DNA
<213> ORGANISM: Artificial Sequence
<220> FEATURE:
<223> OTHER INFORMATION: BG9308

<400> SEQUENCE: 95
aagcttgaaa taatacgact cactataggt gagattatca aaaggatct tcacgtc      57

<210> SEQ ID NO 96
<211> LENGTH: 56
<212> TYPE: DNA
<213> ORGANISM: Artificial Sequence
<220> FEATURE:
<223> OTHER INFORMATION: BG10118

<400> SEQUENCE: 96
aagcttgaaa taatacgact cactatagga gattatcaaa aaggatcttc acgtca      56

<210> SEQ ID NO 97
<211> LENGTH: 60
<212> TYPE: DNA
<213> ORGANISM: Artificial Sequence
<220> FEATURE:
<223> OTHER INFORMATION: BG10119

<400> SEQUENCE: 97
aagcttgaaa taatacgact cactatagga agattatcaa aaggatctt cacgtcatag   60

<210> SEQ ID NO 98
<211> LENGTH: 58
<212> TYPE: DNA
<213> ORGANISM: Artificial Sequence
<220> FEATURE:
<223> OTHER INFORMATION: BG10120

<400> SEQUENCE: 98
aagcttgaaa taatacgact cactatagga ttatcaaaaa ggatcttcac gtcatagt    58

<210> SEQ ID NO 99
<211> LENGTH: 60
<212> TYPE: DNA
<213> ORGANISM: Artificial Sequence
<220> FEATURE:
<223> OTHER INFORMATION: BG10121

<400> SEQUENCE: 99
aagcttgaaa taatacgact cactatagga attatcaaaa aggatcttca cgtcatagtt  60
```

<210> SEQ ID NO 100
<211> LENGTH: 58
<212> TYPE: DNA
<213> ORGANISM: Artificial Sequence
<220> FEATURE:
<223> OTHER INFORMATION: BG10122

<400> SEQUENCE: 100
aagcttgaaa taatacgact cactataggt tatcaaaaag gatcttcacg tcatagtt    58

<210> SEQ ID NO 101
<211> LENGTH: 58
<212> TYPE: DNA
<213> ORGANISM: Artificial Sequence
<220> FEATURE:
<223> OTHER INFORMATION: BG10123

<400> SEQUENCE: 101
aagcttgaaa taatacgact cactataggt atcaaaaagg atcttcacgt catagttc    58

<210> SEQ ID NO 102
<211> LENGTH: 57
<212> TYPE: DNA
<213> ORGANISM: Artificial Sequence
<220> FEATURE:
<223> OTHER INFORMATION: BG10124

<400> SEQUENCE: 102
aagcttgaaa taatacgact cactatagga tcaaaaagga tcttcacgtc atagttc     57

<210> SEQ ID NO 103
<211> LENGTH: 51
<212> TYPE: DNA
<213> ORGANISM: Artificial Sequence
<220> FEATURE:
<223> OTHER INFORMATION: BG9312

<400> SEQUENCE: 103
aaaacgccta agagtgggga atgcccgaag aaagcgggcg ataggcgatc c           51

<210> SEQ ID NO 104
<211> LENGTH: 21
<212> TYPE: DNA
<213> ORGANISM: Artificial Sequence
<220> FEATURE:
<223> OTHER INFORMATION: BG8191

<400> SEQUENCE: 104
aagcttggcg taatcatggt c                                            21

<210> SEQ ID NO 105
<211> LENGTH: 20
<212> TYPE: DNA
<213> ORGANISM: Artificial Sequence
<220> FEATURE:
<223> OTHER INFORMATION: BG8192

<400> SEQUENCE: 105
tcatgagttc ccatgttgtg                                              20

<210> SEQ ID NO 106
<211> LENGTH: 48
<212> TYPE: DNA
<213> ORGANISM: Artificial Sequence
<220> FEATURE:
<223> OTHER INFORMATION: BG8194

```
<400> SEQUENCE: 106
tatggcgaat cacaacatgg gaactcatga gaacatcctc tttcttag                48

<210> SEQ ID NO 107
<211> LENGTH: 50
<212> TYPE: DNA
<213> ORGANISM: Artificial Sequence
<220> FEATURE:
<223> OTHER INFORMATION: BG8195

<400> SEQUENCE: 107
gccgatatca agaccgattt tatacttcat ttaagttacc tcctcgattg             50

<210> SEQ ID NO 108
<211> LENGTH: 22
<212> TYPE: DNA
<213> ORGANISM: Artificial Sequence
<220> FEATURE:
<223> OTHER INFORMATION: BG8196

<400> SEQUENCE: 108
atgaagtata aaatcggtct tg                                           22

<210> SEQ ID NO 109
<211> LENGTH: 18
<212> TYPE: DNA
<213> ORGANISM: Artificial Sequence
<220> FEATURE:
<223> OTHER INFORMATION: BG8197

<400> SEQUENCE: 109
taacggacgg atagtttc                                                18

<210> SEQ ID NO 110
<211> LENGTH: 55
<212> TYPE: DNA
<213> ORGANISM: Artificial Sequence
<220> FEATURE:
<223> OTHER INFORMATION: BG8198

<400> SEQUENCE: 110
gaaagccggg gaaactatcc gtccgttata aatcagacaa aatggcctgc ttatg       55

<210> SEQ ID NO 111
<211> LENGTH: 60
<212> TYPE: DNA
<213> ORGANISM: Artificial Sequence
<220> FEATURE:
<223> OTHER INFORMATION: BG8263

<400> SEQUENCE: 111
gaactatgac actttatttt cagaatggac gtataacggt atccatttta agaataatcc  60

<210> SEQ ID NO 112
<211> LENGTH: 49
<212> TYPE: DNA
<213> ORGANISM: Artificial Sequence
<220> FEATURE:
<223> OTHER INFORMATION: BG8268

<400> SEQUENCE: 112
accgttatac gtccattctg aaaataaagt gtcatagttc ccctgagat              49

<210> SEQ ID NO 113
```

```
<211> LENGTH: 48
<212> TYPE: DNA
<213> ORGANISM: Artificial Sequence
<220> FEATURE:
<223> OTHER INFORMATION: BG8210

<400> SEQUENCE: 113
aacagctatg accatgatta cgccaagctt ccctcccatg cacaatag             48

<210> SEQ ID NO 114
<211> LENGTH: 60
<212> TYPE: DNA
<213> ORGANISM: Artificial Sequence
<220> FEATURE:
<223> OTHER INFORMATION: BG8261

<400> SEQUENCE: 114
gaactatgac atcatggagt tttaaatcca gtataacggt atccatttta agaataatcc    60

<210> SEQ ID NO 115
<211> LENGTH: 49
<212> TYPE: DNA
<213> ORGANISM: Artificial Sequence
<220> FEATURE:
<223> OTHER INFORMATION: BG8266

<400> SEQUENCE: 115
accgttatac tggatttaaa actccatgat gtcatagttc ccctgagat              49

<210> SEQ ID NO 116
<211> LENGTH: 60
<212> TYPE: DNA
<213> ORGANISM: Artificial Sequence
<220> FEATURE:
<223> OTHER INFORMATION: BG8317

<400> SEQUENCE: 116
gaactatgac cacccagctt acatcaacaa gtataacggt atccatttta agaataatcc    60

<210> SEQ ID NO 117
<211> LENGTH: 49
<212> TYPE: DNA
<213> ORGANISM: Artificial Sequence
<220> FEATURE:
<223> OTHER INFORMATION: BG8320

<400> SEQUENCE: 117
accgttatac ttgttgatgt aagctgggtg gtcatagttc ccctgagat              49

<210> SEQ ID NO 118
<211> LENGTH: 20
<212> TYPE: DNA
<213> ORGANISM: Artificial Sequence
<220> FEATURE:
<223> OTHER INFORMATION: BG9075

<400> SEQUENCE: 118
ctatcggcat tacgtctatc                                              20

<210> SEQ ID NO 119
<211> LENGTH: 19
<212> TYPE: DNA
<213> ORGANISM: Artificial Sequence
<220> FEATURE:
<223> OTHER INFORMATION: BG9091
```

<400> SEQUENCE: 119
gcgtcgactt ctgtatagc                                                19

<210> SEQ ID NO 120
<211> LENGTH: 41
<212> TYPE: DNA
<213> ORGANISM: Artificial Sequence
<220> FEATURE:
<223> OTHER INFORMATION: BG9091

<400> SEQUENCE: 120
tgaagtataa aatcggtctt gctatcggca ttacgtctat c                        41

<210> SEQ ID NO 121
<211> LENGTH: 44
<212> TYPE: DNA
<213> ORGANISM: Artificial Sequence
<220> FEATURE:
<223> OTHER INFORMATION: BG9092

<400> SEQUENCE: 121
caagcttcgg ctgtatggaa tcacagcgtc gacttctgta tagc                     44

<210> SEQ ID NO 122
<211> LENGTH: 17
<212> TYPE: DNA
<213> ORGANISM: Artificial Sequence
<220> FEATURE:
<223> OTHER INFORMATION: BG9077

<400> SEQUENCE: 122
gctgtgattc catacag                                                  17

<210> SEQ ID NO 123
<211> LENGTH: 41
<212> TYPE: DNA
<213> ORGANISM: Artificial Sequence
<220> FEATURE:
<223> OTHER INFORMATION: BG9267

<400> SEQUENCE: 123
ggtgcagtag gttgcagcta tgcttgtata acggtatcca t                        41

<210> SEQ ID NO 124
<211> LENGTH: 49
<212> TYPE: DNA
<213> ORGANISM: Artificial Sequence
<220> FEATURE:
<223> OTHER INFORMATION: BG9263

<400> SEQUENCE: 124
aagcatagct gcaacctact gcaccgtcat agttcccctg agattatcg                49

<210> SEQ ID NO 125
<211> LENGTH: 22
<212> TYPE: DNA
<213> ORGANISM: Artificial Sequence
<220> FEATURE:
<223> OTHER INFORMATION: BG9088

<400> SEQUENCE: 125
tcatgaccaa aatcccttaa cg                                            22

<210> SEQ ID NO 126

```
<211> LENGTH: 38
<212> TYPE: DNA
<213> ORGANISM: Artificial Sequence
<220> FEATURE:
<223> OTHER INFORMATION: BG9089

<400> SEQUENCE: 126
ttaagggatt ttggtcatga gaacatcctc tttcttag                         38

<210> SEQ ID NO 127
<211> LENGTH: 28
<212> TYPE: DNA
<213> ORGANISM: Artificial Sequence
<220> FEATURE:
<223> OTHER INFORMATION: BG9090

<400> SEQUENCE: 127
gcaagaccga ttttatactt catttaag                                    28

<210> SEQ ID NO 128
<211> LENGTH: 52
<212> TYPE: DNA
<213> ORGANISM: Artificial Sequence
<220> FEATURE:
<223> OTHER INFORMATION: BG9548

<400> SEQUENCE: 128
ggatcccatg acgctagtat ccagctgggt catagttccc ctgagattat cg         52

<210> SEQ ID NO 129
<211> LENGTH: 63
<212> TYPE: DNA
<213> ORGANISM: Artificial Sequence
<220> FEATURE:
<223> OTHER INFORMATION: BG9601

<400> SEQUENCE: 129
ttcaatattt tttttgaata aaaaatacga tacaataaaa atgtctagaa aaagataaaa   60
atg                                                                63

<210> SEQ ID NO 130
<211> LENGTH: 53
<212> TYPE: DNA
<213> ORGANISM: Artificial Sequence
<220> FEATURE:
<223> OTHER INFORMATION: BG9600

<400> SEQUENCE: 130 tttttttattc aaaaaaaata ttgaatttta aaaatgatgg tgctagtatg aag        53

<210> SEQ ID NO 131
<211> LENGTH: 58
<212> TYPE: DNA
<213> ORGANISM: Artificial Sequence
<220> FEATURE:
<223> OTHER INFORMATION: BG9549

<400> SEQUENCE: 131
ccagctggat actagcgtca tgggatccgt ataacggtat ccattttaag aataatcc    58

<210> SEQ ID NO 132
<211> LENGTH: 20
<212> TYPE: DNA
<213> ORGANISM: Artificial Sequence
<220> FEATURE:
<223> OTHER INFORMATION: BG8552
```

```
<400> SEQUENCE: 132
tcgggggttc gtttcccttg                                               20

<210> SEQ ID NO 133
<211> LENGTH: 22
<212> TYPE: DNA
<213> ORGANISM: Artificial Sequence
<220> FEATURE:
<223> OTHER INFORMATION: BG8553

<400> SEQUENCE: 133
cttacacagc cagtgacgga ac                                            22

<210> SEQ ID NO 134
<211> LENGTH: 20
<212> TYPE: DNA
<213> ORGANISM: Artificial Sequence
<220> FEATURE:
<223> OTHER INFORMATION: BG2365

<400> SEQUENCE: 134
gccggcgtcc cggaaaacga                                               20

<210> SEQ ID NO 135
<211> LENGTH: 35
<212> TYPE: DNA
<213> ORGANISM: Artificial Sequence
<220> FEATURE:
<223> OTHER INFORMATION: BG2366

<400> SEQUENCE: 135
gcaggtcggg ttcctcgcat ccatgccccc gaact                              35

<210> SEQ ID NO 136
<211> LENGTH: 50
<212> TYPE: DNA
<213> ORGANISM: Artificial Sequence
<220> FEATURE:
<223> OTHER INFORMATION: BG2367

<400> SEQUENCE: 136
ggcttcggaa tcgttttccg ggacgccggc acggcattgg caaggccaag              50

<210> SEQ ID NO 137
<211> LENGTH: 35
<212> TYPE: DNA
<213> ORGANISM: Artificial Sequence
<220> FEATURE:
<223> OTHER INFORMATION: BG2368

<400> SEQUENCE: 137
gacacaggca tcggtgcagg gtctcttggc aagtc                              35

<210> SEQ ID NO 138
<211> LENGTH: 35
<212> TYPE: DNA
<213> ORGANISM: Artificial Sequence
<220> FEATURE:
<223> OTHER INFORMATION: BG2369

<400> SEQUENCE: 138
gccaagagac cctgcaccga tgcctgtgtc gaacc                              35

<210> SEQ ID NO 139
```

```
<211> LENGTH: 50
<212> TYPE: DNA
<213> ORGANISM: Artificial Sequence
<220> FEATURE:
<223> OTHER INFORMATION: BG2370

<400> SEQUENCE: 139
cttggcggaa aacgtcaagg tcttttttac acgcgcatca acttcaaggc            50

<210> SEQ ID NO 140
<211> LENGTH: 48
<212> TYPE: DNA
<213> ORGANISM: Artificial Sequence
<220> FEATURE:
<223> OTHER INFORMATION: BG2371

<400> SEQUENCE: 140
atgacgagct gttcaccagc agcgctatta ttgaagcatt tatcaggg              48

<210> SEQ ID NO 141
<211> LENGTH: 23
<212> TYPE: DNA
<213> ORGANISM: Artificial Sequence
<220> FEATURE:
<223> OTHER INFORMATION: BG2372

<400> SEQUENCE: 141
gtaaaaaaga ccttgacgtt ttc                                         23

<210> SEQ ID NO 142
<211> LENGTH: 34
<212> TYPE: DNA
<213> ORGANISM: Artificial Sequence
<220> FEATURE:
<223> OTHER INFORMATION: BG2373

<400> SEQUENCE: 142
tatgaagcgg gccatttgaa gacgaaaggg cctc                             34

<210> SEQ ID NO 143
<211> LENGTH: 49
<212> TYPE: DNA
<213> ORGANISM: Artificial Sequence
<220> FEATURE:
<223> OTHER INFORMATION: BG2374

<400> SEQUENCE: 143
taatagcgct gctggtgaac agctcgtcat agttcccctg agattatcg             49

<210> SEQ ID NO 144
<211> LENGTH: 37
<212> TYPE: DNA
<213> ORGANISM: Artificial Sequence
<220> FEATURE:
<223> OTHER INFORMATION: BG2375

<400> SEQUENCE: 144
tggagtcatg aacatatgaa gtataaaatc ggtcttg                          37

<210> SEQ ID NO 145
<211> LENGTH: 35
<212> TYPE: DNA
<213> ORGANISM: Artificial Sequence
<220> FEATURE:
<223> OTHER INFORMATION: BG2376
```

<400> SEQUENCE: 145 cccttttcgtc ttcaaatggc ccgcttcata agcag                               35

<210> SEQ ID NO 146
<211> LENGTH: 39
<212> TYPE: DNA
<213> ORGANISM: Artificial Sequence
<220> FEATURE:
<223> OTHER INFORMATION: BG2377

<400> SEQUENCE: 146
gattttatac ttcatatgtt catgactcca ttattattg                            39

<210> SEQ ID NO 147
<211> LENGTH: 35
<212> TYPE: DNA
<213> ORGANISM: Artificial Sequence
<220> FEATURE:
<223> OTHER INFORMATION: BG2378

<400> SEQUENCE: 147
gggggcatgg atgcgaggaa cccgacctgc attgg                                35

<210> SEQ ID NO 148
<211> LENGTH: 20
<212> TYPE: DNA
<213> ORGANISM: Artificial Sequence
<220> FEATURE:
<223> OTHER INFORMATION: BG2381

<400> SEQUENCE: 148
acacggcgga tgcacttacc                                                 20

<210> SEQ ID NO 149
<211> LENGTH: 20
<212> TYPE: DNA
<213> ORGANISM: Artificial Sequence
<220> FEATURE:
<223> OTHER INFORMATION: BG2382

<400> SEQUENCE: 149
tggacgtgta cttcgacaac                                                 20

<210> SEQ ID NO 150
<211> LENGTH: 20
<212> TYPE: DNA
<213> ORGANISM: Artificial Sequence
<220> FEATURE:
<223> OTHER INFORMATION: BG2135

<400> SEQUENCE: 150
acacggcgga tgcacttacc                                                 20

<210> SEQ ID NO 151
<211> LENGTH: 20
<212> TYPE: DNA
<213> ORGANISM: Artificial Sequence
<220> FEATURE:
<223> OTHER INFORMATION: BG8196

<400> SEQUENCE: 151
tggacgtgta cttcgacaac                                                 20

<210> SEQ ID NO 152

```
<211> LENGTH: 18
<212> TYPE: DNA
<213> ORGANISM: Artificial Sequence
<220> FEATURE:
<223> OTHER INFORMATION: BG8197

<400> SEQUENCE: 152
taacggacgg atagtttc                                              18

<210> SEQ ID NO 153
<211> LENGTH: 31
<212> TYPE: DNA
<213> ORGANISM: Artificial Sequence
<220> FEATURE:
<223> OTHER INFORMATION: BG6850

<400> SEQUENCE: 153
gcctcatgaa tgcagcgatg gtccggtgtt c                               31

<210> SEQ ID NO 154
<211> LENGTH: 27
<212> TYPE: DNA
<213> ORGANISM: Artificial Sequence
<220> FEATURE:
<223> OTHER INFORMATION: BG6849

<400> SEQUENCE: 154
gcctcatgag ttcccatgtt gtgattc                                    27

<210> SEQ ID NO 155
<211> LENGTH: 19
<212> TYPE: DNA
<213> ORGANISM: Artificial Sequence
<220> FEATURE:
<223> OTHER INFORMATION: BG6769

<400> SEQUENCE: 155
caatccaact gggcttgac                                             19

<210> SEQ ID NO 156
<211> LENGTH: 20
<212> TYPE: DNA
<213> ORGANISM: Artificial Sequence
<220> FEATURE:
<223> OTHER INFORMATION: BG6841

<400> SEQUENCE: 156
caagaacttt attggtatag                                            20

<210> SEQ ID NO 157
<211> LENGTH: 20
<212> TYPE: DNA
<213> ORGANISM: Artificial Sequence
<220> FEATURE:
<223> OTHER INFORMATION: BG6840

<400> SEQUENCE: 157
ttgcagaaat ggttgtcaag                                            20

<210> SEQ ID NO 158
<211> LENGTH: 19
<212> TYPE: DNA
<213> ORGANISM: Artificial Sequence
<220> FEATURE:
<223> OTHER INFORMATION: BG9215
```

```
<400> SEQUENCE: 158
gagataatgc cgactgtac                                               19

<210> SEQ ID NO 159
<211> LENGTH: 19
<212> TYPE: DNA
<213> ORGANISM: Artificial Sequence
<220> FEATURE:
<223> OTHER INFORMATION: BG9216

<400> SEQUENCE: 159
agggctcgcc tttgggaag                                               19

<210> SEQ ID NO 160
<211> LENGTH: 17
<212> TYPE: DNA
<213> ORGANISM: Artificial Sequence
<220> FEATURE:
<223> OTHER INFORMATION: BG9505

<400> SEQUENCE: 160
gttgccaacg ttctgag                                                 17

<210> SEQ ID NO 161
<211> LENGTH: 16
<212> TYPE: DNA
<213> ORGANISM: Artificial Sequence
<220> FEATURE:
<223> OTHER INFORMATION: BG9506

<400> SEQUENCE: 161
aatccacgcc gtttag                                                  16

<210> SEQ ID NO 162
<211> LENGTH: 20
<212> TYPE: DNA
<213> ORGANISM: Artificial Sequence
<220> FEATURE:
<223> OTHER INFORMATION: BG8363

<400> SEQUENCE: 162
acggttatcc acagaatcag                                              20

<210> SEQ ID NO 163
<211> LENGTH: 22
<212> TYPE: DNA
<213> ORGANISM: Artificial Sequence
<220> FEATURE:
<223> OTHER INFORMATION: BG8364

<400> SEQUENCE: 163
cgggattgac ttttaaaaaa gg                                           22

<210> SEQ ID NO 164
<211> LENGTH: 120
<212> TYPE: DNA
<213> ORGANISM: Artificial Sequence
<220> FEATURE:
<223> OTHER INFORMATION: BG9302

<400> SEQUENCE: 164
aaacttcatt tttaatttaa aaggatctag aaccccccgt gaagatcctt tttgataatc   60
tcatgaccaa aatcccttaa cgtgagtttt cgttccactg agcgtcagac cccgtagaaa  120
```

<210> SEQ ID NO 165
<211> LENGTH: 120
<212> TYPE: DNA
<213> ORGANISM: Artificial Sequence
<220> FEATURE:
<223> OTHER INFORMATION: BG9303

<400> SEQUENCE: 165

```
tttctacggg gtctgacgct cagtggaacg aaaactcacg ttaagggatt ttggtcatga      60
gattatcaaa aaggatcttc accccccccaa ctagatcctt ttaaattaaa aatgaagttt    120
```

<210> SEQ ID NO 166
<211> LENGTH: 120
<212> TYPE: DNA
<213> ORGANISM: Artificial Sequence
<220> FEATURE:
<223> OTHER INFORMATION: BG9304

<400> SEQUENCE: 166

```
tttctacggg gtctgacgct cagtggaacg aaaactcacg ttaagggatt ttggtcatga      60
gattatcaaa aaggatcttc acgggggggtt ctagatcctt ttaaattaaa aatgaagttt    120
```

<210> SEQ ID NO 167
<211> LENGTH: 43
<212> TYPE: DNA
<213> ORGANISM: Artificial Sequence
<220> FEATURE:
<223> OTHER INFORMATION: BG7886

<400> SEQUENCE: 167

```
tacttccaat ccaatgcaaa gtataaaatc ggtcttgata tcg                        43
```

<210> SEQ ID NO 168
<211> LENGTH: 50
<212> TYPE: DNA
<213> ORGANISM: Artificial Sequence
<220> FEATURE:
<223> OTHER INFORMATION: BG7887

<400> SEQUENCE: 168

```
ttatccactt ccaatgttat tataacggac ggatagtttc cccggctttc                 50
```

<210> SEQ ID NO 169
<211> LENGTH: 25
<212> TYPE: DNA
<213> ORGANISM: Artificial Sequence
<220> FEATURE:
<223> OTHER INFORMATION: BG9665

<400> SEQUENCE: 169

```
atgacgaaag gagtttctta ttatg                                            25
```

<210> SEQ ID NO 170
<211> LENGTH: 20
<212> TYPE: DNA
<213> ORGANISM: Artificial Sequence
<220> FEATURE:
<223> OTHER INFORMATION: BG9666

<400> SEQUENCE: 170

```
aacggtattc cgtgattaag                                                  20
```

<210> SEQ ID NO 171
<211> LENGTH: 21
<212> TYPE: DNA

```
<213> ORGANISM: Artificial Sequence
<220> FEATURE:
<223> OTHER INFORMATION: Primer 629

<400> SEQUENCE: 171
gactgggcgc aagcggtgat g                                             21

<210> SEQ ID NO 172
<211> LENGTH: 24
<212> TYPE: DNA
<213> ORGANISM: Artificial Sequence
<220> FEATURE:
<223> OTHER INFORMATION: Primer 630

<400> SEQUENCE: 172
cctgttgctg atacaaggtc tagc                                          24

<210> SEQ ID NO 173
<211> LENGTH: 38
<212> TYPE: DNA
<213> ORGANISM: Artificial Sequence
<220> FEATURE:
<223> OTHER INFORMATION: Primer 992

<400> SEQUENCE: 173
ttggatgtga tgctgacttt gaatacaaca aggtgaac                           38

<210> SEQ ID NO 174
<211> LENGTH: 37
<212> TYPE: DNA
<213> ORGANISM: Artificial Sequence
<220> FEATURE:
<223> OTHER INFORMATION: Primer 993

<400> SEQUENCE: 174
attcaaagtc agcatcacat ccaattacat caagcag                            37

<210> SEQ ID NO 175
<211> LENGTH: 20
<212> TYPE: DNA
<213> ORGANISM: Artificial Sequence
<220> FEATURE:
<223> OTHER INFORMATION: Primer 1994

<400> SEQUENCE: 175
aaacaaacca ccgctggtag                                               20

<210> SEQ ID NO 176
<211> LENGTH: 20
<212> TYPE: DNA
<213> ORGANISM: Artificial Sequence
<220> FEATURE:
<223> OTHER INFORMATION: Primer 2125

<400> SEQUENCE: 176
tcttcgatgc gaggaatgtc                                               20

<210> SEQ ID NO 177
<211> LENGTH: 33
<212> TYPE: DNA
<213> ORGANISM: Artificial Sequence
<220> FEATURE:
<223> OTHER INFORMATION: Primer 2208

<400> SEQUENCE: 177
ttttatactt catatgcaac ctcctttatg ttc                                33
```

<210> SEQ ID NO 178
<211> LENGTH: 34
<212> TYPE: DNA
<213> ORGANISM: Artificial Sequence
<220> FEATURE:
<223> OTHER INFORMATION: Primer 2210

<400> SEQUENCE: 178
aggaggttgc atatgaagta taaaatcggt cttg				34

<210> SEQ ID NO 179
<211> LENGTH: 20
<212> TYPE: DNA
<213> ORGANISM: Artificial Sequence
<220> FEATURE:
<223> OTHER INFORMATION: Primer 2400

<400> SEQUENCE: 179
cgataaacgc gaagaaggtg				20

<210> SEQ ID NO 180
<211> LENGTH: 22
<212> TYPE: DNA
<213> ORGANISM: Artificial Sequence
<220> FEATURE:
<223> OTHER INFORMATION: Primer 2401

<400> SEQUENCE: 180
tcatgaccaa aatcccttaa cg				22

<210> SEQ ID NO 181
<211> LENGTH: 52
<212> TYPE: DNA
<213> ORGANISM: Artificial Sequence
<220> FEATURE:
<223> OTHER INFORMATION: Primer 2420

<400> SEQUENCE: 181
aaaactcacg ttaagggatt ttggtcatga ccgattcggc tgttatggag ag				52

<210> SEQ ID NO 182
<211> LENGTH: 54
<212> TYPE: DNA
<213> ORGANISM: Artificial Sequence
<220> FEATURE:
<223> OTHER INFORMATION: Primer 2421

<400> SEQUENCE: 182
tgcgtcggaa caccttcttc gcgtttatcg cggcaaacag agctttaaaa ccag				54

<210> SEQ ID NO 183
<211> LENGTH: 76
<212> TYPE: DNA
<213> ORGANISM: Artificial Sequence
<220> FEATURE:
<223> OTHER INFORMATION: Primer 2489

<400> SEQUENCE: 183
aacttagttg cgtttctata taataagagt tatgttttcc ggacatagta cagtcatagt				60 tccctgaga ttatcg				76

<210> SEQ ID NO 184
<211> LENGTH: 65
<212> TYPE: DNA

```
<213> ORGANISM: Artificial Sequence
<220> FEATURE:
<223> OTHER INFORMATION: Primer 2490

<400> SEQUENCE: 184
actcttatta tatagaaacg caactaagtt aagcattgcc attataacgg acggatagtt    60
tcccc                                                                65

<210> SEQ ID NO 185
<211> LENGTH: 52
<212> TYPE: DNA
<213> ORGANISM: Artificial Sequence
<220> FEATURE:
<223> OTHER INFORMATION: Primer 2501

<400> SEQUENCE: 185
aagagataag ggcaaatgca tagctggcgt catagttccc ctgagattat cg            52

<210> SEQ ID NO 186
<211> LENGTH: 55
<212> TYPE: DNA
<213> ORGANISM: Artificial Sequence
<220> FEATURE:
<223> OTHER INFORMATION: Primer 2502

<400> SEQUENCE: 186
atgacgccag ctatgcattt gcccttatct cttattatat agaaacgcaa ctaag         55

<210> SEQ ID NO 187
<211> LENGTH: 20
<212> TYPE: DNA
<213> ORGANISM: Artificial Sequence
<220> FEATURE:
<223> OTHER INFORMATION: Primer 351

<400> SEQUENCE: 187
caccatgtcc cggacagcac                                                20

<210> SEQ ID NO 188
<211> LENGTH: 22
<212> TYPE: DNA
<213> ORGANISM: Artificial Sequence
<220> FEATURE:
<223> OTHER INFORMATION: Primer 352

<400> SEQUENCE: 188
gcgatgaaat tggaacactg ac                                             22

<210> SEQ ID NO 189
<211> LENGTH: 21
<212> TYPE: DNA
<213> ORGANISM: Artificial Sequence
<220> FEATURE:
<223> OTHER INFORMATION: Primer 2172

<400> SEQUENCE: 189
tcatgaccaa aatcccttaa c                                              21

<210> SEQ ID NO 190
<211> LENGTH: 47
<212> TYPE: DNA
<213> ORGANISM: Artificial Sequence
<220> FEATURE:
<223> OTHER INFORMATION: Primer 2561
```

```
<400> SEQUENCE: 190
tcacgttaag ggattttggt catgagtgag tctggctatt gacctgg          47

<210> SEQ ID NO 191
<211> LENGTH: 36
<212> TYPE: DNA
<213> ORGANISM: Artificial Sequence
<220> FEATURE:
<223> OTHER INFORMATION: Primer 2562

<400> SEQUENCE: 191
atgaaaaaag cgcacgtcgg cacgactcct taattg                      36

<210> SEQ ID NO 192
<211> LENGTH: 38
<212> TYPE: DNA
<213> ORGANISM: Artificial Sequence
<220> FEATURE:
<223> OTHER INFORMATION: Primer 2563

<400> SEQUENCE: 192
attaaggagt cgtgccgacg tgcgcttttt tcattccc                    38

<210> SEQ ID NO 193
<211> LENGTH: 52
<212> TYPE: DNA
<213> ORGANISM: Artificial Sequence
<220> FEATURE:
<223> OTHER INFORMATION: Primer 2570

<400> SEQUENCE: 193
caccttcttc gcgtttatcg cggcacagga tataatggtc gatgtcctgt tg    52

<210> SEQ ID NO 194
<211> LENGTH: 20
<212> TYPE: DNA
<213> ORGANISM: Artificial Sequence
<220> FEATURE:
<223> OTHER INFORMATION: Primer 2571

<400> SEQUENCE: 194
cgataaacgc gaagaaggtg                                        20

<210> SEQ ID NO 195
<211> LENGTH: 54
<212> TYPE: DNA
<213> ORGANISM: Artificial Sequence
<220> FEATURE:
<223> OTHER INFORMATION: Primer 2578

<400> SEQUENCE: 195
taagagtcgg ggatatgaac cggatgactt gtcatagttc ccctgagatt atcg  54

<210> SEQ ID NO 196
<211> LENGTH: 57
<212> TYPE: DNA
<213> ORGANISM: Artificial Sequence
<220> FEATURE:
<223> OTHER INFORMATION: Primer 2579

<400> SEQUENCE: 196
aagtcatccg gttcatatcc ccgactctta ttatatagaa acgcaactaa gttaagc  57

<210> SEQ ID NO 197
```

```
<211> LENGTH: 20
<212> TYPE: DNA
<213> ORGANISM: Artificial Sequence
<220> FEATURE:
<223> OTHER INFORMATION: Primer 2135

<400> SEQUENCE: 197
ccgctttctt cgggcattcc                                               20

<210> SEQ ID NO 198
<211> LENGTH: 20
<212> TYPE: DNA
<213> ORGANISM: Artificial Sequence
<220> FEATURE:
<223> OTHER INFORMATION: Primer 2381

<400> SEQUENCE: 198
acacggcgga tgcacttacc                                               20

<210> SEQ ID NO 199
<211> LENGTH: 20
<212> TYPE: DNA
<213> ORGANISM: Artificial Sequence
<220> FEATURE:
<223> OTHER INFORMATION: Primer 2382

<400> SEQUENCE: 199
tggacgtgta cttcgacaac                                               20

<210> SEQ ID NO 200
<211> LENGTH: 22
<212> TYPE: DNA
<213> ORGANISM: Artificial Sequence
<220> FEATURE:
<223> OTHER INFORMATION: Primer 2459

<400> SEQUENCE: 200
agctgtttcc tgtgtgaaat tg                                            22

<210> SEQ ID NO 201
<211> LENGTH: 20
<212> TYPE: DNA
<213> ORGANISM: Artificial Sequence
<220> FEATURE:
<223> OTHER INFORMATION: Primer 2460

<400> SEQUENCE: 201
ggctggacga cctcgcggag                                               20

<210> SEQ ID NO 202
<211> LENGTH: 50
<212> TYPE: DNA
<213> ORGANISM: Artificial Sequence
<220> FEATURE:
<223> OTHER INFORMATION: Primer 2461

<400> SEQUENCE: 202
gccggtagaa ctccgcgagg tcgtccagcc acggcattgg caaggccaag              50

<210> SEQ ID NO 203
<211> LENGTH: 50
<212> TYPE: DNA
<213> ORGANISM: Artificial Sequence
<220> FEATURE:
<223> OTHER INFORMATION: Primer 2462
```

<400> SEQUENCE: 203
gcggataaca atttcacaca ggaaacagct acgcgcatca acttcaaggc        50

<210> SEQ ID NO 204
<211> LENGTH: 39
<212> TYPE: DNA
<213> ORGANISM: Artificial Sequence
<220> FEATURE:
<223> OTHER INFORMATION: Primer 2467

<400> SEQUENCE: 204
gattttatac ttcatatgtt catgactcca ttattattg                   39

<210> SEQ ID NO 205
<211> LENGTH: 37
<212> TYPE: DNA
<213> ORGANISM: Artificial Sequence
<220> FEATURE:
<223> OTHER INFORMATION: Primer 2468

<400> SEQUENCE: 205
caaggtcttt tttactaagt cgaggggatc ctctagc                     37

<210> SEQ ID NO 206
<211> LENGTH: 57
<212> TYPE: DNA
<213> ORGANISM: Artificial Sequence
<220> FEATURE:
<223> OTHER INFORMATION: Primer 2469

<400> SEQUENCE: 206
ccacacatta tacgagccga tgattaattg tcaacagatg gcccgcttca taagcag    57

<210> SEQ ID NO 207
<211> LENGTH: 37
<212> TYPE: DNA
<213> ORGANISM: Artificial Sequence
<220> FEATURE:
<223> OTHER INFORMATION: Primer 2470

<400> SEQUENCE: 207
tggagtcatg aacatatgaa gtataaaatc ggtcttg                     37

<210> SEQ ID NO 208
<211> LENGTH: 38
<212> TYPE: DNA
<213> ORGANISM: Artificial Sequence
<220> FEATURE:
<223> OTHER INFORMATION: Primer 2471

<400> SEQUENCE: 208
gatcccctcg acttagtaaa aaagaccttg acgttttc                    38

<210> SEQ ID NO 209
<211> LENGTH: 79
<212> TYPE: DNA
<213> ORGANISM: Artificial Sequence
<220> FEATURE:
<223> OTHER INFORMATION: Primer 2742

<400> SEQUENCE: 209
gacaattaat catcggctcg tataatgtgt ggccataccc gcttttccg ccagcgtcat    60 agttcccctg agattatcg                                          79

```
<210> SEQ ID NO 210
<211> LENGTH: 120
<212> TYPE: DNA
<213> ORGANISM: Artificial Sequence
<220> FEATURE:
<223> OTHER INFORMATION: Primer 2101

<400> SEQUENCE: 210
tttcagagtt cttcagactt cttaactcct gtaaaaacaa aaaaaaaaaa aggcatagca      60
atatgacgtt ttattacctt taatcacatt cccacgccat ttcgcattct caccctcata     120

<210> SEQ ID NO 211
<211> LENGTH: 120
<212> TYPE: DNA
<213> ORGANISM: Artificial Sequence
<220> FEATURE:
<223> OTHER INFORMATION: Primer 2102

<400> SEQUENCE: 211
tatgagggtg agaatgcgaa atggcgtggg aatgtgatta aggtaataaa acgtcatat       60 tgctatgcct ttttttttt ttgtttttac aggagttaag aagtctgaag aactctgaaa      120

<210> SEQ ID NO 212
<211> LENGTH: 63
<212> TYPE: DNA
<213> ORGANISM: Artificial Sequence
<220> FEATURE:
<223> OTHER INFORMATION: Primer 2103

<400> SEQUENCE: 212
gcattcccca ctcttaggcg ttttttttgtt ttttatgtct cgggtcttga ggggttttttt    60 gtg                                                                   63

<210> SEQ ID NO 213
<211> LENGTH: 54
<212> TYPE: DNA
<213> ORGANISM: Artificial Sequence
<220> FEATURE:
<223> OTHER INFORMATION: Primer 2104

<400> SEQUENCE: 213
ttatcctata aatataacgt ttttgaacac atggaataat ttgggaattt actc            54

<210> SEQ ID NO 214
<211> LENGTH: 50
<212> TYPE: DNA
<213> ORGANISM: Artificial Sequence
<220> FEATURE:
<223> OTHER INFORMATION: Primer 2105

<400> SEQUENCE: 214
acaaaatgga atatgttcat agggtagacg gatagagatg ggccaatacc                 50

<210> SEQ ID NO 215
<211> LENGTH: 59
<212> TYPE: DNA
<213> ORGANISM: Artificial Sequence
<220> FEATURE:
<223> OTHER INFORMATION: Primer 2106

<400> SEQUENCE: 215
aaaaaacccc tcaagacccg agacataaaa aacaaaaaaa cgcctaagag tggggaatg       59
```

```
<210> SEQ ID NO 216
<211> LENGTH: 64
<212> TYPE: DNA
<213> ORGANISM: Artificial Sequence
<220> FEATURE:
<223> OTHER INFORMATION: Primer 2108

<400> SEQUENCE: 216
gcagtgaaag ataaatgatc gcgttggtca gaggtgtgga gtcatagttc ccctgagatt      60
atcg                                                                  64

<210> SEQ ID NO 217
<211> LENGTH: 50
<212> TYPE: DNA
<213> ORGANISM: Artificial Sequence
<220> FEATURE:
<223> OTHER INFORMATION: Primer 2109

<400> SEQUENCE: 217
aagcataatc atacattatc ttttcaaaga gagattcgat gcccgacgag                 50

<210> SEQ ID NO 218
<211> LENGTH: 50
<212> TYPE: DNA
<213> ORGANISM: Artificial Sequence
<220> FEATURE:
<223> OTHER INFORMATION: Primer 2110

<400> SEQUENCE: 218
atttaaattt ccgaactctc caaggccctc agtctcgacg atccatatcg                 50

<210> SEQ ID NO 219
<211> LENGTH: 56
<212> TYPE: DNA
<213> ORGANISM: Artificial Sequence
<220> FEATURE:
<223> OTHER INFORMATION: Primer 2111

<400> SEQUENCE: 219
aacacagagt aaattcccaa attattccat gtgttcaaaa acgttatatt tatagg         56

<210> SEQ ID NO 220
<211> LENGTH: 53
<212> TYPE: DNA
<213> ORGANISM: Artificial Sequence
<220> FEATURE:
<223> OTHER INFORMATION: Primer 2113

<400> SEQUENCE: 220
ctacaaatgt ggtattggcc catctctatc cgtctaccct atgaacatat tcc            53

<210> SEQ ID NO 221
<211> LENGTH: 67
<212> TYPE: DNA
<213> ORGANISM: Artificial Sequence
<220> FEATURE:
<223> OTHER INFORMATION: Primer 2114

<400> SEQUENCE: 221
aatctcaggg gaactatgac tccacacctc tgaccaacgc gatcatttat ctttcactgc      60
ggagaag                                                               67

<210> SEQ ID NO 222
<211> LENGTH: 57
<212> TYPE: DNA
```

```
<213> ORGANISM: Artificial Sequence
<220> FEATURE:
<223> OTHER INFORMATION: Primer 2115

<400> SEQUENCE: 222
cgctcatttg ctcgtcgggc atcgaatctc tctttgaaaa gataatgtat gattatg       57

<210> SEQ ID NO 223
<211> LENGTH: 63
<212> TYPE: DNA
<213> ORGANISM: Artificial Sequence
<220> FEATURE:
<223> OTHER INFORMATION: Primer 2116

<400> SEQUENCE: 223
gccgatatca agaccgattt tatacttcat tttgtaatta aaacttagat tagattgcta    60
tgc                                                                 63

<210> SEQ ID NO 224
<211> LENGTH: 82
<212> TYPE: DNA
<213> ORGANISM: Artificial Sequence
<220> FEATURE:
<223> OTHER INFORMATION: Primer 2118

<400> SEQUENCE: 224
aatgtaagcg tgacataact aattacatga ttcaccttc ctcttcttct tgggtaacgg     60
acggatagtt tccccggctt tc                                            82

<210> SEQ ID NO 225
<211> LENGTH: 51
<212> TYPE: DNA
<213> ORGANISM: Artificial Sequence
<220> FEATURE:
<223> OTHER INFORMATION: Primer 2119

<400> SEQUENCE: 225
agcaatctaa tctaagtttt aattacaaaa tgaagtataa aatcggtctt g             51

<210> SEQ ID NO 226
<211> LENGTH: 57
<212> TYPE: DNA
<213> ORGANISM: Artificial Sequence
<220> FEATURE:
<223> OTHER INFORMATION: Primer 2120

<400> SEQUENCE: 226
ccgttaccca agaagaagag gaaggtgtaa tcatgtaatt agttatgtca cgcttac       57

<210> SEQ ID NO 227
<211> LENGTH: 20
<212> TYPE: DNA
<213> ORGANISM: Artificial Sequence
<220> FEATURE:
<223> OTHER INFORMATION: Primer 2223

<400> SEQUENCE: 227
ggttgcgaac agagtaaacc                                                20

<210> SEQ ID NO 228
<211> LENGTH: 20
<212> TYPE: DNA
<213> ORGANISM: Artificial Sequence
<220> FEATURE:
<223> OTHER INFORMATION: Primer 2224
```

<400> SEQUENCE: 228
tcgggagcaa gattgttgtg         20

<210> SEQ ID NO 229
<211> LENGTH: 80
<212> TYPE: DNA
<213> ORGANISM: Artificial Sequence
<220> FEATURE:
<223> OTHER INFORMATION: Primer 2580

<400> SEQUENCE: 229
ttcttaggtg catgcgacgg tatccacgtg cagaacaaca tagtctgaag aagggggga         60 tccatcttcg atggatagcg         80

<210> SEQ ID NO 230
<211> LENGTH: 80
<212> TYPE: DNA
<213> ORGANISM: Artificial Sequence
<220> FEATURE:
<223> OTHER INFORMATION: Primer 2581

<400> SEQUENCE: 230
agaagagaaa agggtaaagt taatgcttaa tcttgtcttg cttaaaaag taatatgtac         60 ggtcgcctga cgcatatacc         80

<210> SEQ ID NO 231
<211> LENGTH: 119
<212> TYPE: DNA
<213> ORGANISM: Artificial Sequence
<220> FEATURE:
<223> OTHER INFORMATION: Primer 2665

<400> SEQUENCE: 231
cgcatgtttc ggcgttcgaa acttctccgc agtgaaagat aaatgatcgc acctgggttt         60
ctccaataac ggtcatagtt cccctgagat tatcgctgtg gtataatgaa agttatacc         119

<210> SEQ ID NO 232
<211> LENGTH: 119
<212> TYPE: DNA
<213> ORGANISM: Artificial Sequence
<220> FEATURE:
<223> OTHER INFORMATION: Primer 2666

<400> SEQUENCE: 232
ggtataactt tcattatacc acagcgataa tctcagggga actatgaccg ttattggaga         60
aacccaggtg cgatcattta tctttcactg cggagaagtt tcgaacgccg aaacatgcg         119

<210> SEQ ID NO 233
<211> LENGTH: 43
<212> TYPE: DNA
<213> ORGANISM: Artificial Sequence
<220> FEATURE:
<223> OTHER INFORMATION: Primer 2745

<400> SEQUENCE: 233
ggggactaaa attttttaat ataaatatat aaattaaaaa tag         43

<210> SEQ ID NO 234
<211> LENGTH: 23
<212> TYPE: DNA
<213> ORGANISM: Artificial Sequence
<220> FEATURE:

```
<223> OTHER INFORMATION: non-targeting spacer sequence

<400> SEQUENCE: 234
ttatgttttc cggacatagt aca                                          23

<210> SEQ ID NO 235
<211> LENGTH: 23
<212> TYPE: DNA
<213> ORGANISM: Artificial Sequence
<220> FEATURE:
<223> OTHER INFORMATION: targeting spacer

<400> SEQUENCE: 235
ataagggcaa atgcatagct ggc                                          23

<210> SEQ ID NO 236
<211> LENGTH: 23
<212> TYPE: DNA
<213> ORGANISM: Artificial Sequence
<220> FEATURE:
<223> OTHER INFORMATION: targeting spacer

<400> SEQUENCE: 236
cggggatatg aaccggatga ctt                                          23

<210> SEQ ID NO 237
<211> LENGTH: 23
<212> TYPE: DNA
<213> ORGANISM: Artificial Sequence
<220> FEATURE:
<223> OTHER INFORMATION: targeting spacer

<400> SEQUENCE: 237
ccatacccgc tttttccgcc agc                                          23

<210> SEQ ID NO 238
<211> LENGTH: 21
<212> TYPE: DNA
<213> ORGANISM: Artificial Sequence
<220> FEATURE:
<223> OTHER INFORMATION: nuclear localization signal coding sequence

<400> SEQUENCE: 238
cccaagaaga agaggaaggt g                                            21

<210> SEQ ID NO 239
<211> LENGTH: 23
<212> TYPE: DNA
<213> ORGANISM: Artificial Sequence
<220> FEATURE:
<223> OTHER INFORMATION: targeting spacer

<400> SEQUENCE: 239
gcacctgggt ttctccaata acg                                          23

<210> SEQ ID NO 240
<211> LENGTH: 325
<212> TYPE: DNA
<213> ORGANISM: Artificial Sequence
<220> FEATURE:
<223> OTHER INFORMATION: Chemically Synthesized, tracrRNA t12

<400> SEQUENCE: 240
attgttttcc cctcccatgc acaatagttt tatagtaaaa aagaccttga cgttttccgc   60
caaggtcttc gttcgcctaa gagtggggaa tgcccgaaga aagcgggcga taggcgatcc  120
```

```
ccaacgccac gggtcagtct gcctataggc agaaagccct tatcatagta accctgagat    180
cattgctgtg gtataaccct attactataa taatgtttat atttgggaaa atcaagtcct    240
ttttctatat ttttatact  ttcatttctt cttgcattat gatgatgtga gggaggatag    300
atttctgaca ggaggtttca catcg                                         325
```

<210> SEQ ID NO 241
<211> LENGTH: 36
<212> TYPE: DNA
<213> ORGANISM: Artificial Sequence
<220> FEATURE:
<223> OTHER INFORMATION: Chemically synthesized, repeat gb

<400> SEQUENCE: 241

```
gtcatagttc ccctgagatt atcgctgtgg tataat                              36
```

<210> SEQ ID NO 242
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 242

```
uuggcggugc gaauucuaac cgucccggaa                                     30
```

<210> SEQ ID NO 243
<211> LENGTH: 46
<212> TYPE: DNA
<213> ORGANISM: Geobacillus virus E2

<400> SEQUENCE: 243

```
tgtggtgctt ccgggacggt tagaattcgc accgccaaca tgcgat                   46
```

<210> SEQ ID NO 244
<211> LENGTH: 46
<212> TYPE: DNA
<213> ORGANISM: Geobacillus virus E2

<400> SEQUENCE: 244

```
atcgcatgtt ggcggtgcga attctaaccg tcccggaagc accaca                   46
```

<210> SEQ ID NO 245
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 245

```
uucuaccucu acucucgauu cacgaaucgg                                     30
```

<210> SEQ ID NO 246
<211> LENGTH: 46
<212> TYPE: DNA
<213> ORGANISM: Bacillus alveayuensis strain 24KAM51 LG50_053

<400> SEQUENCE: 246

```
ttggaaaacc gattcgtgaa tcgagagtag aggtagaaag agcagc                   46
```

<210> SEQ ID NO 247
<211> LENGTH: 46
<212> TYPE: DNA

<213> ORGANISM: Bacillus alveayuensis strain 24KAM51 LG50_053

<400> SEQUENCE: 247
gctgctcttt ctacctctac tctcgattca cgaatcggtt ttccaa        46

<210> SEQ ID NO 248
<211> LENGTH: 29
<212> TYPE: RNA
<213> ORGANISM: Artificial Sequence
<220> FEATURE:
<223> OTHER INFORMATION: Chemically synthesized, Crispr RNA

<400> SEQUENCE: 248
ucacggagcu uuacacaaau aaagccgga        29

<210> SEQ ID NO 249
<211> LENGTH: 45
<212> TYPE: DNA
<213> ORGANISM: Anoxybacillus flavithermus WK1

<400> SEQUENCE: 249
ttcgtcgctc cggctttatt tgtgtaaagc tccgtgatct tgtag        45

<210> SEQ ID NO 250
<211> LENGTH: 45
<212> TYPE: DNA
<213> ORGANISM: Anoxybacillus flavithermus WK1

<400> SEQUENCE: 250
ctacaagatc acggagcttt acacaaataa agccggagcg acgaa        45

<210> SEQ ID NO 251
<211> LENGTH: 29
<212> TYPE: RNA
<213> ORGANISM: Artificial Sequence
<220> FEATURE:
<223> OTHER INFORMATION: Chemically synthesized, Crispr RNA

<400> SEQUENCE: 251
ucacggagcu uuacacaaau aaagccgga        29

<210> SEQ ID NO 252
<211> LENGTH: 45
<212> TYPE: DNA
<213> ORGANISM: Geobacillus kaustophilus strain Et23 LG51_086

<400> SEQUENCE: 252
ttcgttgctc cggctttatt tgtgtaaagc tccgtgatct tgtac        45

<210> SEQ ID NO 253
<211> LENGTH: 45
<212> TYPE: DNA
<213> ORGANISM: Geobacillus kaustophilus strain Et23 LG51_086

<400> SEQUENCE: 253
gtacaagatc acggagcttt acacaaataa agccggagca acgaa        45

<210> SEQ ID NO 254
<211> LENGTH: 30
<212> TYPE: RNA
<213> ORGANISM: Artificial Sequence
<220> FEATURE:
<223> OTHER INFORMATION: Chemically synthesized, Crispr RNA -continued

<400> SEQUENCE: 254
caacaccuuc cgcgcugucu cgucuacuuu                              30

<210> SEQ ID NO 255
<211> LENGTH: 46
<212> TYPE: DNA
<213> ORGANISM: Geobacillus virus E2

<400> SEQUENCE: 255
ttcgtaaaaa agtagatgag acagcacgga aggtgttgaa agaagc            46

<210> SEQ ID NO 256
<211> LENGTH: 46
<212> TYPE: DNA
<213> ORGANISM: Geobacillus virus E2

<400> SEQUENCE: 256
gcttctttca acaccttccg tgctgtctca tctactttt tacgaa             46

<210> SEQ ID NO 257
<211> LENGTH: 30
<212> TYPE: RNA
<213> ORGANISM: Artificial Sequence
<220> FEATURE:
<223> OTHER INFORMATION: Chemically synthesized, Crispr RNA

<400> SEQUENCE: 257
uugauuagca auuugacuug ggaauuuagc                              30

<210> SEQ ID NO 258
<211> LENGTH: 46
<212> TYPE: DNA
<213> ORGANISM: Pasteurella bettyae

<400> SEQUENCE: 258
ttggcattac taaattccgc agtcaaattg ctaatcaaat gttaat            46

<210> SEQ ID NO 259
<211> LENGTH: 46
<212> TYPE: DNA
<213> ORGANISM: Pasteurella bettyae

<400> SEQUENCE: 259
attaacattt gattagcaat ttgactgcgg aatttagtaa tgccaa            46

<210> SEQ ID NO 260
<211> LENGTH: 37
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (31)..(37)
<223> OTHER INFORMATION: any nucleotide

<400> SEQUENCE: 260
ggtcatgaga ttatcaaaaa ggatcttcac nnnnnnn                      37

<210> SEQ ID NO 261
<211> LENGTH: 37
<212> TYPE: DNA
<213> ORGANISM: Artificial Sequence
<220> FEATURE:

```
<223> OTHER INFORMATION: Chemically Synthesized
<220> FEATURE:
<221> NAME/KEY: misc_feature
<222> LOCATION: (1)..(7)
<223> OTHER INFORMATION: any nucleotide

<400> SEQUENCE: 261
nnnnnnngtg aagatccttt ttgataatct catgacc                         37

<210> SEQ ID NO 262
<211> LENGTH: 30
<212> TYPE: RNA
<213> ORGANISM: Artificial Sequence
<220> FEATURE:
<223> OTHER INFORMATION: Chemically Synthesized

<400> SEQUENCE: 262
ggucaugaga uuaucaaaaa ggaucuucac                                 30

<210> SEQ ID NO 263
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 263
ggtcatgaga ttatcaaaaa ggatctt                                    27

<210> SEQ ID NO 264
<211> LENGTH: 27
<212> TYPE: DNA
<213> ORGANISM: Artificial Sequence
<220> FEATURE:
<223> OTHER INFORMATION: Chemically Synthesized

<400> SEQUENCE: 264
aagatccttt tgataatct catgacc                                     27

<210> SEQ ID NO 265
<211> LENGTH: 10
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (4)..(10)
<223> OTHER INFORMATION: any nucleotide

<400> SEQUENCE: 265 cacnnnnnnn                                                       10

<210> SEQ ID NO 266
<211> LENGTH: 10
<212> TYPE: DNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(7)
<223> OTHER INFORMATION: any nucleotide

<400> SEQUENCE: 266 nnnnnnngtg                                                       10
```

```
<210> SEQ ID NO 267
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 267
tatgcctcat gagattatca aaaggatct tcaccccccc aa                              42

<210> SEQ ID NO 268
<211> LENGTH: 42
<212> TYPE: DNA
<213> ORGANISM: Artificial Sequence
<220> FEATURE:
<223> OTHER INFORMATION: Chemically Synthesized

<400> SEQUENCE: 268
ttgggggggt gaagatcctt tttgataatc tcatgaggca ta                            42

<210> SEQ ID NO 269
<211> LENGTH: 193
<212> TYPE: RNA
<213> ORGANISM: Artificial Sequence
<220> FEATURE:
<223> OTHER INFORMATION: Chemically Synthesized

<400> SEQUENCE: 269
ugagauuauc aaaaggauc uucacgucau aguuccccug agauuaucgc uguggauaa           60 ugaaaguuau accacagcaa ugaucucagg guuacuauga uaagggcuuu cugccuauag        120
gcagacugac ccguggcguu ggggaucgcc uaucgcccgc uuucuucggg cauucccac         180 ucuuaggcgu uuu                                                           193

<210> SEQ ID NO 270
<211> LENGTH: 28
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(24)
<223> OTHER INFORMATION: any nucleotide
<220> FEATURE:
<221> NAME/KEY: misc_feature
<222> LOCATION: (26)..(26)
<223> OTHER INFORMATION: any nucleotide

<400> SEQUENCE: 270
nnnnnnnnnn nnnnnnnnnn nnnncnaa                                            28

<210> SEQ ID NO 271
<211> LENGTH: 20
<212> TYPE: DNA
<213> ORGANISM: Artificial Sequence
<220> FEATURE:
<223> OTHER INFORMATION: Chemically synthesized
<220> FEATURE:
<221> NAME/KEY: misc_feature
<222> LOCATION: (1)..(20)
<223> OTHER INFORMATION: any nucleotide

<400> SEQUENCE: 271
nnnnnnnnnn nnnnnnnnnn                                                     20

<210> SEQ ID NO 272
```

<211> LENGTH: 184
<212> TYPE: RNA
<213> ORGANISM: Artificial Sequence
<220> FEATURE:
<223> OTHER INFORMATION: Chemically Synthesized
<220> FEATURE:
<221> NAME/KEY: misc_feature
<222> LOCATION: (1)..(20)
<223> OTHER INFORMATION: any nucleotide

<400> SEQUENCE: 272

```
nnnnnnnnnn nnnnnnnnnn gucauaguuc cccugagauu aucgcugugg uauaaugaaa    60
guuauaccac agcaaugauc ucaggguuac uaugauaagg gcuuucugcc uauaggcaga   120
cugacccgug gcguugggga ucgccuaucg cccgcuuucu ucgggcauuc cccacucuua   180
ggcg                                                                184
```

<210> SEQ ID NO 273
<211> LENGTH: 1368
<212> TYPE: PRT
<213> ORGANISM: Streptococcus pyogenes

<400> SEQUENCE: 273

```
Met Asp Lys Lys Tyr Ser Ile Gly Leu Asp Ile Gly Thr Asn Ser Val
 1               5                  10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
    50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp
    130                 135                 140

Ser Thr Asp Lys Ala Asp Leu Arg Leu Ile Tyr Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270
```

```
Asp Asp Leu Asp Asn Leu Leu Ala Gln Ile Gly Asp Gln Tyr Ala Asp
            275                 280                 285

Leu Phe Leu Ala Ala Lys Asn Leu Ser Asp Ala Ile Leu Leu Ser Asp
        290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685
```

```
Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
            725                 730                 735

Ile Leu Gln Thr Val Lys Val Val Asp Glu Leu Val Lys Val Met Gly
                740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
            805                 810                 815

Gln Asn Gly Arg Asp Met Tyr Val Asp Gln Glu Leu Asp Ile Asn Arg
                820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
            885                 890                 895

Phe Asp Asn Leu Thr Lys Ala Glu Arg Gly Gly Leu Ser Glu Leu Asp
                900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
            965                 970                 975

Glu Ile Asn Asn Tyr His His Ala His Asp Ala Tyr Leu Asn Ala Val
                980                 985                 990

Val Gly Thr Ala Leu Ile Lys Lys Tyr Pro Lys Leu Glu Ser Glu Phe
        995                 1000                1005

Val Tyr Gly Asp Tyr Lys Val Tyr Asp Val Arg Lys Met Ile Ala
     1010                1015                1020

Lys Ser Glu Gln Glu Ile Gly Lys Ala Thr Ala Lys Tyr Phe Phe
     1025                1030                1035

Tyr Ser Asn Ile Met Asn Phe Phe Lys Thr Glu Ile Thr Leu Ala
     1040                1045                1050

Asn Gly Glu Ile Arg Lys Arg Pro Leu Ile Glu Thr Asn Gly Glu
     1055                1060                1065

Thr Gly Glu Ile Val Trp Asp Lys Gly Arg Asp Phe Ala Thr Val
     1070                1075                1080

Arg Lys Val Leu Ser Met Pro Gln Val Asn Ile Val Lys Lys Thr
     1085                1090                1095
```

-continued

```
Glu Val Gln Thr Gly Gly Phe Ser Lys Glu Ser Ile Leu Pro Lys
    1100                1105                1110

Arg Asn Ser Asp Lys Leu Ile Ala Arg Lys Lys Asp Trp Asp Pro
    1115                1120                1125

Lys Lys Tyr Gly Gly Phe Asp Ser Pro Thr Val Ala Tyr Ser Val
    1130                1135                1140

Leu Val Val Ala Lys Val Glu Lys Gly Lys Ser Lys Lys Leu Lys
    1145                1150                1155

Ser Val Lys Glu Leu Leu Gly Ile Thr Ile Met Glu Arg Ser Ser
    1160                1165                1170

Phe Glu Lys Asn Pro Ile Asp Phe Leu Glu Ala Lys Gly Tyr Lys
    1175                1180                1185

Glu Val Lys Lys Asp Leu Ile Ile Lys Leu Pro Lys Tyr Ser Leu
    1190                1195                1200

Phe Glu Leu Glu Asn Gly Arg Lys Arg Met Leu Ala Ser Ala Gly
    1205                1210                1215

Glu Leu Gln Lys Gly Asn Glu Leu Ala Leu Pro Ser Lys Tyr Val
    1220                1225                1230

Asn Phe Leu Tyr Leu Ala Ser His Tyr Glu Lys Leu Lys Gly Ser
    1235                1240                1245

Pro Glu Asp Asn Glu Gln Lys Gln Leu Phe Val Glu Gln His Lys
    1250                1255                1260

His Tyr Leu Asp Glu Ile Ile Glu Gln Ile Ser Glu Phe Ser Lys
    1265                1270                1275

Arg Val Ile Leu Ala Asp Ala Asn Leu Asp Lys Val Leu Ser Ala
    1280                1285                1290

Tyr Asn Lys His Arg Asp Lys Pro Ile Arg Glu Gln Ala Glu Asn
    1295                1300                1305

Ile Ile His Leu Phe Thr Leu Thr Asn Leu Gly Ala Pro Ala Ala
    1310                1315                1320

Phe Lys Tyr Phe Asp Thr Thr Ile Asp Arg Lys Arg Tyr Thr Ser
    1325                1330                1335

Thr Lys Glu Val Leu Asp Ala Thr Leu Ile His Gln Ser Ile Thr
    1340                1345                1350

Gly Leu Tyr Glu Thr Arg Ile Asp Leu Ser Gln Leu Gly Gly Asp
    1355                1360                1365
```

<210> SEQ ID NO 274
<211> LENGTH: 1388
<212> TYPE: PRT
<213> ORGANISM: Streptococcus thermophilus

<400> SEQUENCE: 274

```
Met Thr Lys Pro Tyr Ser Ile Gly Leu Asp Ile Gly Thr Asn Ser Val
1               5                   10                  15

Gly Trp Ala Val Thr Thr Asp Asn Tyr Lys Val Pro Ser Lys Lys Met
            20                  25                  30

Lys Val Leu Gly Asn Thr Ser Lys Lys Tyr Ile Lys Lys Asn Leu Leu
        35                  40                  45

Gly Val Leu Leu Phe Asp Ser Gly Ile Thr Ala Glu Gly Arg Arg Leu
    50                  55                  60

Lys Arg Thr Ala Arg Arg Arg Tyr Thr Arg Arg Arg Asn Arg Ile Leu
65                  70                  75                  80

Tyr Leu Gln Glu Ile Phe Ser Thr Glu Met Ala Thr Leu Asp Asp Ala
                85                  90                  95
```

```
Phe Phe Gln Arg Leu Asp Asp Ser Phe Leu Val Pro Asp Asp Lys Arg
                100                 105                 110

Asp Ser Lys Tyr Pro Ile Phe Gly Asn Leu Val Glu Glu Lys Ala Tyr
            115                 120                 125

His Asp Glu Phe Pro Thr Ile Tyr His Leu Arg Lys Tyr Leu Ala Asp
        130                 135                 140

Ser Thr Lys Lys Ala Asp Leu Arg Leu Val Tyr Leu Ala Leu Ala His
145                 150                 155                 160

Met Ile Lys Tyr Arg Gly His Phe Leu Ile Glu Gly Glu Phe Asn Ser
                165                 170                 175

Lys Asn Asn Asp Ile Gln Lys Asn Phe Gln Asp Phe Leu Asp Thr Tyr
            180                 185                 190

Asn Ala Ile Phe Glu Ser Asp Leu Ser Leu Glu Asn Ser Lys Gln Leu
        195                 200                 205

Glu Glu Ile Val Lys Asp Lys Ile Ser Lys Leu Glu Lys Lys Asp Arg
    210                 215                 220

Ile Leu Lys Leu Phe Pro Gly Glu Lys Asn Ser Gly Ile Phe Ser Glu
225                 230                 235                 240

Phe Leu Lys Leu Ile Val Gly Asn Gln Ala Asp Phe Arg Lys Cys Phe
                245                 250                 255

Asn Leu Asp Glu Lys Ala Ser Leu His Phe Ser Lys Glu Ser Tyr Asp
            260                 265                 270

Glu Asp Leu Glu Thr Leu Leu Gly Tyr Ile Gly Asp Asp Tyr Ser Asp
        275                 280                 285

Val Phe Leu Lys Ala Lys Lys Leu Tyr Asp Ala Ile Leu Leu Ser Gly
    290                 295                 300

Phe Leu Thr Val Thr Asp Asn Glu Thr Glu Ala Pro Leu Ser Ser Ala
305                 310                 315                 320

Met Ile Lys Arg Tyr Asn Glu His Lys Glu Asp Leu Ala Leu Leu Lys
                325                 330                 335

Glu Tyr Ile Arg Asn Ile Ser Leu Lys Thr Tyr Asn Glu Val Phe Lys
            340                 345                 350

Asp Asp Thr Lys Asn Gly Tyr Ala Gly Tyr Ile Asp Gly Lys Thr Asn
        355                 360                 365

Gln Glu Asp Phe Tyr Val Tyr Leu Lys Lys Leu Leu Ala Glu Phe Glu
    370                 375                 380

Gly Ala Asp Tyr Phe Leu Glu Lys Ile Asp Arg Glu Asp Phe Leu Arg
385                 390                 395                 400

Lys Gln Arg Thr Phe Asp Asn Gly Ser Ile Pro Tyr Gln Ile His Leu
                405                 410                 415

Gln Glu Met Arg Ala Ile Leu Asp Lys Gln Ala Lys Phe Tyr Pro Phe
            420                 425                 430

Leu Ala Lys Asn Lys Glu Arg Ile Glu Lys Ile Leu Thr Phe Arg Ile
        435                 440                 445

Pro Tyr Tyr Val Gly Pro Leu Ala Arg Gly Asn Ser Asp Phe Ala Trp
    450                 455                 460

Ser Ile Arg Lys Arg Asn Glu Lys Ile Thr Pro Trp Asn Phe Glu Asp
465                 470                 475                 480

Val Ile Asp Lys Glu Ser Ser Ala Glu Ala Phe Ile Asn Arg Met Thr
                485                 490                 495

Ser Phe Asp Leu Tyr Leu Pro Glu Glu Lys Val Leu Pro Lys His Ser
            500                 505                 510
```

```
Leu Leu Tyr Glu Thr Phe Asn Val Tyr Asn Glu Leu Thr Lys Val Arg
        515                 520                 525
Phe Ile Ala Glu Ser Met Arg Asp Tyr Gln Phe Leu Asp Ser Lys Gln
    530                 535                 540
Lys Lys Asp Ile Val Arg Leu Tyr Phe Lys Asp Lys Arg Lys Val Thr
545                 550                 555                 560
Asp Lys Asp Ile Ile Glu Tyr Leu His Ala Ile Tyr Gly Tyr Asp Gly
                565                 570                 575
Ile Glu Leu Lys Gly Ile Glu Lys Gln Phe Asn Ser Ser Leu Ser Thr
            580                 585                 590
Tyr His Asp Leu Leu Asn Ile Ile Asn Asp Lys Glu Phe Leu Asp Asp
        595                 600                 605
Ser Ser Asn Glu Ala Ile Ile Glu Glu Ile Ile His Thr Leu Thr Ile
    610                 615                 620
Phe Glu Asp Arg Glu Met Ile Lys Gln Arg Leu Ser Lys Phe Glu Asn
625                 630                 635                 640
Ile Phe Asp Lys Ser Val Leu Lys Lys Leu Ser Arg Arg His Tyr Thr
                645                 650                 655
Gly Trp Gly Lys Leu Ser Ala Lys Leu Ile Asn Gly Ile Arg Asp Glu
            660                 665                 670
Lys Ser Gly Asn Thr Ile Leu Asp Tyr Leu Ile Asp Asp Gly Ile Ser
        675                 680                 685
Asn Arg Asn Phe Met Gln Leu Ile His Asp Asp Ala Leu Ser Phe Lys
    690                 695                 700
Lys Lys Ile Gln Lys Ala Gln Ile Ile Gly Asp Glu Asp Lys Gly Asn
705                 710                 715                 720
Ile Lys Glu Val Val Lys Ser Leu Pro Gly Ser Pro Ala Ile Lys Lys
                725                 730                 735
Gly Ile Leu Gln Ser Ile Lys Ile Val Asp Glu Leu Val Lys Val Met
            740                 745                 750
Gly Gly Arg Lys Pro Glu Ser Ile Val Val Glu Met Ala Arg Glu Asn
        755                 760                 765
Gln Tyr Thr Asn Gln Gly Lys Ser Asn Ser Gln Arg Leu Lys Arg
    770                 775                 780
Leu Glu Lys Ser Leu Lys Glu Leu Gly Ser Lys Ile Leu Lys Glu Asn
785                 790                 795                 800
Ile Pro Ala Lys Leu Ser Lys Ile Asp Asn Asn Ala Leu Gln Asn Asp
                805                 810                 815
Arg Leu Tyr Leu Tyr Tyr Leu Gln Asn Gly Lys Asp Met Tyr Thr Gly
            820                 825                 830
Asp Asp Leu Asp Ile Asp Arg Leu Ser Asn Tyr Asp Ile Asp His Ile
        835                 840                 845
Ile Pro Gln Ala Phe Leu Lys Asp Asn Ser Ile Asp Asn Lys Val Leu
    850                 855                 860
Val Ser Ser Ala Ser Asn Arg Gly Lys Ser Asp Asp Val Pro Ser Leu
865                 870                 875                 880
Glu Val Val Lys Lys Arg Lys Thr Phe Trp Tyr Gln Leu Leu Lys Ser
                885                 890                 895
Lys Leu Ile Ser Gln Arg Lys Phe Asp Asn Leu Thr Lys Ala Glu Arg
            900                 905                 910
Gly Gly Leu Ser Pro Glu Asp Lys Ala Gly Phe Ile Gln Arg Gln Leu
        915                 920                 925
```

```
Val Glu Thr Arg Gln Ile Thr Lys His Val Ala Arg Leu Leu Asp Glu
    930                 935                 940

Lys Phe Asn Asn Lys Lys Asp Glu Asn Asn Arg Ala Val Arg Thr Val
945                 950                 955                 960

Lys Ile Ile Thr Leu Lys Ser Thr Leu Val Ser Gln Phe Arg Lys Asp
                965                 970                 975

Phe Glu Leu Tyr Lys Val Arg Glu Ile Asn Asp Phe His His Ala His
            980                 985                 990

Asp Ala Tyr Leu Asn Ala Val Val Ala Ser Ala Leu Leu Lys Lys Tyr
        995                 1000                1005

Pro Lys Leu Glu Pro Glu Phe Val Tyr Gly Asp Tyr Pro Lys Tyr
    1010                1015                1020

Asn Ser Phe Arg Glu Arg Lys Ser Ala Thr Glu Lys Val Tyr Phe
    1025                1030                1035

Tyr Ser Asn Ile Met Asn Ile Phe Lys Lys Ser Ile Ser Leu Ala
    1040                1045                1050

Asp Gly Arg Val Ile Glu Arg Pro Leu Ile Glu Val Asn Glu Glu
    1055                1060                1065

Thr Gly Glu Ser Val Trp Asn Lys Glu Ser Asp Leu Ala Thr Val
    1070                1075                1080

Arg Arg Val Leu Ser Tyr Pro Gln Val Asn Val Val Lys Lys Val
    1085                1090                1095

Glu Glu Gln Asn His Gly Leu Asp Arg Gly Lys Pro Lys Gly Leu
    1100                1105                1110

Phe Asn Ala Asn Leu Ser Ser Lys Pro Lys Pro Asn Ser Asn Glu
    1115                1120                1125

Asn Leu Val Gly Ala Lys Glu Tyr Leu Asp Pro Lys Lys Tyr Gly
    1130                1135                1140

Gly Tyr Ala Gly Ile Ser Asn Ser Phe Thr Val Leu Val Lys Gly
    1145                1150                1155

Thr Ile Glu Lys Gly Ala Lys Lys Lys Ile Thr Asn Val Leu Glu
    1160                1165                1170

Phe Gln Gly Ile Ser Ile Leu Asp Arg Ile Asn Tyr Arg Lys Asp
    1175                1180                1185

Lys Leu Asn Phe Leu Leu Glu Lys Gly Tyr Lys Asp Ile Glu Leu
    1190                1195                1200

Ile Ile Glu Leu Pro Lys Tyr Ser Leu Phe Glu Leu Ser Asp Gly
    1205                1210                1215

Ser Arg Arg Met Leu Ala Ser Ile Leu Ser Thr Asn Asn Lys Arg
    1220                1225                1230

Gly Glu Ile His Lys Gly Asn Gln Ile Phe Leu Ser Gln Lys Phe
    1235                1240                1245

Val Lys Leu Leu Tyr His Ala Lys Arg Ile Ser Asn Thr Ile Asn
    1250                1255                1260

Glu Asn His Arg Lys Tyr Val Glu Asn His Lys Lys Glu Phe Glu
    1265                1270                1275

Glu Leu Phe Tyr Tyr Ile Leu Glu Phe Asn Glu Asn Tyr Val Gly
    1280                1285                1290

Ala Lys Lys Asn Gly Lys Leu Leu Asn Ser Ala Phe Gln Ser Trp
    1295                1300                1305

Gln Asn His Ser Ile Asp Glu Leu Cys Ser Ser Phe Ile Gly Pro
    1310                1315                1320
```

Thr Gly Ser Glu Arg Lys Gly Leu Phe Glu Leu Thr Ser Arg Gly
    1325                1330                1335

Ser Ala Ala Asp Phe Glu Phe Leu Gly Val Lys Ile Pro Arg Tyr
    1340                1345                1350

Arg Asp Tyr Thr Pro Ser Ser Leu Leu Lys Asp Ala Thr Leu Ile
    1355                1360                1365

His Gln Ser Val Thr Gly Leu Tyr Glu Thr Arg Ile Asp Leu Ala
    1370                1375                1380

Lys Leu Gly Glu Gly
    1385

<210> SEQ ID NO 275
<211> LENGTH: 1059
<212> TYPE: PRT
<213> ORGANISM: Wolinella succinogenes

<400> SEQUENCE: 275

Met Ile Glu Arg Ile Leu Gly Val Asp Leu Gly Ile Ser Ser Leu Gly
1               5                   10                  15

Trp Ala Ile Val Glu Tyr Asp Lys Asp Asp Glu Ala Ala Asn Arg Ile
            20                  25                  30

Ile Asp Cys Gly Val Arg Leu Phe Thr Ala Ala Glu Thr Pro Lys Lys
        35                  40                  45

Lys Glu Ser Pro Asn Lys Ala Arg Arg Glu Ala Arg Gly Ile Arg Arg
    50                  55                  60

Val Leu Asn Arg Arg Val Arg Met Asn Met Ile Lys Lys Leu Phe
65                  70                  75                  80

Leu Arg Ala Gly Leu Ile Gln Asp Val Asp Leu Asp Gly Glu Gly Gly
                85                  90                  95

Met Phe Tyr Ser Lys Ala Asn Arg Ala Asp Val Trp Glu Leu Arg His
            100                 105                 110

Asp Gly Leu Tyr Arg Leu Leu Lys Gly Asp Glu Leu Ala Arg Val Leu
        115                 120                 125

Ile His Ile Ala Lys His Arg Gly Tyr Lys Phe Ile Gly Asp Asp Glu
    130                 135                 140

Ala Asp Glu Glu Ser Gly Lys Val Lys Lys Ala Gly Val Val Leu Arg
145                 150                 155                 160

Gln Asn Phe Glu Ala Ala Gly Cys Arg Thr Val Gly Glu Trp Leu Trp
                165                 170                 175

Arg Glu Arg Gly Ala Asn Gly Lys Lys Arg Asn Lys His Gly Asp Tyr
            180                 185                 190

Glu Ile Ser Ile His Arg Asp Leu Leu Val Glu Glu Val Glu Ala Ile
        195                 200                 205

Phe Val Ala Gln Gln Glu Met Arg Ser Thr Ile Ala Thr Asp Ala Leu
    210                 215                 220

Lys Ala Ala Tyr Arg Glu Ile Ala Phe Phe Val Arg Pro Met Gln Arg
225                 230                 235                 240

Ile Glu Lys Met Val Gly His Cys Thr Tyr Phe Pro Glu Glu Arg Arg
                245                 250                 255

Ala Pro Lys Ser Ala Pro Thr Ala Glu Lys Phe Ile Ala Ile Ser Lys
            260                 265                 270

Phe Phe Ser Thr Val Ile Ile Asp Asn Glu Gly Trp Glu Gln Lys Ile
        275                 280                 285

Ile Glu Arg Lys Thr Leu Glu Glu Leu Leu Asp Phe Ala Val Ser Arg
    290                 295                 300

Glu Lys Val Glu Phe Arg His Leu Arg Lys Phe Leu Asp Leu Ser Asp
305                 310                 315                 320

Asn Glu Ile Phe Lys Gly Leu His Tyr Lys Gly Lys Pro Lys Thr Ala
                325                 330                 335

Lys Lys Arg Glu Ala Thr Leu Phe Asp Pro Asn Glu Pro Thr Glu Leu
            340                 345                 350

Glu Phe Asp Lys Val Glu Ala Glu Lys Lys Ala Trp Ile Ser Leu Arg
        355                 360                 365

Gly Ala Ala Lys Leu Arg Glu Ala Leu Gly Asn Glu Phe Tyr Gly Arg
    370                 375                 380

Phe Val Ala Leu Gly Lys His Ala Asp Glu Ala Thr Lys Ile Leu Thr
385                 390                 395                 400

Tyr Tyr Lys Asp Glu Gly Gln Lys Arg Arg Glu Leu Thr Lys Leu Pro
                405                 410                 415

Leu Glu Ala Glu Met Val Glu Arg Leu Val Lys Ile Gly Phe Ser Asp
            420                 425                 430

Phe Leu Lys Leu Ser Leu Lys Ala Ile Arg Asp Ile Leu Pro Ala Met
        435                 440                 445

Glu Ser Gly Ala Arg Tyr Asp Glu Ala Val Leu Met Leu Gly Val Pro
    450                 455                 460

His Lys Glu Lys Ser Ala Ile Leu Pro Pro Leu Asn Lys Thr Asp Ile
465                 470                 475                 480

Asp Ile Leu Asn Pro Thr Val Ile Arg Ala Phe Ala Gln Phe Arg Lys
                485                 490                 495

Val Ala Asn Ala Leu Val Arg Lys Tyr Gly Ala Phe Asp Arg Val His
            500                 505                 510

Phe Glu Leu Ala Arg Glu Ile Asn Thr Lys Gly Glu Ile Glu Asp Ile
        515                 520                 525

Lys Glu Ser Gln Arg Lys Asn Glu Lys Glu Arg Lys Glu Ala Ala Asp
    530                 535                 540

Trp Ile Ala Glu Thr Ser Phe Gln Val Pro Leu Thr Arg Lys Asn Ile
545                 550                 555                 560

Leu Lys Lys Arg Leu Tyr Ile Gln Gln Asp Gly Arg Cys Ala Tyr Thr
                565                 570                 575

Gly Asp Val Ile Glu Leu Glu Arg Leu Phe Asp Glu Gly Tyr Cys Glu
            580                 585                 590

Ile Asp His Ile Leu Pro Arg Ser Arg Ser Ala Asp Asp Ser Phe Ala
        595                 600                 605

Asn Lys Val Leu Cys Leu Ala Arg Ala Asn Gln Gln Lys Thr Asp Arg
    610                 615                 620

Thr Pro Tyr Glu Trp Phe Gly His Asp Ala Ala Arg Trp Asn Ala Phe
625                 630                 635                 640

Glu Thr Arg Thr Ser Ala Pro Ser Asn Arg Val Arg Thr Gly Lys Gly
                645                 650                 655

Lys Ile Asp Arg Leu Leu Lys Lys Asn Phe Asp Glu Asn Ser Glu Met
            660                 665                 670

Ala Phe Lys Asp Arg Asn Leu Asn Asp Thr Arg Tyr Met Ala Arg Ala
        675                 680                 685

Ile Lys Thr Tyr Cys Glu Gln Tyr Trp Val Phe Lys Asn Ser His Thr
    690                 695                 700

Lys Ala Pro Val Gln Val Arg Ser Gly Lys Leu Thr Ser Val Leu Arg
705                 710                 715                 720

-continued

Tyr Gln Trp Gly Leu Glu Ser Lys Asp Arg Glu Ser His Thr His His
                    725                 730                 735

Ala Val Asp Ala Ile Ile Ile Ala Phe Ser Thr Gln Gly Met Val Gln
            740                 745                 750

Lys Leu Ser Glu Tyr Tyr Arg Phe Lys Glu Thr His Arg Glu Lys Glu
        755                 760                 765

Arg Pro Lys Leu Ala Val Pro Leu Ala Asn Phe Arg Asp Ala Val Glu
    770                 775                 780

Glu Ala Thr Arg Ile Glu Asn Thr Glu Thr Val Lys Glu Gly Val Glu
785                 790                 795                 800

Val Lys Arg Leu Leu Ile Ser Arg Pro Pro Arg Ala Arg Val Thr Gly
                805                 810                 815

Gln Ala His Glu Gln Thr Ala Lys Pro Tyr Pro Arg Ile Lys Gln Val
            820                 825                 830

Lys Asn Lys Lys Lys Trp Arg Leu Ala Pro Ile Asp Glu Glu Lys Phe
        835                 840                 845

Glu Ser Phe Lys Ala Asp Arg Val Ala Ser Ala Asn Gln Lys Asn Phe
    850                 855                 860

Tyr Glu Thr Ser Thr Ile Pro Arg Val Asp Val Tyr His Lys Lys Gly
865                 870                 875                 880

Lys Phe His Leu Val Pro Ile Tyr Leu His Glu Met Val Leu Asn Glu
                885                 890                 895

Leu Pro Asn Leu Ser Leu Gly Thr Asn Pro Glu Ala Met Asp Glu Asn
            900                 905                 910

Phe Phe Lys Phe Ser Ile Phe Lys Asp Asp Leu Ile Ser Ile Gln Thr
        915                 920                 925

Gln Gly Thr Pro Lys Lys Pro Ala Lys Ile Ile Met Gly Tyr Phe Lys
    930                 935                 940

Asn Met His Gly Ala Asn Met Val Leu Ser Ser Ile Asn Asn Ser Pro
945                 950                 955                 960

Cys Glu Gly Phe Thr Cys Thr Pro Val Ser Met Asp Lys Lys His Lys
                965                 970                 975

Asp Lys Cys Lys Leu Cys Pro Glu Glu Asn Arg Ile Ala Gly Arg Cys
            980                 985                 990

Leu Gln Gly Phe Leu Asp Tyr Trp Ser Gln Glu Gly Leu Arg Pro Pro
        995                 1000                1005

Arg Lys Glu Phe Glu Cys Asp Gln Gly Val Lys Phe Ala Leu Asp
    1010                1015                1020

Val Lys Lys Tyr Gln Ile Asp Pro Leu Gly Tyr Tyr Tyr Glu Val
    1025                1030                1035

Lys Gln Glu Lys Arg Leu Gly Thr Ile Pro Gln Met Arg Ser Ala
    1040                1045                1050

Lys Lys Leu Val Lys Lys
    1055

<210> SEQ ID NO 276
<211> LENGTH: 1082
<212> TYPE: PRT
<213> ORGANISM: Neisseria meningitidis

<400> SEQUENCE: 276

Met Ala Ala Phe Lys Pro Asn Ser Ile Asn Tyr Ile Leu Gly Leu Asp
1               5                   10                  15

Ile Gly Ile Ala Ser Val Gly Trp Ala Met Val Glu Ile Asp Glu Glu
            20                  25                  30

```
Glu Asn Pro Ile Arg Leu Ile Asp Leu Gly Val Arg Val Phe Glu Arg
            35                  40                  45

Ala Glu Val Pro Lys Thr Gly Asp Ser Leu Ala Met Ala Arg Arg Leu
 50                  55                  60

Ala Arg Ser Val Arg Arg Leu Thr Arg Arg Ala His Arg Leu Leu
 65                  70                  75                  80

Arg Thr Arg Arg Leu Leu Lys Arg Glu Gly Val Leu Gln Ala Ala Asn
                    85                  90                  95

Phe Asp Glu Asn Gly Leu Ile Lys Ser Leu Pro Asn Thr Pro Trp Gln
                100                 105                 110

Leu Arg Ala Ala Ala Leu Asp Arg Lys Leu Thr Pro Leu Glu Trp Ser
                115                 120                 125

Ala Val Leu Leu His Leu Ile Lys His Arg Gly Tyr Leu Ser Gln Arg
                130                 135                 140

Lys Asn Glu Gly Glu Thr Ala Asp Lys Glu Leu Gly Ala Leu Leu Lys
145                 150                 155                 160

Gly Val Ala Gly Asn Ala His Ala Leu Gln Thr Gly Asp Phe Arg Thr
                    165                 170                 175

Pro Ala Glu Leu Ala Leu Asn Lys Phe Glu Lys Glu Ser Gly His Ile
                180                 185                 190

Arg Asn Gln Arg Ser Asp Tyr Ser His Thr Phe Ser Arg Lys Asp Leu
                195                 200                 205

Gln Ala Glu Leu Ile Leu Leu Phe Glu Lys Gln Lys Glu Phe Gly Asn
                210                 215                 220

Pro His Val Ser Gly Leu Lys Glu Gly Ile Glu Thr Leu Leu Met
225                 230                 235                 240

Thr Gln Arg Pro Ala Leu Ser Gly Asp Ala Val Gln Lys Met Leu Gly
                    245                 250                 255

His Cys Thr Phe Glu Pro Ala Glu Pro Lys Ala Ala Lys Asn Thr Tyr
                    260                 265                 270

Thr Ala Glu Arg Phe Ile Trp Leu Thr Lys Leu Asn Asn Leu Arg Ile
                275                 280                 285

Leu Glu Gln Gly Ser Glu Arg Pro Leu Thr Asp Thr Glu Arg Ala Thr
290                 295                 300

Leu Met Asp Glu Pro Tyr Arg Lys Ser Lys Leu Thr Tyr Ala Gln Ala
305                 310                 315                 320

Arg Lys Leu Leu Gly Leu Glu Asp Thr Ala Phe Phe Lys Gly Leu Arg
                325                 330                 335

Tyr Gly Lys Asp Asn Ala Glu Ala Ser Thr Leu Met Glu Met Lys Ala
                340                 345                 350

Tyr His Ala Ile Ser Arg Ala Leu Glu Lys Glu Gly Leu Lys Asp Lys
                355                 360                 365

Lys Ser Pro Leu Asn Leu Ser Pro Glu Leu Gln Asp Glu Ile Gly Thr
370                 375                 380

Ala Phe Ser Leu Phe Lys Thr Asp Glu Asp Ile Thr Gly Arg Leu Lys
385                 390                 395                 400

Asp Arg Ile Gln Pro Glu Ile Leu Glu Ala Leu Leu Lys His Ile Ser
                405                 410                 415

Phe Asp Lys Phe Val Gln Ile Ser Leu Lys Ala Leu Arg Arg Ile Val
                420                 425                 430

Pro Leu Met Glu Gln Gly Lys Arg Tyr Asp Glu Ala Cys Ala Glu Ile
                435                 440                 445
```

```
Tyr Gly Asp His Tyr Gly Lys Lys Asn Thr Glu Glu Lys Ile Tyr Leu
    450             455                 460
Pro Pro Ile Pro Ala Asp Glu Ile Arg Asn Pro Val Val Leu Arg Ala
465             470                 475                 480
Leu Ser Gln Ala Arg Lys Val Ile Asn Gly Val Val Arg Arg Tyr Gly
                485                 490                 495
Ser Pro Ala Arg Ile His Ile Glu Thr Ala Arg Glu Val Gly Lys Ser
            500                 505                 510
Phe Lys Asp Arg Lys Glu Ile Glu Lys Arg Gln Glu Glu Asn Arg Lys
        515                 520                 525
Asp Arg Glu Lys Ala Ala Ala Lys Phe Arg Glu Tyr Phe Pro Asn Phe
    530                 535                 540
Val Gly Glu Pro Lys Ser Lys Asp Ile Leu Lys Leu Arg Leu Tyr Glu
545                 550                 555                 560
Gln Gln His Gly Lys Cys Leu Tyr Ser Gly Lys Glu Ile Asn Leu Gly
                565                 570                 575
Arg Leu Asn Glu Lys Gly Tyr Val Glu Ile Asp His Ala Leu Pro Phe
            580                 585                 590
Ser Arg Thr Trp Asp Asp Ser Phe Asn Asn Lys Val Leu Val Leu Gly
        595                 600                 605
Ser Glu Asn Gln Asn Lys Gly Asn Gln Thr Pro Tyr Glu Tyr Phe Asn
    610                 615                 620
Gly Lys Asp Asn Ser Arg Glu Trp Gln Glu Phe Lys Ala Arg Val Glu
625                 630                 635                 640
Thr Ser Arg Phe Pro Arg Ser Lys Lys Gln Arg Ile Leu Leu Gln Lys
                645                 650                 655
Phe Asp Glu Asp Gly Phe Lys Glu Arg Asn Leu Asn Asp Thr Arg Tyr
            660                 665                 670
Val Asn Arg Phe Leu Cys Gln Phe Val Ala Asp Arg Met Arg Leu Thr
        675                 680                 685
Gly Lys Gly Lys Lys Arg Val Phe Ala Ser Asn Gly Gln Ile Thr Asn
    690                 695                 700
Leu Leu Arg Gly Phe Trp Gly Leu Arg Lys Val Arg Ala Glu Asn Asp
705                 710                 715                 720
Arg His His Ala Leu Asp Ala Val Val Val Ala Cys Ser Thr Val Ala
                725                 730                 735
Met Gln Gln Lys Ile Thr Arg Phe Val Arg Tyr Lys Glu Met Asn Ala
            740                 745                 750
Phe Asp Gly Lys Thr Ile Asp Lys Glu Thr Gly Glu Val Leu His Gln
        755                 760                 765
Lys Thr His Phe Pro Gln Pro Trp Glu Phe Phe Ala Gln Glu Val Met
    770                 775                 780
Ile Arg Val Phe Gly Lys Pro Asp Gly Lys Pro Glu Phe Glu Glu Ala
785                 790                 795                 800
Asp Thr Leu Glu Lys Leu Arg Thr Leu Leu Ala Glu Lys Leu Ser Ser
                805                 810                 815
Arg Pro Glu Ala Val His Glu Tyr Val Thr Pro Leu Phe Val Ser Arg
            820                 825                 830
Ala Pro Asn Arg Lys Met Ser Gly Gln Gly His Met Glu Thr Val Lys
        835                 840                 845
Ser Ala Lys Arg Leu Asp Glu Gly Val Ser Val Leu Arg Val Pro Leu
    850                 855                 860
```

```
Thr Gln Leu Lys Leu Lys Asp Leu Glu Lys Met Val Asn Arg Glu Arg
865                 870                 875                 880

Glu Pro Lys Leu Tyr Glu Ala Leu Lys Ala Arg Leu Glu Ala His Lys
                885                 890                 895

Asp Asp Pro Ala Lys Ala Phe Ala Glu Pro Phe Tyr Lys Tyr Asp Lys
            900                 905                 910

Ala Gly Asn Arg Thr Gln Gln Val Lys Ala Val Arg Val Glu Gln Val
        915                 920                 925

Gln Lys Thr Gly Val Trp Val Arg Asn His Asn Gly Ile Ala Asp Asn
    930                 935                 940

Ala Thr Met Val Arg Val Asp Val Phe Glu Lys Gly Asp Lys Tyr Tyr
945                 950                 955                 960

Leu Val Pro Ile Tyr Ser Trp Gln Val Ala Lys Gly Ile Leu Pro Asp
                965                 970                 975

Arg Ala Val Val Gln Gly Lys Asp Glu Glu Asp Trp Gln Leu Ile Asp
            980                 985                 990

Asp Ser Phe Asn Phe Lys Phe Ser Leu His Pro Asn Asp Leu Val Glu
        995                 1000                1005

Val Ile Thr Lys Lys Ala Arg Met Phe Gly Tyr Phe Ala Ser Cys
    1010                1015                1020

His Arg Gly Thr Gly Asn Ile Asn Ile Arg Ile His Asp Leu Asp
    1025                1030                1035

His Lys Ile Gly Lys Asn Gly Ile Leu Glu Gly Ile Gly Val Lys
    1040                1045                1050

Thr Ala Leu Ser Phe Gln Lys Tyr Gln Ile Asp Glu Leu Gly Lys
    1055                1060                1065

Glu Ile Arg Pro Cys Arg Leu Lys Lys Arg Pro Pro Val Arg
    1070                1075                1080

<210> SEQ ID NO 277
<211> LENGTH: 1101
<212> TYPE: PRT
<213> ORGANISM: Actinomyces naeslundii

<400> SEQUENCE: 277

Met Trp Tyr Ala Ser Leu Met Ser Ala His His Leu Arg Val Gly Ile
1               5                   10                  15

Asp Val Gly Thr His Ser Val Gly Leu Ala Thr Leu Arg Val Asp Asp
                20                  25                  30

His Gly Thr Pro Ile Glu Leu Leu Ser Ala Leu Ser His Ile His Asp
            35                  40                  45

Ser Gly Val Gly Lys Glu Gly Lys Lys Asp His Asp Thr Arg Lys Lys
        50                  55                  60

Leu Ser Gly Ile Ala Arg Arg Ala Arg Arg Leu Leu His Arg Arg
65                  70                  75                  80

Thr Gln Leu Gln Gln Leu Asp Glu Val Leu Arg Asp Leu Gly Phe Pro
                85                  90                  95

Ile Pro Thr Pro Gly Glu Phe Leu Asp Leu Asn Glu Gln Thr Asp Pro
            100                 105                 110

Tyr Arg Val Trp Arg Val Arg Ala Arg Leu Val Glu Glu Lys Leu Pro
        115                 120                 125

Glu Glu Leu Arg Gly Pro Ala Ile Ser Met Ala Val Arg His Ile Ala
    130                 135                 140
```

```
Arg His Arg Gly Trp Arg Asn Pro Tyr Ser Lys Val Glu Ser Leu Leu
145                 150                 155                 160

Ser Pro Ala Glu Glu Ser Pro Phe Met Lys Ala Leu Arg Glu Arg Ile
            165                 170                 175

Leu Ala Thr Thr Gly Glu Val Leu Asp Asp Gly Ile Thr Pro Gly Gln
            180                 185                 190

Ala Met Ala Gln Val Ala Leu Thr His Asn Ile Ser Met Arg Gly Pro
            195                 200                 205

Glu Gly Ile Leu Gly Lys Leu His Gln Ser Asp Asn Ala Asn Glu Ile
            210                 215                 220

Arg Lys Ile Cys Ala Arg Gln Gly Val Ser Pro Asp Val Cys Lys Gln
225                 230                 235                 240

Leu Leu Arg Ala Val Phe Lys Ala Asp Ser Pro Arg Gly Ser Ala Val
                245                 250                 255

Ser Arg Val Ala Pro Asp Pro Leu Pro Gly Gln Gly Ser Phe Arg Arg
            260                 265                 270

Ala Pro Lys Cys Asp Pro Glu Phe Gln Arg Phe Arg Ile Ile Ser Ile
            275                 280                 285

Val Ala Asn Leu Arg Ile Ser Glu Thr Lys Gly Glu Asn Arg Pro Leu
            290                 295                 300

Thr Ala Asp Glu Arg Arg His Val Val Thr Phe Leu Thr Glu Asp Ser
305                 310                 315                 320

Gln Ala Asp Leu Thr Trp Val Asp Val Ala Glu Lys Leu Gly Val His
                325                 330                 335

Arg Arg Asp Leu Arg Gly Thr Ala Val His Thr Asp Asp Gly Glu Arg
            340                 345                 350

Ser Ala Ala Arg Pro Pro Ile Asp Ala Thr Asp Arg Ile Met Arg Gln
            355                 360                 365

Thr Lys Ile Ser Ser Leu Lys Thr Trp Trp Glu Glu Ala Asp Ser Glu
370                 375                 380

Gln Arg Gly Ala Met Ile Arg Tyr Leu Tyr Glu Asp Pro Thr Asp Ser
385                 390                 395                 400

Glu Cys Ala Glu Ile Ile Ala Glu Leu Pro Glu Glu Asp Gln Ala Lys
                405                 410                 415

Leu Asp Ser Leu His Leu Pro Ala Gly Arg Ala Ala Tyr Ser Arg Glu
            420                 425                 430

Ser Leu Thr Ala Leu Ser Asp His Met Leu Ala Thr Thr Asp Asp Leu
            435                 440                 445

His Glu Ala Arg Lys Arg Leu Phe Gly Val Asp Asp Ser Trp Ala Pro
            450                 455                 460

Pro Ala Glu Ala Ile Asn Ala Pro Val Gly Asn Pro Ser Val Asp Arg
465                 470                 475                 480

Thr Leu Lys Ile Val Gly Arg Tyr Leu Ser Ala Val Glu Ser Met Trp
                485                 490                 495

Gly Thr Pro Glu Val Ile His Val Glu His Val Arg Asp Gly Phe Thr
            500                 505                 510

Ser Glu Arg Met Ala Asp Glu Arg Asp Lys Ala Asn Arg Arg Arg Tyr
            515                 520                 525

Asn Asp Asn Gln Glu Ala Met Lys Lys Ile Gln Arg Asp Tyr Gly Lys
            530                 535                 540

Glu Gly Tyr Ile Ser Arg Gly Asp Ile Val Arg Leu Asp Ala Leu Glu
545                 550                 555                 560
```

```
Leu Gln Gly Cys Ala Cys Leu Tyr Cys Gly Thr Thr Ile Gly Tyr His
                565                 570                 575
Thr Cys Gln Leu Asp His Ile Val Pro Gln Ala Gly Pro Gly Ser Asn
                580                 585                 590
Asn Arg Arg Gly Asn Leu Val Ala Val Cys Glu Arg Cys Asn Arg Ser
                595                 600                 605
Lys Ser Asn Thr Pro Phe Ala Val Trp Ala Gln Lys Cys Gly Ile Pro
                610                 615                 620
His Val Gly Val Lys Glu Ala Ile Gly Arg Val Arg Gly Trp Arg Lys
625                 630                 635                 640
Gln Thr Pro Asn Thr Ser Ser Glu Asp Leu Thr Arg Leu Lys Lys Glu
                645                 650                 655
Val Ile Ala Arg Leu Arg Arg Thr Gln Glu Asp Pro Glu Ile Asp Glu
                660                 665                 670
Arg Ser Met Glu Ser Val Ala Trp Met Ala Asn Glu Leu His His Arg
                675                 680                 685
Ile Ala Ala Ala Tyr Pro Glu Thr Thr Val Met Val Tyr Arg Gly Ser
                690                 695                 700
Ile Thr Ala Ala Ala Arg Lys Ala Ala Gly Ile Asp Ser Arg Ile Asn
705                 710                 715                 720
Leu Ile Gly Glu Lys Gly Arg Lys Asp Arg Ile Asp Arg Arg His His
                725                 730                 735
Ala Val Asp Ala Ser Val Val Ala Leu Met Glu Ala Ser Val Ala Lys
                740                 745                 750
Thr Leu Ala Glu Arg Ser Ser Leu Arg Gly Glu Gln Arg Leu Thr Gly
                755                 760                 765
Lys Glu Gln Thr Trp Lys Gln Tyr Thr Gly Ser Thr Val Gly Ala Arg
                770                 775                 780
Glu His Phe Glu Met Trp Arg Gly His Met Leu His Leu Thr Glu Leu
785                 790                 795                 800
Phe Asn Glu Arg Leu Ala Glu Asp Lys Val Tyr Val Thr Gln Asn Ile
                805                 810                 815
Arg Leu Arg Leu Ser Asp Gly Asn Ala His Thr Val Asn Pro Ser Lys
                820                 825                 830
Leu Val Ser His Arg Leu Gly Asp Gly Leu Thr Val Gln Gln Ile Asp
                835                 840                 845
Arg Ala Cys Thr Pro Ala Leu Trp Cys Ala Leu Thr Arg Glu Lys Asp
                850                 855                 860
Phe Asp Glu Lys Asn Gly Leu Pro Ala Arg Glu Asp Arg Ala Ile Arg
865                 870                 875                 880
Val His Gly His Glu Ile Lys Ser Ser Asp Tyr Ile Gln Val Phe Ser
                885                 890                 895
Lys Arg Lys Lys Thr Asp Ser Asp Arg Asp Glu Thr Pro Phe Gly Ala
                900                 905                 910
Ile Ala Val Arg Gly Gly Phe Val Glu Ile Gly Pro Ser Ile His His
                915                 920                 925
Ala Arg Ile Tyr Arg Val Glu Gly Lys Lys Pro Val Tyr Ala Met Leu
                930                 935                 940
Arg Val Phe Thr His Asp Leu Leu Ser Gln Arg His Gly Asp Leu Phe
945                 950                 955                 960
Ser Ala Val Ile Pro Pro Gln Ser Ile Ser Met Arg Cys Ala Glu Pro
                965                 970                 975
```

```
Lys Leu Arg Lys Ala Ile Thr Thr Gly Asn Ala Thr Tyr Leu Gly Trp
                980                 985                 990

Val Val Val Gly Asp Glu Leu Glu  Ile Asn Val Asp Ser  Phe Thr Lys
            995                 1000                1005

Tyr Ala  Ile Gly Arg Phe Leu  Glu Asp Phe Pro Asn  Thr Thr Arg
    1010                1015                1020

Trp Arg  Ile Cys Gly Tyr Asp  Thr Asn Ser Lys Leu  Thr Leu Lys
    1025                1030                1035

Pro Ile  Val Leu Ala Ala Glu  Gly Leu Glu Asn Pro  Ser Ser Ala
    1040                1045                1050

Val Asn  Glu Ile Val Glu Leu  Lys Gly Trp Arg Val  Ala Ile Asn
    1055                1060                1065

Val Leu  Thr Lys Val His Pro  Thr Val Val Arg Arg  Asp Ala Leu
    1070                1075                1080

Gly Arg  Pro Arg Tyr Ser Ser  Arg Ser Asn Leu Pro  Thr Ser Trp
    1085                1090                1095

Thr Ile  Glu
    1100

<210> SEQ ID NO 278
<211> LENGTH: 1082
<212> TYPE: PRT
<213> ORGANISM: Geobacillus thermodenitrificans

<400> SEQUENCE: 278

Met Lys Tyr Lys Ile Gly Leu Asp Ile Gly Ile Thr Ser Ile Gly Trp
1               5                   10                  15

Ala Val Ile Asn Leu Asp Ile Pro Arg Ile Glu Asp Leu Gly Val Arg
                20                  25                  30

Ile Phe Asp Arg Ala Glu Asn Pro Lys Thr Gly Glu Ser Leu Ala Leu
            35                  40                  45

Pro Arg Arg Leu Ala Arg Ser Ala Arg Arg Arg Leu Arg Arg Arg Lys
    50                  55                  60

His Arg Leu Glu Arg Ile Arg Arg Leu Phe Val Arg Glu Gly Ile Leu
65                  70                  75                  80

Thr Lys Glu Glu Leu Asn Lys Leu Phe Glu Lys Lys His Glu Ile Asp
                85                  90                  95

Val Trp Gln Leu Arg Val Glu Ala Leu Asp Arg Lys Leu Asn Asn Asp
                100                 105                 110

Glu Leu Ala Arg Ile Leu Leu His Leu Ala Lys Arg Arg Gly Phe Arg
            115                 120                 125

Ser Asn Arg Lys Ser Glu Arg Thr Asn Lys Glu Asn Ser Thr Met Leu
    130                 135                 140

Lys His Ile Glu Glu Asn Gln Ser Ile Leu Ser Ser Tyr Arg Thr Val
145                 150                 155                 160

Ala Glu Met Val Val Lys Asp Pro Lys Phe Ser Leu His Lys Arg Asn
                165                 170                 175

Lys Glu Asp Asn Tyr Thr Asn Thr Val Ala Arg Asp Asp Leu Glu Arg
            180                 185                 190

Glu Ile Lys Leu Ile Phe Ala Lys Gln Arg Glu Tyr Gly Asn Ile Val
    195                 200                 205

Cys Thr Glu Ala Phe Glu His Glu Tyr Ile Ser Ile Trp Ala Ser Gln
    210                 215                 220
```

```
Arg Pro Phe Ala Ser Lys Asp Asp Ile Glu Lys Lys Val Gly Phe Cys
225                 230                 235                 240

Thr Phe Glu Pro Lys Glu Lys Arg Ala Pro Lys Ala Thr Tyr Thr Phe
            245                 250                 255

Gln Ser Phe Thr Val Trp Glu His Ile Asn Lys Leu Arg Leu Val Ser
                260                 265                 270

Pro Gly Gly Ile Arg Ala Leu Thr Asp Asp Glu Arg Leu Ile Tyr
            275                 280                 285

Lys Gln Ala Phe His Lys Asn Lys Ile Thr Phe His Asp Val Arg Thr
            290                 295                 300

Leu Leu Asn Leu Pro Asp Asp Thr Arg Phe Lys Gly Leu Leu Tyr Asp
305                 310                 315                 320

Arg Asn Thr Thr Leu Lys Glu Asn Glu Lys Val Arg Phe Leu Glu Leu
                325                 330                 335

Gly Ala Tyr His Lys Ile Arg Lys Ala Ile Asp Ser Val Tyr Gly Lys
                340                 345                 350

Gly Ala Ala Lys Ser Phe Arg Pro Ile Asp Phe Asp Thr Phe Gly Tyr
            355                 360                 365

Ala Leu Thr Met Phe Lys Asp Asp Thr Asp Ile Arg Ser Tyr Leu Arg
370                 375                 380

Asn Glu Tyr Glu Gln Asn Gly Lys Arg Met Glu Asn Leu Ala Asp Lys
385                 390                 395                 400

Val Tyr Asp Glu Glu Leu Ile Glu Glu Leu Leu Asn Leu Ser Phe Ser
                405                 410                 415

Lys Phe Gly His Leu Ser Leu Lys Ala Leu Arg Asn Ile Leu Pro Tyr
                420                 425                 430

Met Glu Gln Gly Glu Val Tyr Ser Thr Ala Cys Glu Arg Ala Gly Tyr
            435                 440                 445

Thr Phe Thr Gly Pro Lys Lys Lys Gln Lys Thr Val Leu Leu Pro Asn
            450                 455                 460

Ile Pro Pro Ile Ala Asn Pro Val Val Met Arg Ala Leu Thr Gln Ala
465                 470                 475                 480

Arg Lys Val Val Asn Ala Ile Ile Lys Lys Tyr Gly Ser Pro Val Ser
                485                 490                 495

Ile His Ile Glu Leu Ala Arg Glu Leu Ser Gln Ser Phe Asp Glu Arg
            500                 505                 510

Arg Lys Met Gln Lys Glu Gln Glu Gly Asn Arg Lys Lys Asn Glu Thr
            515                 520                 525

Ala Ile Arg Gln Leu Val Glu Tyr Gly Leu Thr Leu Asn Pro Thr Gly
            530                 535                 540

Leu Asp Ile Val Lys Phe Lys Leu Trp Ser Glu Gln Asn Gly Lys Cys
545                 550                 555                 560

Ala Tyr Ser Leu Gln Pro Ile Glu Ile Glu Arg Leu Leu Glu Pro Gly
                565                 570                 575

Tyr Thr Glu Val Asp His Val Ile Pro Tyr Ser Arg Ser Leu Asp Asp
                580                 585                 590

Ser Tyr Thr Asn Lys Val Leu Val Leu Thr Lys Glu Asn Arg Glu Lys
            595                 600                 605

Gly Asn Arg Thr Pro Ala Glu Tyr Leu Gly Leu Gly Ser Glu Arg Trp
            610                 615                 620

Gln Gln Phe Glu Thr Phe Val Leu Thr Asn Lys Gln Phe Ser Lys Lys
625                 630                 635                 640
```

```
Lys Arg Asp Arg Leu Leu Arg Leu His Tyr Asp Glu Asn Glu Glu Asn
                645                 650                 655

Glu Phe Lys Asn Arg Asn Leu Asn Asp Thr Arg Tyr Ile Ser Arg Phe
            660                 665                 670

Leu Ala Asn Phe Ile Arg Glu His Leu Lys Phe Ala Asp Ser Asp Asp
        675                 680                 685

Lys Gln Lys Val Tyr Thr Val Asn Gly Arg Ile Thr Ala His Leu Arg
    690                 695                 700

Ser Arg Trp Asn Phe Asn Lys Asn Arg Glu Glu Ser Asn Leu His His
705                 710                 715                 720

Ala Val Asp Ala Ala Ile Val Ala Cys Thr Thr Pro Ser Asp Ile Ala
                725                 730                 735

Arg Val Thr Ala Phe Tyr Gln Arg Arg Glu Gln Asn Lys Glu Leu Ser
            740                 745                 750

Lys Lys Thr Asp Pro Gln Phe Pro Gln Pro Trp Pro His Phe Ala Asp
        755                 760                 765

Glu Leu Gln Ala Arg Leu Ser Lys Asn Pro Lys Glu Ser Ile Lys Ala
    770                 775                 780

Leu Asn Leu Gly Asn Tyr Asp Asn Glu Lys Leu Glu Ser Leu Gln Pro
785                 790                 795                 800

Val Phe Val Ser Arg Met Pro Lys Arg Ser Ile Thr Gly Ala Ala His
                805                 810                 815

Gln Glu Thr Leu Arg Arg Tyr Ile Gly Ile Asp Glu Arg Ser Gly Lys
            820                 825                 830

Ile Gln Thr Val Val Lys Lys Leu Ser Glu Ile Gln Leu Asp Lys
        835                 840                 845

Thr Gly His Phe Pro Met Tyr Gly Lys Glu Ser Asp Pro Arg Thr Tyr
    850                 855                 860

Glu Ala Ile Arg Gln Arg Leu Leu Glu His Asn Asn Asp Pro Lys Lys
865                 870                 875                 880

Ala Phe Gln Glu Pro Leu Tyr Lys Pro Lys Lys Asn Gly Glu Leu Gly
                885                 890                 895

Pro Ile Ile Arg Thr Ile Lys Ile Ile Asp Thr Thr Asn Gln Val Ile
            900                 905                 910

Pro Leu Asn Asp Gly Lys Thr Val Ala Tyr Asn Ser Asn Ile Val Arg
        915                 920                 925

Val Asp Val Phe Glu Lys Asp Gly Lys Tyr Tyr Cys Val Pro Ile Tyr
    930                 935                 940

Thr Ile Asp Met Met Lys Gly Ile Leu Pro Asn Lys Ala Ile Glu Pro
945                 950                 955                 960

Asn Lys Pro Tyr Ser Glu Trp Lys Glu Met Thr Glu Asp Tyr Thr Phe
                965                 970                 975

Arg Phe Ser Leu Tyr Pro Asn Asp Leu Ile Arg Ile Glu Phe Pro Arg
            980                 985                 990

Glu Lys Thr Ile Lys Thr Ala Val  Gly Glu Glu Ile Lys  Ile Lys Asp
        995                 1000                1005

Leu Phe Ala Tyr Tyr Gln Thr  Ile Asp Ser Ser Asn  Gly Gly Leu
    1010                1015                1020

Ser Leu Val Ser His Asp Asn  Asn Phe Ser Leu Arg  Ser Ile Gly
    1025                1030                1035

Ser Arg  Thr Leu Lys Arg Phe  Glu Lys Tyr Gln Val  Asp Val Leu
    1040                1045                1050
```

```
Gly Asn Ile Tyr Lys Val Arg Gly Glu Lys Arg Val Gly Val Ala
    1055            1060            1065

Ser Ser Ser His Ser Lys Ala Gly Glu Thr Ile Arg Pro Leu
    1070            1075            1080

<210> SEQ ID NO 279
<211> LENGTH: 25
<212> TYPE: DNA
<213> ORGANISM: Artificial Sequence
<220> FEATURE:
<223> OTHER INFORMATION: Chemically synthesized

<400> SEQUENCE: 279
aagcatagct gcaacctact gcacc                                           25

<210> SEQ ID NO 280
<211> LENGTH: 73
<212> TYPE: DNA
<213> ORGANISM: Artificial Sequence
<220> FEATURE:
<223> OTHER INFORMATION: Chemically synthesized

<400> SEQUENCE: 280
atgaaaaaag aaaaagtaaa tcgtgttgta gtcgttggaa ctggtgcagt aggttgcagc     60
tatgcttact ccc                                                        73

<210> SEQ ID NO 281
<211> LENGTH: 72
<212> TYPE: DNA
<213> ORGANISM: Artificial Sequence
<220> FEATURE:
<223> OTHER INFORMATION: Chemically synthesized

<400> SEQUENCE: 281
ggagtaagca tagctgcaac ctactgcacc agttccaacg actacaacac gatttacttt     60 ttctttttc at                                                          72
```